US012734530B2

(12) United States Patent
Smith et al.

(10) Patent No.: US 12,734,530 B2
(45) Date of Patent: Sep. 15, 2026

(54) CENTRIFUGAL SEPARATORS AND SKID FOR SEPARATING BIOCOMPONENTS AND METHODS OF USE

(71) Applicant: Life Technologies Corporation, Carlsbad, CA (US)

(72) Inventors: Mark T. Smith, Nibley, UT (US); Joe Loveless, Logan, UT (US); Norman Ballhause, Osterode (DE); Jacob D. Lee, Logan, UT (US)

(73) Assignee: Life Technologies Corporation, Carlsbad, CA (US)

(*) Notice: Subject to any disclaimer, the term of this patent is extended or adjusted under 35 U.S.C. 154(b) by 672 days.

(21) Appl. No.: 18/253,350

(22) PCT Filed: Nov. 19, 2021

(86) PCT No.: PCT/US2021/072534
§ 371 (c)(1),
(2) Date: Nov. 9, 2023

(87) PCT Pub. No.: WO2022/109612
PCT Pub. Date: May 27, 2022

(65) Prior Publication Data

US 2023/0405611 A1 Dec. 21, 2023

Related U.S. Application Data

(60) Provisional application No. 63/219,339, filed on Jul. 7, 2021, provisional application No. 63/115,938, filed on Nov. 19, 2020.

(51) Int. Cl.
*B04B 15/00* (2006.01)
*B04B 5/04* (2006.01)
(Continued)

(52) U.S. Cl.
CPC ............ *B04B 15/00* (2013.01); *B04B 5/0442* (2013.01); *B04B 7/02* (2013.01); *B04B 9/02* (2013.01); *B04B 9/12* (2013.01); *C12M 47/02* (2013.01)

(58) Field of Classification Search
CPC ........... B04B 1/08; B04B 11/02; B04B 11/06; B04B 15/00; B04B 5/0442; B04B 5/12;
(Continued)

(56) References Cited

U.S. PATENT DOCUMENTS

| | | | |
|---|---|---|---|
| 5,851,169 | A | 12/1998 | Meresz et al. |
| 6,083,587 | A | 7/2000 | Smith et al. |

(Continued)

FOREIGN PATENT DOCUMENTS

| | | | |
|---|---|---|---|
| JP | 2009-291335 A | 12/2009 | |
| WO | WO-2019226618 A1 | 11/2019 | |
| WO | WO-2019236895 A1 | 12/2019 | |

OTHER PUBLICATIONS

International Search Report and Written Opinion issued in International Application No. PCT/US2021/072534, mailed May 11, 2022. 22 pages.

(Continued)

*Primary Examiner* — Lydia Edwards

(57) ABSTRACT

A skid (700) for use in separating biocomponents includes a housing (701) bounding a compartment (708), the compartment being partially bounding by a mounting platform (709); and a loading assembly (800) secured to the housing so as to communicate with the compartment. The loading assembly (800) includes an alignment plate (808) having a top surface with cavity (814) recessed therein, the cavity communicating with the compartment; a drive rotor (15) rotatably disposed below the alignment plate and at least partially encircling the cavity, the drive rotor including one or more magnets; a motor (169) coupled to the drive rotor
(Continued)

for selectively rotating the drive rotor about the cavity; and a mount at least partially encircling the drive rotor and communicating with the compartment, the mount including a mounting plate having one or more mounting elements upstanding therefrom, the mount being movable between a raised position wherein the mounting plate is aligned with the alignment plate and a second lowered position wherein the mounting plate is disposed at an elevation lower than the alignment plate.

20 Claims, 60 Drawing Sheets

(51) Int. Cl.

| | |
|---|---|
| ***B04B 7/02*** | (2006.01) |
| ***B04B 9/02*** | (2006.01) |
| ***B04B 9/12*** | (2006.01) |
| ***C12M 1/00*** | (2006.01) |

(58) Field of Classification Search
CPC .... B04B 7/00; B04B 7/02; B04B 7/08; B04B 7/14; B04B 9/02; B04B 9/04; B04B 9/08; B04B 9/12; C12M 23/14; C12M 23/44; C12M 29/18; C12M 47/02
See application file for complete search history.

(56) References Cited

U.S. PATENT DOCUMENTS

| | | | |
|---|---|---|---|
| 7,384,783 | B2 | 6/2008 | Kunas et al. |
| 7,682,067 | B2 | 3/2010 | West et al. |
| 9,982,226 | B2 | 5/2018 | Tijsterman |
| 2003/0077466 | A1 | 4/2003 | Smith et al. |
| 2006/0196501 | A1 | 9/2006 | Bibbo et al. |

OTHER PUBLICATIONS

EP25192241.5, Partial European Search Report and Provisional Opinion, Mar. 27, 2026, 21 pages.

CENTRIFUGAL SEPARATORS AND SKID FOR SEPARATING BIOCOMPONENTS AND METHODS OF USE

CROSS-REFERENCE TO RELATED APPLICATIONS

This application is a U.S. National Phase Application under 35 U.S.C. § 371 of International Patent Application Number PCT/US2021/072534, filed Nov. 19, 2021, which claims the benefit of U.S. Provisional Application No. 63/115,938, filed Nov. 19, 2020, and U.S. Provisional Application No. 63/219,339, filed Jul. 7, 2021, which are incorporated herein by specific reference.

BACKGROUND OF THE DISCLOSURE

1. The Field of the Disclosure

The present disclosure relates to centrifugal separators used in the bioproduction industry and, more specifically, to single use continuous flow centrifugal separators for separating biological fluids, solids, mixtures, solutions and suspensions and to modular skids into which the separators can be incorporated.

2. The Relevant Technology

Bioreactors and fermenters are used to grow a variety of different types of biological suspensions. Such suspensions are broadly defined as comprising cells or microorganisms and a liquid medium in which they are suspended. Once a suspension has been sufficiently grown, it is common to separate the biological suspension into components and then harvest the separate components for subsequent analysis or use. Centrifugation is a technique often employed during isolation or analysis of various cells, organelles, and biopolymers, including proteins, nucleic acids, lipids, and carbohydrates dissolved or dispersed in biological suspension.

In one approach to centrifugation, quantities of a suspension are dispensed from a bioreactor or fermenter into an open-top bottle. The bottle is then closed by manually applying a lid and then spun using a centrifuge rotor. The centrifuge force created by spinning of the rotor causes the solids within the suspension, e.g., the cells or microorganisms, to sediment out towards the bottom of the bottle while the lighter components collect toward the top of the bottle. Once the bottle is removed from the centrifuge rotor, the lighter component is poured out of the bottle for harvesting following which, the solids are removed from the bottle for harvesting.

Although the above process is effective, it has a number of shortcomings. For example, in the above process the bottles are reused. Accordingly, after each use it is necessary to clean and sterilize each bottle. This process is time consuming, labor intensive and requires special sterilizing equipment, like an autoclave. Furthermore, although the bottles are cleaned and sterilized between each use, the bottles are used as open-top containers. Thus, both the suspension and the interior of the bottles are openly exposed to the surrounding environment as the suspension is initially dispensed into the bottles. In turn, the separated components are again openly exposed to the surrounding environment as the separated components are removed from the bottles. This open exposure to the environment increases the probability of the suspension and/or the separated components becoming contaminated. Subsequent purification steps can thus be required to remove any contaminates from one or both of the separated components. In addition to the above, it can be difficult in conventional systems to effectively separate from the bottle the light components from the heavier components without some mixing between the two.

Furthermore, because the above process operates by consecutively separating discrete portions of a volume of suspension, the process cannot be used where it is desired to have a continuous flow perfusion system. Likewise, where it is desired to harvest the cells/microorganisms for reuse, such as in an inoculum, the extended removal of the cells/microorganisms out of a reactor for separation can stress the cells/microorganisms and decrease their viability.

In one alternative to the above, a centrifuge rotor is provided having a cavity with an inlet and an outlet. As the centrifuge rotor is spun, a suspension is delivered into the cavity through the inlet. The heavier components of the suspension collect within the cavity against the outside walls of the rotor while the lighter components flow out of the cavity through the outlet. Once a determined quantity of the heavier components has been collected within the cavity, the inflow of suspension is stopped and a portion of the heavier components is removed from the cavity. The inflow then resumes and the process is repeated until an entire batch of a suspension has been sufficiently separated. The cavity of the centrifuge rotor is then cleaned and sterilized for use with a next batch of a suspension.

Although this latter process is more efficient than the first, it still has a number of shortcomings. For example, this latter process still collects the heavier components in a batch type mode and thus cannot function in a continuous flow perfusion system. In addition, because the cells/microorganisms are collected within rotor, the cells/microorganisms are again maintained out of a reactor for an extended period of time which can decrease their viability. The centrifuge rotor is also typically a very robust piece of machinery that is made primary of metal and has many different parts that are assembled. Once use of the rotor is finished, it must be cleaned and sterilized for subsequent use. As such, the centrifuge rotor is both expensive to produce and labor intensive to maintain.

Accordingly, what is needed in the art are improved separators, systems, and methods that solve all or some of the above and other existing shortcomings.

SUMMARY OF THE DISCLOSURE

A first independent aspect of the disclosure includes a skid for use in separating biocomponents, the skid comprising:

a housing bounding a compartment, the compartment being partially bounded by a mounting platform; and a loading assembly secured to the housing so as to communicate with the compartment, the loading assembly comprising:

an alignment plate having a top surface with cavity recessed therein, the cavity communicating with the compartment;

a drive rotor rotatably disposed below the alignment plate and at least partially encircling the cavity, the drive rotor including one or more magnets;

a motor coupled to the drive rotor for selectively rotating the drive rotor about the cavity; and a mount at least partially encircling the drive rotor and communicating with the compartment, the mount including a mounting plate having one or more mounting elements upstanding therefrom, the mount being movable between a raised position wherein the mounting plate is aligned with the alignment plate and a second lowered position wherein the mounting plate is disposed at an elevation lower than the alignment plate.

An alternative embodiment further includes:

a doorway formed on the housing and communicating with the compartment; and a door mounted on the housing, the door being movable between an open position wherein the doorway is openly exposed and a closed position wherein the door covers the doorway.

In another embodiment, a notch is recessed into an exterior surface of the housing and extending between a side face of the housing and the doorway, the notch bounding a channel the communicates with the compartment whether the door is in the open position or the closed position.

Another embodiment further includes:

the mounting platform having an opening extending therethrough; and the loading assembly being secured to the housing so that the alignment plate is aligned with the opening extending through the mounting platform.

In another embodiment, at least a portion of a top surface of the mounting platform, a top surface of the alignment plate, and a top surface of the mounting plate are horizontally aligned when the mount is in the raised position.

In another embodiment, the loading assembly further comprises:

an annular inner sleeve that encircles an opening, the inner sleeve having an upper end with the alignment plate mounted thereon;

a receiver extending from a bottom surface of the alignment plate and projecting into the opening of the annular sleeve, the receiver bounding the cavity; and the drive rotor being at least partially disposed within the opening of the inner sleeve.

Another embodiment further includes the loading assembly further comprising an annular outer sleeve encircling the inner sleeve, the outer sleeve having an upper end with the mounting plate mounted thereon, the outer sleeve and the mounting plate being movable relative to the inner sleeve.

Another embodiment further includes:

a support from which the inner sleeve upstands;

a pivot mount block secured to the support at a location spaced apart from the inner sleeve;

a pair of pivot arms each having a first end pivotably mounted to the pivot mount block so that the pair of pivot arms extend along opposing sides of the outer sleeve; and a pair of support pins outwardly projecting from the opposing sides of the outer sleeve and coupling with corresponding ones of the pair of pivot arms.

Another embodiment further includes a linear actuator positioned to selectively raise and lower the outer sleeve relative to the inner sleeve.

In another embodiment, the one or more mounting elements comprise one or more L-shaped clips upstanding from the mounting plate and facing toward the cavity.

Another embodiment further includes one or more peristaltic pumps mounted on an exterior surface of the housing.

Another embodiment further includes one or more pinch valves mounted on an exterior surface of the housing.

Another embodiment further includes one or more of a pressure sensor, conductivity sensor, flow meter sensor, pH sensor, temperature sensor, or turbidity sensor mounted on an exterior surface of the housing.

Another independent aspect of the present disclosure includes a system for separating biocomponents, the system comprising:

the skid as recited above with or without any of the alternative features recited above or otherwise within the present application; and a centrifugal separator removably disposed within the compartment of the skid, the centrifugal separator being supported on the mounting plate of the loading assembly.

Another embodiment further includes a first fluid line fluid coupled to the centrifugal separator within the compartment of the skid, the first fluid line passing out of the compartment and being removably secured to an exterior surface of the housing.

In another embodiment, the first fluid line is removably coupled to a peristaltic pump and/or a pinch valve secured to the exterior surface of the housing.

Another embodiment further includes a sensor mounted on the first fluid line, the sensor being removably plugged into an electrical outlet formed on the exterior surface of the housing.

In another embodiment, the centrifugal separator is at least partially secured to the mounting plate by a magnetic force produced by the one or more magnets of the drive rotor.

Another embodiment further includes:

the centrifugal separator comprising:

a separation stator that bounds a chamber, the separation stator having a floor with a receiver outwardly projecting therefrom, the receiver bounding a recess that communicates with the chamber of the separation stator;

a separation rotor rotatably disposed within chamber of the separation stator;

a drive coupling coupled to and extending from the separation rotor so as to project into the recess of the receiver; and a driver sleeve that outwardly projects from a floor of the separation stator and at least partially encircles the receiver of the separation stator;

wherein the centrifugal separator is positioned so that receiver of the separation rotor is aligned with the cavity of the alignment plate and the one or more mounting elements engage the driver sleeve.

In another embodiment, the receiver of the separation stator is received within the cavity of the alignment plate when the mounting plate is moved to the lowered position and the receiver of the separation stator is removed from within the cavity of the alignment plate when the mounting plate is moved to the raised position.

In another embodiment, the driver sleeve has one or more apertures or recesses in which a portion of the one or more mounting elements are received.

In another embodiment, with the one or more mounting elements engaging the driver sleeve, moving the mounting plate to the lowered position rigidly locks the centrifugal separator to the housing of the skid.

Another independent aspect of the present disclosure includes a method for separating biocomponents, the method comprising:

positioning a centrifugal separator on a top surface of the mounting platform of the skid as recited above with or without any of the alternative features recited above or otherwise within the present application;

laterally moving the centrifugal separator within the compartment of the housing so that the centrifugal separator is supported on the mounting plate of the mount and the mounting elements engage the centrifugal separator;

moving the mounting plate to the lowered position so that centrifugal separator is lowered relative to the alignment plate, a drive coupling of the centrifugal separator being received within the cavity of the alignment plate as the mounting plate is moved to the lowered position; and activating the motor to rotate the drive rotor which magnetically rotates a separation rotor of the centrifugal separator.

In another embodiment, laterally moving the centrifugal separator comprises laterally sliding the centrifugal separator on the mounting platform proximate a magnetic field produced by the one or more magnets of the drive rotor, wherein the magnetic field assists in positioning of the centrifugal separator.

In another embodiment, moving the mounting plate to the lowered position rigidly locks the centrifugal separator to the housing of the skid.

In another embodiment, the step of positioning a centrifugal separator on the top surface of the mounting platform comprises:

passing the centrifugal separator through a doorway formed on the housing and into the compartment; and closing a door that covers the doorway after the centrifugal separator is within the compartment.

In another embodiment, the centrifugal separator is positioned on the top surface of the mounting platform so that a first fluid line coupled with centrifugal separator passes out of the compartment of the housing, the method further comprising removably securing the first fluid line to a pinch valve and/or a peristaltic pump mounted on an exterior surface of the housing.

Another independent aspect of the present disclosure includes a centrifugal separator incudes:

a separation stator bounding a chamber, the separation stator having an inlet opening, a first outlet opening and a second outlet opening;

a separation rotor bounding a compartment, the separation rotor being at least partially disposed within the chamber of the separation stator and being rotatable therein about a rotational axis, the separation rotor having a floor with an interior surface and an opposing bottom surface, a bowl being formed on and outwardly projecting from the bottom surface of the floor, the bowl bounding a recess formed on the interior surface of the floor and communicating with the compartment of the separation rotor; and an annular bearing assembly extending between the separation stator and the separation rotor so as to enable the separation rotor to rotate relative to the separation stator, the annular bearing assembly encircling and being disposed directly against the exterior surface of the bowl so as to encircle at least a portion of the recess.

In another embodiment, during operation, a fluid flowing between the inlet opening and the first and second outlet openings passes through the recess of the bowl so as to form a heat sink for the bearing.

Another embodiment further includes a plurality of fins downwardly projecting from the bottom surface of the floor and radially outwardly projecting away from the bowl.

Another independent aspect of the present disclosure includes a centrifugal separator includes:

a separation stator bounding a chamber, the separation stator having an inlet opening, a first outlet opening and a second outlet opening; and a separation rotor bounding a compartment, the separation rotor being at least partially disposed within the chamber of the separation stator and being rotatable therein about a rotational axis, a heavy component collection recess and light component collection recess being disposed between the separation stator and the separation rotor at spaced apart positions, the heavy component collection recess communicating with the first outlet opening and light component collection recess communicating with the second outlet opening, the separation rotor comprising:

a floor;

a sidewall assembly upstanding from the floor and encircling the compartment, the sidewall assembly comprising a plurality of separated heavy component fluid paths that each communicate upstream with the inlet opening and downstream with the heavy component collection recess; and a plurality of upper partitions radially inwardly projecting from sidewall assembly into the compartment so as to at least partially divide the compartment into a plurality of separated light component fluid paths that each communicate upstream with the inlet opening and downstream with the light component collection recess, wherein each light component fluid path communicates with at least two of the separated heavy component fluid paths but is isolated from at least some of the plurality of separated heavy component fluid paths.

In another embodiment, each of the plurality of separated light component fluid paths extend along a length and are isolated from each other along their length.

In another embodiment, at least some of the plurality of separated heavy component fluid paths are isolated from others of the plurality of separated heavy component fluid paths upstream of the heavy component collection recess.

In another embodiment, each light component fluid path communicates with two or three of the separated heavy component fluid paths but is isolated from a remainder of the plurality of separated heavy component fluid paths.

In another embodiment, the sidewall assembly comprises an annular outer sidewall and an annular inner sidewall that is encircled by the outer sidewall, the plurality of separated heavy component fluid paths being bounded between the inner sidewall and the outer sidewall.

Another embodiment further includes a plurality of dividers extending between the inner sidewall and the outer sidewall that separate the heavy component fluid paths from each other.

In another embodiment, the outer sidewall extends to the floor and the inner sidewall is spaced apart from the floor.

In another embodiment, at least a portion of outer sidewall has a frustoconical configuration.

In another embodiment, at least a portion of inner sidewall has a frustoconical configuration.

In another embodiment, the plurality of upper partitions radially inwardly project from the outer sidewall and the inner sidewall.

Another embodiment further includes a tubular conduit disposed within the compartment of the separation stator along the rotational axis, the tubular conduit having a first end coupled to the inlet opening of the separation stator and an opposing second end.

Another embodiment further includes a dispersion member disposed within the compartment of the separation rotor, the dispersion member having a body location above the floor so that a space is formed between the floor and the body of the dispersion member.

In another embodiment, the dispersion member has an opening centrally passing therethrough, the second end of the conduit being coupled to or passing through the opening of the dispersion member, the conduit being configured so that a fluid passing through the conduit from the inlet opening exits the conduit in the space formed between the floor and the body of the dispersion member.

In another embodiment, the plurality of upper partitions radially extend out from the conduit and extend along a top surface of the body of the dispersion member.

In another embodiment, the body of the dispersion member has a flat plate configuration or a frustoconical configuration.

Another embodiment further includes a plurality of lower partitions extending between the body of the dispersion member and the floor, the plurality of lower partitions radially outwardly extending from the opening of the dispersion member.

In another embodiment, the lower partitions extend to the sidewall assembly and are aligned with corresponding ones of the plurality of upper partitions.

In another embodiment, the second end of the conduit is disposed outside of the separation rotor and is rotatably secured to the separation stator by a bearing assembly.

Another embodiment further includes:

- a drive coupling secured to the floor of the separation rotor so as to outwardly project therefrom; and
- a drive rotor encircling the drive coupling, the drive rotor producing a magnetic field on the drive coupling so that rotation of the drive rotor facilitates rotation of the drive coupling.

In another embodiment, the drive coupling is disposed within the separation stator and the drive rotor is disposed outside of the separation stator.

In another embodiment, the separation rotor further comprises a stem assembly coupled to a first end of the sidewall assembly, the stem assembly comprises a stem comprising:

- a tubular spout having an interior surface and an opposing exterior surface, the interior surface bounding a light collection channel providing fluid communication between each of the light component fluid paths and the light component collection recess; and
- a plurality of partition sections radially outwardly projecting from the exterior surface of the tubular spout and at least partially bounding a plurality heavy collection channels, the heavy collection channels being in fluid communication with the heavy component fluid paths.

In another embodiment, the stem assembly further comprises a tubular sleeve encircling the stem, the tubular sleeve having an interior surface and an opposing exterior surface with a plurality of radially spaced apart openings passing through the tubular sleeve between the interior surface and exterior surface, each of the plurality of openings providing fluid communication between the heavy collection channels and the heavy component collection recess.

In another embodiment, the sleeve and the stem are comprised of different materials.

In another embodiment, the material of the sleeve is more thermally conductive than the material of the stem.

In another embodiment, the sleeve is comprised of a metal and the stem is comprised of a polymer.

Another embodiment further includes one or more seals disposed between the separation stator and the sleeve.

Another embodiment further includes a first end of the tubular spout flaring radially outward away from the rotational axis and terminating at and annular end face, the sleeve being disposed against the annular end face of the spout.

Another embodiment further includes one or more bearing assemblies disposed between the separation stator and the separation rotor.

In another embodiment, the chamber of the separation stator extends between a first end and an opposing second end, the inlet opening, the first outlet opening, and the second outlet opening each being disposed at or toward the first end.

In another independent aspect of the present disclosure, a centrifugal separator includes:

- a separation stator bounding a chamber, the separation stator having an inlet opening, a first outlet opening and a second outlet opening; and
- a separation rotor bounding a compartment, the separation rotor being at least partially disposed within the chamber of the separation stator and being rotatable therein about a rotational axis, the separation rotor comprising:
  - a floor;
  - a sidewall assembly upstanding from the floor and encircling the compartment, the sidewall assembly comprising a plurality of separated heavy component fluid paths that each communicate upstream with the inlet opening and downstream with the first outlet opening; and
  - a plurality of upper partitions radially inwardly projecting from sidewall assembly into the compartment so as to at least partially divide the compartment into a plurality of separated light component fluid paths that each communicate upstream with the inlet opening and downstream with the second outlet opening; and
  - a stem assembly coupled with a first end of the sidewall assembly, the stem assembly comprising:
    - a stem being made of a material and comprising a tubular spout having an interior surface and an opposing exterior surface, the interior surface bounding at least one light collection channel providing fluid communication between the light component fluid paths and second outlet opening; and
    - a tubular sleeve encircling the stem an having an interior surface and an opposing exterior surface, at least one heavy collection channel being disposed between the stem and the sleeve and providing fluid communication between the plurality of heavy component fluid paths and the first outlet.

In another embodiment, the tubular sleeve comprises a first heat dissipation section having an interior surface and an opposing exterior surface, the interior surface of the first heat dissipation section directly bounding a portion of the at least one heavy collection channel.

Another embodiment further includes a seal disposed between the separation stator and the tubular sleeve, the seal directly biasing against the interior surface of the first heat dissipation section of the sleeve.

In another embodiment, the tubular sleeve comprises a second heat dissipation section having an interior surface and an opposing exterior surface, the interior surface of the second heat dissipation section directly bounding a portion of the at least one light collection channel.

Another embodiment further includes a seal disposed between the separation stator and the tubular sleeve, the seal directly biasing against the interior surface of the second heat dissipation section of the sleeve.

In another embodiment, the tubular sleeve is made of a material that is more thermally conductive than the material of the stem.

In another embodiment, the tubular sleeve has a thickness extending between the interior surface and the exterior surface thereof that is less than 2.5 mm.

Another embodiment further includes:

the stem further comprises a plurality of partition sections radially outwardly projecting from the exterior surface of the tubular spout; and the at least one heavy collection channel comprising a plurality of heavy collection channels that are separated by the plurality of partition sections.

Another embodiment further includes the tubular sleeve having a first end and an opposing second end and having a plurality of radially spaced apart openings passing through the tubular sleeve between the interior surface and exterior surface so as to be disposed between the first end and the second end, each of the plurality of openings being aligned with a corresponding one of the plurality of heavy collection channels so as to provide fluid communication between the heavy collection channels and the first outlet.

Another embodiment further includes:

a first seal disposed between the separation stator and the tubular sleeve, the first seal being disposed directly against an exterior surface of the tubular sleeve at the first end thereof so as to provide liquid tight seal therebetween; and a second seal disposed between the separation stator and the tubular sleeve, the second seal being disposed directly against an exterior surface of the tubular sleeve at the second end thereof so as to provide liquid tight seal therebetween.

Another embodiment further includes a heavy component collection recess disposed between the separation stator and the separation rotor, the heavy component collection recess being in fluid communication upstream with each of the plurality of separated heavy component fluid paths and being in fluid communication downstream with the first fluid outlet.

Another embodiment further includes a light component collection recess disposed between the separation stator and the separation rotor, the light component collection recess being in fluid communication upstream with each of the plurality of separated light component fluid paths and being in fluid communication downstream with the second fluid outlet.

In another embodiment, the plurality of light component fluid paths are separated from and disposed radially inward of the plurality of heavy component fluid paths.

In another independent aspect of the present disclosure, a centrifugal separator includes:

a separation stator bounding a chamber, the separation stator having an inlet opening, a first outlet opening and a second outlet opening; and a separation rotor bounding a compartment, the separation rotor being at least partially disposed within the chamber of the separation stator and being rotatable therein about a rotational axis, the separation rotor comprising:

a floor;

a sidewall assembly upstanding from the floor and encircling the compartment, the sidewall assembly comprising an annular outer sidewall and an annular inner sidewall that is encircled by the outer sidewall, a plurality of separated heavy component fluid paths being bounded between the inner sidewall and the outer sidewall, the outer sidewall comprising an upper sidewall portion having an interior surface with a frustoconical configuration, the interior surface of the upper sidewall portion being sloped at an angle in a range between 400 and 50° relative to the rotational axis, the plurality of separated heavy component fluid paths each communicate upstream with the inlet opening and downstream with the first outlet; and a plurality of upper partitions radially inwardly projecting from sidewall assembly into the compartment so as to at least partially divide the compartment into a plurality of separated light component fluid paths that each communicate upstream with the inlet opening and downstream with the second outlet.

In another embodiment, the outer sidewall extends to the floor and the inner sidewall is spaced apart from the floor.

In another embodiment, at least a portion of inner sidewall has a frustoconical configuration.

Another embodiment further includes a tubular conduit disposed within the compartment of the separation stator along the rotational axis, the tubular conduit having a first end coupled to the inlet opening of the separation stator and an opposing second end.

Another embodiment further includes a dispersion member disposed within the compartment of the separation rotor at a location above the floor so that a space is formed between the floor and the dispersion member.

In another embodiment, the dispersion member has an opening centrally passing therethrough, the second end of the conduit being coupled to or passing through the opening of the dispersion member, the conduit being configured so that a fluid passing through the conduit from the inlet opening exits the conduit in the space formed between the floor and the dispersion member.

In another independent aspect of the present disclosure, a centrifugal separator includes:

a separation stator bounding a chamber, the separation stator having an inlet opening, a first outlet opening and a second outlet opening; and a separation rotor bounding a compartment, the separation rotor being at least partially disposed within the chamber of the separation stator and being rotatable therein about a rotational axis, the separation rotor comprising:

a floor;

a sidewall assembly upstanding from the floor and encircling the compartment, sidewall assembly comprises an annular outer sidewall and an annular inner sidewall that is encircled by the outer sidewall, the outer sidewall extending to the floor and the inner sidewall being spaced apart from the floor, a plurality of separated heavy component fluid paths being bounded between the inner sidewall and the outer sidewall, the plurality of separated heavy component fluid paths each communicating upstream with the inlet opening and downstream with the first outlet;

a dispersion member disposed within the compartment of the separation rotor at a location above the floor so that a space comprising a portion of the compartment is formed between the floor and the dispersion member, the dispersion member having a top surface and an opposing bottom surface, an opening centrally passing through the dispersion member between the top surface and the bottom surface;

a tubular conduit at least partially disposed within the compartment of the separation stator along the rotational axis, the tubular conduit having a first end coupled to the inlet opening of the separation stator and an opposing second end being coupled to or passing through the opening of the dispersion member, the conduit being configured so that a fluid passing through the conduit from the inlet opening exits the conduit in the space formed between the floor and the dispersion member;

a plurality of upper partitions extending between the inner sidewall and the upper surface of the dispersion member and radially outwardly projecting from the tubular conduit, the plurality of upper partitions dividing at least a portion of the compartment into a plurality of separated light component fluid paths that each communicate upstream with the inlet opening and downstream with the second outlet; and a plurality of lower partitions that extend between the floor and lower surface of the dispersion member and radially inwardly project from the outer sidewall in alignment with the rotational axis, the plurality of lower partitions at least partially dividing the space into a plurality of separated inlet fluid paths that each communicate upstream with the inlet opening and downstream with both the plurality of separated light component fluid paths and the plurality of separated heavy component fluid paths.

In another embodiment, each of the plurality of separated inlet fluid paths communicates with at least two of the plurality of separated heavy component fluid paths but is isolated from at least some of the plurality of separated heavy component fluid paths.

In another embodiment, at least a portion of outer sidewall has a frustoconical configuration and at least a portion of inner sidewall has a frustoconical configuration.

In another embodiment, at least some of the upper partitions extend to the outer sidewall and intersect with a corresponding one of the lower partitions.

In another embodiment, the tubular conduit passes through the floor of the separation rotor and the plurality of lower partitions radially outwardly project from the conduit.

In another independent aspect of the present disclosure, a method for separating a biological suspension includes:

growing biological cells or microorganism of a suspension within a container of a reactor, the suspension further comprising a growth medium; and passing an inlet stream of the suspension from the container of the reactor to the inlet opening of the centrifugal separator recited in claim 1, 30, 43, or 49, the centrifugal separator separating the inlet stream into a first outlet stream that passes out of the centrifugal separator through the first outlet opening and a second outlet stream that passes out of the centrifugal separator through the second outlet opening, the first outlet stream having a greater density or percent solids than the second outlet stream.

Another embodiment further includes passing the first outlet stream back into the container of the reactor.

Another embodiment further includes passing the first outlet stream into a collection container that is separate from the reactor.

Another embodiment further includes continuously operating the centrifugal separator to separate the suspension into the first outlet stream and the second outlet stream for a time period of at least 20 minutes, 1 hour, 3 hours, 6 hours, 12 hours, 24 hours or 48 hours.

Another embodiment further includes:

using a first pump to control a flow rate of the first outlet stream out of the first outlet opening; and using a second pump to control a flow rate of the second outlet stream out of the second outlet opening.

Another embodiment further includes:

using a first control valve to control a flow rate of the first outlet stream out of the first outlet opening; and using a second control valve to control a flow rate of the second outlet stream out of the second outlet opening.

Another embodiment further includes mixing the suspension within the container of the reactor while operating the centrifugal separator.

In another embodiment, the first outlet stream and the second outlet stream are concurrently flowing out of the centrifugal separator as the inlet stream flows into the centrifugal separator.

Another embodiment further includes passing the second outlet stream into a second centrifugal separator.

In another independent aspect of the present disclosure, a method for separating a biological suspension includes:

growing biological cells or microorganism of a suspension within a container of a reactor, the suspension further comprising a growth medium; and passing an inlet stream of the suspension from the container of the reactor to an inlet opening of a centrifugal separator, the centrifugal separator separating the inlet stream into a first outlet stream that passes out of the centrifugal separator through a first outlet opening and a second outlet stream that passes out of the centrifugal separator through a second outlet opening, the first outlet stream having a greater density or percent solids than the second outlet stream.

In another independent aspect of the present disclosure, a modular system for separating biocomponents includes:

a skid comprising a base, sidewalls and a top forming a housing with a housing compartment;

a motor positioned at least partially in the housing compartment;

a magnetic driver comprising a drive rotor mechanically coupled to the motor, the drive rotor comprising an interior surface bounding a cavity and at least one magnet mounted to the interior surface, the magnet generating a magnetic field; and a centrifugal separator assembly comprising:

a stator comprising a base, sidewalls and a top forming a stator chamber, the stator comprising a fluid inlet port and at least two fluid outlet ports;

a separation rotor rotatably coupled to the stator chamber and in fluid communication with the inlet port and the at least two outlet ports of the stator, the separation rotor forming a separation container;

a drive coupling comprising a first end mechanically coupled to and extending from the separation rotor and a second magnetic end magnetically coupled to the drive rotor, the second magnetic end positioned proximate the magnetic field to generate an aligning force that aligns a central axis of the separation rotor with a central axis of the drive rotor; and Wherein the stator chamber forms an aseptic seal and a hermetic seal around the separation rotor and the drive coupling.

In another embodiment, at least a portion of the magnetic driver and the drive coupling are arranged within the housing compartment.

In another embodiment, the stator further comprises a recess forming a containment shroud that extends from the bottom surface of the stator to receive and contain the drive coupling.

In another embodiment, the stator comprises a mounting surface and the housing comprises a mounting clip extending from a surface of the housing and engaging the mounting surface to mechanically couple the stator to the housing.

In another embodiment, the mounting clip is positioned to apply a downward force to the mounting surface and the stator.

In another embodiment, the mounting surface is a flange, slot, cavity or elbow.

Another embodiment further includes a loading assembly comprising:

- a mounting platform coupled to and extending laterally across the housing compartment, the mounting platform comprising a recess and a movable mounting plate coupled to the mounting platform and positioned at least partially within the recess;
- a mounting clip protruding from a surface of the mounting plate; and
- a linear actuator comprising an arm with a first end coupled to the movable mounting plate; wherein the linear actuator is configured to move the arm and movable mounting plate to move the mounting clip into the locked and unlocked position.

Another embodiment further includes an inlet pump coupled to the housing compartment and in fluid communication with the fluid inlet port of the stator.

In another embodiment, inlet pump is a centrifugal pump.

Another embodiment further includes at least one outlet pump coupled to the housing compartment and in fluid communication with the at least two fluid outlet ports.

In another embodiment, the outlet pump is a peristaltic pump.

In another embodiment, the centrifugal separator assembly is removably attached to the housing by the magnetic field.

Another embodiment further includes a programmable power source in wired or wireless communication with a controller comprising a memory, a processor, and a non-transitory computer-readable medium containing instruction executed by the processor to control the programmable power source to supply power to the motor.

Another embodiment further includes a programmable power source in wired or wireless communication with a controller comprising a memory, a processor, and a non-transitory computer-readable medium containing instruction executed by the processor to control the programmable power source to supply power to the inlet and outlet pumps.

In another independent aspect of the present disclosure, a method for separating biocomponents includes:

- pumping a culture comprising media and cells or microorganisms from a bioprocess vessel to a centrifugal separator with an inlet pump through an inlet line,
- wherein the centrifugal separator comprises a stator with an inlet port, a light outlet port, a heavy outlet port and a separation rotor rotatably coupled to the stator and in fluid communication with the inlet port, the light outlet port and the heavy outlet port, and
- wherein the inlet pump is located downstream from the bioprocess vessel and upstream from the centrifugal separator and in fluid communication with the bioprocess vessel and centrifugal separator;
- displacing gas out of the inlet line, the inlet pump and the centrifugal separator with the culture;
- measuring a turbidity downstream from the centrifugal separator with a turbidity sensor; and
- rotating the separation rotor and applying a rotational force to the culture based on the turbidity downstream from the centrifugal separator.

Another embodiment further includes measuring a pressure downstream of the centrifugal separator with a pressure sensor and providing a first power input to the inlet pump based on the pressure downstream of the centrifugal separator.

Another embodiment further includes:

- providing a first power input, based on the turbidity downstream from the centrifugal separator, to a light outlet pump in fluid communication with the light outlet port; and
- providing a second power input, based on the turbidity downstream from the centrifugal separator, to a heavy outlet pump in fluid communication with the heavy outlet port.

Another embodiment further includes:

- providing a second power input, based on the turbidity and pressure downstream from the centrifugal separator, to a light outlet pump in fluid communication with the light outlet port; and
- providing a third power input, based on the turbidity and pressure downstream from the centrifugal separator, to a heavy outlet pump in fluid communication with the heavy outlet port.

Another embodiment further includes removably loading the centrifugal separator to a skid that houses the inlet pump.

In another embodiment, removably loading the centrifugal separator comprises moving the centrifugal separator proximate to a magnetic field at a surface of the skid that provides a magnetic force coupling the centrifugal separator to the skid.

Another embodiment further includes measuring the inlet pressure at an inlet of the centrifugal separator with an inlet pressure sensor and stopping operation of the centrifugal separator when the inlet pressure reaches a predetermined shutdown inlet pressure.

In another embodiment, the inlet pump is a centrifugal pump.

In another independent aspect of the present disclosure, a controller comprises a memory, a processor, and a non-transitory computer-readable medium containing instructions executed by the processor to:

- pump a culture comprising media and cells or microorganisms from a bioprocess vessel to a centrifugal separator with an inlet pump through an inlet line,
- wherein the centrifugal separator comprises a stator with an inlet port, a light outlet port, a heavy outlet port and a separation rotor rotatably coupled to the stator and in fluid communication with the inlet port, the light outlet port and the heavy outlet port, and
- wherein the inlet pump is located downstream from the bioprocess vessel and upstream from the centrifugal separator and in fluid communication with the bioprocess vessel and centrifugal separator;
- displace gas out of the inlet line, the inlet pump and the centrifugal separator with the culture;
- measure a turbidity downstream from the centrifugal separator with a turbidity sensor; and
- rotate the separation rotor and apply a rotational force to the culture based on the turbidity downstream from the centrifugal separator.

It is understood that each of the independent aspects recited herein may include any of the features, options and possibilities recited in association with the other independent aspects recited herein or as recited elsewhere within this document.

BRIEF DESCRIPTION OF THE DRAWINGS

Various embodiments of the present disclosure will now be discussed with reference to the appended drawings. It is appreciated that these drawings depict only typical embodiments of the disclosure and are therefore not to be considered limiting of its scope.

DETAILED DESCRIPTION OF THE PREFERRED EMBODIMENTS

Figure 1:
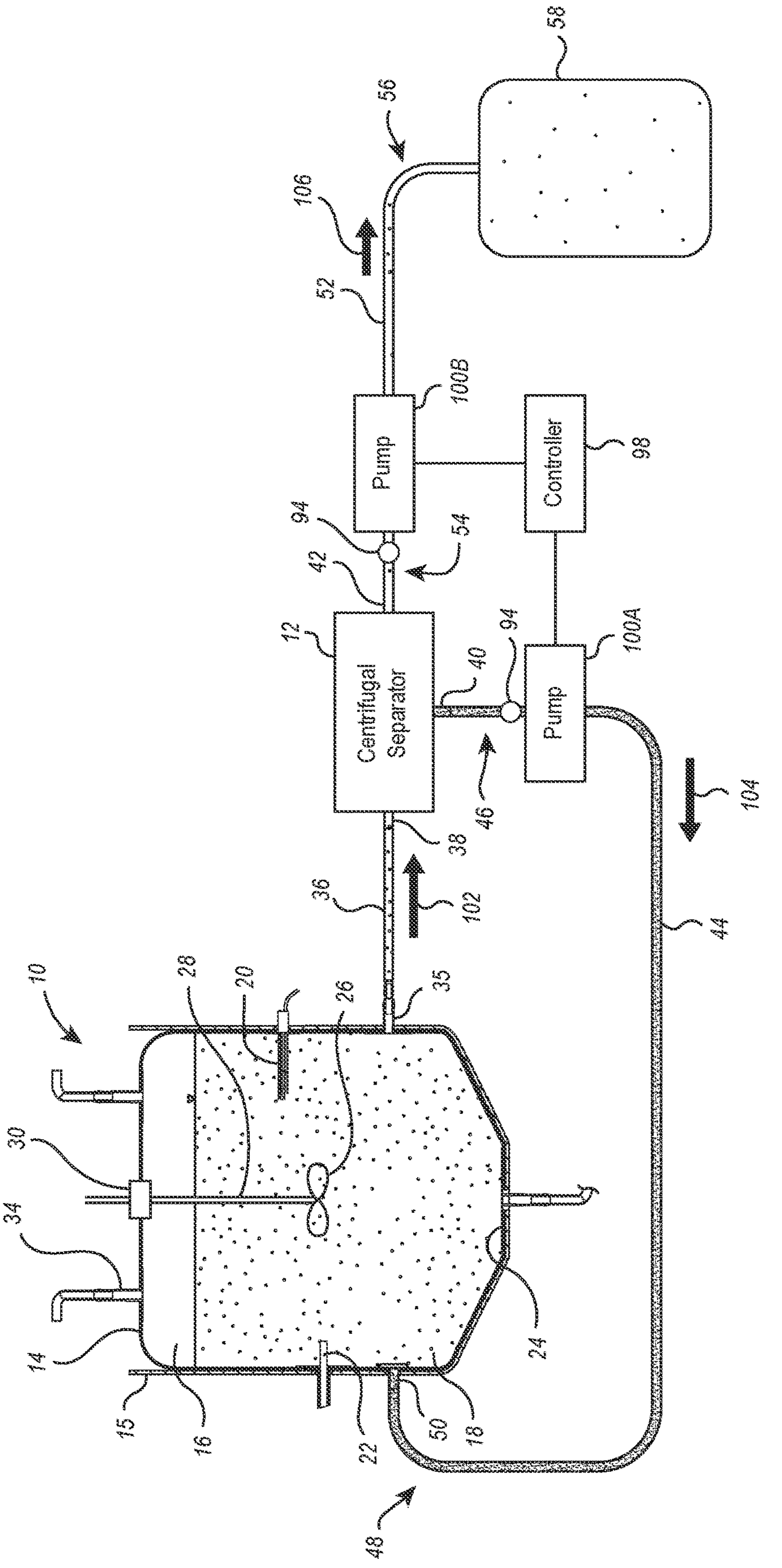
FIG. 1 is a schematic representation of a system incorporating a reactor and a continuous flow centrifugal separator.

Before describing the present disclosure in detail, it is to be understood that this disclosure is not limited to particularly exemplified apparatus, systems, methods, or process parameters that may, of course, vary. It is also to be understood that the terminology used herein is only for the purpose of describing particular embodiments of the present disclosure and is not intended to limit the scope of the disclosure in any manner.

All publications, patents, and patent applications cited herein, whether supra or infra, are hereby incorporated by reference in their entirety to the same extent as if each individual publication, patent, or patent application was specifically and individually indicated to be incorporated by reference.

The term "comprising" which is synonymous with "including," "containing," or "characterized by," is inclusive or open-ended and does not exclude additional, unrecited elements or method steps.

It will be noted that, as used in this specification and the appended claims, the singular forms "a," "an" and "the" include plural referents unless the content clearly dictates otherwise. Thus, for example, reference to a "partition" includes one, two, or more partitions.

As used in the specification and appended claims, directional terms, such as "top," "bottom," "left," "right," "up," "down," "upper," "lower," "proximal," "distal" and the like are used herein solely to indicate relative directions and are not otherwise intended to limit the scope of the disclosure or claims.

Where possible, like numbering of elements have been used in various figures. Furthermore, multiple instances of an element and or sub-elements of a parent element may each include separate letters appended to the element number. For example, two instances of a particular element "10" or two alternative embodiments of a particular element may be labeled as "10A" and "10B". In that case, the element label may be used without an appended letter (e.g., "10") to generally refer to all instances of the element or any one of the elements. Element labels including an appended letter (e.g., "10A") can be used to refer to a specific instance of the element or to distinguish or draw attention to multiple uses of the element. Furthermore, an element label with an appended letter can be used to designate an alternative design, structure, function, implementation, and/or embodiment of an element or feature without an appended letter. Likewise, an element label with an appended letter can be used to indicate a sub-element of a parent element. For instance, an element "12" can comprise sub-elements "12A" and "12B."

Various aspects of the present devices and systems may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present. Furthermore, as used herein, the terms "connection," "connected," and the like do not necessarily imply direct contact between the two or more elements.

Various aspects of the present devices, systems, and methods may be illustrated with reference to one or more exemplary embodiments. As used herein, the term "embodiment" means "serving as an example, instance, or illustration," and should not necessarily be construed as preferred or advantageous over other embodiments disclosed herein.

Unless defined otherwise, all technical and scientific terms used herein have the same meaning as commonly understood by one of ordinary skill in the art to which the present disclosure pertains. Although a number of methods and materials similar or equivalent to those described herein can be used in the practice of the present disclosure, the preferred materials and methods are described herein.

In general, the present disclosure relates to centrifugal separator systems used in the bioproduction industry to separate biocomponents. More specifically, the present disclosure is directed to centrifugal separators for separating biocomponents, such as biological fluids, solids, mixtures, solutions and suspensions comprising, for example, media, cells, blood, plasma, organelles, proteins, nucleic acids, lipids, plasmids, viral vectors, nucleic acids and/or carbohydrates dissolved or dispersed in biological mixtures, solutions and suspensions. The centrifugal separators can be manually portable, single-use, continuous flow, and/or closed-system centrifugal separators used in separating biocomponents. The present disclosure also relates to methods, systems and modular skids which can incorporate such centrifugal separators.

Although the apparatus and methods disclosed herein are primarily designed for use with biological processes, the apparatus and methods of the present disclosure can also be used with non-biological processes where it is desired to separate solids from liquids using a centrifuge. Such applications can be found in the production of chemicals, medicines, food products and other products. Accordingly, the discussions and examples set forth herein of separating biological components and harvesting the separated biocomponents are also applicable to and should be considered as disclosure for separating non-biological components and harvesting the separated components thereof.

The exemplary centrifugal separator systems/skids can provide a hermetically sealed and sterile environment for continuous flow separation of biocomponents in the liquid, solid, gas and mixed phased separation. The disclosed embodiments herein can be modular, sterile, portable and continuous-flow centrifugal separator systems, including centrifugal separator skids, that enhance process efficiency, product purification and yield.

The exemplary centrifugal separator systems/skids can also be portable and easily transported to a bioproduction facility and integrated into bioproduction processes, typically downstream, to purify the biological product. To account for a diverse set of bioproduction processes, equipment and control requirements, the exemplary centrifugal separator systems/skids can incorporate mounting arrangements and single-use, disposable and modular separators and other components that are easily installed and removed to increase the versatility, efficiency and yield of continuous flow centrifugal separation. For example, in one embodiment the exemplary mounting arrangements can include controller mounts, pump mounts, sensor ports, valve ports, terminals and manifolds, bulkhead connectors, motor mounts, tube holders and cable management systems. These mounts can facilitate portability, universal compatibility and easy installation across a broad range of bioproduction process equipment, tubing, cables, controllers, motors, pumps, sensors and valves.

In addition, the exemplary centrifugal separator systems/skids can be equipped with a loading assembly that can magnetically, mechanically and/or releasably load, mount, center and lock the centrifugal separator to the skid. Preferably, the centrifugal separator is a single use and disposable assembly that can be easily and quickly removed, disposed and replaced with a sterile separator to increase efficiency in continues flow processes.

Depicted in FIG. 1 is one exemplary embodiment of a system incorporating features of the present disclosure and used for separating a biological suspension or other mixture and harvesting one or more of the components thereof. More specifically, FIG. 1 depicts a bioproduction vessel 10 fluid coupled with a continuous flow, centrifugal separator 12. Bioproduction vessel 10 is configured for growing a biological suspension and can comprise one or more bioreactors, fermenters, storage vessels, fluid management systems, cell culture equipment or any other device designed for growing or producing cells and/or other biological products. One example of such other devices can include the Cell Factory multi-plate growth chamber produced by Thermo Fisher Scientific. It is also appreciated that bioproduction vessel 10 can comprise any conventional type of bioreactor, fermenter, or cell culture device such as a stirred-tank reactor, rocker type reactor, paddle mixer reactor, or the like.

In the exemplary embodiment depicted, bioproduction vessel 10 comprises a container 14 bounding a chamber 16. Container 14 is supported by a rigid support housing 15. Disposed within chamber 16 is a liquid suspension 18. Suspension 18 typically comprises a biological suspension that includes cells or microorganisms and a growth medium in which the cells or microorganisms are suspended and grown. By way of example and not by limitation, suspension 18 can include one or more biocomponents, including bacteria, fungi, algae, plant cells, animal cells, protozoans, nematodes, plasmids, viral vectors and the like. Examples of some common biologics that are grown include *E. coli*, yeast, *bacillus*, and CHO cells. Suspension 18 can also comprise cell-therapy cultures and can comprise cells and microorganisms that are aerobic or anaerobic and are adherent or non-adherent. Different media compositions known in the art can be used to accommodate the specific cells or microorganisms grown and the desired end-product. In some uses, bioproduction vessel 10 is used primarily only to grow and recover cells for subsequent use (e.g., preparing vaccine materials from the cells themselves). But in many uses, the ultimate purpose of growing cells in bioproduction vessel 10 is to produce and later recover biological products (such as recombinant proteins) that are exported from the cells into the growth medium. It is also common to use bioproduction vessel 10 to grow cells in a master batch to prepare aliquots of cells for subsequent use as an inoculant for multiple subsequent batches of cells grown to recover biological products.

In one exemplary embodiment, container 14 comprises a flexible, collapsible bag. For example, container 14 can be comprised of one or more sheets of a flexible, water impermeable polymeric film such as a low-density polyethylene. The polymeric film can have a thickness that is at least or less than 0.02 mm, 0.05 mm, 0.1 mm, 0.2 mm, 0.5 mm, 1 mm, 2 mm, 3 mm or in a range between any two of the foregoing. Other thicknesses can also be used. The film is sufficiently flexible that it can be rolled into a tube without plastic deformation and can be folded over an angle of at least 90°, 180°, 270°, or 360° without plastic deformation.

The film can be comprised of a single ply material or can comprise two or more layers that are either sealed together or separated to form a double wall container. Where the layers are sealed together, the material can comprise a laminated or extruded material. The laminated material comprises two or more separately formed layers that are subsequently secured together by an adhesive. One example of an extruded material that can be used in the present disclosure is the Thermo Scientific CX3-9 film available from Thermo Fisher Scientific. The Thermo Scientific CX3-9 film is a three-layer, 9 mil cast film produced in a cGMP facility. The outer layer is a polyester elastomer coextruded with an ultra-low-density polyethylene product contact layer. Another example of an extruded material that can be used in the present disclosure is the Thermo Scientific CX5-14 cast film also available from Thermo Fisher Scientific. The Thermo Scientific CX5-14 cast film comprises a polyester elastomer outer layer, an ultra-low-density polyethylene contact layer, and an EVOH barrier layer disposed therebetween.

The material can be approved for direct contact with living cells and be capable of maintaining a solution sterile. In such an embodiment, the material can also be sterilizable such as by ionizing radiation. Examples of materials that can be used in different situations are disclosed in U.S. Pat. No. 6,083,587 which issued on Jul. 4, 2000 and United States Patent Publication No. US 2003-0077466 A1, published Apr. 24, 2003, which are hereby incorporated by specific reference.

In one embodiment, container 14 comprise a two-dimensional pillow style bag wherein two sheets of material are placed in overlapping relation and the two sheets are bounded together at their peripheries to form chamber 16. Alternatively, a single sheet of material can be folded over and seamed around the periphery to form the internal compartment. In another embodiment, container 14 can be formed from a continuous tubular extrusion of polymeric material that is cut to length and is seamed closed at the ends. In still other embodiments, container 14 can comprise a three-dimensional bag that not only has an annular side wall but also a two-dimensional top end wall and a two-dimensional bottom end wall.

It is appreciated that container 14 can be manufactured to have virtually any desired size, shape, and configuration. For example, container 14 can be formed having chamber 16 sized to 0.5 liters, 1 liter, 5 liters, 10 liters, 30 liters, 50 liters, 100 liters, 250 liters, 500 liters, 750 liters, 1,000 liters, 1,500 liters, 3,000 liters, 5,000 liters, 10,000 liters or other desired volumes. The size of chamber 16 can also be in the range between any two of the above volumes. In other embodiments, chamber 16 can have a larger or smaller volume. Although in the above discussed embodiment container 14 is described as a flexible, collapsible, bag, in alternative embodiments it is appreciated that container 14 can comprise any form of collapsible container or semi-rigid container. In some embodiments, container 14 can comprise a rigid container, such as comprised of metal, molded plastic or a composite. In this embodiment, support housing 15 can be eliminated as container 14 is self-supporting.

As needed, sensors 20 and probes 22 can be coupled with container 14 for detecting properties of suspension 18. By way of example and not by limitations, sensors 20 and probes 22 can comprise temperature probes, pH probes, $CO_2$ sensors, oxygen sensors, pressure sensors, and the like. If needed, a sparger 24 can be coupled with container 14 for delivering gas to suspension 18 within chamber 16.

In one exemplary embodiment of the present disclosure, means are provided for mixing suspension 18 within container 14. In the depicted embodiment, a movable mixing element 26 is disposed within chamber 16 and is for used for mixing suspension 18. In one exemplary embodiment, mixing element 26 can comprise an impeller coupled with a drive shaft 28. Drive shaft 28 couples with container 14 through a dynamic seal 30. A motor can be coupled with drive shaft 28 for rotating mixing element 26 to facilitate mixing of suspension 18.

In another embodiment, drive shaft 28 can project into container 14 through a flexible tube having one end rotatably connected to container 14 and an opposing second end connected to mixing element 26. Drive shaft 28 passes through the flexible tube and removably couples with mixing element 26 so that drive shaft 28 can rotate mixing element 26 without directly contacting suspension 18. Examples of this mixing system are disclosed in U.S. Pat. No. 7,384,783, issued Jun. 10, 2008 and U.S. Pat. No. 7,682,067, issued Mar. 23, 2010 which are incorporated herein by specific reference. In another alternative embodiment, drive shaft 28 can be configured to repeatedly raise and lower mixing element 26 located within container 14 for mixing the suspension 18. Alternatively, mixing element 26 can comprise a magnetic stir bar or impeller disposed within chamber 16 of container 14 and rotated by a magnetic mixer disposed outside of container 14. In yet other embodiments, mixing element 26 can comprise a stir bar, paddle, or the like that projects into chamber 16 of container 14 and can be pivoted, swirled, shook or otherwise moved to mix suspension 18. In addition, the mixing can be accomplished by circulating fluid through chamber 16, such as by using a peristaltic pump to move the fluid into and out of chamber 16 through a tube having opposing ends sealed to container 14. Gas bubbles can also be passed through suspension 18 to achieve the desired mixing. Finally, support housing 15 and container 14 can be pivoted, rocked, rotated or otherwise moved so as to mix suspension 18 within container 14. Other conventional mixing techniques can also be used. Specific examples of how to incorporate a mixer into a flexible bag, such as container 14, are disclosed in U.S. Pat. No. 7,384,783, issued Jun. 10, 2008; U.S. Pat. No. 7,682,067, issued Mar. 23, 2010; and US Patent Publication No. 2006/0196501, issued Sep. 7, 2006 which are incorporated herein by specific reference.

A plurality of ports 34 are coupled with container 14 for delivering material into or removing material from chamber 16. A port 35 is disposed at a lower end of container 14 and is fluid coupled with centrifugal separator 12. It is noted that reactor 10 is not necessarily drawn to scale with regard to centrifugal separator 12. Chamber 16 of reactor 10 will commonly have a fluid capacity that is at least 3, 5, 10, 20, 50, 100, 200 or more times the fluid capacity of centrifugal separator 12.

In the system depicted in FIG. 1, container 14 is fluid coupled with centrifugal separator 12 by a fluid line 36 extending from port 35 to an inlet port 38 of centrifugal separator 12. Fluid line 36 and other fluid lines discussed herein typically comprise flexible, polymeric tubing that can be coiled without plastic deformation. In other embodiments, however, the fluid lines can comprise other flexible or rigid conduits. Centrifugal separator 12 also has a first outlet port 40 and a second outlet port 42. A fluid line 44 has a first end 46 coupled with first outlet port 40 of centrifugal separator 12 and an opposing second end 48 fluid coupled with chamber 16 of container 14, such as through a port 50 mounted on container 14. Likewise, a fluid line 52 has a first end 54 coupled with second outlet port 42 of centrifugal separator 12 and an opposing second end 56 fluid coupled with a collection container 58. Collection container 58 typically comprises a collapsible bag made of one or more sheets of polymeric film. Collection container 58 can be made of the same materials, using the same methods, and have the same properties as container 14 discussed above. For example, collection container 58 can comprise a two-dimensional pillow style bag or a larger three-dimensional bag. Collection container 58 can have a volume that is the same as, smaller than or larger than container 14. For example, collection container 58 can have a volume that is less than 0.7, 0.5 or 0.2 times the volume container 14 or greater than 1.2, 1.5, 2, or 3 times the volume of container 14. Where collection container 58 is a flexible bag, collection container 58 can be supported in a rigid support housing. In other embodiments, collection container 58 can comprise a rigid or semi-rigid container.

Figure 2:
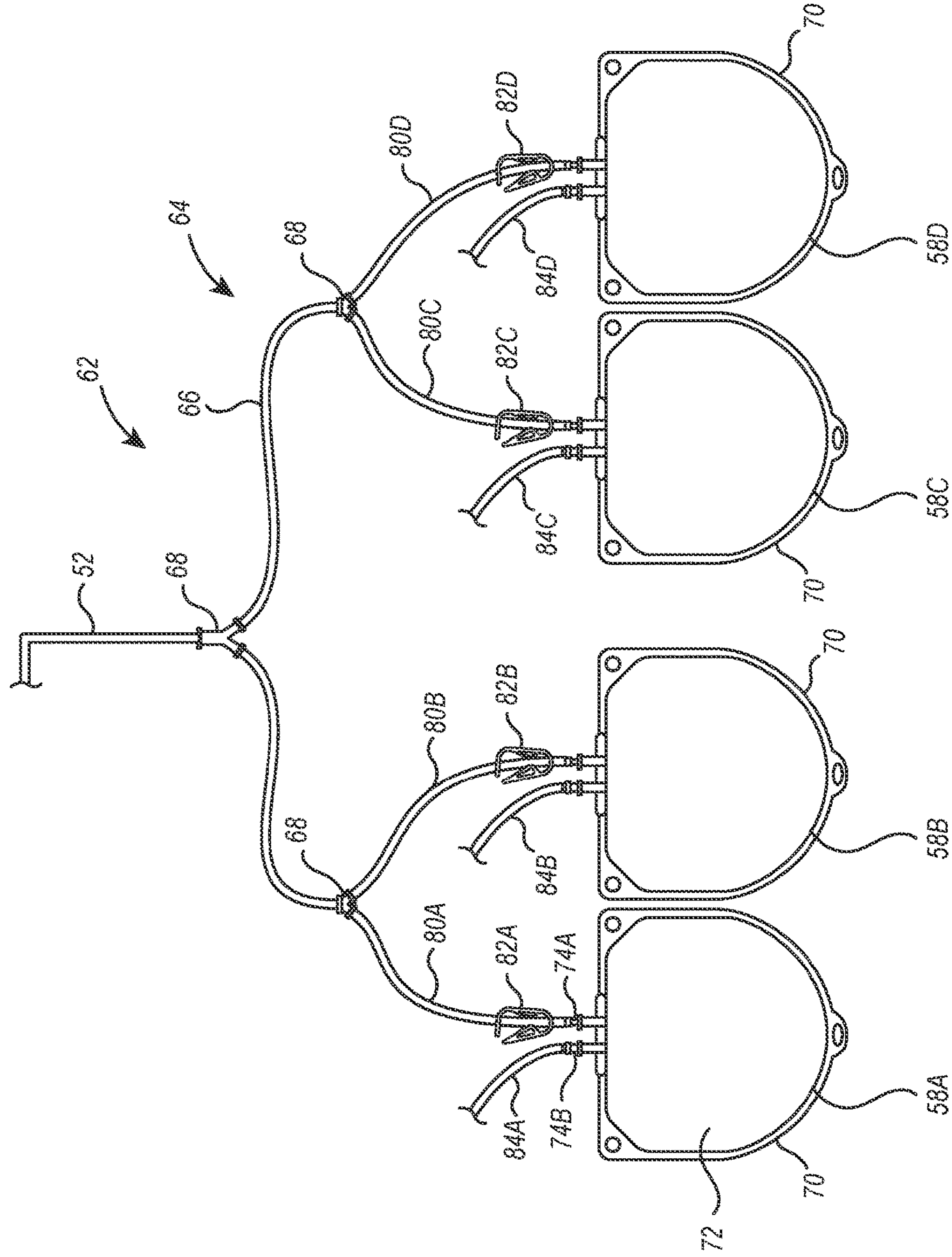
FIG. 2 is an elevated front view of a manifold assembly that can be used in the system of FIG. 1.

In one alternative embodiment, single collection container 58 can be replaced with a manifold system 62 as depicted in FIG. 2. In general, manifold system 62 comprises a manifold 64 fluid coupled to a plurality of collection containers 58A, 58B, 58C, and 58D. In one embodiment, manifold 64 comprises a plurality of separate sections of fluid line 66, such as flexible tubing, that are coupled together by fittings 68, such as Y-connectors, so that fluid flowing from fluid line 52 can be delivered to each of collection containers 58A-58D along sterile pathways.

Each collection container 58A-58D can comprise a flexible, collapsible bag 70 bounding a compartment 72. Each collection container 58A-58D further comprises a first port 74A and a second port 74B coupled to bag 70 and communicating with compartment 72. Although two ports 74A and 74B are shown, other numbers of ports, such as one, three, four or more ports, could be used. Bags 70 are commonly sized so that compartment 72, when fully inflated, has a volume of at least or less than 0.5 liters, 1 liter, 1.5 liters, 2 liters, 2.5 liters, 3 liters, 5 liters, 10 liters or in a range between any two of the foregoing. Other volumes can also be used.

Fluid line 66 includes inlet lines 80A-80D that are fluid coupled with ports 74A disposed on bags 70. Clamps 82A-82D are mounted on inlet lines 80A-80D, respectively. Clamps 82A-82D can be manually adjusted to regulate the flow of a fluid stream through inlet lines 80A-80D and can seal off inlet lines 80A-80D to prevent fluid flow therethrough. In addition, outlet lines 84A-84D are coupled with ports 74B disposed on bags 70. Each outlet line 84 has a terminal end that can be sealed closed, such as by welding or crimp, or by having a fitting mounted thereon, such as an aseptic connector, that can be selectively coupled to another fluid line.

During use, once a bag 70 has been filled with a desired amount of fluid, a portion of inlet line 80 upstream of clamp 82 is sealed closed and then cut, thereby separating each bag 70 from manifold 64. Collection containers 58A-58D are coupled to manifold 64 in parallel, as opposed to in series. Accordingly, by selectively opening and closing clamps 82, transfer of fluid from container 14 to select collection containers 58A-58D can be controlled. For example, all of clamps 82 can be concurrently opened to allow all of collection containers 58A-58D to be concurrently filled. Alternatively, by closing all of clamps 82 and then opening clamps 82 consecutively, collection containers 58A-58D can be filled in consecutive order. It is appreciated that clamps 82, valves, or other flow regulating devices can also be positioned at other location on manifold 64 to control the flow of fluid therethrough.

In the depicted embodiment, manifold 64 is fluid coupled with four collection containers 58A-58D. In alternative embodiments, manifold 64 can be fluid coupled with or to at least 2, 3, 5, 6, 8, 12, 16, or any other number of collection containers 58. In yet another alternative embodiment, collection containers 58A-D could be fluid coupled with manifold 64 in series rather than in parallel.

In yet another alternative to the embodiment depicted in FIG. 1, collection container 58 can be eliminated and fluid line 52 can be directly coupled to downstream processing equipment such as filtration systems, e.g., depth or sterile filters.

Returning to FIG. 1, a first pump 100A is coupled with fluid line 44 and a second pump 100B is coupled with fluid line 52. As discussed below in greater detail, pumps 100 are used to control the flow rate of suspension 18 through centrifugal separator 12. In one embodiment, pumps 100 can comprise peristaltic pumps that pump fluid through fluid lines 44 and 52 but do not directly contact the fluid. As such, pumps 100 can be reused without cleaning. However, other types of pumps, such as positive displacement pumps, can also be used.

Figure 3:
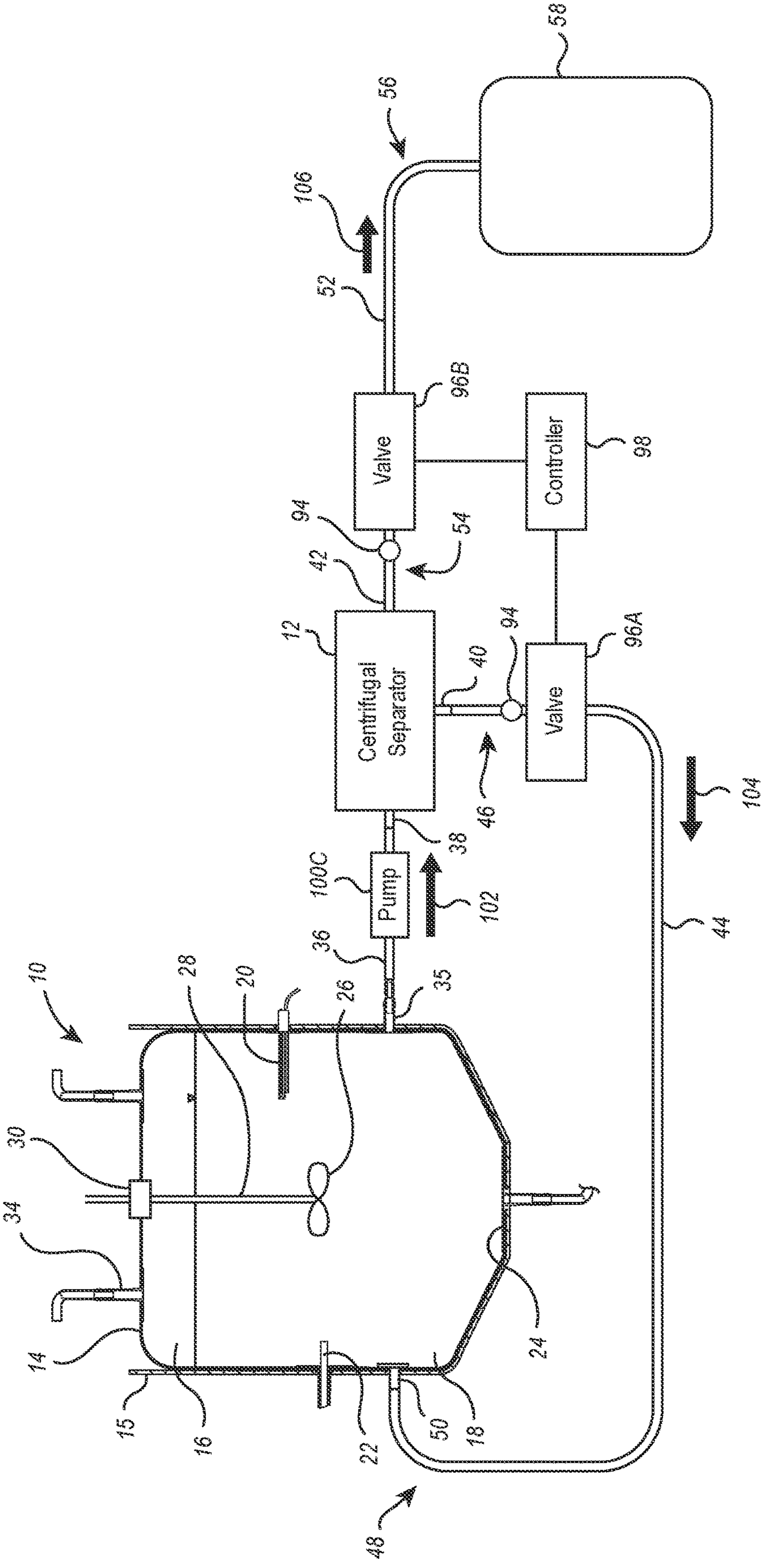
FIG. 3 is a schematic representation of the system shown in FIG. 1 having modified flow control components.

In one exemplary embodiment, a controller 98 can be used to automatically and separately control the operation of pumps 100A and 100B so as to selectively and separately control and adjust the flow rate of fluid within fluid lines 44 and 52. Controller 98 can comprise a programmable processor and non-transitory memory. In an alternative embodiment as shown in FIG. 3, the flow rate of fluid through centrifugal separator 12 can be controlled by having a single pump 100C coupled with fluid line 36 and having a control valve 96A coupled with fluid line 44 and/or a control valve 96B coupled with fluid line 52. Pump 100C and control valves 96A and 96B could also be controlled by controller 98. In another alternative, container 14 could be pressurized or elevated to achieve flow of suspension 18 into centrifugal separator 12 while control valves 96 on one or both of fluid lines 44 and 52 can be used to control the flow rate through fluid lines 44 and 52. In still another alternative, pumps 100A and 100B could be retained as in FIG. 1 while pump 100C is added to fluid line 36. The fluid flow would then be controlled by the three pumps regulated by controller 98.

As shown in FIGS. 1 and 3, controller 98 can control the operation of pumps 100 and/or valves 98 based on inputs from sensors 94 mounted to fluid line 44 and/or 52 or otherwise sensing properties of the outlet streams flowing therethrough. Depending on the intended method of operation, sensors 94 can comprise pressure sensors, flow rate sensors, turbidity sensors, capacitance sensors, conductivity sensors, in-line spectroscopy sensors, and the like.

In one method of operation, the function of centrifugal separator 12 is to continuously separate suspension 18 received from container 14 into a first outlet stream and a second outlet stream where the first outlet stream has a higher concentration of cells or microorganism, and thus a greater density or higher percentage of solids, than the second outlet stream. More specifically, during one use as shown in FIG. 1, pumps 100 can be operated so that an inlet stream of suspension 18, designated by arrow 102, flows through fluid line 36 from container 14 and into centrifugal separator 12 through an inlet at inlet port 38. In turn, centrifugal separator 12 separates inlet stream 102 into a first outlet stream, designated by arrow 104, that passes out of centrifugal separator 12 through an outlet at outlet port 40. Centrifugal separator 12 also separates inlet stream 102 into a second outlet stream, designated by arrow 106, that passes out of centrifugal separator 12 through an outlet at outlet port 42 and into fluid line 52. As discussed above, first outlet stream 104 has a higher concentration or volume of cells or microorganism, i.e., a higher percentage of solids, per unit volume, than second outlet stream 106.

Figure 4:
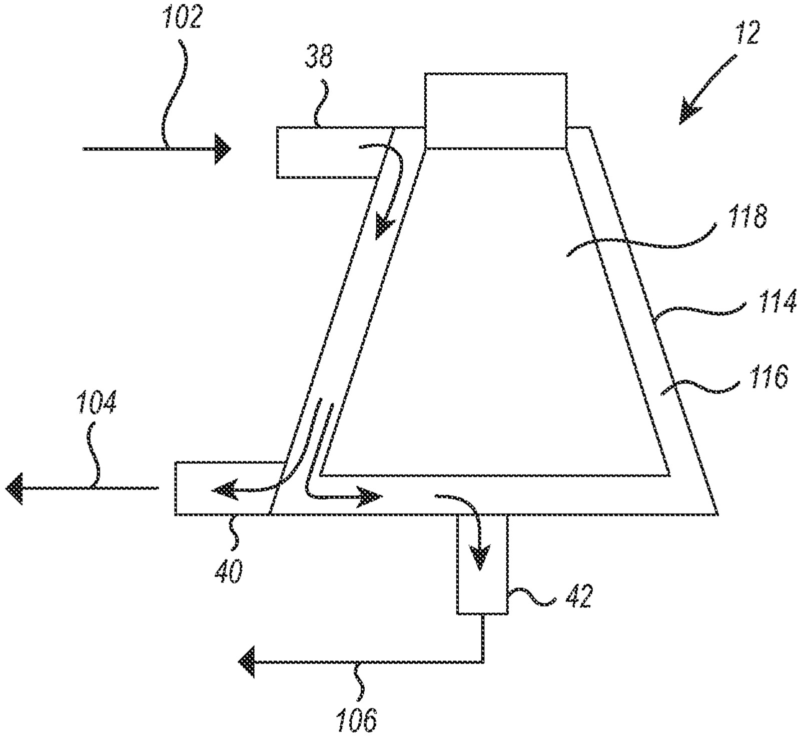
FIG. 4 is a cross sectional view of one embodiment of the centrifugal separator shown in FIG. 1.

Depicted in FIG. 4 is one simplified embodiment of centrifugal separator 12 incorporating features of the present disclosure. In general, centrifugal separator 12 comprises a separation stator 114 that bounds a chamber 116. Rotatably disposed within chamber 116 of separation stator 114 is a separation rotor 118. Means, such as a magnetic driver, are provided for rotating separation rotor 118 within separation stator 114. Ports 38, 40 and 42 are mounted on separation stator 114 so as to communicate with chamber 116. As inlet stream 102 flows into chamber 116 through inlet port 38, the rotation of separation rotor 118 causes suspension 18 to rotate within chamber 116 so that suspension 18 is subject to a centrifugal force. Because of the centrifugal force, the heavier components of suspension 18 collect toward the interior surface of separation stator 114 and exit as first outlet stream 104 through outlet port 40. The lighter components of suspension 18 collect toward the exterior surface of separation rotor 114 and exit as second outlet stream 106 through outlet port 42.

It is appreciated that in some embodiments second outlet stream 106 could be free of cells or microorganism which have been separated out into the first outlet stream 104. Typically, however, some cells or microorganism remain in second outlet stream 106 when suspension 18 is passed through a single centrifugal separator. The remaining cells or microorganism can then be removed from second outlet stream 106 by passing second outlet stream 106 through one or more additional centrifugal separators, as discussed below in greater detail, and/or by passing second outlet stream 106 through other conventional filtration systems.

In the embodiment depicted in FIG. 1, first outlet stream 104 is pumped back into container 14 through fluid line 44 so as to help retain cells or microorganism within container 14 while second outlet stream 106 is harvested through collection container(s) 58 for subsequent use. The system in FIG. 1 is thus a perfusion system where cells or microorganisms are retained within container 14 for continued growth while the medium and byproduct from the cells or microorganisms is continuously being harvested. To compensate for the loss of medium through the harvesting, new medium is added continuously or as needed into container 14 through ports 34.

Figure 5:
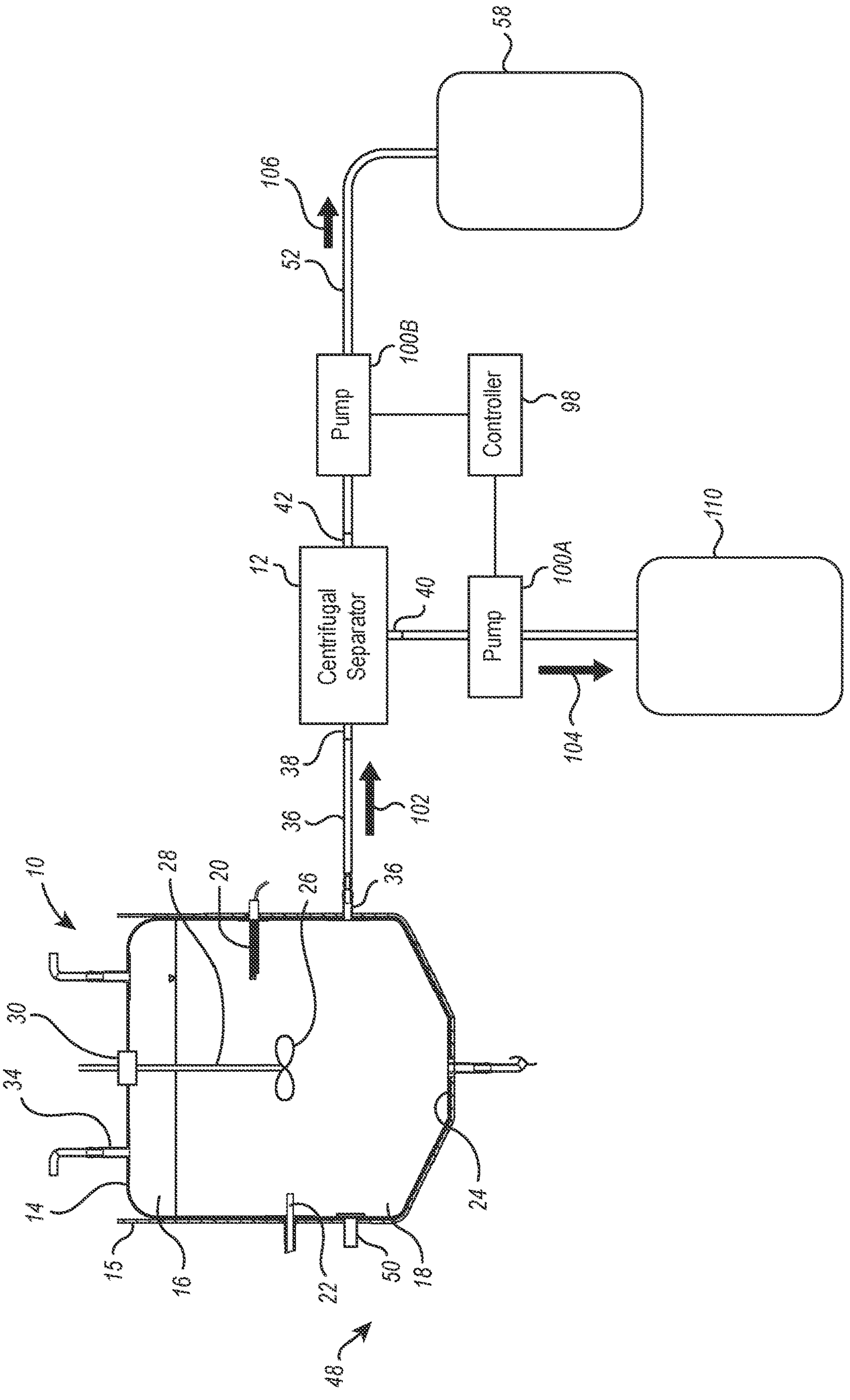
FIG. 5 is a schematic representation of a modified version of the system shown in FIG. 1.

Turning to FIG. 5, in contrast to returning first outlet stream 104 to container 14, first outlet stream 104 can be harvested by being collected within a collection container 110. Collection container 110 typically comprises a collapsible bag made of one or more sheets of polymeric film. Collection container 110 can be made of the same materials, using the same methods, and have the same properties, sizes and alternatives as collection container 58, discussed above. For example, collection container 110 can comprise a two-dimensional pillow style bag or a larger three-dimensional bag. Where collection container 110 is a flexible bag, collection container 110 can be supported in a rigid support housing. In other embodiments, collection container 110 can comprise a rigid or semi-rigid container.

In one alternative embodiment, single collection container 110 can be replaced with manifold system 62 as previously discussed above with regard to FIG. 2. As such, first outlet stream 104 can be collected in separate collection container 58A-58D. All of the above discussed uses and alternatives of manifold system 62 discussed above with regard to the harvesting of second outlet stream 106 is also applicable to the harvesting of first outlet stream 104. Furthermore, the system in FIG. 5 operates in the same way as discussed above with regard to the system in FIG. 1 except that that first outlet stream 104 is harvested rather than returned to container 14.

In another alternative to the system depicted in FIG. 5, container 14 need not form part of a reactor for growing biologics. Rather, container 14 can simply comprise a rigid or flexible container that is simply holding previously prepared suspension 18.

Figure 6:
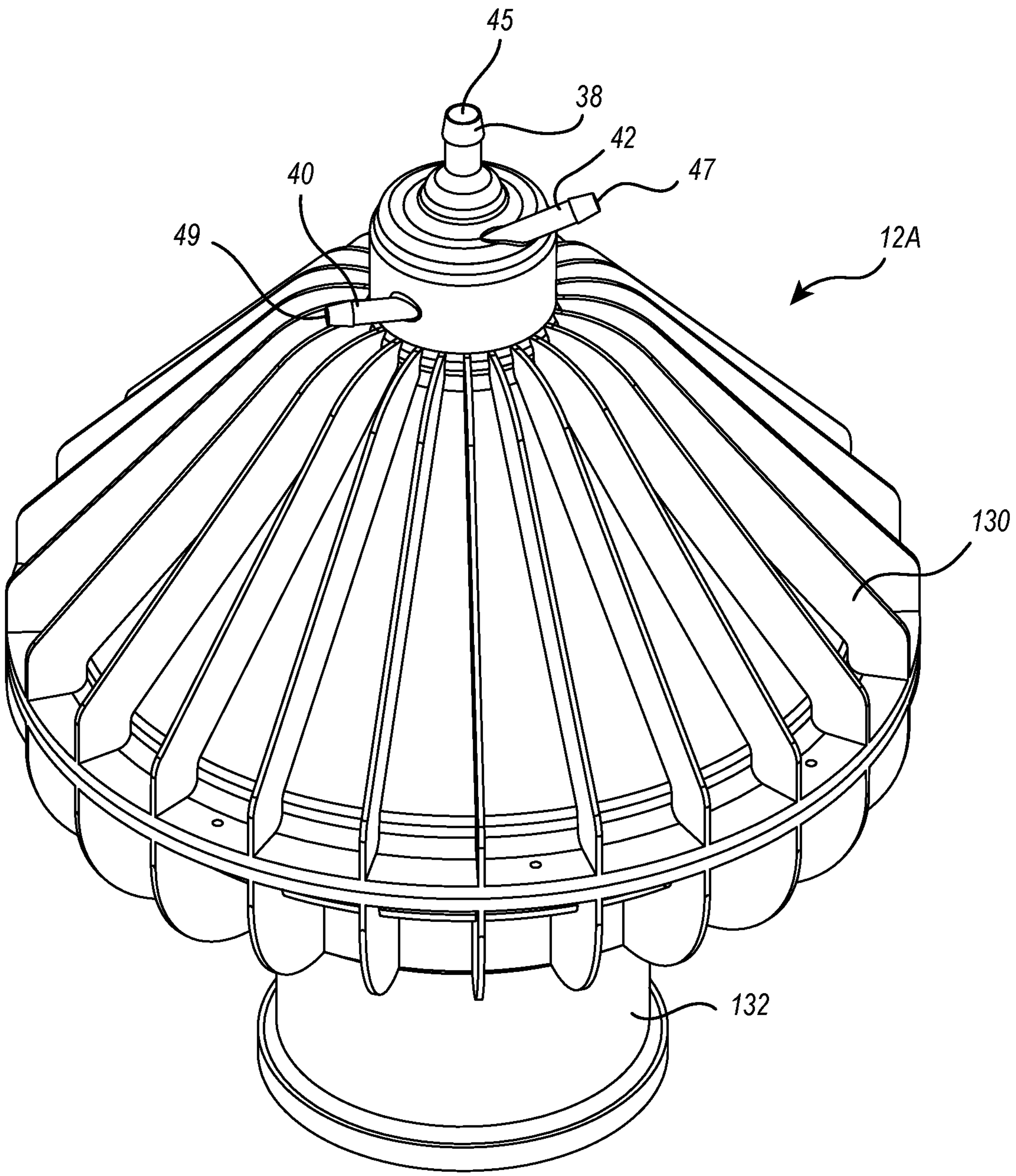
FIG. 6 is a top perspective view of a centrifugal separator that can be used in the systems of FIGS. 1, 3 and 5.
Figure 7:
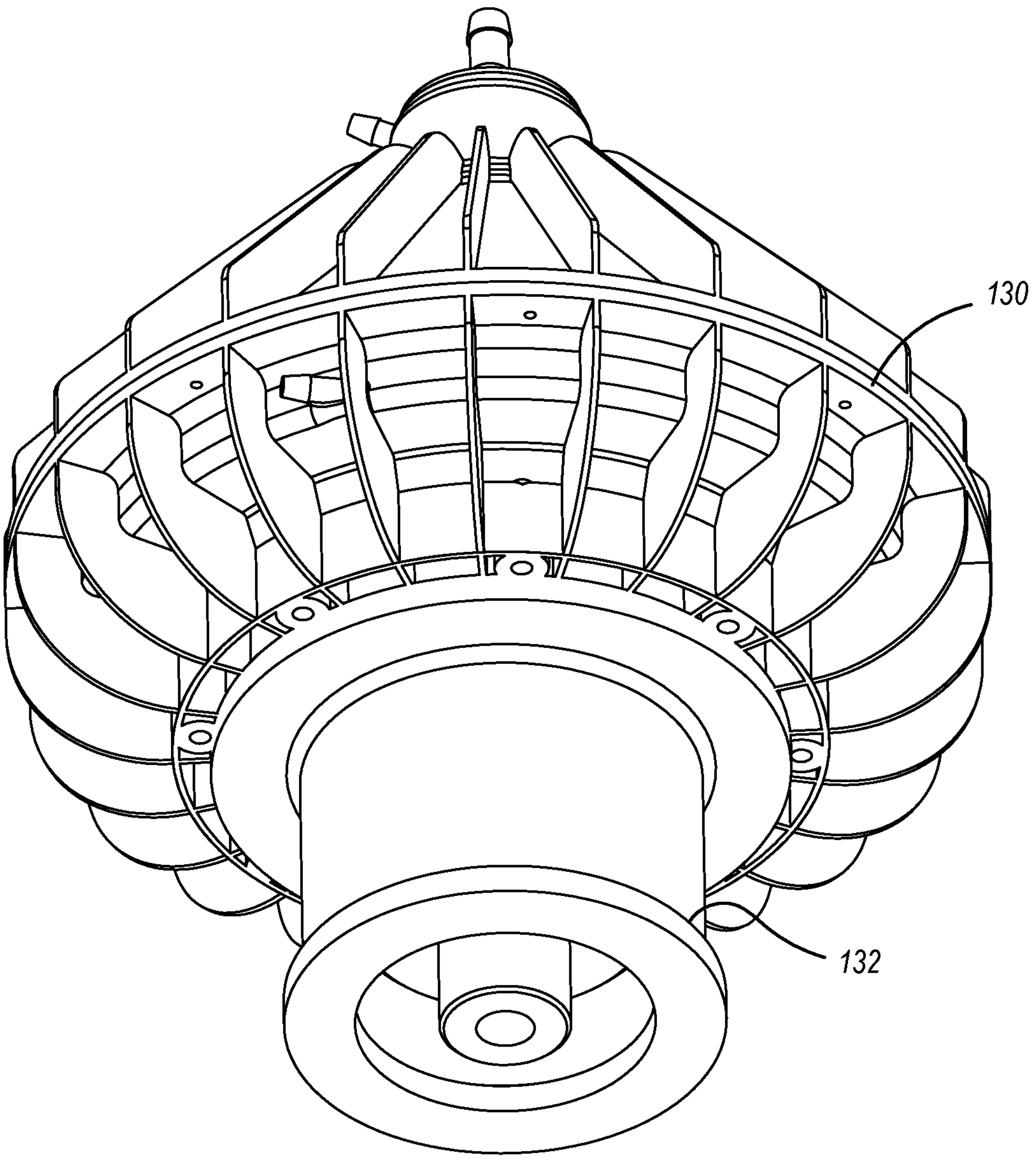
FIG. 7 is a bottom perspective view of the centrifugal separator shown in FIG. 6.

Depicted in FIGS. 6 and 7 is one detailed exemplary embodiment of a continuous flow, centrifugal separator 12A that can be used as centrifugal separator 12 in the systems and alternatives discussed above with regard to FIGS. 1-5. In general, centrifugal separator 12A comprises a body assembly 130 and a driver sleeve 132 that is integrally formed with, releasably attached to, or otherwise interacts with body assembly 130. During operation, a magnetic driver 148 (FIG. 8) is received and rotated within driver sleeve 132 to facilitate operation of centrifugal separator 12A during use. As discussed below in more detail, body assembly 130/centrifugal separator 12A includes inlet port 38, first outlet port 40 and second outlet port 42.

Figure 8:
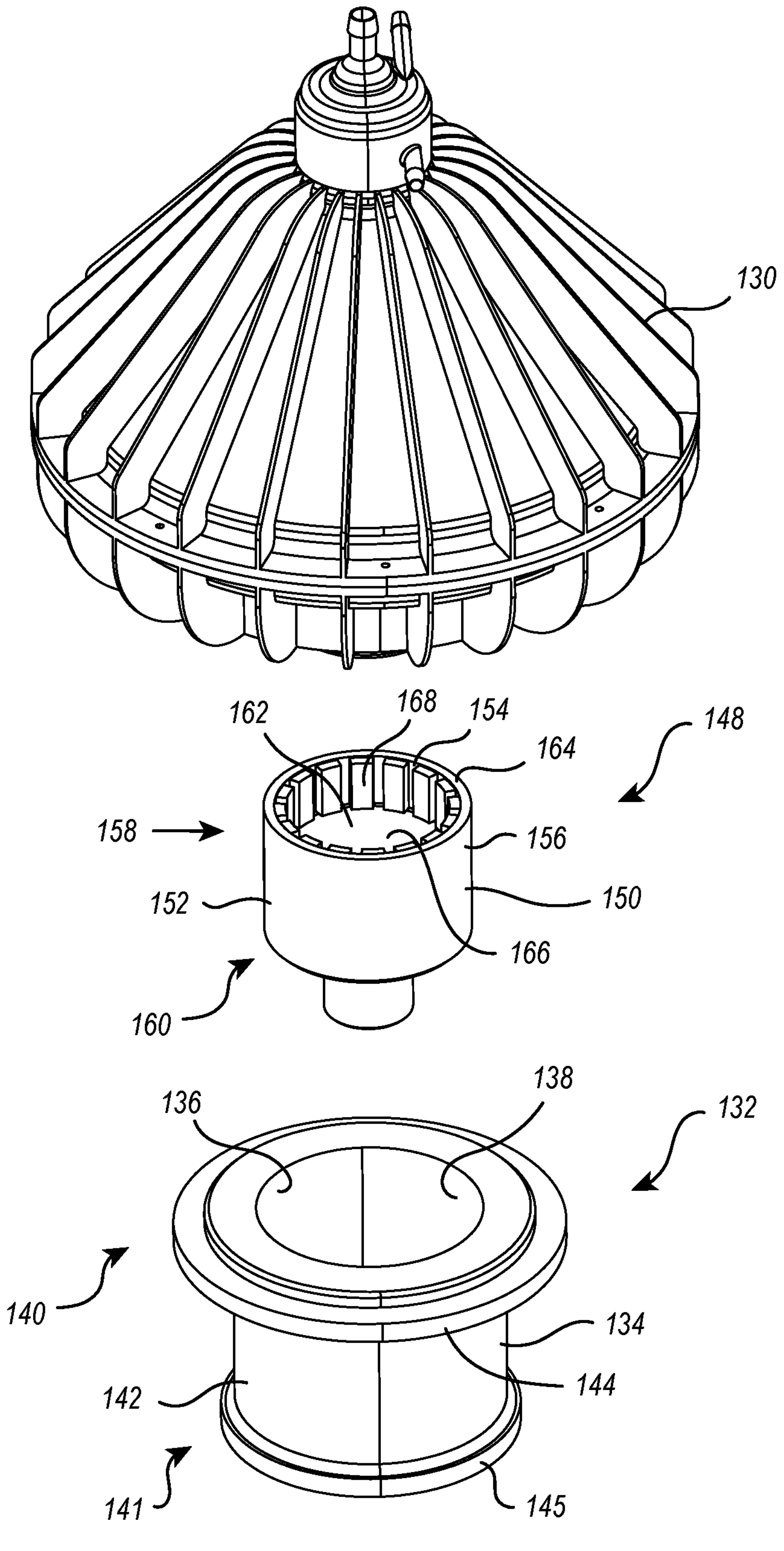
FIG. 8 is a partially exploded view of the centrifugal separator shown in FIG. 6.

Turing to FIG. 8, driver sleeve 132 comprises an exterior surface 134 and an interior surface 136 that encircles an opening 138. Driver sleeve 132 has a first end 140 through which opening 138 extends and which, in one embodiment, can be releasably coupled with body assembly 130. For example, first end 140 can be releasably coupled to body assembly 130 by fasteners, such as screws or bolts, clamps, threaded connection, or a twist connection, such as bayonet connection. In other exemplary embodiments, driver sleeve could be integrally formed with body assembly 130 may only be positioned against or adjacent to body assembly 130. For example, one purpose of driver sleeve 132 is to function as a protective covering of magnetic driver 148. Thus, driver sleeve 132 could be formed as a portion of separator 12A that interacts with magnetic driver 148 or could be formed as a portion of magnetic driver 148 that interacts with separator 12A. In other embodiments, driver sleeve 132 could be eliminated.

In one embodiment, driver sleeve 132 can comprise a tubular sleeve body 142 having a flange 144 outwardly projecting from first end 140 thereof. Flange 140 can be used for coupling with body assembly 130. In one exemplary embodiment, sleeve body 142 can have a second end 141 opposite first end 140 from which a flange 145 outwardly projects. Flange 145 can be used for securing separator 12A to a separate structure, such as a skid or other framework that supports magnetic driver 148. In other embodiments, driver sleeve 132 need not be in the form of a tubular sleeve.

Magnet driver 148 comprises a drive rotor 150 that aligns with body assembly 130, as discussed below, and is rotatably disposed within opening 138 of driver sleeve 132. Drive rotor 150 includes sleeve 152 having an interior surface 154 and an opposing exterior surface 156 that extend between a first end 158 and an opposing second end 160. Interior surface 154 bounds a cavity 162. For example, in one embodiment, sleeve 152 is annular and encircles cavity 162. In other embodiments, sleeve 152 need not completely encircle cavity 162. First end 158 of sleeve 152 terminates at an end face 164 which bounds an opening 166 to cavity 162. Secured to interior surface 154 of sleeve 152 is a magnet 168. In the depicted embodiment, magnet 168 comprises a plurality of magnet sections 170 that are spaced apart and secured to interior surface 154 of sleeve 152 so as to encircle cavity 162. In one embodiment, magnet 168 can comprise at least 2, 4, 6, 12, 18, 24, or 30 separate magnet sections 170 or can be in a range between any two of the foregoing values. Magnetic sections 170 can be vertically orientated with respect to the axis of rotation, such that the poles of a magnetic section are axially oriented. In such an embodiment, the poles of each magnetic section 170 are preferentially alternated in axially orientation.

In other embodiments, magnet 168 can comprise a magnetic ring secured to interior surface 154 so as to encircle cavity 162. In such an embodiment, the magnetic ring can be dipole, quadripole, hexapole, or octapole. In such a magnetic ring, the poles are preferentially radially disposed. The magnetic coupling can be comprised of any magnetic pairing that provides sufficient torque to meet the torque requirements to overcome the power losses and rotor and fluid acceleration. For example, torque requirements in one example embodiment range from 10 to 70 in-$lb_f$. Magnets can be comprised of material capable of carrying a permanent magnetic field on the rotor side and either a permanent magnet or electro-magnet on the motor side of the coupling. In one embodiment, the magnets can be comprised of neodymium Turing to FIG. 9, magnet driver 148 further comprises a motor 169 that couples to and selectively rotates drive rotor 150/sleeve 153. For example, in one embedment, drive rotor 150 further comprises a stem 172 projecting from second end 160 of sleeve 152 and is coupled to motor 169 for rotation of drive rotor 150. Motor 169 can be housed within or at least partially housed within housing 134. As previously mentioned, driver sleeve 132 is optional and can function in part as a protective cover for drive rotor 150 and/or motor 169.

Figure 9:
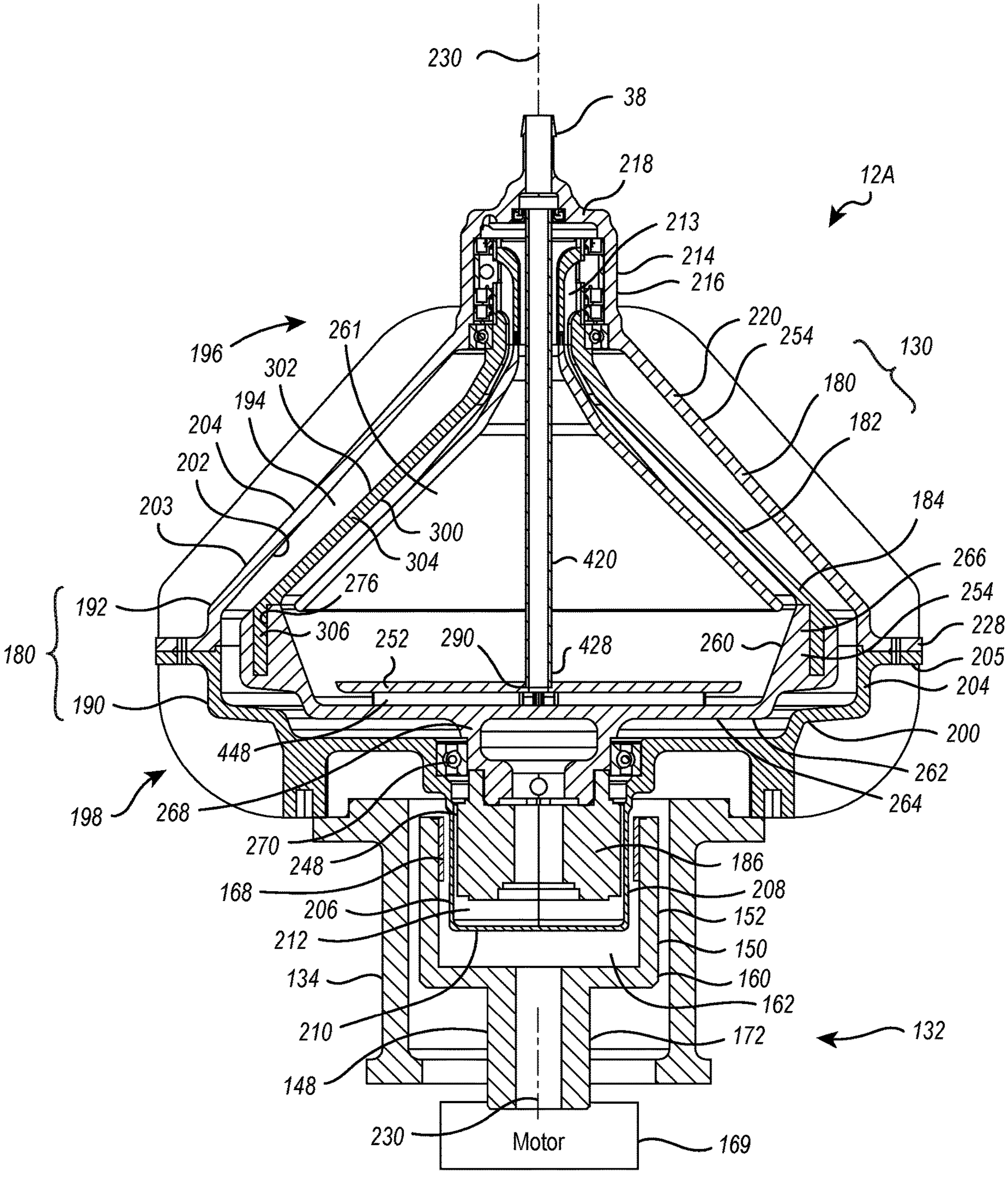
FIG. 9 is a front elevational cross-sectional view of the centrifugal separator shown in FIG. 6.

With continued reference to FIG. 9, separator 12A/body assembly 130 generally comprises a separation stator 180 and a rotor assembly 182 that is rotatable disposed within separation stator 180. Rotor assembly 182 comprises a separation rotor 184 that is rotatable disposed within separation stator 180 and a drive coupling 186 that is coupled with separation rotor 184 and may also rotatably disposed within separation stator 180. A central axis 230 centrally passes through separation stator 180 and rotor assembly 182 and coincides with a rotational axis, also identified by reference number 230, about which rotor assembly 182 rotates. As such, "central axis 230" and "rotational axis 230" are used synonymously herein.

Figure 10:
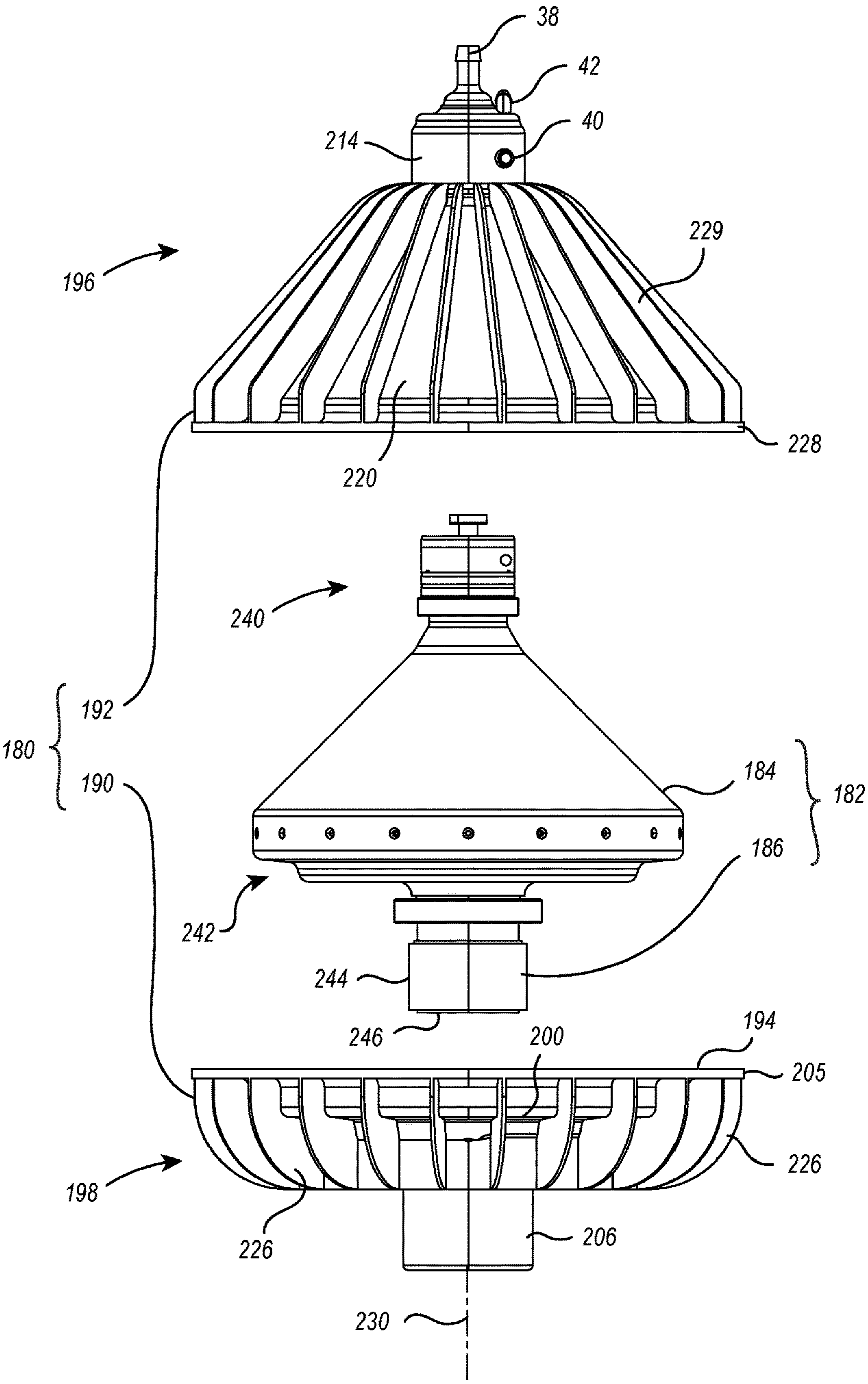
FIG. 10 is front elevational view of the separation stator of the centrifugal separator shown in FIG. 9 being exploded off of the rotor assembly.

As depicted in FIGS. 9 and 10, in one embodiment, separation stator 180 comprises a base 190 and a head 192 that are coupled together prior to use. Separation stator 180 has an interior surface 202 and an opposing exterior surface 203. Interior surface 202 bounds a chamber 194 in which rotor assembly 182 is at least partially received. Assembled separation stator 180 has a first end 196 where head 192 is disposed and an opposing second end 198 where base 190 is disposed. Central axis 230 extends between first end 196 and second end 198. Separation stator 180 includes inlet port 38, first outlet port 40 and second outlet port 42 each located on head 192 at first end 196.

With continued reference to FIG. 9, base 190 (or second end 198 of separation stator 180) comprises a floor 200 that radially outwardly extends to an annular sidewall 204. Sidewall 204 upstands from floor 200 and projects toward first end 196. An annular mounting flange 205 outwardly projects from sidewall 204. In one embodiment, interior surface 202 of sidewall 204 is cylindrical. In other embodiments, interior surface 202 of sidewall 204 may outwardly slope. Centrally disposed on floor 200 so as to outwardly project from exterior surface 203 thereof is a receiver 206. Receiver 206 bounds a recess 212 which forms a portion of chamber 194. In one embodiment, receiver 206 comprises a sidewall 208 projecting from floor 200 and terminating at an end wall 210. In one embodiment, sidewall 208 and recess 212 each have a cylindrical configuration. As depicted in FIG. 9 and discussed below, receiver 206 is configured so that it can be received within opening 166 of drive rotor 150.

With reference to FIG. 10, base 190 (or first end 198 of separation stator 180) also comprises a plurality of fins 226 that outwardly project from the exterior surface of floor 200 in parallel alignment with central axis 230 and are equally spaced apart around receiver 206. Fins 226 longitudinally extend from mounting flange 205 to or toward receiver 206. In one embodiment, centrifugal separator 12A is designed so as to be disposable after a single use. To that end, separation stator 180, and more particularly, base 190 and head 192 are typically made from a polymeric material, such as polyvinylidene fluoride or polyvinylidene difluoride (PVDF), high density polyethylene (HDPE), polyetherimide (PEI), polyether ether ketone (PEEK) or the like, and are commonly molded, such as by injection or rotational molding. These materials and method of production enable separation stator 180 to be produced less expensively that if separation stator 180 was made from metal. In part, fins 226 function to add strength and stability to separation stator 180 when made from a lower strength polymeric material. However, in an alternative embodiment, separation stator 180 could be made from a higher strength metal, such as aluminum or stainless steel or, alternatively, a higher strength polymer, such as liquid crystal polymers or polycarbonate. In such case, fins 226 may be eliminated.

Returning to FIG. 9, head 192 of separation stator 180 includes a nose 214 disposed at first end 196. Nose 214 has a sidewall 216 that terminates at an end wall 218. Nose 214 bounds a recess 213. In one embodiment, interior surface 202 of sidewall 216 that bounds recess 213 can have a cylindrical configuration. Centrally outwardly projecting from end wall 218 is inlet port 38. First outlet port 40 and second outlet port 42 outwardly project from sidewall of nose 214. Head 192 also include an annular mounting flange 228 and an annular transition wall 220 that extends between mounting flange 228 and sidewall 216 of nose 214. In one embodiment, at least a portion of transition wall 220 has a frustoconical configuration wherein interior surface 202 thereof is typically disposed at an angle relative to central axis 230 that is at least or is less than 30°, 40°, 50°, or 60° or is in a range between any two of the foregoing. In the depicted embodiment, a portion of transition wall 220 extending from mounting flange 228 can be cylindrical or have a different configuration than the remainder of transition wall 220. As with base 190, head 192 is also shown as being formed with fins 229 (FIG. 10) that outwardly project from transition wall 220 so as to extend between mounting flange 228 and nose 214. Fins 229 also extend in parallel alignment in central axis 230 and are equally spaced around transition wall 220. As discussed above, where separation stator 180 is made from a plastic material, fins 229 add structural strength and stability while adding minimal material and cost. Where separation stator 180 is being made from a higher strength material, fins 229 can be eliminated.

During assembly, mounting flanges 205 and 228 are coupled together so that rotor assembly 182/separation rotor 184 is captured within separation stator 180. Mounting flanges 205 and 228 can be coupled together by welding, clamps, fasteners, such as screws or bolts, or by using other fastening techniques.

Rotor assembly 182 is rotatably positioned within chamber 194 of separation stator 180 and is used for separating inlet stream 102 (FIGS. 1-5) of the biological suspension into first outlet stream 104 and second outlet stream 106. With reference to FIG. 10, as previously noted, rotor assembly 182 includes separation rotor 184 and drive coupling 186 extending therefrom. More specifically, separation rotor 184 has a first end 240 and an opposing second end 242 between which central axis/rotational axis 230 centrally extends. Drive coupling 186 is centrally mounted to and outwardly projects from second end 242 of separation rotor 184 so that central axis 230 centrally passes therethrough. Drive coupling 186 typically has an encircling side face 244 that terminates at an end face 246. In one embodiment, drive coupling 186 has a cylindrical configuration and, as depicted in FIG. 9, is configured so that it can be rotatably received within recess 212 of receiver 206. A gap 248 is formed between side face 244 of drive coupling 186 and sidewall 208 of receiver 206 so that drive coupling 186 can freely rotate within receive 206.

In one embodiment, gap 248 is less than 10 mm, 8 mm, 6 mm, 4 mm, 2 mm, or in a range between any two of the foregoing. It is typically desired to minimize the size of gap 248 to help facilitate the magnetic rotation of drive coupling 186. Drive coupling 186 is comprised of a material and configured so that it can be controlled by a magnetic field produced by magnet 168. For example, drive coupling 186 can comprise another magnet or a material that is attracted to a magnet such as iron or an iron composite. During operation, drive coupling is positioned within receiver 206 while receiver 206 is received within cavity 162 of drive rotor 150. Rotation of drive rotor 150 by motor 169 facilitates concurrent rotation of drive coupling as a result of the magnetic force produced by magnet 168 on drive coupling 186. In turn, rotation of drive coupling 186 facilitate concurrent rotation of separation rotor 184 to which it is attached. In alternative embodiments, it is appreciated that receiver 206, which commonly functions as a protective cover, can be eliminated. In this case, drive coupling 186 would be directly received within cavity 162 of drive rotor 150.

Figure 11:
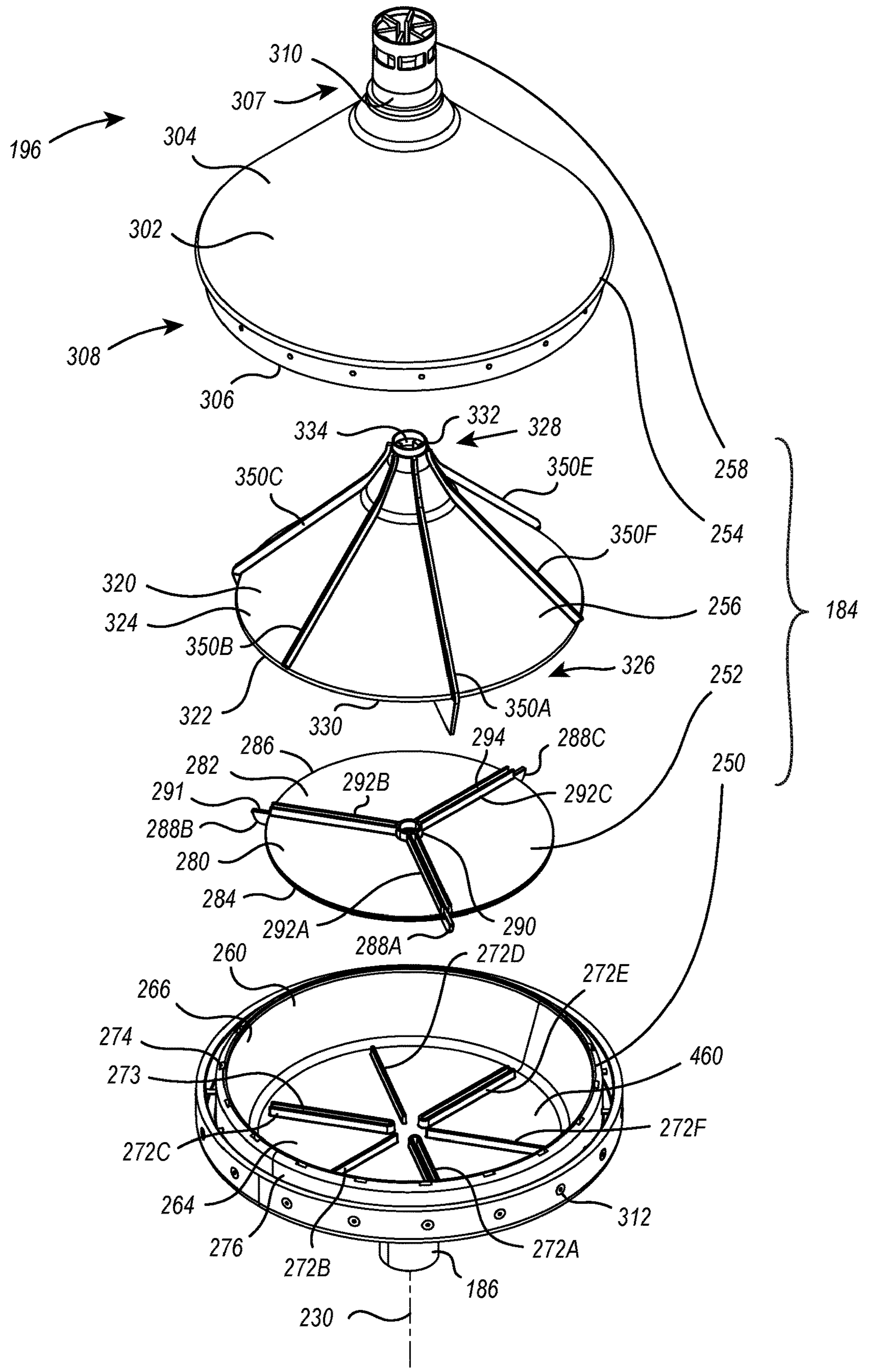
FIG. 11 a perspective exploded view of the separation rotor shown in FIG. 10.

Turning to FIG. 11, separation rotor 184 comprises a base 250 to which drive coupling 186 is attached, a dispersion member 252 that sits on base 250, a cap 254 that couples with base 250, an insert 256 that is captured between cap 254 and base 250, and a stem assembly 258 disposed on cap 254. The various elements of separation rotor 184 will now be discussed in further detail.

As better seen in FIG. 9, base 250 has an interior surface 260 that partially bounds a compartment 261 and has an opposing exterior surface 262. Base 250 comprises a floor 264 and an annular sidewall 266 that upwardly projects from an outer perimeter of floor 264 toward cap 254. Sidewall 266 is referred to hereinafter as lower sidewall 266. A mount 268 outwardly projects from exterior surface 262 of floor 264 in alignment with central axis 230. Drive coupling 186 is secured to mount 268 such as by adhesive, press fitting, fasteners, threaded coupling, or the like. An annular bearing assembly 270, such as a race bearing or the like, extends between mount 268 and base 190 of separation stator 180. Bearing assembly 270 functions to both center and stabilize separation rotor 184 relative to separation stator 180 and enables easy rotation of separation rotor 184 relative to separation stator 180.

Returning to FIG. 11, upwardly projecting from interior surface 260 of floor 264 are a plurality of spacers 272A-F. Spacers 272 are evenly spaced apart and radially outwardly project in alignment with central axis 230. Spacers 272A, C, and E are also formed with an elongated slot 273 formed along the length thereof. As will be discussed below in greater detail, spacers 272 function to both space dispersion member 252 from interior surface 260 of floor 264 and secure dispersion member 252 to base 250 so that base 250 and dispersion member 252 rotate concurrently. Interior surface 260 of lower sidewall 266 has an annular, frusto-conical configuration that outwardly slopes from an outer perimeter edge of floor 264 to annular lip 274. In one embodiment, lower sidewall 266 slopes at an outward angle relative to central axis 230 that is at least or less than 10°, 15°, 20°, 25°, 30°, 350 or is in a range between any two of the foregoing angles. An annular slot 276 is recessed into lip 275 and, as will be discussed below in greater detail, is used for coupling cap 254 to base 250.

As discussed herein, dispersion member 252 can have a variety of different configurations. In the current depicted embodiment, dispersion member 252 comprises a body 280 in the form of a circular plate having a top surface 282 and an opposing bottom surface 284 that each extend to an outer perimeter edge 286. An opening 290 centrally extends through body 280 in alignment with central axis 230 so as to pass between opposing surfaces 282 and 284. Projecting from bottom surface 284 of body 280 are lower partitions 288A, B, and C which are typically equally spaced. Lower partitions 288 are linear and radially outwardly project from opening 290. Lower partitions 288 are configured to be received within slots 273 of spacers 272A, C, and E and terminate at a terminal end 291 that projects out beyond perimeter edge 286. During assembly, dispersion member 252 is placed on top of spacers 272 of base 250 so that lower partitions 288A, B, and C are received within slots 273 and so that terminal ends 291 are butted against or disposed directly adjacent to interior surface 260 of lower sidewall 266 of base 250. This assembly centers dispersion member 252 on floor 264 so as to ensure that perimeter edge 286 is evenly spaced apart from lower sidewall 266 and also interlocks dispersion member 252 with base 250 such that rotation of base 250 facilitates concurrent annular rotation of dispersion member 252. In addition, as will be discussed below in further detail, lower partitions 288 and spacers 272 function to form inlet fluid channels that radially flow outward from between dispersion member 252 and floor 264 to help facilitate separation of the biological suspension. It is appreciated that a variety of other structural designs could be used for securing and centering dispersion member 252 on floor 264 while forming the inlet fluid channels. However, the current depicted embodiment is uniquely configured to enable quick and easy positioning of dispersion member 252 without the required use of separate fasteners.

As also shown in FIG. 11, dispersion member 252 further comprises retention rails 292A-C that are equally spaced apart on top surface 282 of body 280 and radially outwardly project from opening 290 to perimeter edge 286. Each retention rail 292 has a slot 294 extending along the length thereof.

Figure 12:
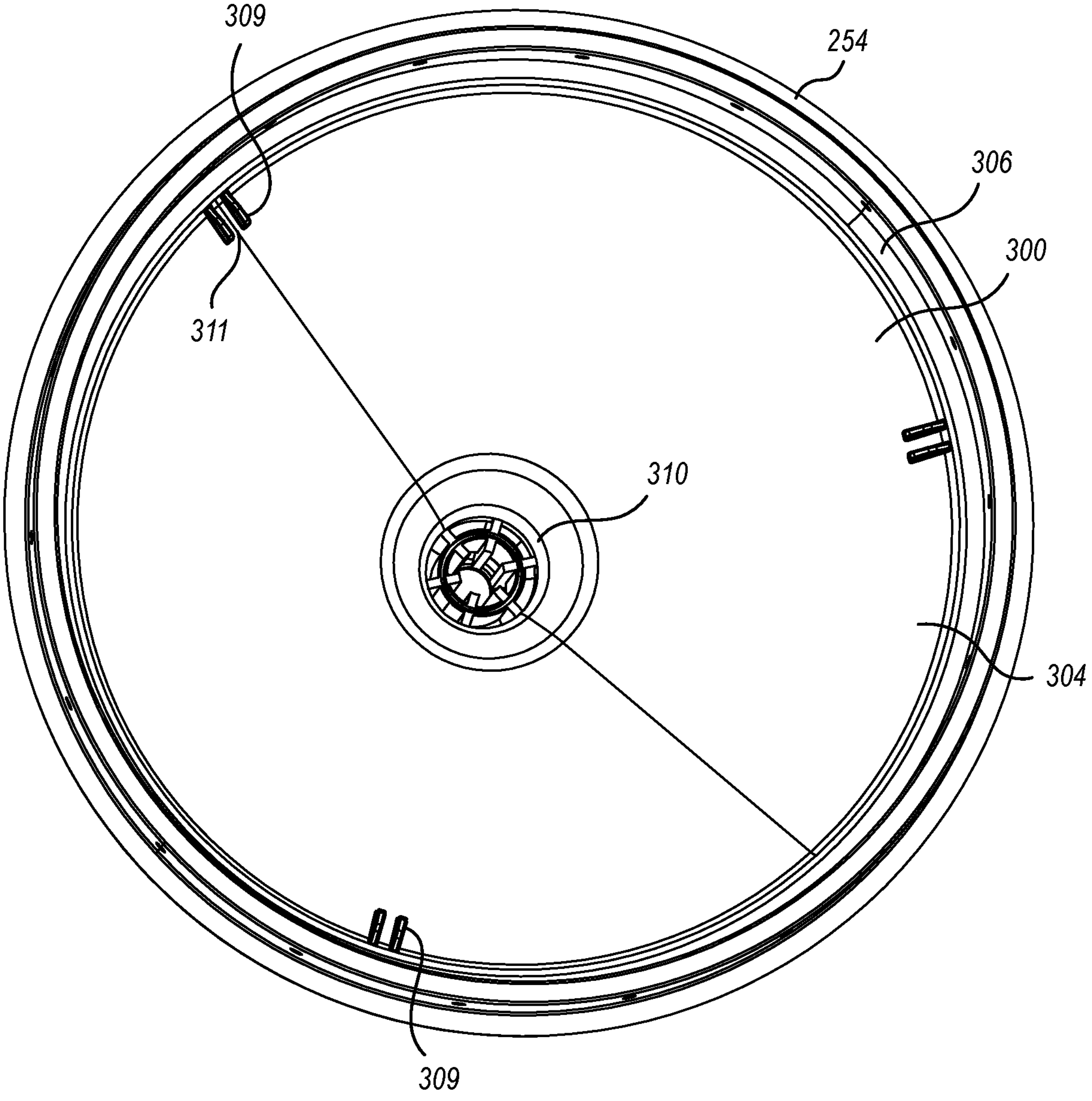
FIG. 12 is a bottom perspective view of the cap of the separation rotor shown in FIG. 11.

With reference to FIGS. 9, 11 and 12, cap 254 has an interior surface 300 and an opposing exterior surface 302 that extend between a first end 307 and an opposing second end 308. Cap 254 includes an annular sidewall 304 that extends from an annular lip 306 formed at second end 308 to an annular lip 310 disposed at first end 307. Sidewall 304 is hereinafter referred to as "upper sidewall 304." Upper sidewall 304 and interior surface 300 thereof have a frustoconical configuration that inwardly constricts from annular lip 306 to an annular lip 310. In one embodiment, sidewall 304 is configured so that interior surface 300 thereof slopes relative to central axis 230 at an angle in a range between 35° and 55° and more commonly between 40° and 50° or between 42° and 48°. A plurality of spaced apart guides 309 radially inwardly project from interior surface 300 at second end 308. Each guide 309 bounds a slot 311 is configured to engage with insert 256 as discussed below.

Figure 13:
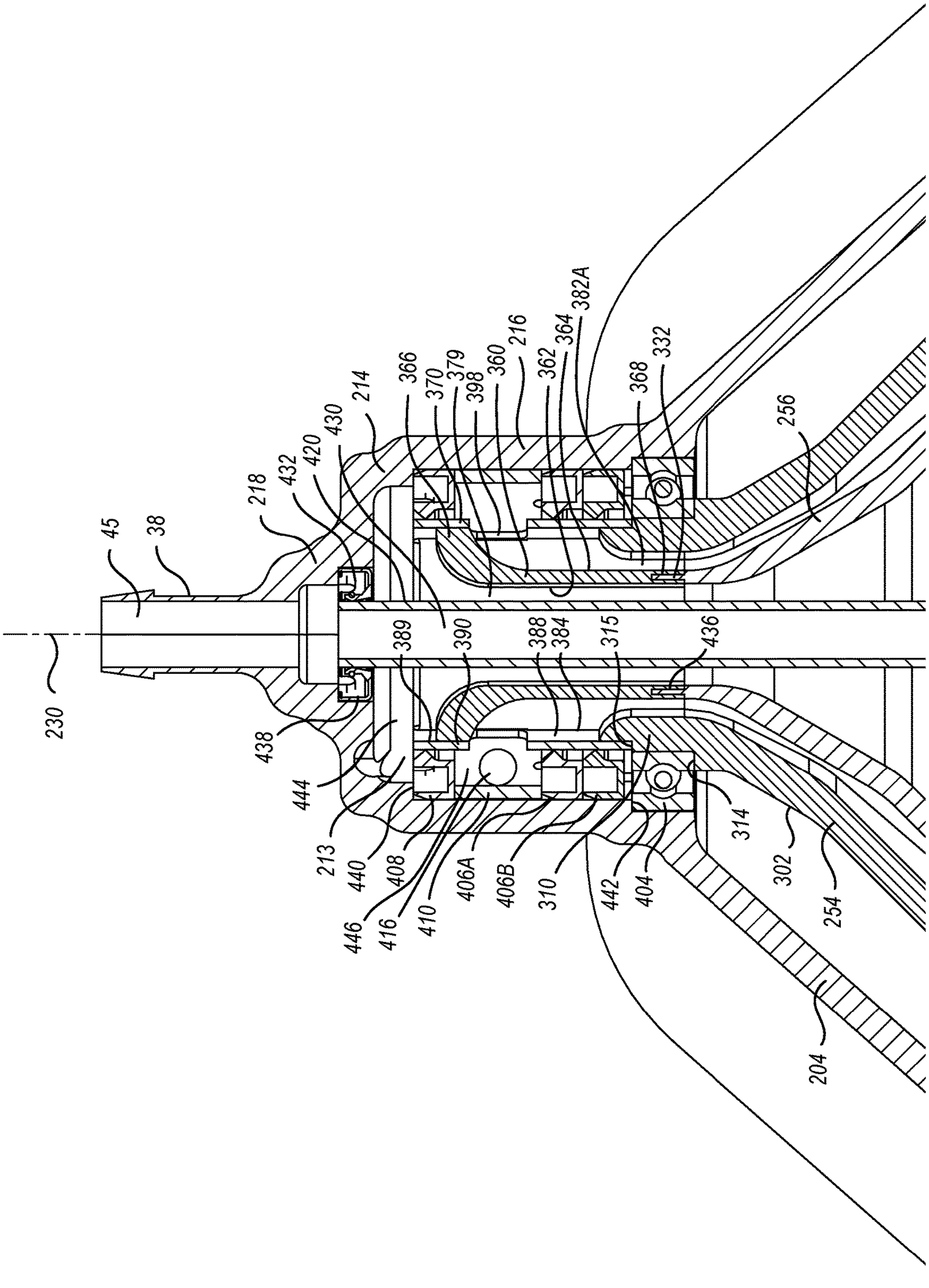
FIG. 13 is an enlarged cross-sectional view of a first end of the centrifugal separator shown in FIG. 9.

As best seen in FIG. 9, lip 306 can have a cylindrical configuration that is configured to fit within and have a configuration complimentary to slot 276 formed on base 250. This configuration helps to facilitate a liquid tight seal between base 250 and cap 254. Fasteners 312 (FIG. 11), such as screws or bolts, extend into sidewall of base 250 from exterior surface 262 and pass through lip 306 to facilitate a secure engagement. As best depicted in FIG. 13, annular lip 310 at first end 196 of cap 254 has an annular first shoulder 314 recessed into exterior surface 302 and an annular second shoulder 315 recessed into exterior surface 302, with shoulder 315 being spaced apart from shoulder 314.

Figure 14:
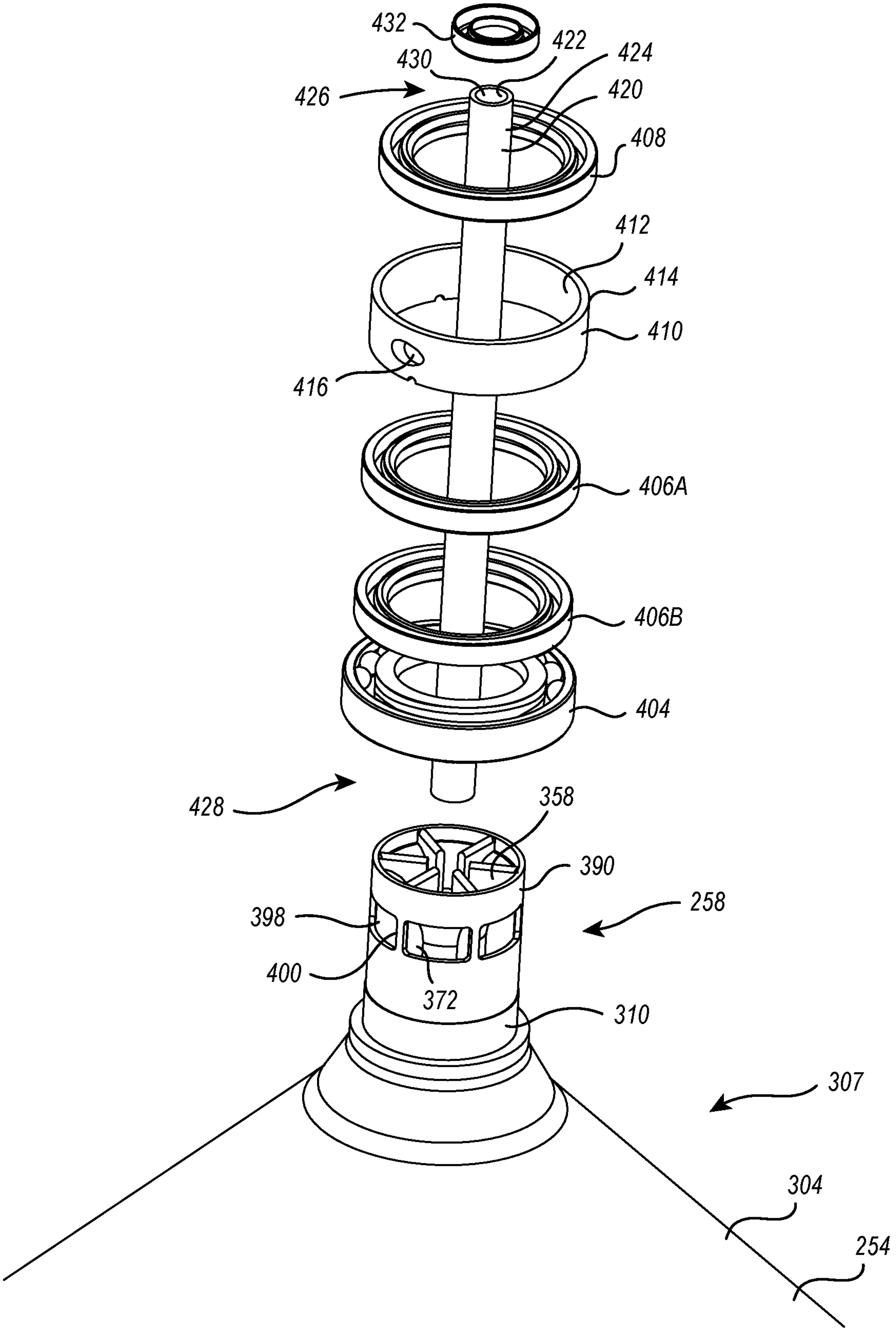
FIG. 14 is a partially exploded view the first end of the centrifugal separator shown in FIG. 13.
Figure 15:
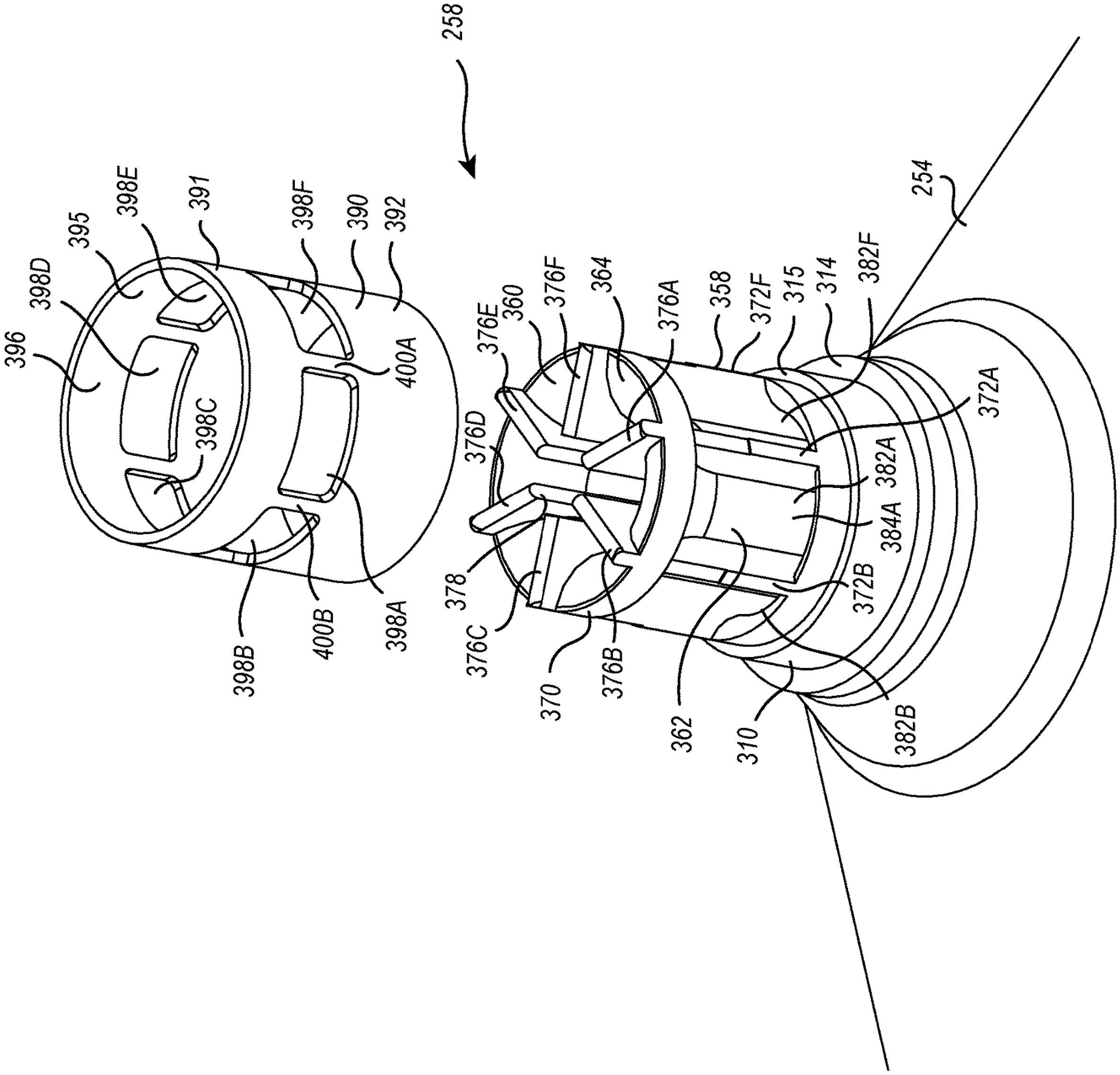
FIG. 15 is an exploded view of the stem assembly shown in FIG. 14.

With reference to FIGS. 14 and 15, stem assembly 258 is coupled to lip 310 at first end 307 of cap 254. Stem assembly 258 comprises a stem 358 and a sleeve 390 mounted thereon. Specifically, in the depicted embodiment, stem 358 has a substantially cylindrical configuration and outwardly projects from annular lip 310 so that central axis 230 centrally passes therethrough. In the depicted embodiment, stem 358 is integrally formed as a single, unitary member with cap 254. However, in other embodiments, stem 358 can be separately mounted and secured to cap 254. With reference to FIGS. 13 and 15, stem 358 comprises a tubular spout 360 having an interior surface 362 and an opposing exterior surface 364 that extend between a first end 366 and an opposing second end 368. Interior surface 362 bounds a light collection channel 379 that centrally passes through spout 360. As discussed below, second end 368 of spout 360 is connected to insert 256. First end 366 of spout 360 flares radially outward and terminates at an annular end face 370. End face 370 encircles central axis 230 and is typically disposed parallel thereto. Partition segments 372A-F outwardly project from exterior surface 364 of spout 360 and are equally spaced about spout 360. Partition segments 372 are typically disposed parallel to central axis 230 and longitudinally extend between annular end face 370 and annular lip 310 of cap 254.

Extending between spout 360 and annular lip 310 of cap 254 are heavy collection channels 382A-F that are separated by partition segments 372. For example, heavy collection channel 382A passes between annular lip 310 of cap 254 and exterior surface 364 of spout 360 at first end 366 while also being bounded between partition segments 372A and 372B. As heavy collection channel 382A extends upward toward first end 366, heavy collection channel 382A communicates with an opening 384A formed on an exterior side of stem 358. Opening 384A is bounded between partition segments 372A and 372B and also between annular lip 310 and end face 370. Heavy collection channels 382B-F are similarly configured and communicate with corresponding openings 384B-F, respectively. In alternative embodiments, it is appreciated that other numbers of partition segments 372 and heavy collection channels 382 can be formed. For example, in one embodiment, partition segments 372A can be eliminated so that only a single heavy collection channel 382 is formed that is bounded in part between exterior surface 364 of spout 360 and sleeve 390.

In one embodiment, a plurality of braces 376A-F inwardly project from interior surface 362 of spout 360 and extend between first end 366 and second end 368. Braces 376A-F are equally spaced apart around spout 360 and are typically linear and extending in parallel alignment with central axis 230. Each brace 376 terminates at an interior face 378 that is spaced part from central axis 230. In one embedment, braces 376 can divide light collection channel 379 into a plurality of separate light collection channel 379. In other embodiments, braces 376 can be eliminated so that only a single, unitary light collection channel 379 is formed.

Although stem 358 is shown having six partition segments 372, six openings 384, six heavy collection channels 382, and six braces 376, in alternative embodiments, such as discussed below in further detail, other numbers can be used such as at least 2, 3, 4, 5, 6, 7, 8, 9, or 10 or a range between any two of the foregoing.

Sleeve 390 has an exterior surface 394 and an opposing interior surface 395 that extend between a first end 391 and an opposing second end 392. Interior surface 395 bounds a passage 396 extending therethrough that is configured to receive stem 358. Specifically, sleeve 390 is configured to receive stem 358 so that second end 392 of sleeve 390 sits on shoulder 315 while sitting flush against and spanning between annular lip 310 and annular end face 370. Sleeve 390 spans over openings 384 of stem 358 that are disposed between annular lip 310 and annular end face 370. A plurality of equally spaced part openings 398A-F extend through sleeve 390 around the circumference of sleeve 390 and are configured so that each opening 398A-F aligns with a corresponding opening 384A-F/heavy collection channel 382A-F, respectively. However, openings 398 of sleeve 390 are smaller than openings 384 of stem 358. As such a portion of sleeve 390 directly bounds a portion of heavy collection channels 382. Specifically, sleeve 390 includes an annular heat dissipation section 388 that encircles spout 360 and extends between annular lip 310 and openings 398 of sleeve 390. Interior surface 395 of heat dissipation section 388 directly bounds a portion of heavy collection channels 382. Sleeve 390 also includes an annular heat dissipation section 389 that is disposed on the side of annular end face 370 of spout 360 opposite of opening 398. That is, annular heat dissipation section 389 projects out beyond spout 360 and encircles central axis 230. Heat dissipation section 389 extends between annular end face 370 and a terminal end of sleeve 390 Interior surface 395 of heat dissipation section 389 directly encircles and bounds a portion of light collection channel 379. The function of heat dissipation sections 388 and 389 will be discussed below. A segment 400 of sleeve 390 is disposed between each adjacent pair of openings 398 and aligns with a corresponding partition segment 372, as depicted in FIG. 14.

Stem 358, base 250, dispersion member 252, insert 256, and cap 254 are each typically made of a polymeric material, such as a liquid crystal polymer, polycarbonate, PVDF, HDPE, PEI, PEEK or the like. The different parts can be made of the same materials or different materials. As previously mentioned, making the parts from a polymeric material minimizes the cost of the centrifugal separator so that it can be economically disposed of after a single use, thereby avoid the need for subsequent sterilization or other cleaning. In alternative embodiments, however, one or more of the parts can also be made of a metal, such as aluminum or stainless steel. For reasons as will be discussed below in more detail, in one embodiment, sleeve 390 is made of a material that is more thermally conductive than the material used to form stem 358. For example, in one embodiment, stem 358 is formed from a polymeric material while sleeve 390 is formed from a metal, such as aluminum, copper, brass, stainless steel, or an alloy thereof, that is more thermally conductive than the polymer used to form stem 358. In other embodiments, sleeve 390 can be formed from a non-metal such as a composite, polymer, or other material that is more thermally conductive than the material used to form stem 358.

Figure 16:
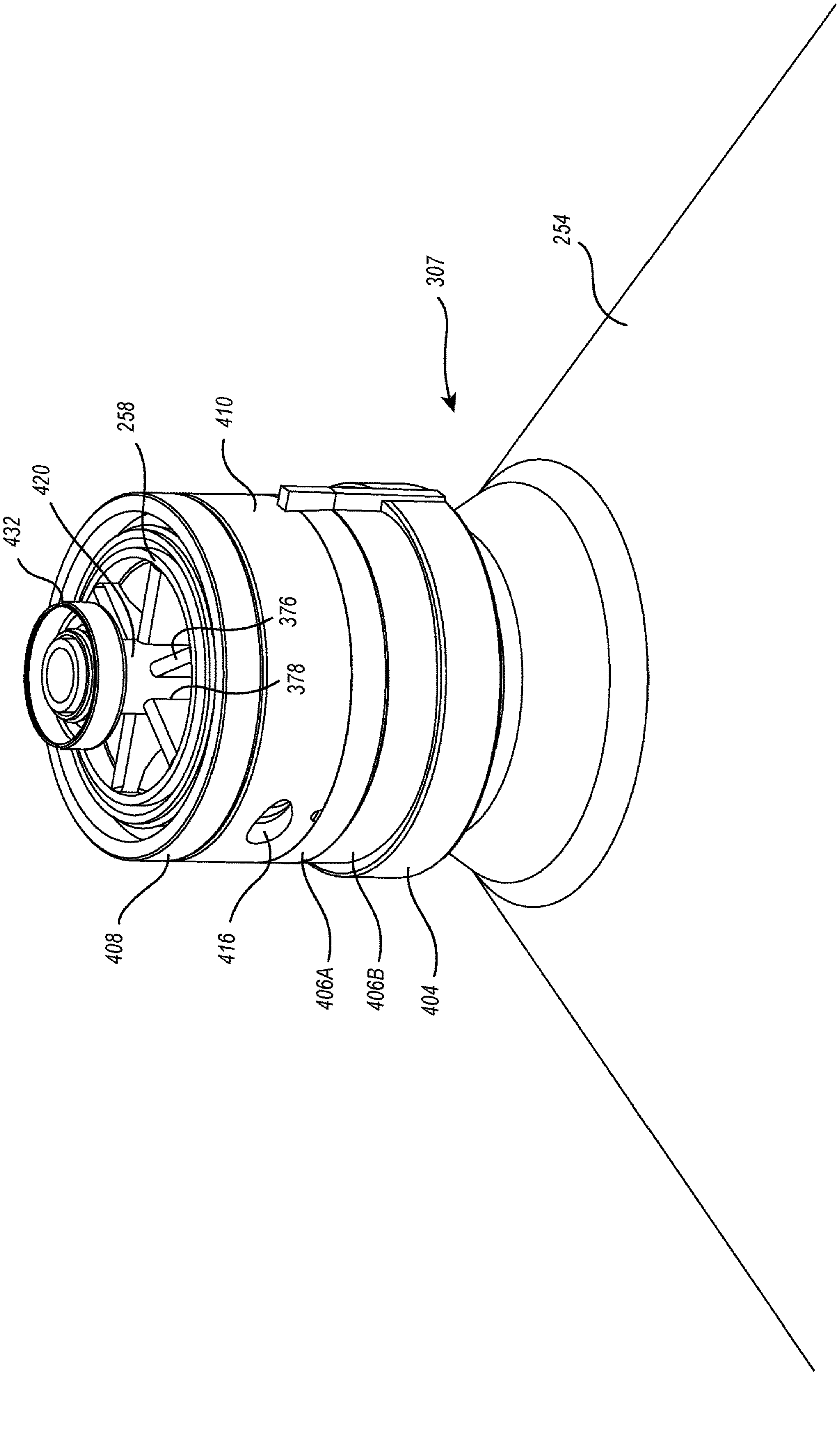
FIG. 16 is a perspective view of the assembled parts shown in FIG. 14.

Stem assembly 258 rotates concurrently with cap 254 and thus forms a portion of separation rotor 184. Centrifugal separator 12A also includes elements that are disposed between separation rotor 184 and separation stator 180. For example, as depicted in FIGS. 13, 14, and 16, such elements include an annular bearing assembly 404, such as a race bearing or other bearing assembly, that encircles annular lip 310 and sits on shoulder 314. Annular seals 406A and 406B, such as lip seals or other types of annular seals, that encircle stem 358 above bearing assembly 404. Seals 406 typically seal directly against exterior surface 394 of sleeve 390 at second end 392 below openings 398. More specifically, one or both of seals 406 are typically disposed directly against exterior surface 394 of heat dissipation section 388.

An annular seal 408, such as a lip seal or other type of annular seals, encircles stem 358 and seals directly against exterior surface 394 of sleeve 390 at first end 391 above openings 398. More specifically, seals 408 is typically disposed directly against exterior surface 394 of heat dissipation section 389. A cylindrical ring 410 has an interior surface 412 and an opposing exterior surface 414 and encircles sleeve 390 in alignment with openings 398. Ring 410 is disposed between seal 408 and seal 406A and has a passage 416 that laterally extends therethrough between an interior surface 412 and an opposing exterior surface 414.

As will be discussed further below, centrifugal separator 12A also includes a tubular conduit 420 having an interior surface 412 and an opposing exterior surface 414 that extend between a first end 426 and an opposing second end 428. Interior surface 422 bounds a passageway 430 extending therethrough. Encircling first end 426 of conduit 420 is a dynamic seal 432. Dynamic seal 432 effects a liquid tight seal with conduit 420 while permitting conduit 420 to rotate relative to seal 432.

Figure 17:
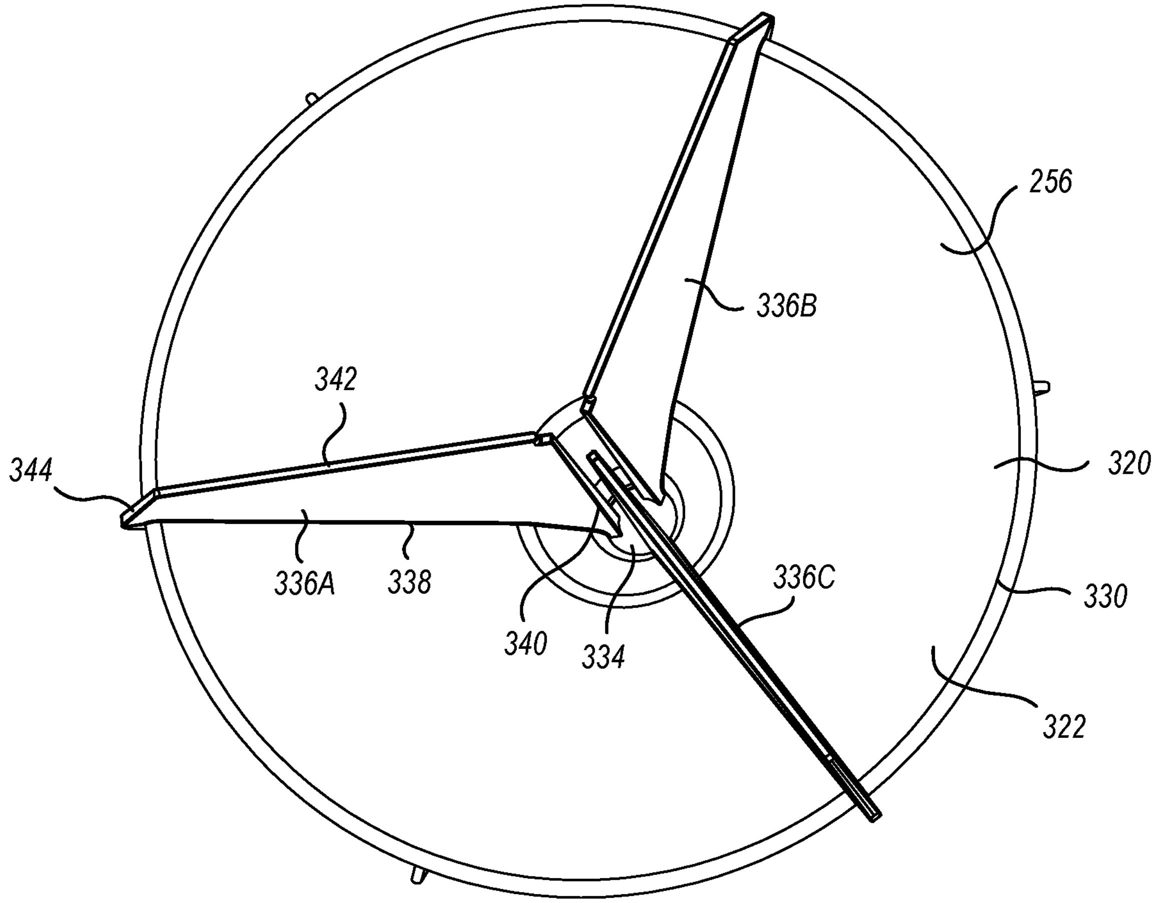
FIG. 17 is bottom perspective view of the insert shown in FIG. 11.

With reference to FIGS. 11 and 17, insert 256 comprises an annular, frustoconical sidewall 320 which is referred to herein as inner sidewall 320. Inner sidewall 320 has an interior surface 322 and an opposing exterior surface 324 that inwardly constrict from a second end 326 to an opposing first end 238. Second end 326 of inner sidewall 320 terminates at a perimeter edge 330 while first end 328 terminates at an annular lip 332. Lip 332 encircles an opening 334 that centrally passes through insert 256 along central axis 230. In one embodiment, interior surface 322 of inner sidewall 320 can be disposed at the same angle as interior surface 300 of sidewall 304. For example, interior surface 322 of inner sidewall 320 can slope relative to central axis 230 at an angle in a range between 35° and 55° and more commonly between 40° and 50° or between 42° and 48°. Other angles can also be used.

Insert 256 also includes three radially spaced apart upper partitions 336A-C that are equally spaced apart. Upper partitions 336A-C project away from interior surface 322 and radially outwardly extend in alignment with central axis 230 to perimeter edge 330 and beyond. More specifically, each partition 336 has a top edge that extends along interior surface 322 from perimeter edge 330 to opening 334, an inside edge 340 that extends parallel to central axis 230 along opening 334, a bottom edge 342 that projects down below inner sidewall 320 and is configured to be received within slots 294 (FIG. 11) of dispersion member 252 and an outside edge 344 that is sloped to butt against interior surface 260 of sidewall 266 of base 250. Upper partitions 336B and 336C have the same configuration and elements as upper partition 336A and thus like elements between each of upper partitions 336 are identified by like reference numbers.

Outwardly projecting from exterior surface 324 of inner sidewall 320 are a plurality of radially spaced part dividers 350A-F. Dividers 350 are in the form of linear rails that radially outwardly extend from annular lip 332 to perimeter edge 330 and are equally spaced apart.

During assembly, with reference to FIGS. 9 and 11, dispersion member 252 is disposed on and is interlocked with spacers 272 of base 250 by lower partitions 288 being received within slots 276. In this configuration, dispersion member 252 is secured to base 250 such that rotation of base 250 about central axis 230 facilitates rotation of dispersion member 252. However, body 280 of dispersion member 252 is spaced apart from floor 264 of base 250 so that a space 448 is formed therebetween.

Insert 256 is set on and interlocked with dispersion member 252 by bottom edges 342 of upper partitions 336 (FIG. 17) being received within slots 294 of retention rails 292. As a result, rotation of base 250 also facilitates current rotation of insert 256. Cap 254 having stem assembly 258 disposed thereon, as discussed above, is the secured to base 250 by securing lip 306 of cap 254 within slot 276 of base 250, as previously discussed. Slots 311 of guides 309 (FIG. 12) receive corresponding dividers 350 of insert 256 so as to help ensure proper centering, alignment and engagement between cap 254 and insert 256. As a result of the assembly, insert 256 and dispersion member 252 are enclosed between base 250 and cap 254. As base 250 is secured to cap 254, lip 332 at first end 328 of insert 256 is secured to second end 368 of spout 360 (FIG. 13). For example, in the depicted embodiment, an annular slot 436 is formed at second end 368 of spout 360 in which lip 332 can be securely received. In other embodiments, second end 368 of spout 360 can be secured to lip 332 of insert 256 by adhesive, threaded engagement, press fit connection, snap fit connection, through the use of fasteners or other conventional mechanisms.

During further assembly, as depicted in FIGS. 14 and 16, bearing assembly 404, seals 406 and 408, and ring 410 are disposed on stem assembly 258, as previously discussed. Conduit 420 is also positioned. Specifically, with reference to FIG. 9, second end 428 of conduit 420 is secured within opening 290 that central extends through dispersion member 252. This coupling can be by press fit connection, threaded connection, adhesive, or other forms of connection. The remainder of conduit 420 centrally projects along central axis 230 through opening 334 of insert 256 and centrally up through light collection channel 379 of spout 360. In this position, conduit 420 is laterally supported by interior faces 378 of braces 376 (FIG. 16). During operation, conduit 420 rotates concurrently with the remainder of separation rotor 184 relative to separation stator 180.

The assembled separation rotor 184 is enclosed within separation stator 180. Specifically, with reference to FIG. 13, inlet port 38 outwardly projects from end wall 218 of nose 214 and bounds a passage 45 that is aligned with central axis 230. Passage 45 passes through end wall 218 to interior surface 202. An annular groove 438 is recessed on interior surface 202 of end wall 218 so as to encircle passage 45. Dynamic seal 432 is received and secured within groove 438. Stem assembly 258 having bearing assembly 404, seals 406 and 408, and ring 410 disposed thereon is received within recess 213 of nose 214, thereby rotatably fluid coupling first end 426 of conduit 420 to passage 45 of inlet port 38 by dynamic seal 432.

With continued reference to FIG. 13, an annular upper shoulder 440 inwardly projects from interior surface of 202 of sidewall 216 of nose 214 toward end wall 218. A light component collection recess 444 is formed between upper shoulder 440 and end wall 218. Second outlet port 42 (FIG. 6) bounds a passage 47 that communicates with light component collection recess 444. Seal 408 rests against upper shoulder 440 while each of seal 408, ring 410, and seals 406A and 406B rest against interior surface of 202 of sidewall 216 of nose 214. As such, each of seal 408, ring 410, and seals 406A and 406B are captured between sidewall 216 of nose 214 and sleeve 390. More specifically, seals 406 and 408 form a dynamic, liquid tight seal directly against sleeve 390 which enables sleeve 390 and the remainder of separation rotor 184 to rotate relative to separation stator 180 and relative to seals 406 and 408 while maintaining a liquid tight seal therebetween.

An annular heavy component collection recess 446 encircles sleeve 390 and is bound between sleeve 390 and ring 410 and also between seal 408 and 406A. First outlet port 42 (FIG. 6) bounds a passage 49 that aligns with passage 416 of ring 410 so as to communicates with heavy component collection recess 446. In alternative embodiments, ring 410 can be eliminated so that heavy component collection recess 446 is bound directly between nose 214 of separation stator 180 and sleeve 390. Heavy component collection recess 446 aligns with and thus communicates with openings 398 of sleeve 390 and heavy collection channels 382.

An annular lower shoulder 442 inwardly projects from interior surface 202 of sidewall 216 of nose 214. Bearing assembly 404 sits against shoulders 442 and 314 and is captured between lip 310 of cap 254 and head 192 of separation stator 180. As with bearing assembly 270 (FIG. 9) bearing assembly 404 functions to both center and stabilize separation rotor 184 within separation stator 180 so that separation rotor 184 can freely rotate within separation stator 180.

Figure 18:
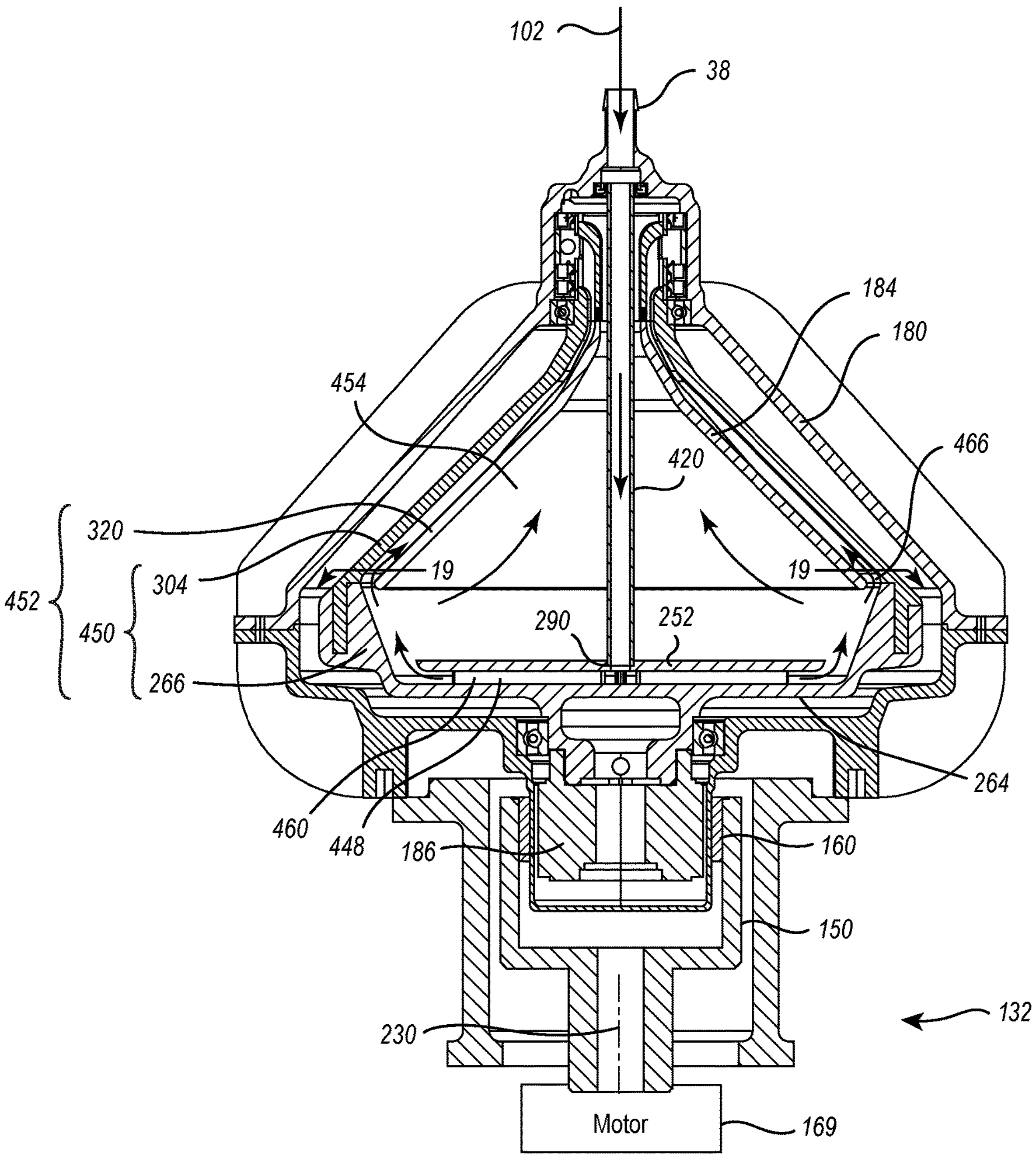
FIG. 18 is a front elevational cross-sectional view of the centrifugal separator shown in FIG. 6.

Turning to FIG. 18, during operation motor 169 is active so as to rotate drive rotor 150 relative to separation stator 180 about central axis 230. In turn, the magnetic force produced by magnet 168 acts on drive coupling 186, as previously discussed, so as to concurrently rotate drive coupling 186 and separation rotor 184 about central axis 230 and relative to separation stator 180. During operation, separation rotor 184 typically rotates at a rate of at least 1,000; 2,000; 2,500; 3,000; or 3,500 rotations per minute (RPM) or in a range between any two of the foregoing values. Depending on the application, other speeds can also be used.

Once rotation of separation rotor 184 is activated, inlet stream 102 (FIGS. 1, 3, and 5) of suspension 18 is passed into inlet port 38 and travels through conduit 420 along central axis 230 and through opening 290 of dispersion member 252 so as to enter space 448 between dispersion member 252 and floor 264 of separation rotor 184. Inlet stream 102 radially outwardly flows in all directions within space 448 toward the perimeter edge 286 of dispersion member 252. In part, dispersion member 252 functions to force inlet stream 102 to flow radially outward away from central axis 230 so as to maximize the rate and force at which inlet stream 102 begins to separate into a heavy component and a light component. Specifically, as inlet stream 102 moves radially outward away from central axis 230, inlet stream 102 become subject to an increasing greater centrifugal force caused by the rotation of separation rotor 184. Thus, as inlet stream 102 passes around perimeter edge 286 of dispersion member 252, the centrifugal force causes inlet stream 102 to separate into a heavier component that travels radially outward and a lighter component that travels radially inward.

In addition, radially extending spacers 272 and lower partitions 288 (FIG. 11) extend between dispersion member 252 and floor 264 so as to divide space 448 in a plurality of inlet fluid paths 460 that extend from conduit 420 to perimeter edge 286 of dispersion member 252. Each inlet fluid path 460 is bounded between an adjacent pair of spacers 272/lower partitions 288 so as to force inlet stream 102 to flow radially outward along a generally linear path as opposed to swirling in a circle within space 448 about central axis 230. This linear, radial flow of inlet stream 102 again assists to quickly move inlet stream 102 away from central axis 230 so as to increase the rate of separation of inlet stream 102 into heavier and lighter components. In addition, the linear, radial flow helps to maintain inlet stream in a laminar flow, as opposed to a turbulent flow, which further assists in the separation of inlet stream 102 into the heavier and lighter components. In the depicted embodiment, six inlet fluid path 460 (FIG. 11) are formed. In alternative embodiments, other numbers of inlet fluid paths 460 can be formed, such as at least 3, 4, 5, 6, 7, 8, 9, or 10 or in a range between any two of the foregoing numbers.

Lower sidewall 266 of base 250 and upper sidewall 304 of cap 254 combine to form an outer sidewall 450 of separation rotor 184 while inner sidewall 320 of insert 256 forms an inner sidewall 320 of separation rotor 184. Outer sidewall 450 and inner sidewall 320 combine to form a sidewall assembly 452 of separation rotor 184 that encircles a compartment 454 of which space 448 forms a portion.

Figure 19:
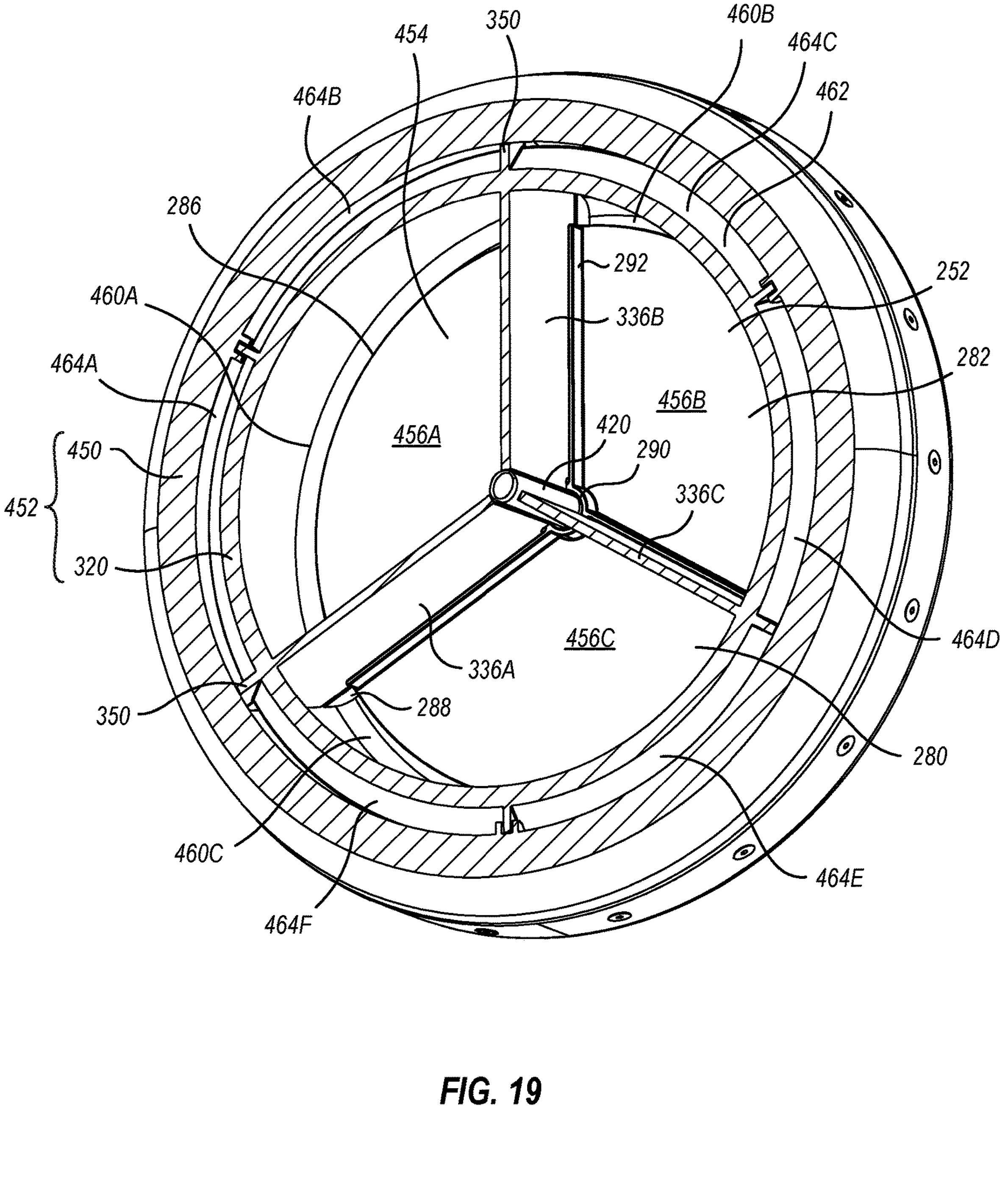
FIG. 19 is a cross-section view of the separation rotor shown in FIG. 18 taken along lines 19-19.

As better depicted in the cross-sectional view of FIG. 19, lower partitions 288 radially outwardly project within space 448 from or toward opening 290 of dispersion member 252 to sidewall assembly 452 and, more specifically, to outer sidewall 450/lower sidewall 216. As a result, lower partitions 288 also extending between body 280 of dispersion member 252 and floor 264, lower partitions 288 create three isolated inlet fluid paths 460 that do not openly communicate downstream of opening 290.

Similarly, upper partitions 336 radially outwardly project from conduit 420 along top surface 282 of dispersion member 252 to sidewall assembly 452 and, more specifically, to inner sidewall 320 and along the length thereof and to outer sidewall 450 below inner sidewall 320 (lower sidewall 266). As a result, upper partitions 336 in combination with rails 292 divide compartment 454 above dispersion member 252 into a plurality of light component fluid paths 456A-C. In one embodiment, light component fluid paths 456A-C are substantially isolated from each other so that fluid cannot freely flow between light component fluid paths 456A-C.

Furthermore, each upper partition 336 also radially extends along top surface 282 of dispersion member 252 from conduit 420 to perimeter edge 286 and then aligns and intersects with a corresponding one of lower partitions 288 as upper partitions 336 extend from perimeter edge 286 to sidewall assembly 452. As a result, each inlet fluid path 460 bounded between adjacent lower partitions 288 aligns with a corresponding light component fluid path 456 and fluid does not mix as it passes therebetween. That is fluid traveling along an inlet fluid path 460 to a corresponding light component fluid path 456 does not mix with a separated fluid traveling along a separate inlet fluid path 460 to a separate corresponding light component fluid path 456. Again, this configuration helps the fluid to continually flow along a generally linear path as opposed to swirling in a circle around conduit 420/central axis 230 and helps to keep the fluid flowing in a more laminar flow, as opposed to a turbulent flow, both of which help separation of the fluid into the heavy component and the light component. In the depicted embodiment, three upper partitions 336 and three lower partitions 288 are shown. In alternative embodiments, separation rotor 184 can be formed with at least 3, 4, 5, 6, 7, 8, 9, 12, 15, 18, 21 or more upper partitions 336 and lower partitions 288 or in a range between any two of the foregoing.

Again, as previously mentioned, as a result of the centrifugal force produced by the rotation of separation rotor 184, the lighter components of inlet stream 102 passing around perimeter edge 286 of dispersion member 252 flow radially inward into a corresponding one of light component fluid paths 456 at second end 242 of separation rotor 184. As depicted in FIGS. 13 and 18, the separated light components the flow toward first end 240 of separation rotor 184 by flowing through light component fluid paths 456, through light collection channel 379 bounded between spout 360 and conduit 420 and into light component collection recess 444. The light components from each light component fluid paths 456 combine within light component collection recess 444. Finally, the light components pass out of light component collection recess 444 through second outlet port 42 as second outlet stream 106 (FIGS. 1, 3, and 5,) and can be further processed or transferred as previously discussed.

With continued reference to FIG. 13, during operation, seal 408 is stationary and rides against sleeve 390 which is rotating with the remainder of separation rotor 184. Frictional engagement between seal 408 and sleeve 390 can heat seal 408 and reduce its effective life span. To help minimize heating of seal 408 and thus prolong its effective life, seal 408 directly biases against heat dissipation section 389 of sleeve 390. As previously discussed, interior surface 395 of heat dissipation section 389 bounds a portion of light collection channel 379. As such, as the light components of the fluid flow through light collection channel 379 and into light component collection recess 444, the fluid flows over interior surface 395 of heat dissipation section 389 so as to cool heat dissipation section 389/sleeve 390 and thereby also cool seal 408. Furthermore, by making sleeve 390 out of a material that is relatively highly thermally conductive, as previously discussed, the heat from sleeve 390 is more rapidly dissipated, thereby further improving the cooling of sleeve 390 and seal 408.

In contrast to the light components which flow radially inward into light component fluid paths 456, the heavier components, which typically include the cells, microorganism, particles thereof, and other solids, flow radially outward toward sidewall assembly 452/outer sidewall 450. As a result of dividers 350 outwardly projecting from exterior surface 324 insert 256, an annular, frustoconical gap 462 is formed between insert 256 and cap 254. The outer edge of dividers 350 sit against interior surface 300 of cap 254 so that dividers 350 divide annular, frustoconical gap 462 into a plurality of separate heavy component fluid paths 464A-F. That is, sidewall assembly 452 bounds the plurality of separate heavy component fluid paths 464. Each heavy component fluid paths 464 has an opening 466 disposed at perimeter edge 330 of insert 256/inner sidewall 320.

During operation, once inlet stream 102 flows out through an inlet fluid path 460 between floor 264 and dispersion member 252, the heavy components of the fluid flow radially outward toward sidewall assembly 452/outer sidewall 450 and flow into a corresponding heavy component fluid paths 464 through an opening 466. The heavy components then flow within heavy component fluid paths 464 toward first end 196 of separation rotor 184. With reference to FIGS. 13 and 18, as the heavy components reach stem assembly 258, the heavy components flow into corresponding heavy collection channels 382, out through openings 398 on sleeve 390 and into heavy component collection recess 446. The heavy components from each of the different heavy component fluid paths 464 combine together within heavy component collection recess 446. Finally, the heavy components pass through passage 416 on ring 410 and then out through first outlet port 40 as first outlet stream 104 (FIGS. 1, 3, and 5,) where it can be further processed or transferred as previously discussed.

With continued reference to FIG. 13, during operation, seal 406 are stationary and ride against sleeve 390 which is rotating with the remainder of separation rotor 184. Frictional engagement between seals 406 and sleeve 390 can heat seal 406 and reduce their effective life span. To help minimize heating of seal 406 and thus prolong their effective life, seals 406 directly biases against heat dissipation section 388 of sleeve 390. As previously discussed, interior surface 395 of heat dissipation section 388 bounds a portion of heavy collection channels 382. As such, as the heavy components of the fluid flow through heavy collection channels 382 and into heavy component collection recess 446, the fluid flows over interior surface 395 of heat dissipation section 388 so as to cool heat dissipation section 388/sleeve 390 and thereby also cool seals 406. Furthermore, by making sleeve 390 out of a material that is relatively highly thermally conductive, as previously discussed, the heat from sleeve 390 is more rapidly dissipated, thereby further improving the cooling of sleeve 390 and seals 406.

Again, using dividers 350 to form and isolate heavy component fluid paths 464 helps the heavy component flowing into and along heavy component fluid paths 464 to continually flow along a generally linear path, as opposed to swirling in a circle around central axis 230 and also assists with keeping the heavy components in a more laminar flow, as opposed to a turbulent flow, both of which help separation of the fluid and which also limits the application of undue force on the separated cells or microorganisms which can be damaging or detrimental. In the depicted embodiment, six dividers 350 are used forming six heavy component fluid paths 464. In alternative embodiments, separation rotor 184 can be formed with at least 3, 4, 5, 6, 7, 8, 9, 12, 15, 18, 21, 26, 32, 38 or more dividers 350 and/or heavy component fluid paths 464 or can be in a range between any two of the foregoing.

As depicted in FIG. 19, aligned upper partitions 336 and lower partitions 288 also radially align with corresponding dividers 350. As a result, fluid flowing from an inlet fluid path 460 to a corresponding aligned light component fluid path 456 can only communicate with corresponding aligned heavy component fluid paths 464. For example, as shown in FIG. 19, inlet fluid path 460A, light component fluid path 456A, and heavy component fluid paths 464A and 464B are aligned and communicate with each other. However, they are restricted by upper partitions 336, lower partitions 288, and dividers 350 from freely communicating with the other inlet fluid paths 460B and C, the other light component fluid path 456B and C, and the other heavy component fluid paths 464C-F. This configuration and isolation of the fluid paths helps to assist in the separation of the heavy and light components.

Development of the present disclosure has also discovered surprising and unexpected result. For example, when using upper partitions 336, lower partitions 288, and dividers 350, as discussed herein, to isolate fluid communication between select inlet fluid paths 460, light component fluid paths 456, and heavy component fluid paths 464, it has been discovered that having each light component fluid path 456 in fluid communication with increasing numbers of heavy component fluid paths 464 increases the separation efficiency of solids. For example, set forth below is a table setting forth parameters and results of three tests operating three different separation rotor designs.

| | # Heavy Outlets | Rotor rpm | Feed Rate (L/Min) | Feed Solids (%) | Light-Solids (%) | Heavy-Solids (%) |
|---|---|---|---|---|---|---|
| Test 1 | 1 | 2,500 | 3 | 10 | 21.8 | 78.2 |
| Test 2 | 2 | 2,500 | 3 | 10 | 11.1 | 88.9 |
| Test 3 | 4 | 2,500 | 3 | 10 | 3.4 | 96.6 |

In each of the above three tests, the rotation of the separation rotor was set at 2,500 rotations per minute, the feed rate of delivering the inlet stream into the centrifugal separator was set at 3 liters per minute and the percent solids within the inlet stream was retained at 10%. Furthermore, in each of the three tests, the separation rotor was design similar to separation rotor 184, previously disclosed herein, so as to have three separated light component fluid paths 456A-C that are separated by three spaced apart upper partitions 336A-C. However, the number of heavy component fluid paths 464 that communicated with each light component fluid path 456 varied for each test.

In Test 1, the separation rotor 184 was designed so that the sidewall assembly 452 only included three dividers 350 that were each aligned with corresponding upper partition 336. As such, each light component fluid path 456 only communicated with a single heavy component fluid path 464. In this test, 78.2% of the solids were collected in the first outlet stream 104 that collects the heavier components and 21.8% of the solids were collected in the second outlet stream 106 that collects the lighter components.

In Test 2, with all other variables held constant, the separation rotor 184 was designed the same as in the present disclosure wherein sidewall assembly 452 included six dividers 350 with every other divider being aligned with a corresponding upper partition 336. As such, each light component fluid path 456 communicated with a two heavy component fluid path 464. In this test, 88.9% of the solids were collected in the first outlet stream 104 that collects the heavier components and 11.1% of the solids were collected in the second outlet stream 106 that collects the lighter components.

Finally, in Test 3, with all other variables held constant, the separation rotor 184 was designed similar to the present disclosure except that sidewall assembly 452 included twelve dividers 350 with every fourth divider being aligned with a corresponding upper partition 336. As such, each light component fluid path 456 communicated with four heavy component fluid path 464. In this test, 96.6% of the solids were collected in the first outlet stream 104 that collects the heavier components and 3.4% of the solids were collected in the second outlet stream 106 that collects the lighter components.

The test results support that increasing the number of heavy component fluid paths 464 relative to aligned light component fluid paths 456 increases the solids separation efficiency. Thus, although in one embodiment of the present disclosure separation rotor 184 can be formed so that the ratio of heavy component fluid paths 464 to light component fluid paths 456 is 1:1 in other embodiments, to help improve solids separation efficiency, the separation rotor 184 can be designed so that the ratio is at least 2:1, 3:1, 4:1, 5:1, 6:1, 8:1, 10:1, 20:1, 40:1 or is in range between any two of the foregoing ratios.

Furthermore, some common centrifugal separators employ angled sidewalls to assist in separation. Commonly, the angling of the sidewalls is for two purposes: 1) to encourage the heavy component to funnel to a colocalized volume for collection and potential discharge, and 2) to shorten the separation time for heavy components by shortening the radial distance through which the separating material must travel for separation. The present disclosure, however, also employs an angled upper and/or lower sidewall for an additional purpose of mitigating inertial fluid flow effects that can disrupt separation.

Fluid flowing radially through a chamber that is rotating will be subject to Coriolis effects (i.e., inertial effects). Coriolis effects impact the flowing fluid in a manner primarily perpendicular to the axis of rotation. For example, as fluid flows radially inward, the radial velocity of the fluid accelerates with respect to the radial velocity of the rotating chamber due to the inertia of the fluid imparted by the chamber at the larger radius. This difference in velocity can cause the fluid to overtake the chamber at some radius smaller than the outermost radius, which then drives the fluid back towards the outermost radius. Overall, the Coriolis (inertial) effect imparts a flow dynamic that leads to vortex formation in the plane perpendicular to the axis of rotation. Such vortices can develop flows that are disruptive to the centrifugal separation. In a chamber with upper and lower sidewalls that remain axially equidistant, such as in one embodiment of the present disclosure, the radial cross-sectional area changes linearly with respect to radius. Thus, radially flowing fluid in such a chamber accelerates to maintain a flow rate through a given radial cross-sectionally area of the chamber. In such a chamber, the radial acceleration of the fluid exacerbates the Coriolis effect and enlarges and increases the fluid flow velocities in developing vortices.

To assist in mitigating these above described effects, embodiments of the present disclosure can employ an upper or lower sidewall, or both, that extend the axial distance between them as the radius decreases. In one embodiment, the upper sidewall, e.g. interior surface 322 of inner sidewall 320 (FIGS. 17 and 18), can be angled in a range between 40° and 50° and more commonly between 42° and 48° or between 43° and 47° with respect to the central axis 230, i.e., the axis of rotation. This resulting frustoconical shape can help to mitigate the above described flow effects. That is, the expanding chamber height counteracts changes in the radial cross-sectional area through which fluid flows radially, decreasing, eliminating, or reversing the acceleration of the fluid as it flows radially. The additional axial dimension of the chamber can thus function to disrupt vortex formation from Coriolis effect by encouraging fluid to flow out of the plane perpendicular to the axis of rotation. The combined mitigation prevents the compounding acceleration of the fluid that leads to strong vortex formation capable of disrupting separations in the chamber.

Figure 20:
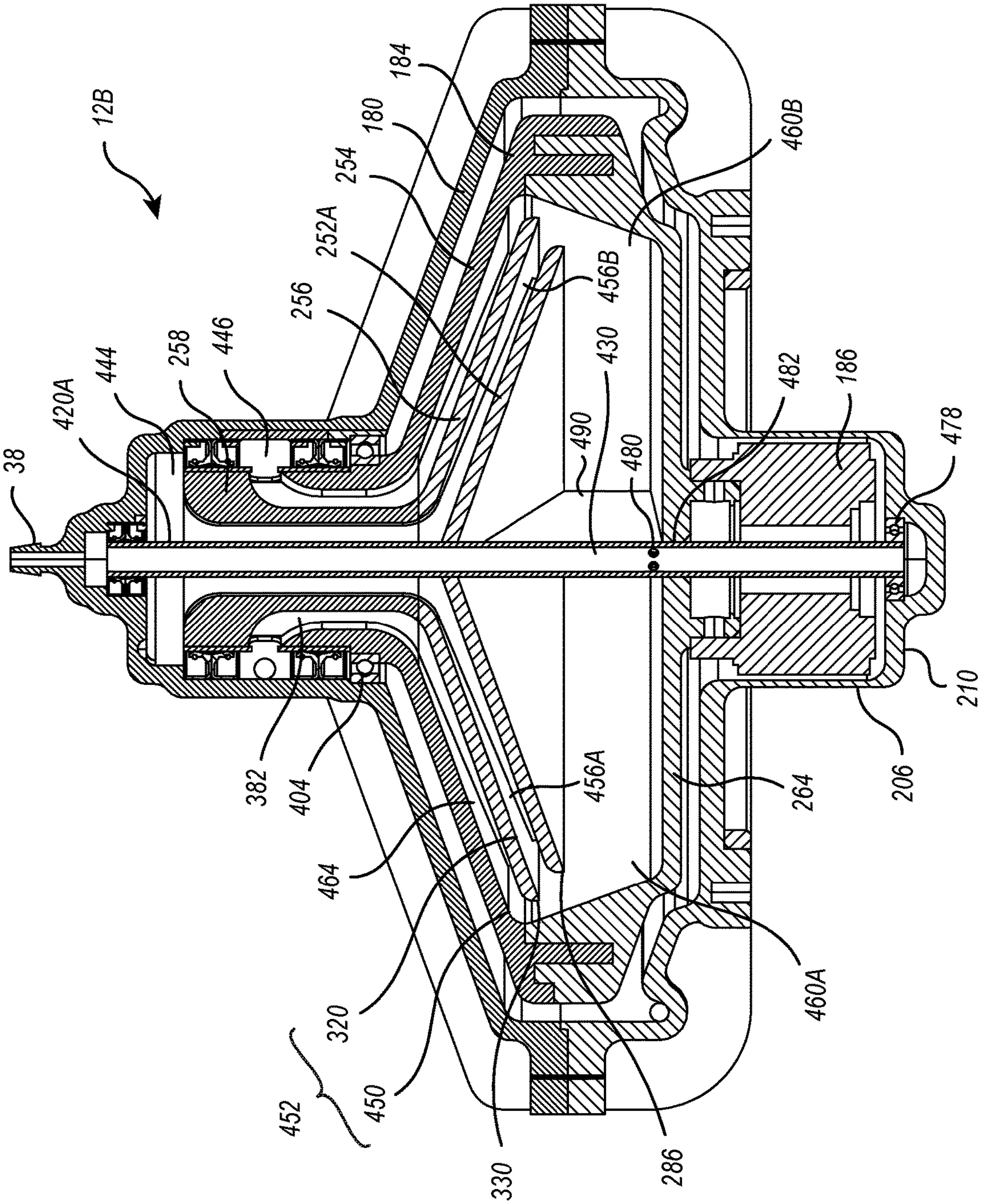
FIG. 20 is a front elevational cross-sectional view of an alternative embodiment of a centrifugal separator.

Depicted in FIG. 20 is another alternative embodiment of a centrifugal separator 12B that can be used as centrifugal separator 12 in the systems and alternatives discussed above with regard to FIGS. 1-5. Centrifugal separator 12B is substantially similar to centrifugal separator 12A and like elements are identified by like reference characters. Furthermore, unless otherwise described and/or depicted, it is appreciated that like elements between centrifugal separator 12B function in the same way and can have the same alternatives as corresponding elements of centrifugal separator 12A.

Figure 21:
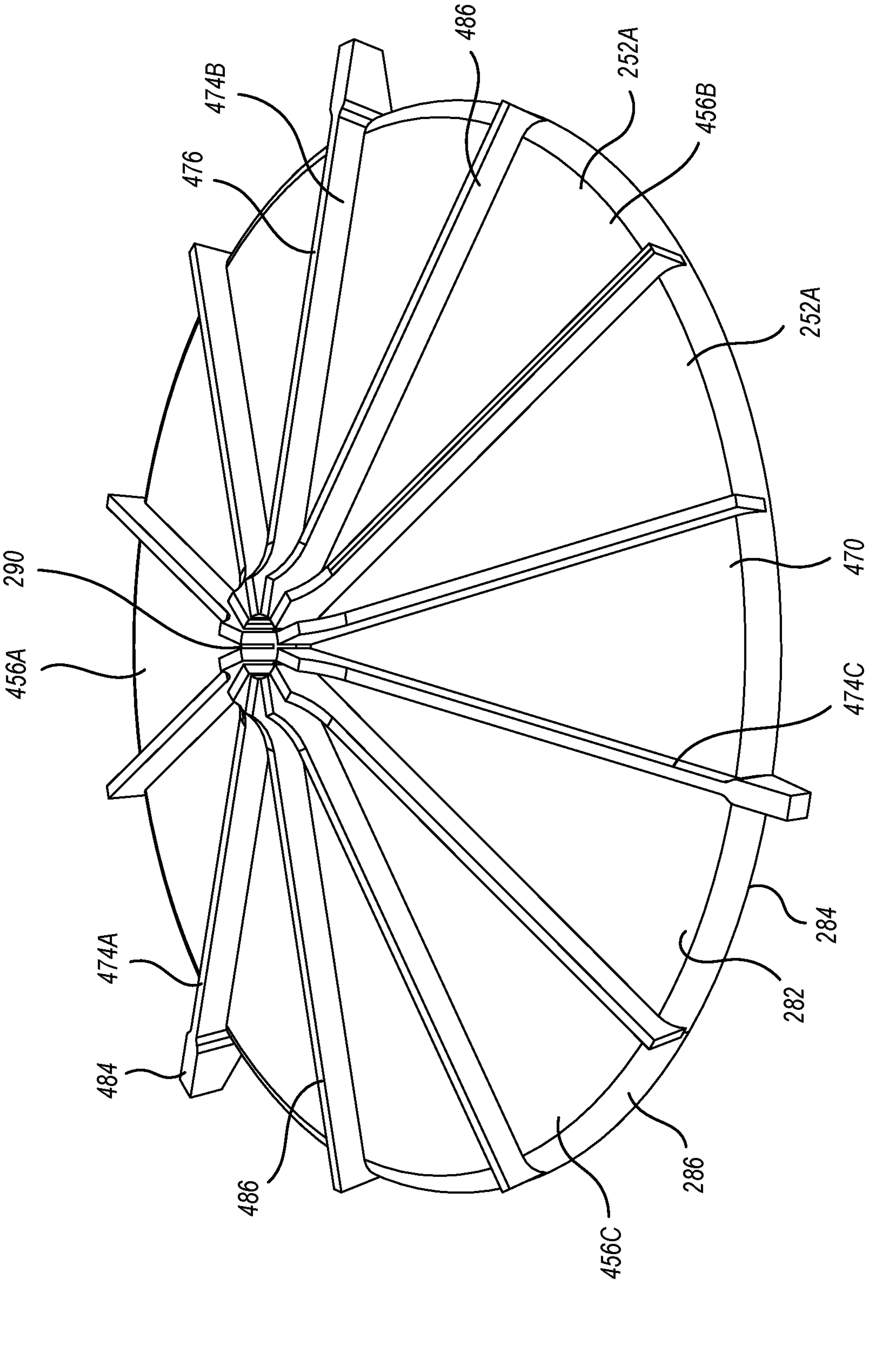
FIG. 21 is a top perspective view of the dispersion member shown in FIG. 20

As depicted in FIG. 20, centrifugal separator 12B includes separation rotor 184 that rotates within separation stator 180 and functions to separate inlet stream 102 into a heavy component and a light component. Separation rotor 184 includes base 250, a dispersion member 252A, insert 256, cap 254, and stem assembly 258. In contrast to dispersion member 252 having a body 280 in the form of a flat plate, dispersion member 252A, as shown in FIGS. 20 and 21, comprises a body 470 having a frustoconical configuration and opening 290 centrally extending therethrough. Body 470 has top surface 282 and opposing bottom surface 284 that outwardly slope from opening 290 to outer perimeter edge 286. Three upper partitions 474A-C outwardly project from top surface 282. Upper partitions 474A-C radially extend out from opening 290 and terminate at a free end 484 that extends past perimeter edge 286. Free ends 484 are deigned to butt against outer sidewall 450. Each upper partition 474 has an outer edge 476 that is configured to sit against the interior surface of insert 256 such that light component fluid paths 456A-C are formed between each adjacent pair of upper partitions 474 through which the light components pass to stem assembly 258. In the depicted embodiment, a plurality of elongated dividers 486 also outwardly project from top surface 282 of dispersion member 252A between each adjacent pair of upper partitions 474. Dividers radially extend out from opening 290 to perimeter edge 286. However, dividers 486 do not extend to outer sidewall 450. Dividers 486 partially subdivide each light component fluid paths 456A-C. However, some fluid communication is permitted between the subdivisions for each light component fluid paths 456A-C. In contrast, fluid communication is restricted between the different light component fluid paths 456A-C. In the depicted embodiment, three dividers 486 are formed between each pair of upper partitions 474. Other numbers of dividers 486 such as at least 1, 2, 4, 5, 6, 8, or 10 can also be used.

Centrifugal separator 12B is also formed with a conduit 420A. First end 426 of conduit 420A is rotatably sealed to end wall 218 of nose 214 by a pair of dynamic seals 432A and 432B. In contrast to centrifugal separator 12A, second end 428 of conduit 420A centrally passes through floor 264 and drive coupling 186 and is rotatably secured by an annular bearing assembly 478, such as a race bearing, to end wall 210 of receiver 206. A seal 482 is formed between conduit 420A and floor 264 so as to prevent liquid from leaking therebetween. Bearing assembly 270 has been eliminated and thus bearing assemblies 404 and 478 are now used to support and stabilize separation rotor 184 within separation stator 180. A plurality of openings 480 radially extend through conduit 420A between floor 264 and dispersion member 252A so as to communicate with passageway 430. Three equally spaced lower partitions 490 extend between floor 264 and dispersion member 252A and radially outwardly project from conduit 420A to outer sidewall 450. Lower partitions 490 align with and intersect with corresponding upper partitions 474. Lower partitions 490 divide space into separate and isolated inlet fluid paths 460A-C that communicate with corresponding light component fluid paths 456A-C.

It is noted that outer perimeter edge 330 of insert 256 is disposed radially outward from outer perimeter edge of dispersion member 252A. During operation, separation rotor 184 is rotated with separation stator 180 through the use of drive coupling 186, as previously discussed. Inlet stream 102 is delivered in inlet port 38 where it passes down through conduit 420A and out through openings 480 into inlet fluid paths 460. The fluid stream flow radially outward toward outer sidewall 450. The lighter components flow into light component fluid paths 456, through spout 360 of stem assembly 258, into light component collection recess 444, and out through second outlet port 42, as previously discussed with regard to centrifugal separator 12A. Likewise, the heavier components flow radially outward so as to flow into heavy component fluid paths 464, through heavy collection channels 382, into heavy component collection recess 446 and out through first outlet port 40, as previously discussed with regard to centrifugal separator 12A.

Figure 22:
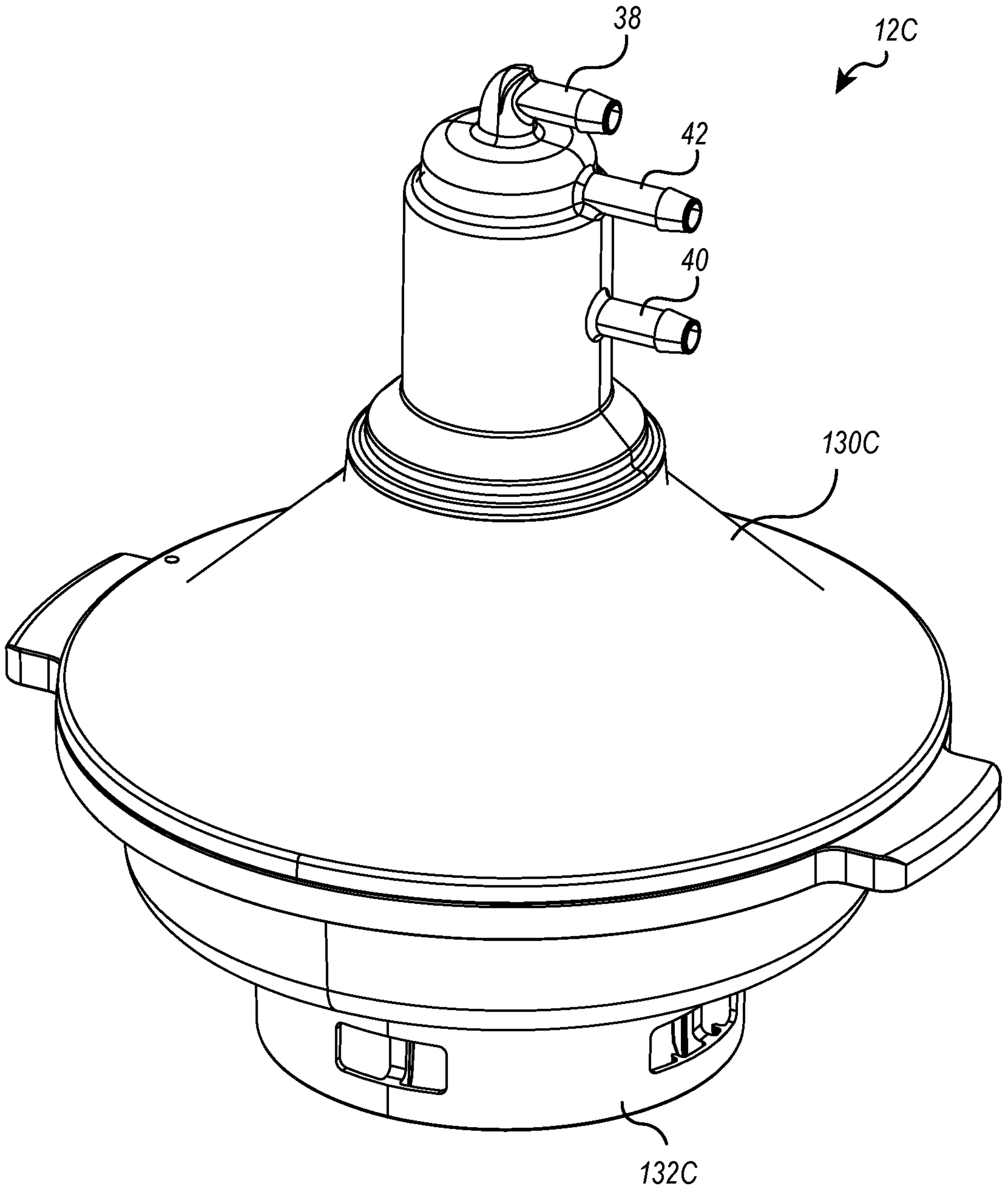
FIG. 22 is a top perspective view of an alternative embodiment a centrifugal separator.
Figure 23:
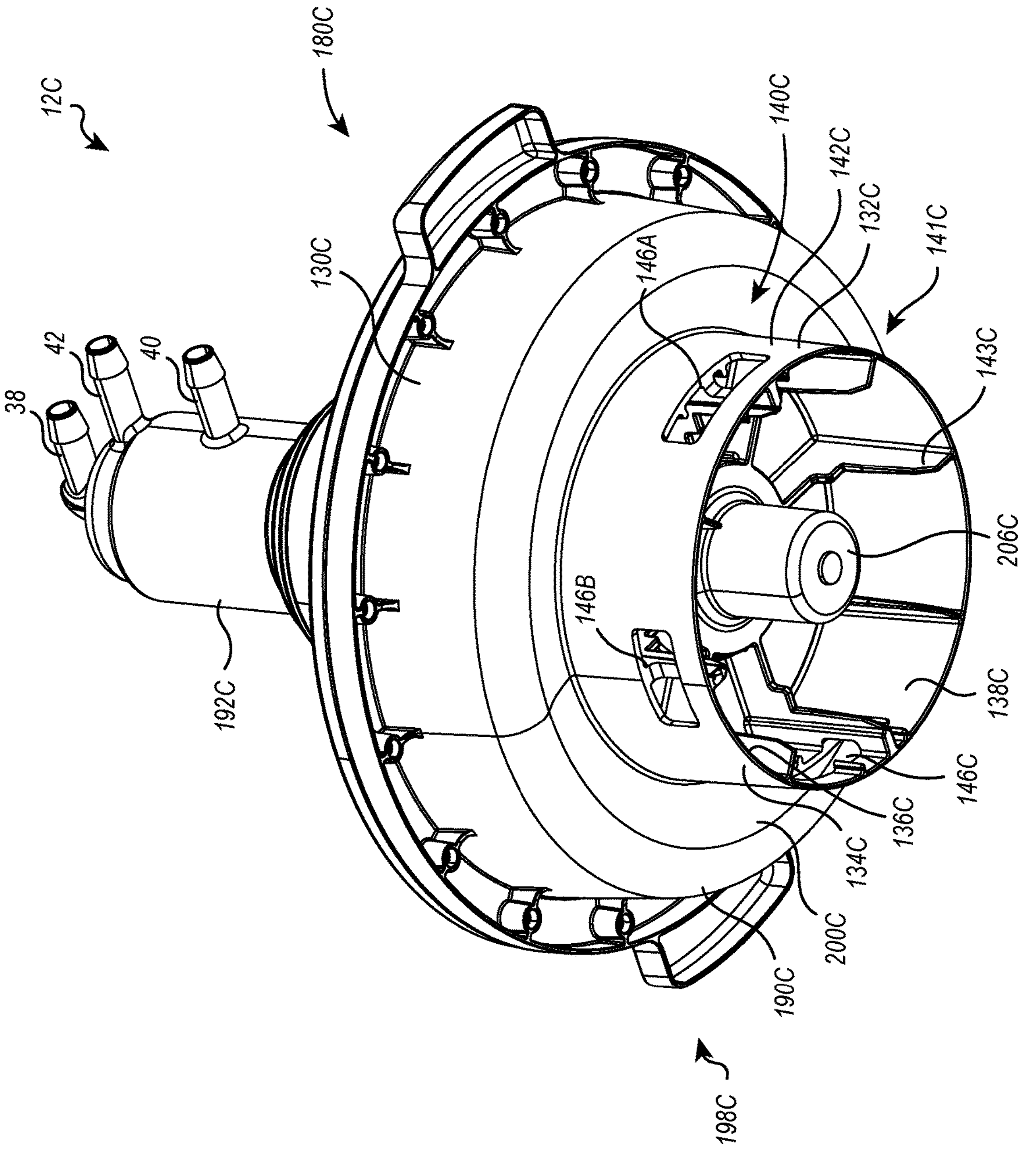
FIG. 23 is a bottom perspective view of the centrifugal separator shown in FIG. 22.

Depicted in FIGS. 22 and 23 is an exemplary embodiment of another alternative continuous flow, centrifugal separator 12C that can be used as centrifugal separator 12 in the systems and alternatives discussed above with regard to FIGS. 1-5. Separator 12C has components similar to and operates in a manner similar to separator 12A. As such, like elements between separators 12A and 12C are identified by like reference characters. Furthermore, the alternatives, modifications, operations, properties, and functions discussed above with regard to the prior separators are also applicable to separator 12C, unless expressly or inherently understood otherwise.

In general, centrifugal separator 12C comprises a body assembly 130C and a driver sleeve 132C outwardly projecting therefrom. In the exemplary depicted embodiment, driver sleeve 132C is integrally formed as a single unity member with a portion of body assembly 130C. However, in other embodiments, driver sleeve 132C could be secured to body assembly 130C in the same manner as previously discussed with regard to driver sleeve 132 (FIG. 8). Again, as will be discussed below in greater detail, during operation of centrifugal separator 12A, magnet driver 148 (FIG. 8) can be positioned and rotated within driver sleeve 132. As will also be discussed below in more detail, body assembly 130C/centrifugal separator 12C includes inlet port 38, first outlet port 40 and second outlet port 42.

With continued reference to FIG. 23, driver sleeve 132C comprises an exterior surface 134C and an interior surface 136C that encircle an opening 138C. Driver sleeve 132C has a first end 140C extending from body assembly 130C and an opposing second end 141C. In the exemplary embodiment, driver sleeve 132C includes a cylindrical sleeve body 142C and a plurality of spaced apart reinforcing fins 143C that radially inwardly project from interior surface 136C and outwardly project along a floor of body assembly 130C. Fins 143C add reinforcing and structural stability to both driver sleeve 132C and body assembly 130C.

Spaced apart apertures 146A-C extend through driver sleeve 132C between exterior surface 134C and an interior surface 136C and, as will be discussed below in greater detail, can be used for releasably securing separator 12C to a skid or other structures. In this embodiment, all three apertures 146A-C are formed on one half of driver sleeve 132C. In other embodiments, apertures 146A-C could be replaced with two apertures or four or more apertures. In still other embodiments, apertures 146A-C could be replaced with one or more recesses extending into exterior surface 134C or one or more flanges outwardly projecting from exterior surface 134C, such as flange 145 (FIG. 8).

Figure 24:
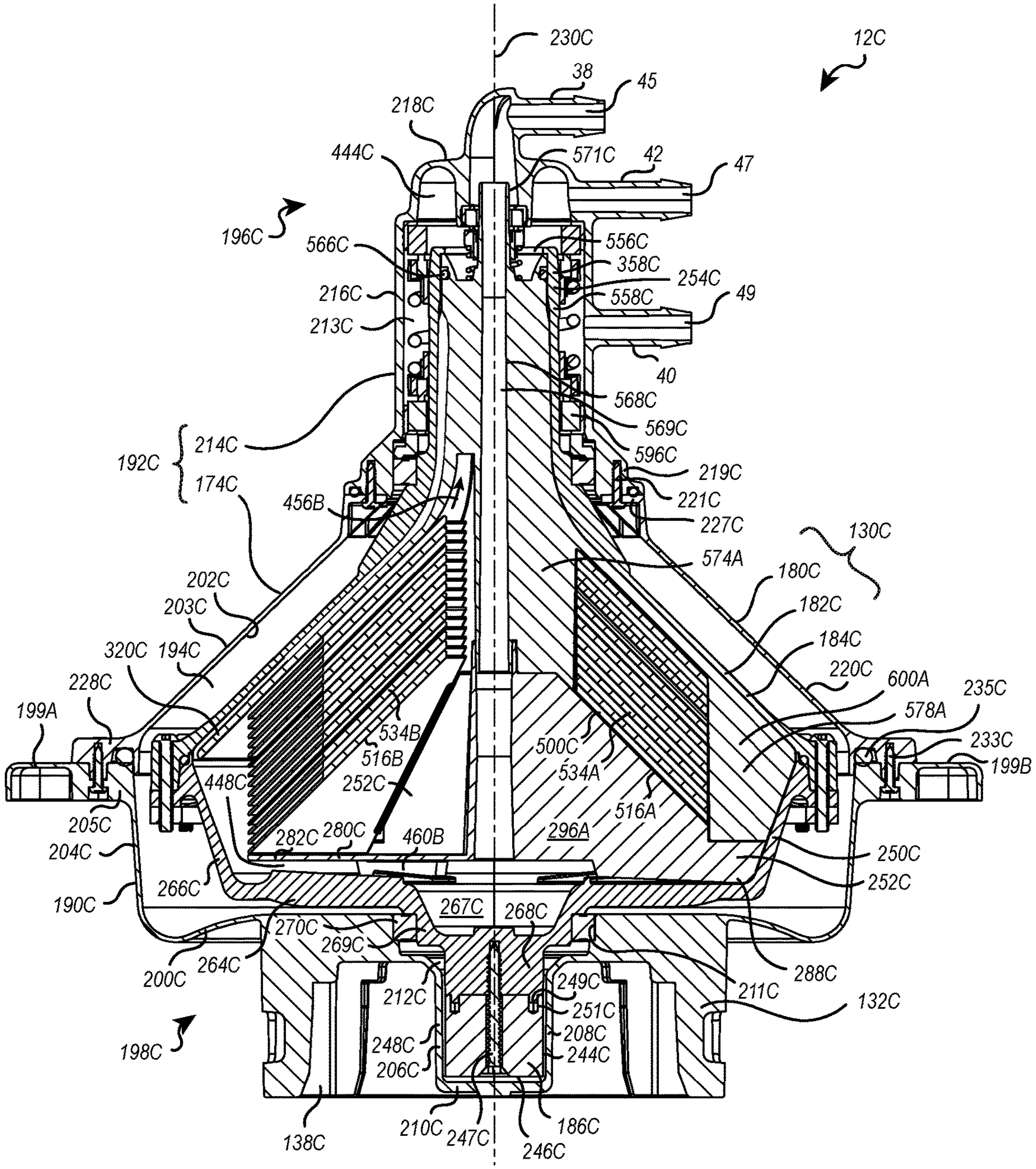
FIG. 24 is a cross sectional view of the centrifugal separator shown in FIG. 22.

With reference to FIG. 24, separator 12C/body assembly 130C generally comprises a separation stator 180C and a rotor assembly 182C that is rotatable disposed within separation stator 180C. Rotor assembly 182C comprises a separation rotor 184C that is rotatable disposed within separation stator 180 and a drive coupling 186C that is coupled with separation rotor 184C and may also be rotatably disposed within separation stator 180C. A central axis 230C centrally passes through separation stator 180C and rotor assembly 182C and coincides with a rotational axis, also identified by reference number 230C, about which rotor assembly 182C rotates. As such, "central axis 230C" and "rotational axis 230C" are used synonymously herein.

Figure 25:
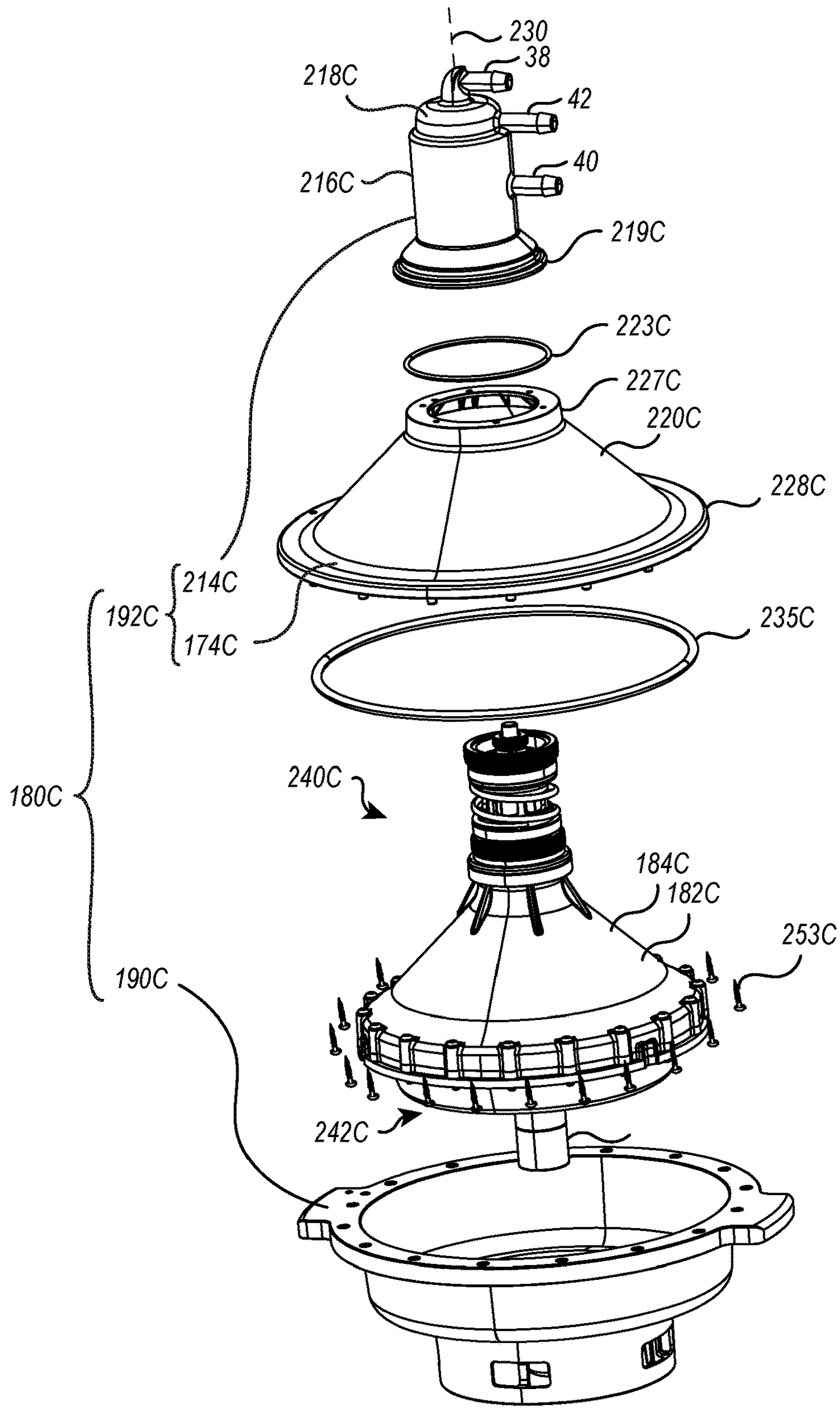
FIG. 25 is a partially exploded view of centrifugal separator shown in FIG. 22.

As depicted in FIGS. 24 and 25, in one exemplary embodiment, separation stator 180C comprises a base 190C and a head 192C that are coupled together prior to use. In one exemplary embodiment, head 192C includes a tapered neck 174C having a nose 214C coupled thereto. Separation stator 180C has an interior surface 202C and an opposing exterior surface 203C. Interior surface 202C bounds a chamber 194C in which rotor assembly 182C is at least partially received. Assembled separation stator 180C has a first end 196C where head 192C/nose 214C is disposed and an opposing second end 198C where base 190C is disposed. Central axis 230C extends between first end 196C and second end 198C. Separation stator 180C includes inlet port 38, first outlet port 40 and second outlet port 42 each located on head 192/nose 214C at first end 196C.

With continued reference to FIG. 24, base 190C (or second end 198C of separation stator 180C) comprises a floor 200C that radially outwardly extends to an annular sidewall 204C. Sidewall 204C upstands from floor 200C and projects toward first end 196C. An annular mounting flange 205C outwardly projects from sidewall 204C. A pair of handles 199A and 199B radially outwardly project form opposing sides of flange 205C. Handles 199 are used to manually lift and transport separator 12C. In one embodiment, interior surface 202C of sidewall 204C is cylindrical. In other embodiments, interior surface 202C of sidewall 204C may outwardly slope. Driver sleeve 132C is typically centered on and outwardly projects from floor 200C. Centrally disposed on floor 200C so as to outwardly project from exterior surface 203C thereof is a receiver 206C. Receiver 206C is disposed within opening 138C of driver sleeve 132C so as to be encircled by driver sleeve 132C. In one exemplary embodiment, receiver 206C is concentrically disposed within driver sleeve 132C. Receiver 206C bounds a recess 212C which forms a portion of chamber 194C. In one embodiment, receiver 206C comprises a sidewall 208C projecting from floor 200C and terminating at an end wall 210C. In one embodiment, sidewall 208C and recess 212C each have a cylindrical configuration. An annular notch 211C can be recessed into sidewall 208C at the intersection with floor 200C for receiving a bearing assembly 270C, as will be discussed below in further detail. Receiver 206C is configured so that it can be received within opening 166 of magnetic driver 148/drive rotor 150 (FIG. 8) while magnetic driver 148/drive rotor 150 is received within opening 138C of driver sleeve 132C.

Returning to FIG. 23, base 190C (or first end 198C of separation stator 180C) also comprises fins 143C, as previously discussed, that outwardly project from the exterior surface of floor 200C. Fins 143C can be in parallel alignment with central axis 230C (FIG. 24) and be equally spaced apart around receiver 206C.

In one embodiment, centrifugal separator 12C is designed so as to be disposable after a single use. To that end, separation stator 180C, and more particularly, base 190C, head 192C, and driver sleeve 132C are typically made from a polymeric material, such as polyvinylidene fluoride or polyvinylidene difluoride (PVDF), high density polyethylene (HDPE), polyetherimide (PEI), polyether ether ketone (PEEK) or the like, and are commonly molded, such as by injection or rotational molding. These materials and method of production enable separation stator 180C to be produced less expensively than if separation stator 180C was made from metal. In part, fins 143C function to add strength and stability to separation stator 180C and driver sleeve 132C and when made from a lower strength polymeric material. However, in an alternative embodiment, separation stator 180C could be made from a higher strength metal, such as aluminum or stainless steel or, alternatively, a higher strength polymer, such as liquid crystal polymers or polycarbonate. In such case, fins 143C may be eliminated.

With reference to FIGS. 24 and 25, nose 214C of head 192C has a sidewall 216C that terminates at an end wall 218C at an upper end and has an annular outwardly projecting flange 219C at an opposing lower end. Nose 214C bounds a recess 213C. In 30 one embodiment, interior surface 202C of sidewall 216C that bounds recess 213C can have a substantially cylindrical configuration. Centrally outwardly projecting from end wall 218C is inlet port 38. First outlet port 40 and second outlet port 42 outwardly project from sidewall of nose 214C. Inlet port 38 bounds passage 45 while outlet ports 40 and 42 bound passages 47 and 49, respectively. Recessed into end wall 218C so as to encircle passage 45 and communicate with recess 213C is an annular light component collection recess 444C. Light component collection recess 444C communicates directly with passage 47 of second outlet port 42.

Neck 174C of head 192C include an annular transition wall 220C that extends between an annular mounting flange 227C at an upper end and annular mounting flange 228C at an opposing lower end. Flanges 219C and 227C are coupled together by fasteners 221C, such as screw, bolts, clamps, or the like, with an O-ring 223C disposed therebetween so as to form a hermetic seal between nose 214C and neck 174C. In one embodiment, at least a portion of transition wall 220C has a frustoconical configuration wherein interior surface 202C thereof is typically disposed at an angle relative to central axis 230C that is at least or is less than 30°, 40°, 50°, or 60° or is in a range between any two of the foregoing. In the depicted embodiment, a portion of transition wall 220C extending from mounting flange 227C and/or 228C can be cylindrical or have a different configuration than the remainder of transition wall 220. Forming nose 214C and neck 174C as two separate members that are secured together by fasteners can simplify production of head 192C and assembly with separator 12C. However, in other embodiments, nose 214C and neck 174C can be integrally formed as one unitary member, thereby eliminating the need for fasteners.

During assembly, mounting flanges 205C and 228C are coupled together so that rotor assembly 182C/separation rotor 184C is captured within separation stator 180C. Mounting flanges 205C and 228C can be coupled together by fasteners 233C such as screws, bolts, clamps, or other fasteners or fastening techniques. An O-ring 235C is disposed between flanges 205C and 228C so as to form a hermetic seal therebetween.

Rotor assembly 182C is rotatably positioned within chamber 194C of separation stator 180C and is used for separating inlet stream 102 (FIGS. 1-5) of the biological suspension or other mixture into first outlet stream 104 and second outlet stream 106. With reference to FIG. 25, as previously noted, rotor assembly 182C includes separation rotor 184C and drive coupling 186C extending therefrom. More specifically, separation rotor 184C has a first end 240C and an opposing second end 242C between which central axis/rotational axis 230 centrally extends. Drive coupling 186C is centrally mounted to and outwardly projects from second end 242C of separation rotor 184C so that central axis 230 centrally passes therethrough. Turning to FIG. 24, drive coupling 186C typically has an encircling side face 244C that terminates at an end face 246C. A fastener 247C, such as a screw, bolt, or the like, can extend trough an opening formed on drive coupling 186C and engage with separation rotor 184C, such as by threaded connection or other techniques, so as to secure drive coupling 186C to separation rotor 184C. In the exemplary embodiment, sheer pins 249C project from separation rotor 184C into openings 251C formed on drive coupling 186C. The engagement between sheer pins 249C and drive coupling 186C help ensure that separation rotor 184C and drive coupling 186C concurrently rotate. In an alternative embodiment, sheer pins 249C could outwardly project from drive coupling 186C and project into openings 251C formed on separation rotor 184C.

Drive coupling 186C typically has a cylindrical configuration and, as depicted in FIG. 24, is configured so that it can be rotatably received within recess 212C of receiver 206C. A gap 248C is formed between side face 244C of drive coupling 186C and sidewall 208C of receiver 206C so that drive coupling 186C can freely rotate within receive 206C.

In one exemplary embodiment, gap 248C is less than 10 mm, 8 mm, 6 mm, 4 mm, 2 mm, or in a range between any two of the foregoing. It is typically desired to minimize the size of gap 248C to help facilitate the magnetic rotation of drive coupling 186C. Drive coupling 186C is comprised of a material and configured so that it can be controlled by a magnetic field produced by magnet 168 of magnetic driver 148 (FIG. 8). For example, drive coupling 186 can comprise another magnet or a material that is attracted to a magnet such as iron or an iron composite. During operation, drive coupling 186C is positioned within receiver 206C while receiver 206C is received within cavity 162 of drive rotor 150 (FIG. 8). Rotation of drive rotor 150 by motor 169 facilitates concurrent rotation of drive coupling 186C as a result of the magnetic force produced by magnet 168 on drive coupling 186C. In turn, rotation of drive coupling 186C facilitate concurrent rotation of separation rotor 184C to which it is attached. In alternative embodiments, it is appreciated that receiver 206C, which commonly functions as a protective cover, can be eliminated. In this case, drive coupling 186C would be directly received within cavity 162 of drive rotor 150.

Figure 26:
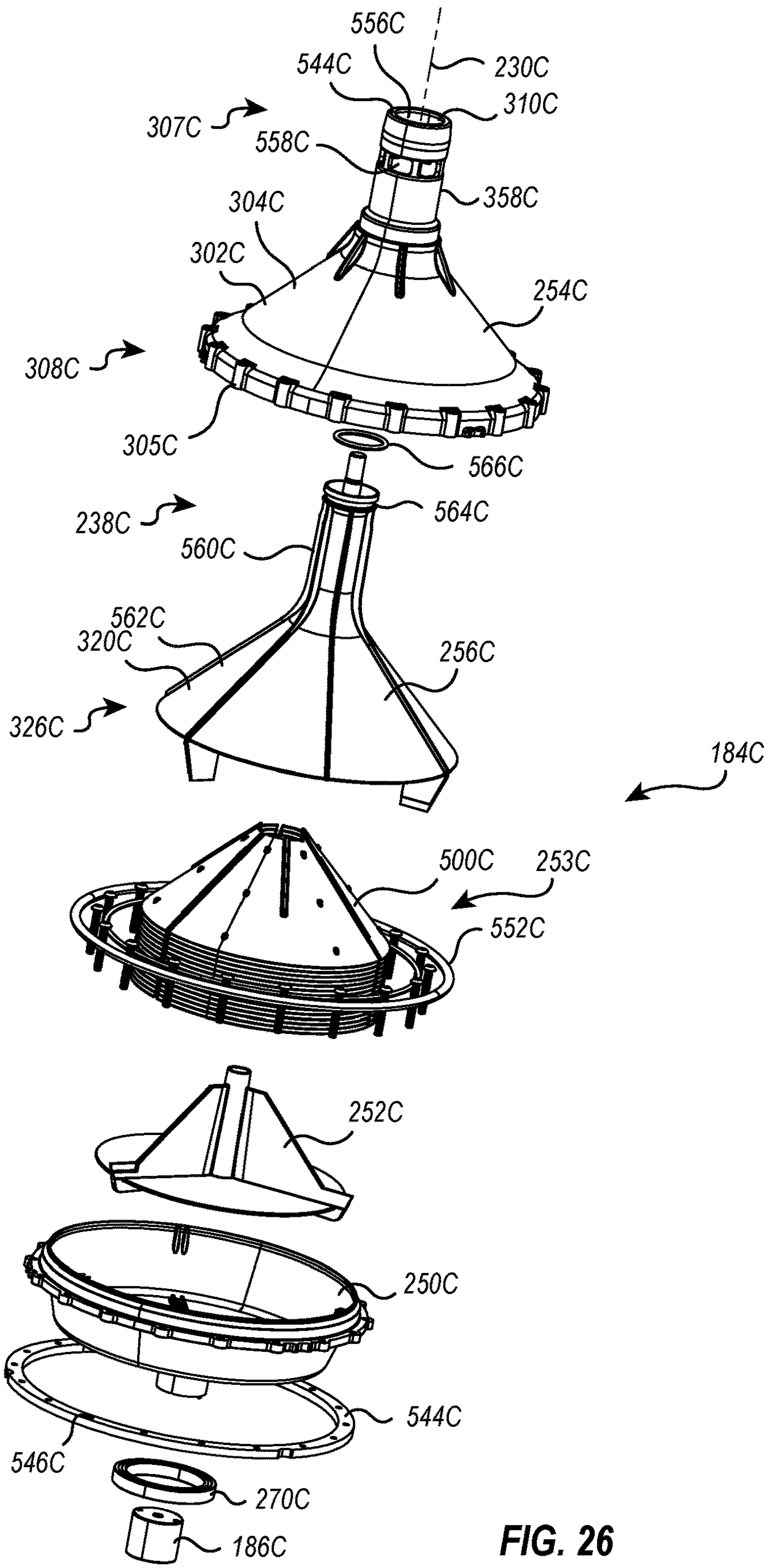
FIG. 26 is an exploded view of the separation rotor shown in FIG. 25.

Turning to FIG. 26, separation rotor 184C generally comprises a base 250C to which drive coupling 186C is attached, a dispersion member 252C that sits on base 250C, a disc stack 253C that is disposed on dispersion member 252C, a cap 254C that couples with base 250C, and an insert 256C that is captured between cap 254C and disc stack 253C. The various elements of separation rotor 184C will now be discussed in further detail.

Figure 27:
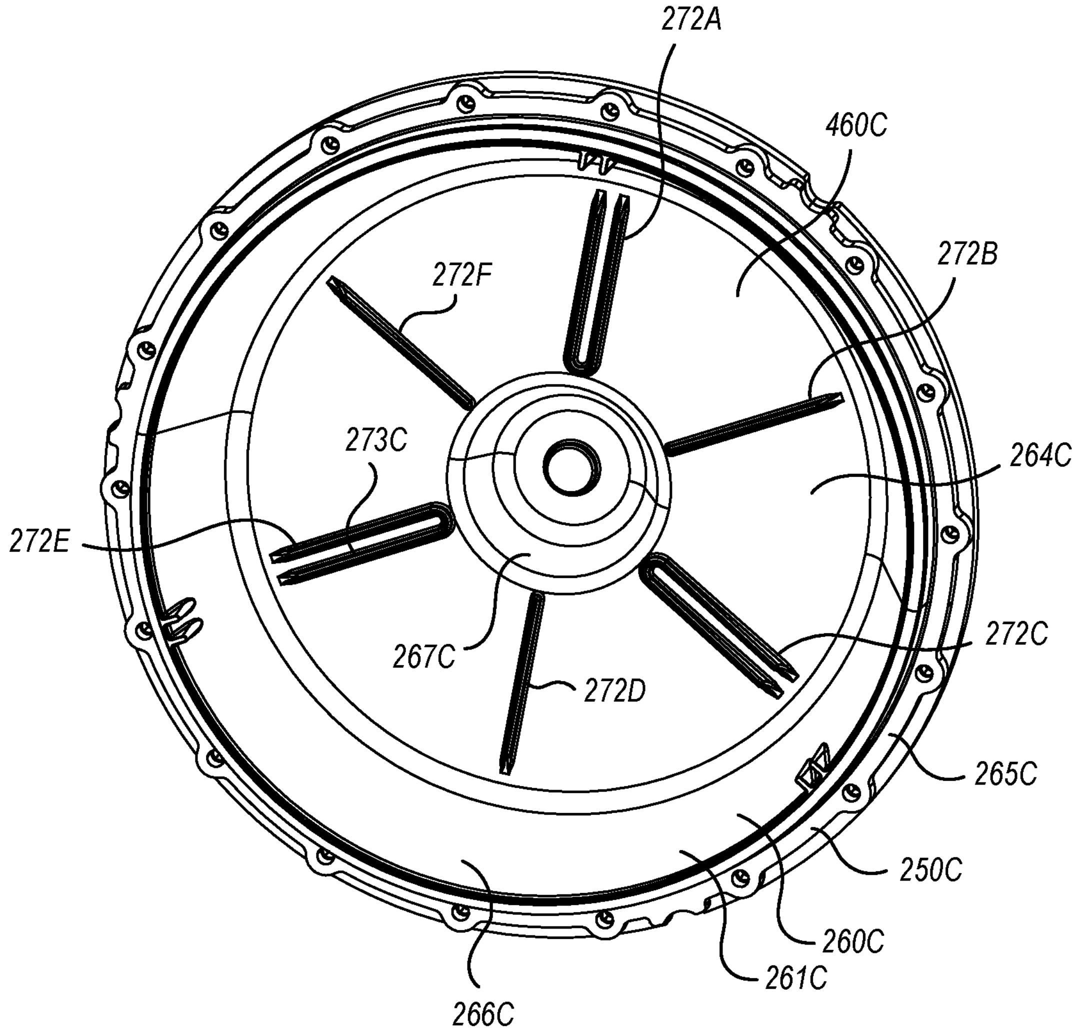
FIG. 27 is a perspective view of the interior of the base of the separation rotor shown in FIG. 26.
Figure 28:
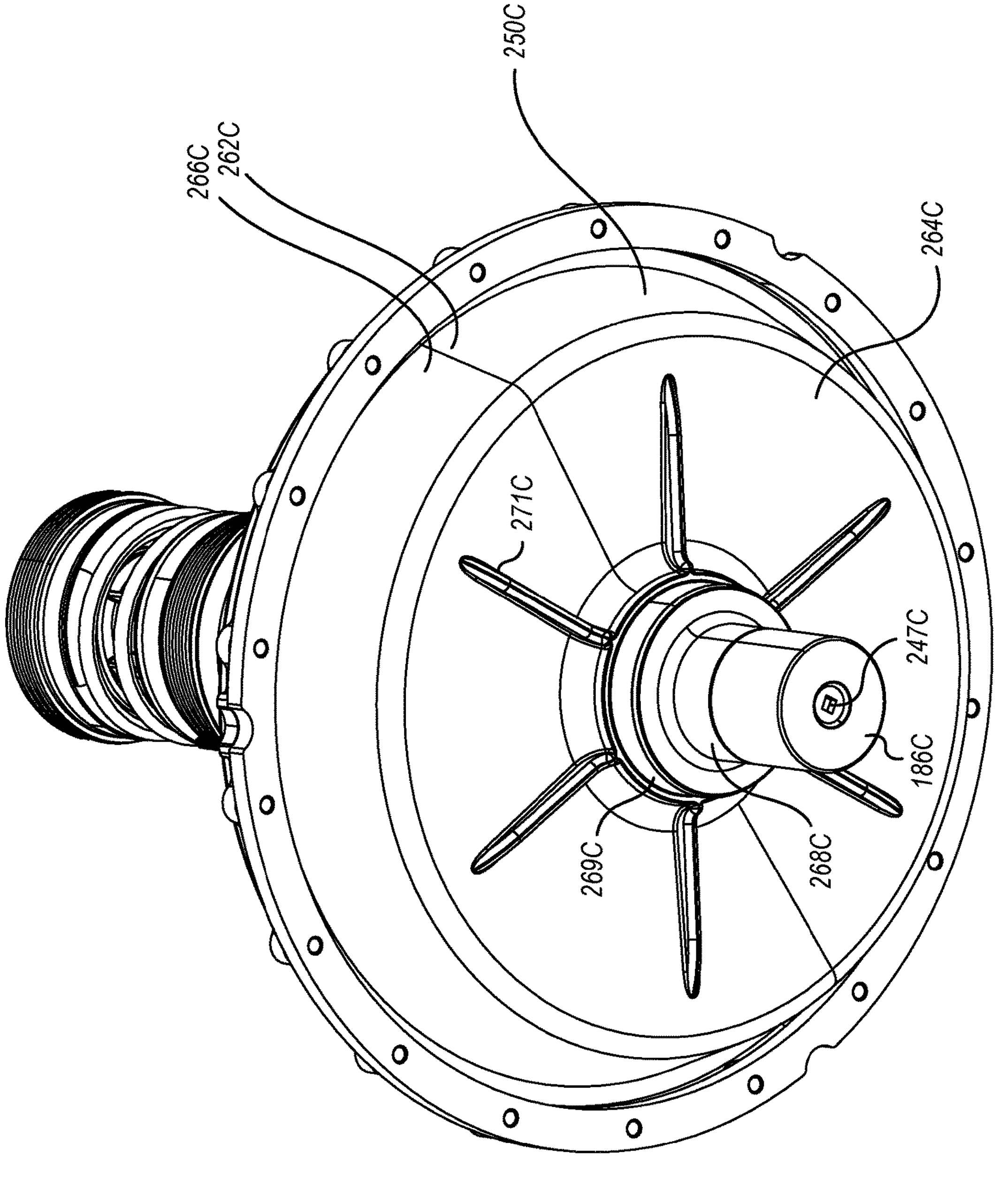
FIG. 28 is a perspective view of a bottom view of the base shown in FIG. 27.

As depicted in FIGS. 27 and 28, base 250C has an interior surface 260C that partially bounds a compartment 261C and has an opposing exterior surface 262C. Base 250C includes a floor 264C and an annular sidewall 266C that upwardly projects from an outer perimeter of floor 264C toward cap 254C. Sidewall 266C is referred to hereinafter as lower sidewall 266. A mounting flange 265C encircles and radially outwardly projects from an upper end sidewall 266. A recess 267C is centrally formed on interior surface 260C of floor 264C and communicates with compartment 261C. More specifically, in one exemplary embodiment a bowl 269C is centrally formed on and outwardly projects from exterior surface 262C of floor 264C. Recess 167C is formed into bowl 269C. In one embodiment, both bowl 269C and recess 267C can be circular. A mount 268C outwardly projects from exterior surface 262C of bowl 269C in alignment with central axis 230A. Bowl 269C and recess 167C are optional and can be eliminated. Where not used, mount 268C can outwardly project directly from exterior surface 262C of floor 264C in alignment with central axis 230C. Drive coupling 186C is secured to mount 268C such as by fastener 247C, as previously discussed, or by other fastening techniques such as adhesive, press fitting, threaded coupling, or the like.

A plurality of optional cooling fins 271C are formed on and outwardly project from floor 264C. In one exemplary embodiment, fins 271C are spaced apart and radially outwardly project away from bowl 269C. Fins 271C can be linear or curved. Where bowl 269C is not used, fins 271C can radially outwardly project away from central axis 230C. Base 250C can be formed with at least 1, 3, 5, 6, 8, or more fins 271C or in a range between any two of the foregoing.

Returning to FIG. 24, annular bearing assembly 270C, such as a race bearing or the like, is received within annular notch 211C and extends between base 250C of separation rotor 184C and base 190C of separation stator 180C. Bearing assembly 270C functions to support, center and stabilize separation rotor 184C relative to separation stator 180C and enables easy rotation of separation rotor 184C relative to separation stator 180C. In one exemplary embodiment, bearing assembly 270C is secured against the exterior of bowl 269C or is secured directly adjacent thereto. As discussed below in more detail, one of the functions of bowl 269C/recess 267C is that during operation when separation rotor 184C is rotating relative to separation stator 180C through the use of bearing assembly 270C, the biological suspension or other mixture being processed can flow through recess 267C and thereby help to cool adjacent bearing assembly 270C. That is, bowl 269C/recess 267C functions as a heat sink. In one embodiment, bearing assembly 270C is horizontally aligned with and/or encircles a portion of recess 276C and/or bowl 269C.

Cooling fins 271C (FIG. 28) can also help assist in the cooling of bearing assembly 270C. That is, as separation rotor 184C is rotating relative to separation stator 180C through the use of bearing assembly 270C, fins 271C are rotated within the gap between separation rotor 184C and separation stator 180C. Fins 271C move the air within the gap over bearing assembly 270C and thereby help to cool bearing assembly 270A.

Returning to FIG. 27, upwardly projecting from interior surface 260C of floor 264C are a plurality of spacers 272A-F. Spacers 272 are evenly spaced apart and radially outwardly project in alignment with central axis 230 and/or recess 267C. Spacers 272A, C, and E are also formed with an elongated slot 273 formed along the length thereof. As will be discussed below in greater detail, spacers 272 function to both space dispersion member 252C from interior surface 260C of floor 264C and secure dispersion member 252C to base 250C so that base 250C and dispersion member 252C rotate concurrently. Interior surface 260C of lower sidewall 266C can have an annular, frustoconical configuration that outwardly slopes from an outer perimeter edge of floor 264C to annular flange 265C. In one embodiment, the interior surface of lower sidewall 266C slopes at an outward angle relative to central axis 230 that is at least or less than 10°, 15°, 20°, 25°, 30°, 35°, or is in a range between any two of the foregoing angles.

Figure 29:
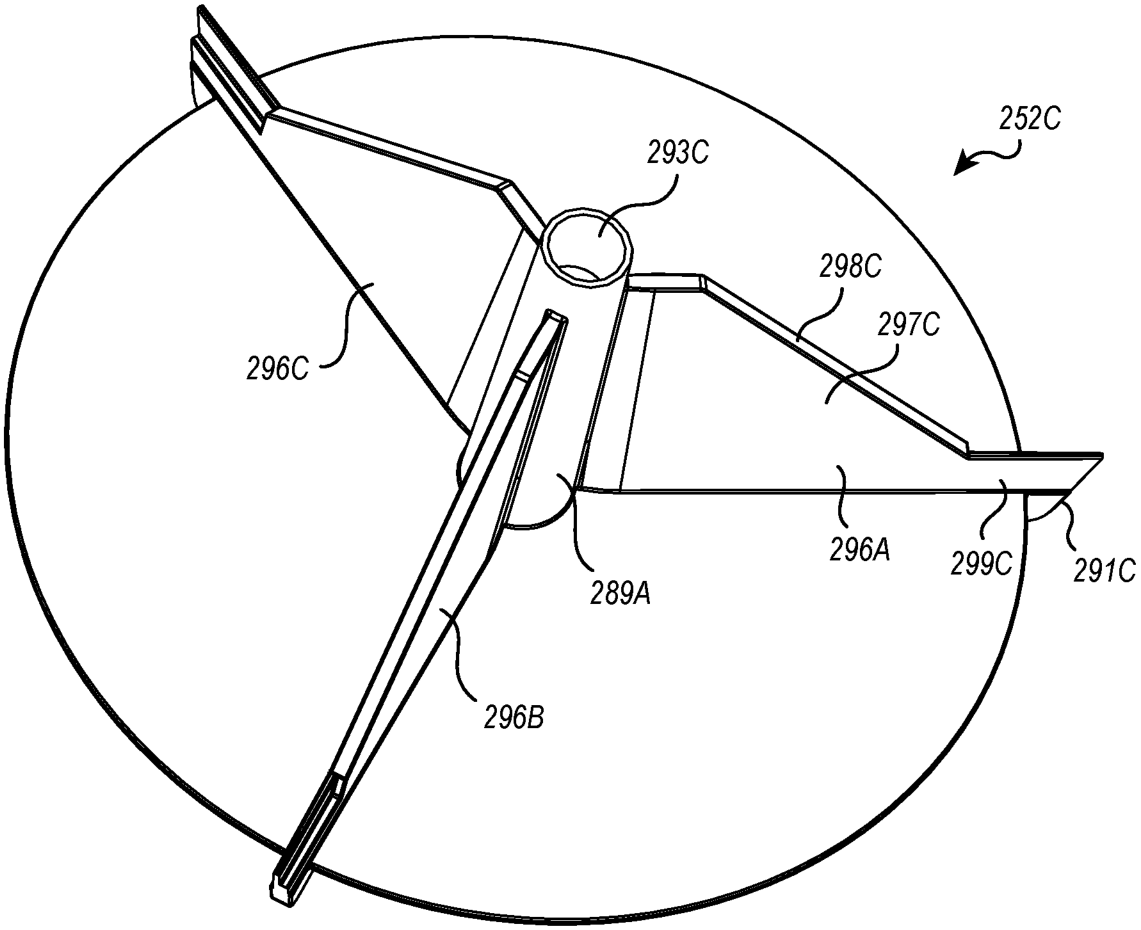
FIG. 29 is a top perspective view of a dispersion member shown in FIG. 26.
Figure 30:
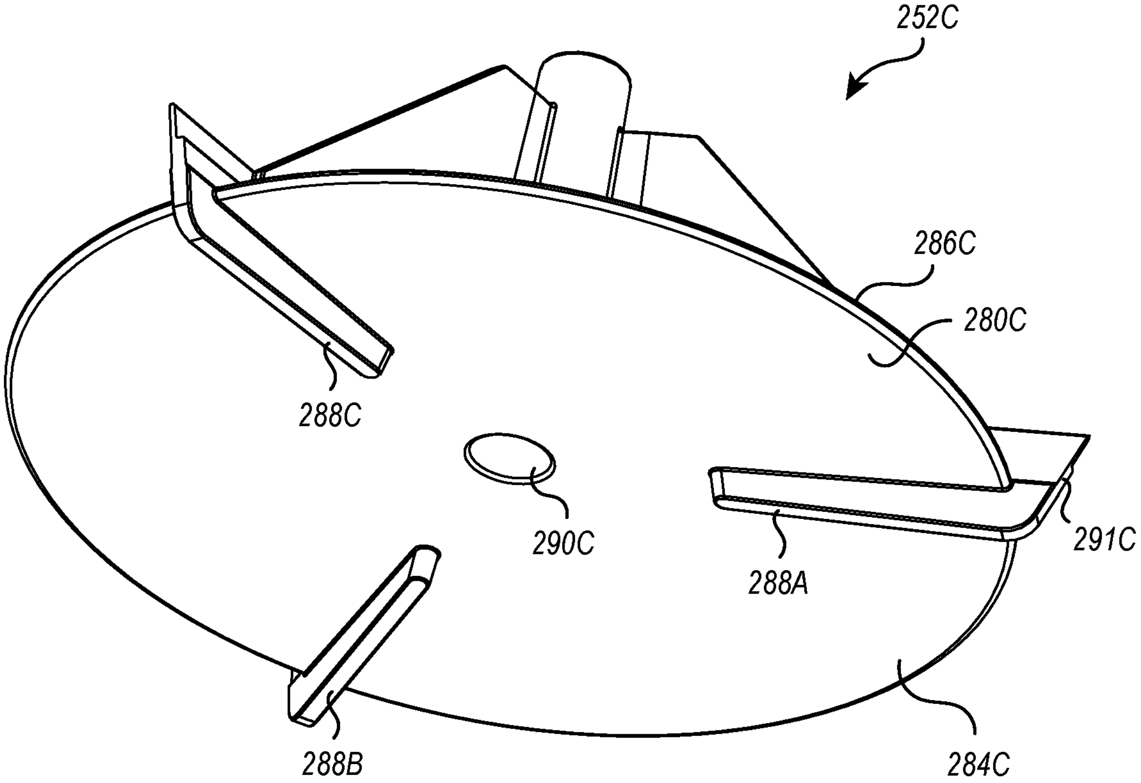
FIG. 30 is a bottom perspective view of a dispersion member shown in FIG. 29.

Turning to FIGS. 29 and 30, as discussed herein, dispersion member 252C can have a variety of different configurations. In the current depicted embodiment, dispersion member 252C comprises a body 280C in the form of a circular plate having a top surface 282C and an opposing bottom surface 284C that each extend to an outer perimeter edge 286C. An opening 290C centrally extends through body 280C in alignment with central axis 230C so as to pass between opposing surfaces 282C and 284C. Projecting from bottom surface 284C of body 280C are lower partitions 288A, B, and C which are typically equally spaced. Lower partitions 288 are linear and radially outwardly project away from opening 290C. Lower partitions 288 are configured to be received within slots 273C of spacers 272A, C, and E and terminate at a terminal end 291C that projects out beyond perimeter edge 286C.

During assembly, dispersion member 252C is disposed on and interlocked with base 250C (FIG. 26) by lower partitions 288A-C of dispersion member 252C (FIG. 30) being received within slots 273C of spacers 272 A, C, and E (FIG. 27). Terminal ends 291C are butted against or disposed directly adjacent to interior surface 260C of lower sidewall 266C of base 250C. This assembly centers dispersion member 252C on floor 264C so as to ensure that perimeter edge 286C is evenly spaced apart from lower sidewall 266C and also interlocks dispersion member 252C with base 250C such that rotation of base 250C about central axis 230C facilitates concurrent annular rotation of dispersion member 252C. In addition, body 280C of dispersion member 252C is spaced apart from floor 264C of base 250C so that a space 448C is formed therebetween. As will be discussed below in further detail, lower partitions 288 and spacers 272 function to form inlet fluid channels that radially flow outward through space 448C between dispersion member 252C and floor 264C to help facilitate separation of the biological suspension. It is appreciated that a variety of other structural designs could be used for securing and centering dispersion member 252C on floor 264C while forming the inlet fluid channels. However, the current depicted embodiment is uniquely configured to enable quick and easy positioning of dispersion member 252C without the required use of separate fasteners.

As also shown in FIG. 29, dispersion member 252C further comprises a tubular stem portion 289C that outwardly projects from top surface 282C of body 280C in aligned with opening 290C. Specifically, stem portion 289C bounds a passage 293C that communicates with opening 290C. Retention rails 296A-C upwardly extend from top surface 282C and radially outwardly project from stem portion 289C in alignment with lower partitions 288A-C, respectively. Each retention rail 296A-C intersects with a corresponding lower partition 288A-C outside of perimeter edge 286C and can extend to terminal end 291C. Each retention rail 296 includes a support portion 297C having triangular shape with a top edge 298C that upwardly slopes toward stem portion 289C and an extension portion 299C that outwardly projects from support portion 297C past perimeter edge 286C.

Figure 31:
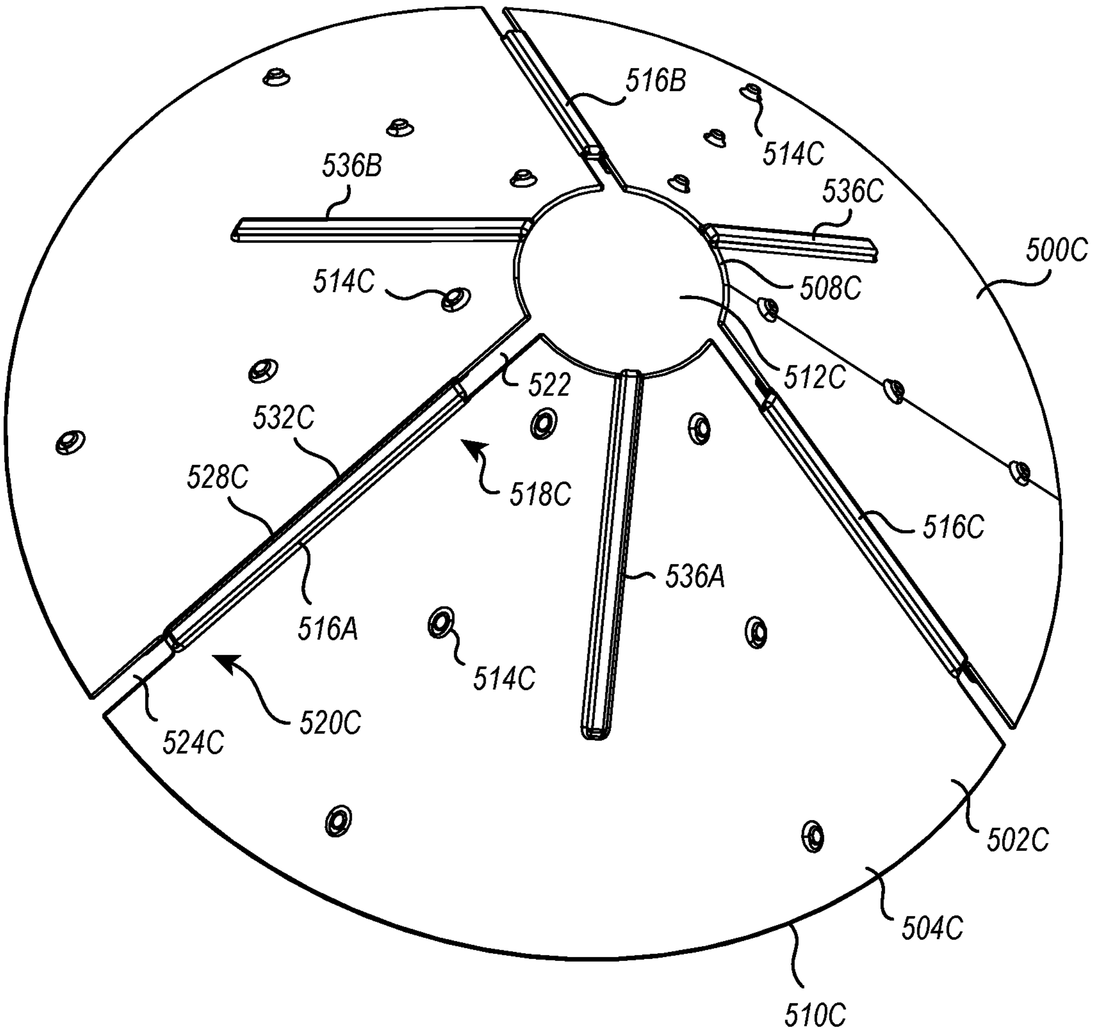
FIG. 31 is a top perspective view of a disk shown in FIG. 26.
Figure 32:
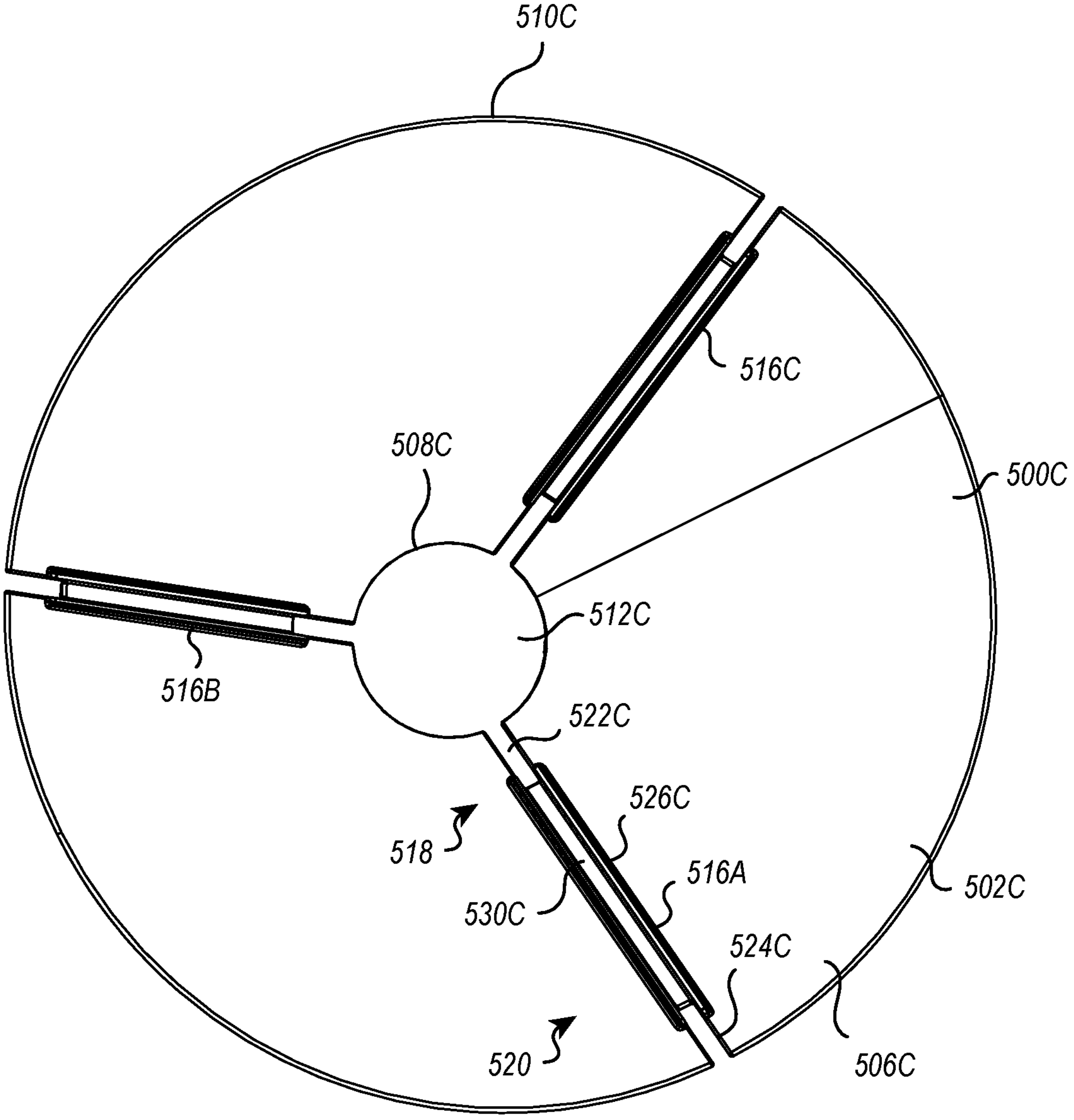
FIG. 32 is a bottom perspective view of the disk shown in FIG. 31.

Disc stack 253C (FIG. 26) comprises a plurality of discs 500C that are nested together. As depicted in FIGS. 31 and 32, each disc 500C comprises a disc body 502C having a top face 504C and an opposing bottom face 506C each having complementary frustoconical configurations. Disc body 502C extends between a central inner edge 508C and an outer perimeter edge 510C. Inner edge 508C is circular and encircles an opening 512C through which axis 230C centrally passes. Perimeter edge 510C is also typically circular. Outwardly projecting from top face 504C are a plurality of spaced apart spacers 514C. Spacers 514C function to keep discs 500C spaced apart when nested together into disc stack 253C and especially when disc stack 253C is being rotated at high velocities.

Formed on disc body 502C are three radially spaced apart guides 516A-C. Each guide 516A-C is radially aligned with axis 230C and is disposed between inner edge 508C and perimeter edge 510C. More specifically, each guide 516A-C is elongated having a first end 518C disposed toward inner edge 508C and an opposing second end 520C disposed toward perimeter edge 510C. An upper notch 522C passes through disc body 502C and extends from first end 518C to inner edge 508C while a lower notch 524C extends from second end 520C to perimeter edge 510C. Each guide 516A-C has an inside face 526 formed on bottom face 506C of disc body 502C and an outside face 528C formed on top face 504C of disc body 502C. A guide slot 530C is recessed into inside face 526 and extends between opposing ends 518C and 520C. A guide rail 532C outwardly projects from outside face 528C and extends between opposing ends 518C and 520C. As discs 500C are nested together, guide rails 532C of one disc 500C are received within guide slots 530C of the adjacent disc 500C. The coupling between guide rails 532C and guide slots 530C functions, in part, to help interlock each of discs 500C so that they rotate concurrently. In addition, guide rails 532C and guide slots 530C are sized to help achieve and maintain proper spacing between discs 500C so that fluid can flow therebetween. Although spacing between discs 500C can vary based on intended use and operation, in one embedment the spacing between each adjacent pair of nested discs 500C is typically less than 1.5 cm, 1 cm, 0.8 cm, 0.6 cm, or 0.4 cm or is in a range between any two of the foregoing values. The number of discs 500C can also vary depending on intended use. In one embodiment, the number of discs 500C used in a separator can be at least or less than 1, 3, 5, 7, 10, 12, 15, or 20 or in a range between any two of the foregoing numbers. Finally, the interlocking between guides 516, i.e., the interlocking between guide rails 532C and guide slots 530C, forms a continuous wall portion along nested discs 500C which prevents fluid from flowing radially around discs 500C. For example, FIG. 24 show stacked guides 516A and 516B which form wall portions 534A and 534B, respectively.

As depicted in FIG. 31, each discs 500C also includes elongated flow rails 536A-C. Each flow rail 536A-C is positioned between an adjacent pair of guides 516A-C and is radially aligned with opening 512C/axis 230C. Flow rails 536A-C extend partially between inner edge 508C and perimeter edge 510C but do not extend fully therebetween. In one exemplary embodiment, the linear radial distance from inner edge 508C to perimeter edge 510C is "D." Each flow rail 536A-C extends in a range between 20% and 90% of radial distance D and more commonly in range between 30% and 80% or 40% and 70% of radial distance D. Other dimensions can also be used. Flow rails 536A-C are typically spaced apart from perimeter edge 510C and extend to inner edge 508C. However, in other embodiments, flow rails 536 can also be spaced apart from inner edge 508C. As will be discussed below in more detail, during operation, liquid radially flows in opposing directions between perimeter edge 510C and inner edge 508C along separate channels bounded between guides 516. The formation of flow rails 536, which is optional, helps to limit or eliminate the fluid from swirling in a vortex within the sperate channels. The swirling of the fluid in a vortex can enhance turbulent flow which decreases settling and separation of the fluid. Expressed in other terms, flow rails 536 help to maintain radial and laminar flow which assists in separation. Spacing flow rails 536A-C back from perimeter edge 510C enables the fluid to freely flow into each of the separate channels.

During assembly, discs 500C are stacked on top of dispersion member 252C so as to interlock therewith. Discs 500C can be staked progressively or as a group, i.e., disc stack 253C. With reference to FIGS. 29 and 32, discs 500C are stacked so that top edge 298C of support portions 297C of retention rails 296 are received within corresponding guide slots 530 on the bottom disc 500C and extension portions 299C of retention rails 296 are received within lower notch 524C of the bottom few discs 500C. This positioning interlocks discs 550C with dispersion member 252C so that they rotate concurrently and also results in retention rails 296 vertically extending the wall formed by stacked guides 516C down to body 280C of dispersion member 252C.

Figure 35:
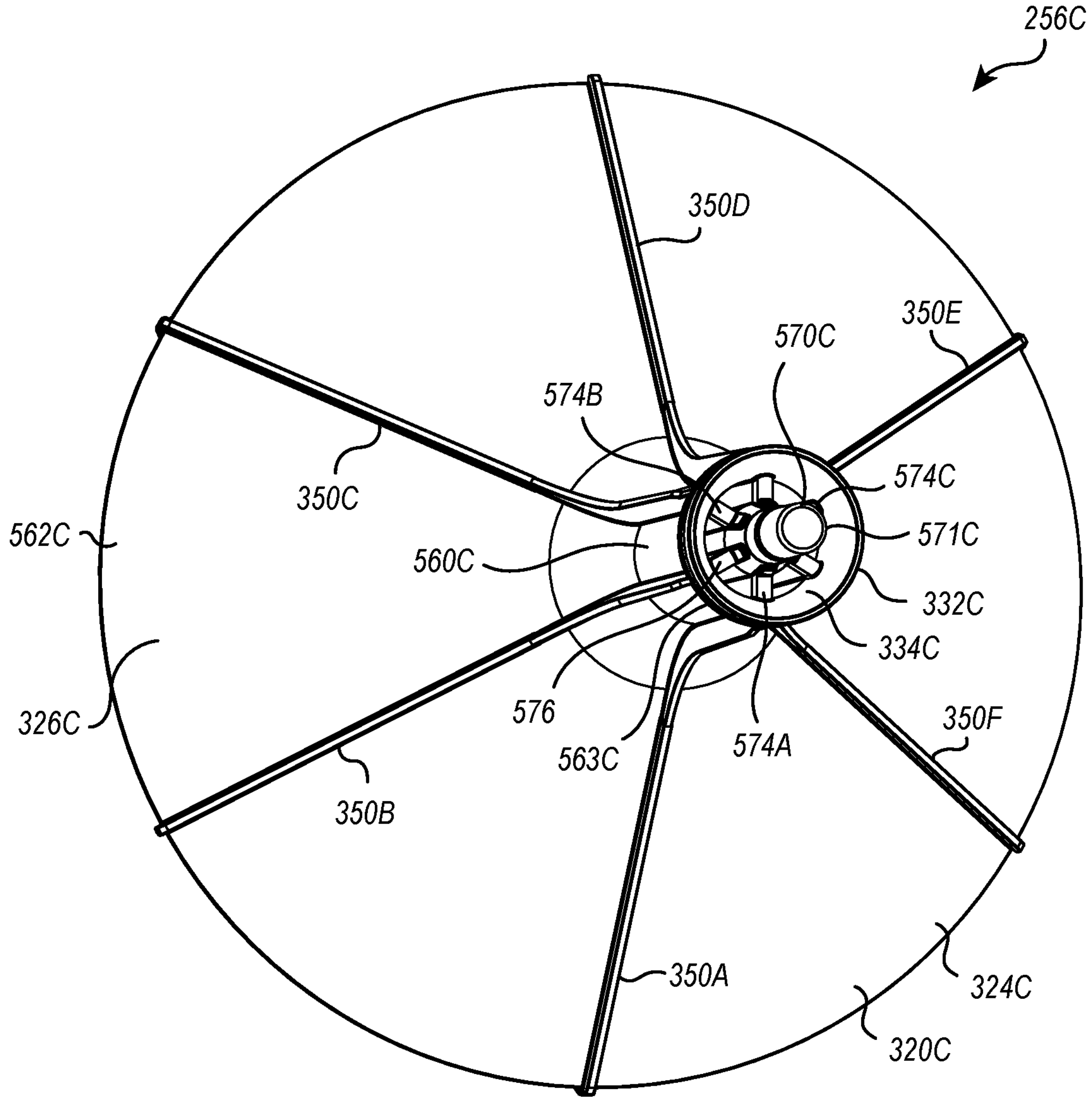
FIG. 35 is a top perspective view of an insert shown in FIG. 26.
Figure 36:
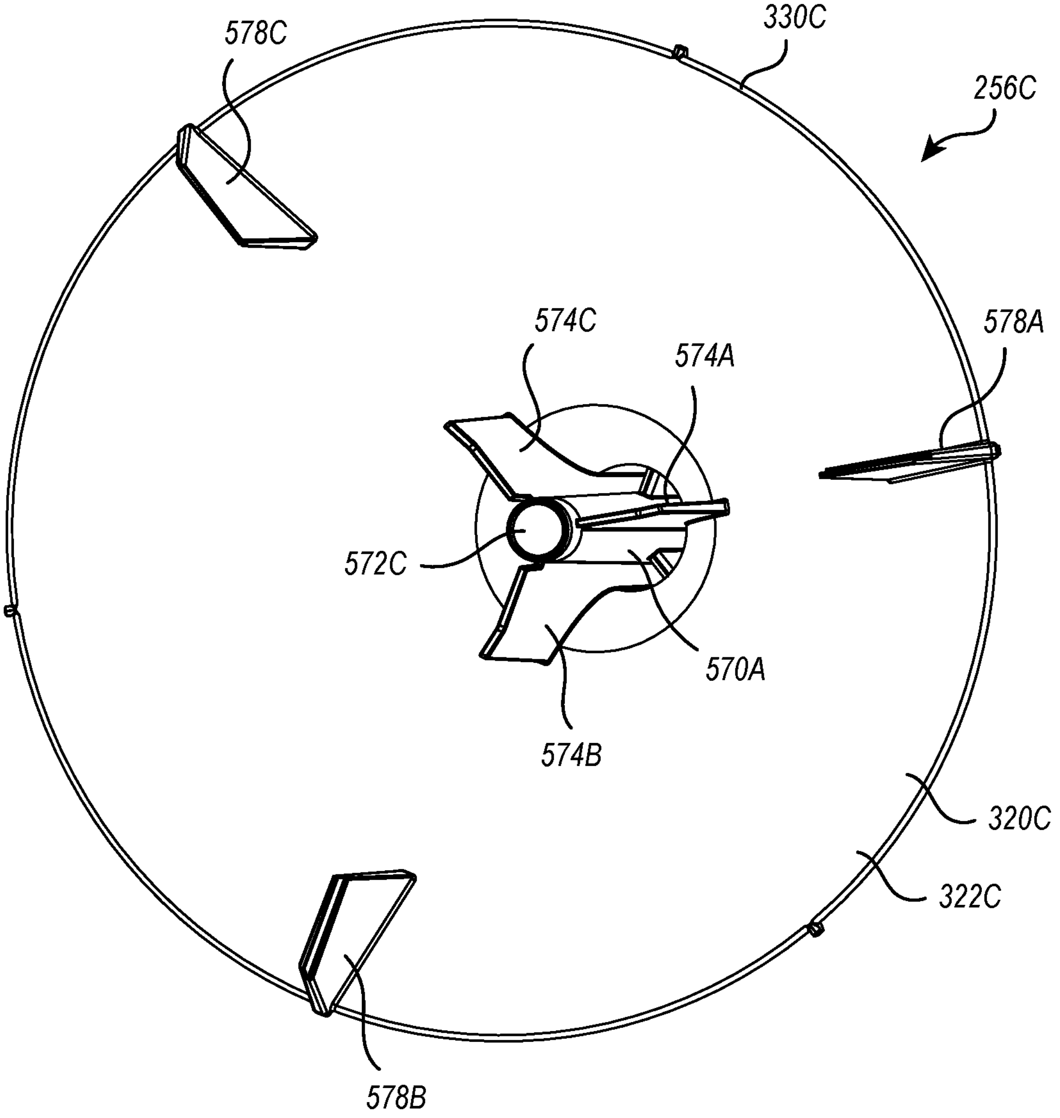
FIG. 36 is a bottom perspective view of the insert shown in FIG. 35.

With reference to FIGS. 26, 35 and 36, insert 256C comprises an annular sidewall 320C which is referred to herein as inner sidewall 320C. Inner sidewall 320C has an interior surface 322C and an opposing exterior surface 324C that extend between first end 238C and an opposing second end 326C. Inner sidewall 320C includes an annular first portion 560C at first end 238 having a substantially cylindrical configuration that is configured to be received within cap 254C. Inner sidewall 320C also includes an annular second portion 562C at second end 326C having a substantially frustoconical configuration that inwardly tapers toward first portion 560C. In one embodiment, interior surface 322C of second portion 562C of inner sidewall 320C can be sloped relative to central axis 230 at an angle in a range between 35° and 55° and more commonly between 40° and 50° or between 42° and 48°. Other angles can also be used. Second end 326C of inner sidewall 320C terminates at a perimeter edge 330C while first end 328 terminates at an annular lip 332C. Lip 332C encircles an opening 334C that centrally passes through insert 256C along central axis 230C. An annular flange 563C encircles and radially outwardly project sidewall 320C at first end 238C. An annular groove 564C encircles and is recessed into flange 563C just below lip 332C. Annular groove 564C is configured to receive an O-ring 566C.

Insert 256C further comprises a tubular conduit portion 570C that is disposed within opening 334C of insert 256C so as to extend along first portion 560C of inner sidewall 320C and along at least a section of second portion 562C of inner sidewall 320C. A free end 571C of conduit portion 570C projects out of opening 334C at first end 238C. Conduit portion 570C bounds a passageway portion 572C through which axis 230C extends. Three upper partitions 574A-C radially outward project from along a length of conduit portion 570C to interior surface 322C of inner sidewall 320C. Upper partitions 574A-C function in part to secure conduit portion 570C to inner sidewall 320C and to separate opening 334 passing through first portion 560C into three separate channels. A brace 576C also radially extends between conduit portion 570C and sidewall 320C between each adjacent pair of upper partitions 574A-C. Braces 576C function to further support conduit portion 570C at first end 238C but typically do not extend the length of conduit portion 570C and are typically not as long as upper partitions 574A-C. As shown in FIG. 36, radially aligned with but spaced apart from upper partitions 574A-C are outer partitions 578A-C. Outer partitions 578A-C outwardly project from interior surface 322C at second end 326C of inner sidewall 320C so as to project out beyond perimeter edge 330C. Outer partitions 578A-C radially align with upper partitions 574A-C, respectively.

Outwardly projecting from exterior surface 324C of inner sidewall 320D are a plurality of radially spaced part dividers 350A-F. Dividers 350 are in the form of linear rails that radially outwardly extend from the exterior of inner sidewall 320C in alignment with axis 230C and longitudinally extend from flange 563C at first end 238C to perimeter edge 330C at second end 326C. Dividers 350A, C and E align with upper partitions 574A-C and outer partitions 578A-C, respectively, and also intersect with outer partitions 578A-C, respectively.

During assembly, insert 256C is set on and interlocked with both discs 500 and dispersion member 252. Specifically, with reference to FIGS. 29, 31, and 36, insert 256C is nested on top of disc stack 253C so that upper partitions 574A-C pass through corresponding upper notches 522 of discs 500C and engage with the upper end of retention rails 296A-C, respectively, of dispersion member 252C. Concurrently, the lower end of conduit portion 570C passes through opening 512 of discs 500C and couples with the upper end of stem portion 289C of dispersion member 252C. Conduit portion 570C and stem portion 289C combine to form a conduit 568C that bounds a passage 569C (FIG. 24). Outer partitions 578A-C of insert 256C pass down through lower notches 524C of discs 500C and engage with extension portions 299C of retention rails 296A-C, respectively. In this nested configuration, rotation of base 250C also facilitates current rotation of each of dispersion member 252C, discs 500C and insert 256C.

Figure 33:
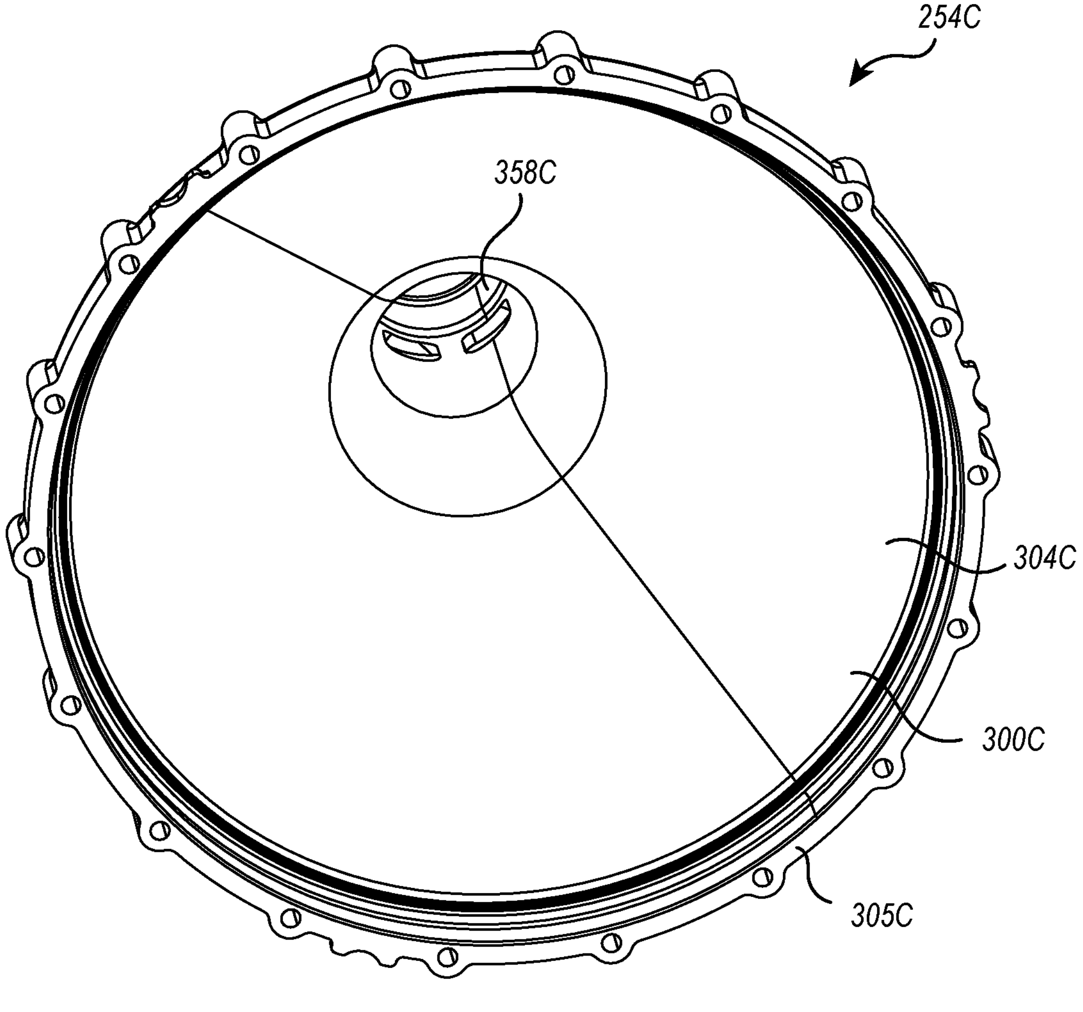
FIG. 33 is a bottom perspective view of a cap shown in FIG. 26.

With reference to FIGS. 26 and 33, cap 254C has an interior surface 300C and an opposing exterior surface 302C that extend between a first end 307C and an opposing second end 308C. Cap 254 includes a tubular stem 358C disposed at first end 307C and an annular sidewall 304C disposed at second end 308C. Sidewall 304C is hereinafter referred to as "upper sidewall 304C." Upper sidewall 304C and interior surface 300C thereof have a frustoconical configuration that inwardly constricts from an annular flange 305C at a lower end to stem 358C. In one embodiment, sidewall 304C is configured so that interior surface 300C thereof slopes relative to central axis 230C at an angle in a range between 35° and 55° and more commonly between 40° and 50° or between 42° and 48°. Other angles can also be used.

Figure 34:
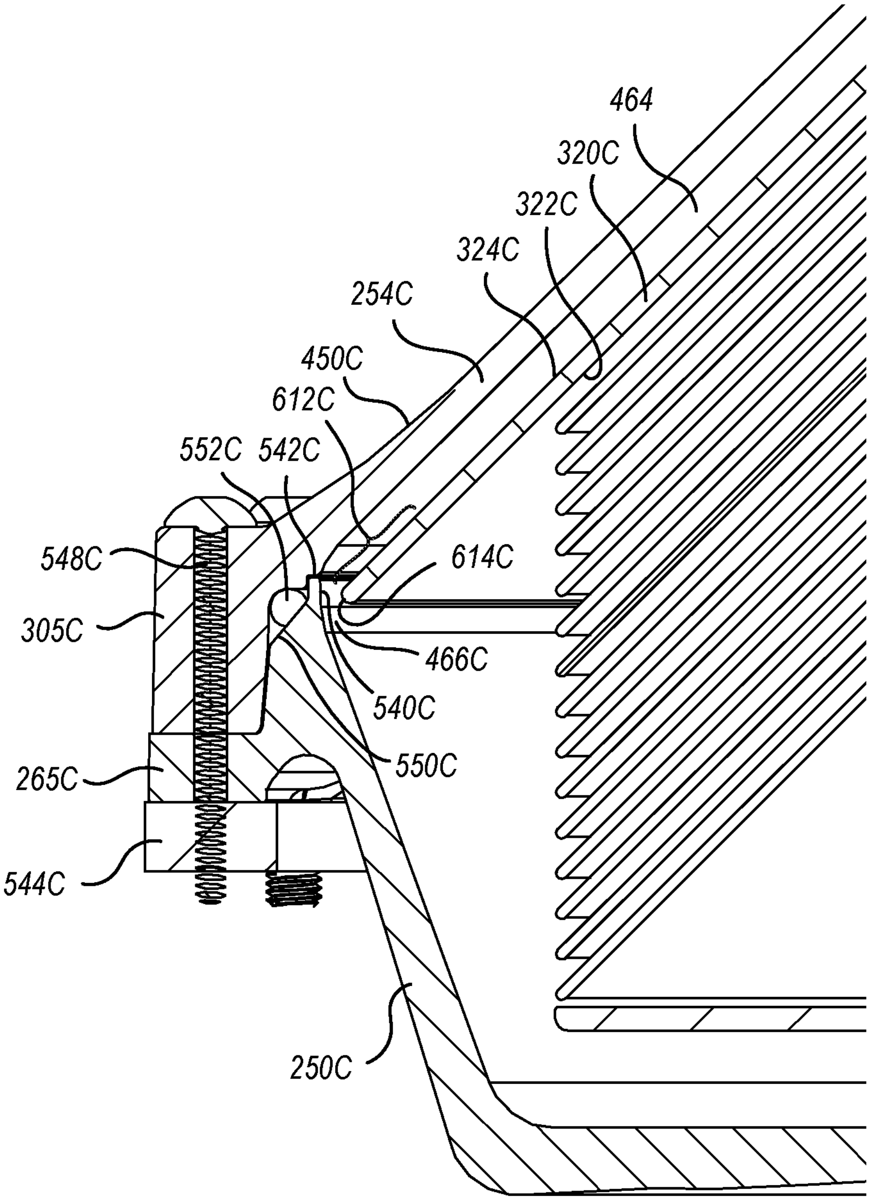
FIG. 34 is an enlarged cross sectional side view of a perimeter edge of the separation rotor shown in FIG. 22.

As best seen in FIG. 34, during assembly, cap 254C is coupled to base 250C by overlaying flanges 256C and 305C. To help ensure proper alignment and centering, an annular ridge 540C upstanding from flange 265C can be received within an annular slot 542C formed on flange 305C. In an alternative embodiment, ridge 540C and slot 542C can be reversed. With flanges 256C and 305C overlayed, an annular mounting ring 544C having threaded holes 546C (FIG. 26) extending therethrough can be positioned against a bottom face of flange 265C. Fasteners 548, such as screws, bolts or the like, can then be advanced down through aligned openings in flanges 305C and 265C and threaded into holes 546 on mounting ring 544. Mounting ring 544C is typically made of a metal, such as aluminum or stainless steel, and provides an enhanced uniform compression between flanges 256C and 305C while adding increased structural stability. Formed between flanges 256C and 305C is an annular slot 550C that tapers, such as in the form of a triangle or wedge. An O-ring 552C is received and compressed within slot 550C so as to form a hermetic seal between cap 254C and base 250C. As a result of slot 550C being tapered, as fluid pressure increases within separation rotor 184C, O-ring 552C is pressed further into constricting slot 550C which further enhances the sealing effect of O-ring 552C.

Returning to FIG. 26, stem 358C has a substantially cylindrical configuration and outwardly projects from upper sidewall 304C so that central axis 230 centrally passes therethrough. In the depicted embodiment, stem 358C is integrally formed as a single, unitary member with cap 254C. However, in other embodiments, stem 358C can be separately mounted and secured to cap 254C. As will be discussed below in further detail, stem 358C terminates at an end face 544C having an end opening 556C extending therethrough in alignment with axis 230C. Laterally extending through stem 358C between interior surface 300C and exterior surface 302C are a plurality of radially spaced apart side openings 558C. In one embodiment, six side openings 558C are formed with all of side opening 558C being disposed in a common plane that is orthogonal to axis 230C. Other numbers of side openings 558C can also be formed.

Turning to FIG. 21, as cap 254C is placed over insert 256C and secured to base 250C, as previously discussed, first portion 560C of insert 256C is received within stem 358C of cap 254C. Free end 571C of conduit 568C projects out through end opening 556C of stem 348C while O-ring 566C forms a seal between first portion 560C of insert 256C and the interior surface of stem 358C above side openings 556C. In the assembled state, base 250C, dispersion member 252C, insert 256C, discs 500C, and cap 254C are secured together and concurrently rotate as base 250C is rotated.

The assembled separation rotor 184C is enclosed within separation stator 180C. Specifically, as previously discussed, base 250C of separation rotor 184C is seated within base 190C of separation stator 180C so as to be supported on bearing assembly 270C. In this position, drive coupling 186C is freely disposed within receiver 206C. Neck 174C of head 192C is secured to base 190C using fasteners 233C and O-ring 235C, as previously discussed. Concurrently with or subsequent to mounting neck 174C, nose 214C of head 192C is secured to neck 174C using fasteners 221C and O-ring 223C, as previously discussed.

Base 250C, dispersion member 252C, discs 500C, insert 256C, and cap 254C are each typically made of a polymeric material, such as a liquid crystal polymer, polycarbonate, PVDF, HDPE, PEI, PEEK or the like. The different parts can be made of the same materials or different materials. As previously mentioned, making the parts from a polymeric material minimizes the cost of the centrifugal separator so that it can be economically disposed of after a single use, thereby avoid the need for subsequent sterilization or other cleaning. In alternative embodiments, however, one or more of the parts can also be made of a metal, such as aluminum or stainless steel.

Figure 37:
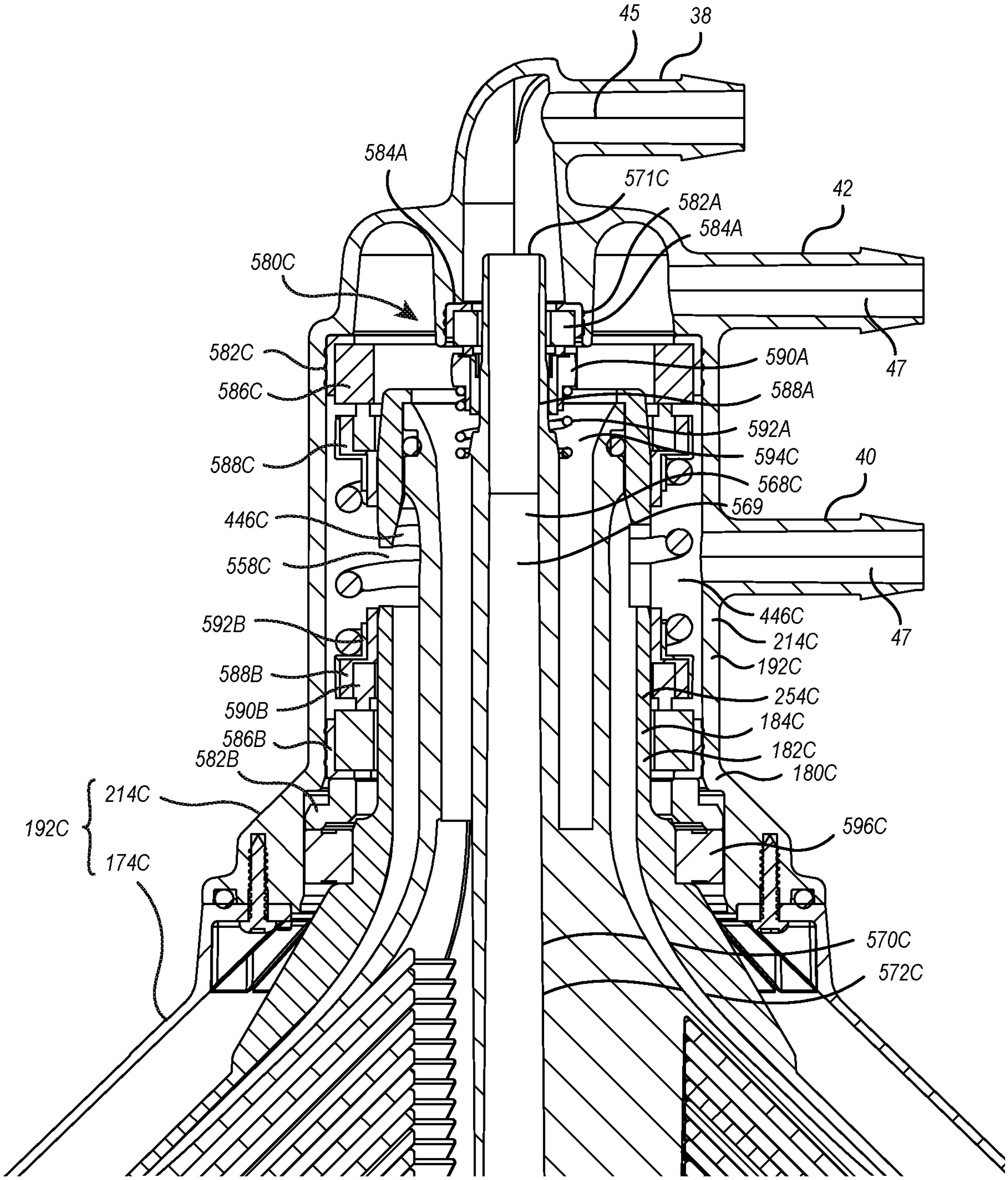
FIG. 37 is an enlarged cross sectional view of an upper end of the centrifugal separator shown in FIG. 22.

Turning to FIG. 37, during assembly a bearing assembly and various seals are positioned between nose 214C/head 192C and the upper end of rotor assembly 182C. Specifically, free end 571C of conduit 568C/conduit portion 570C is received within passage 45 of inlet port 38 during assembly. A dynamic seal 580C is used to form a seal between conduit 568C and head 192C/nose 214C that allows conduit 568C to rotate relative to head 192C/nose 214C. In one exemplary embodiment, dynamic seal 580C can be spring loaded. For example, in the depicted embodiment, dynamic seal 580C comprises a spring loaded rotary face seal. Other types of dynamic seals can also be used.

Dynamic seal 580A includes an annular mount 582A that is received and secured within an annular notch 584A that encircles passage 45 of inlet port 38. Secured to mount 582A so as to encircle free end of conduit 568C is an annular static sealing element 586A. In one embodiment, static sealing element 586A comprises a ceramic ring. Secured around the exterior of conduit 570C is an annular mount 588A. Secured to mount 588A so as to sit against static sealing element 586A is an annular dynamic sealing element 590A. Dynamic sealing element 590A is made of a material that will form a wearable seal with static sealing element 586A as dynamic sealing element 590A is rotated on static sealing element 586A. The material for static sealing element 586A and dynamic sealing element 590A can be the same as those used for conventional rotary pump seals. Mount 582A and/or mount 588A are typically made of a flexible, elastomeric material and is commonly more flexible than static sealing element 586A and dynamic sealing element 590A. One end of a spring 592A is disposed within a recess 594C formed at the end of insert 256C so as to sit against braces 576C and/or upper partitions 574 (FIG. 35). The opposing end of spring 594A resiliently presses against dynamic sealing element 590A so as to load or press dynamic sealing element 590A against static sealing element 586A. The flexibility of mount 588A enables dynamic sealing element 590A to float or move along axis 230A while being pressed by spring 592A so as to accommodate expansion and/or contraction of rotor assembly 182C during use and to account for wear of dynamic sealing element 590A and/or static sealing element 586A while still achieving a liquid tight seal therebetween. In view of dynamic seal 580C, fluid entering inlet port 38 and traveling along passage 45 is forced to enter and travel down passage 569C of conduit 568C.

A bearing assembly 596C, such as a race bearing, extends between cap 254C of separation rotor 184C and head 192C/nose 214C. Bearing assemblies 596C and 270C (FIG. 24) support and stabilize rotor assembly 182C/separation rotor 184C within separation stator 180C while enabling rotor assembly 182C/separation rotor 184C to rotate within separation stator 180A. A dynamic seal 580B extends between head 192C/nose 214C and separation rotor 184C below side opening 558C while a dynamic seal 580C extends between head 192C/nose 214C and separation rotor 184C above side opening 558C. In one embodiment, dynamic seals 580B and 580C can again be spring loaded and include a spring loaded rotary face seal. Other types of dynamic seals can also be used. Dynamic seals 580B and 580C are depicted having substantially the same elements as dynamic seal 580A. As such, like elements are identified by like reference characters but with letters of the corresponding seal. For example, dynamic seal 580B includes an annular mount 582B secured to head 192C/nose 214C and an annular static sealing element 586B secured to mount 582B. An annular spacer 582B can extend between bearing assembly 596C and mount 586C. In turn, an annular mount 588B is secured to separation rotor 184C with an annular dynamic sealing element 590B secured to mount 588B. Dynamic sealing element 590B is disposed against static sealing element 586B to form a seal therebetween. Again, mounts 582B and/or 588B can be made of a flexible elastomeric material that is more flexible than dynamic sealing element 590B or static sealing element 586B, thereby allowing floating or movement of dynamic seals 580B. Dynamic seal 580C is similarly structured on the opposing side of side openings 558C. A single spring 592B has one end biased against mount 588B and an opposing second end mounted against mount 588C so as to load or press against dynamic seals 580B and 580C. As a result, a single spring 592B is able to operate with two separate dynamic seals. Spring 592B is positioned within an annular heavy component collection recess 446C that encircles cap 254C and extends between dynamic seals 580B and 580C. First outlet port 40 is aligned with and communicates with heavy component collection recess 446C while heavy component collection recess 446C is aligned with and communicates with side openings 558C. As such, fluid flowing out through side openings 558C is forced to flow out through passage 49 of first outlet port 40.

Figure 38:
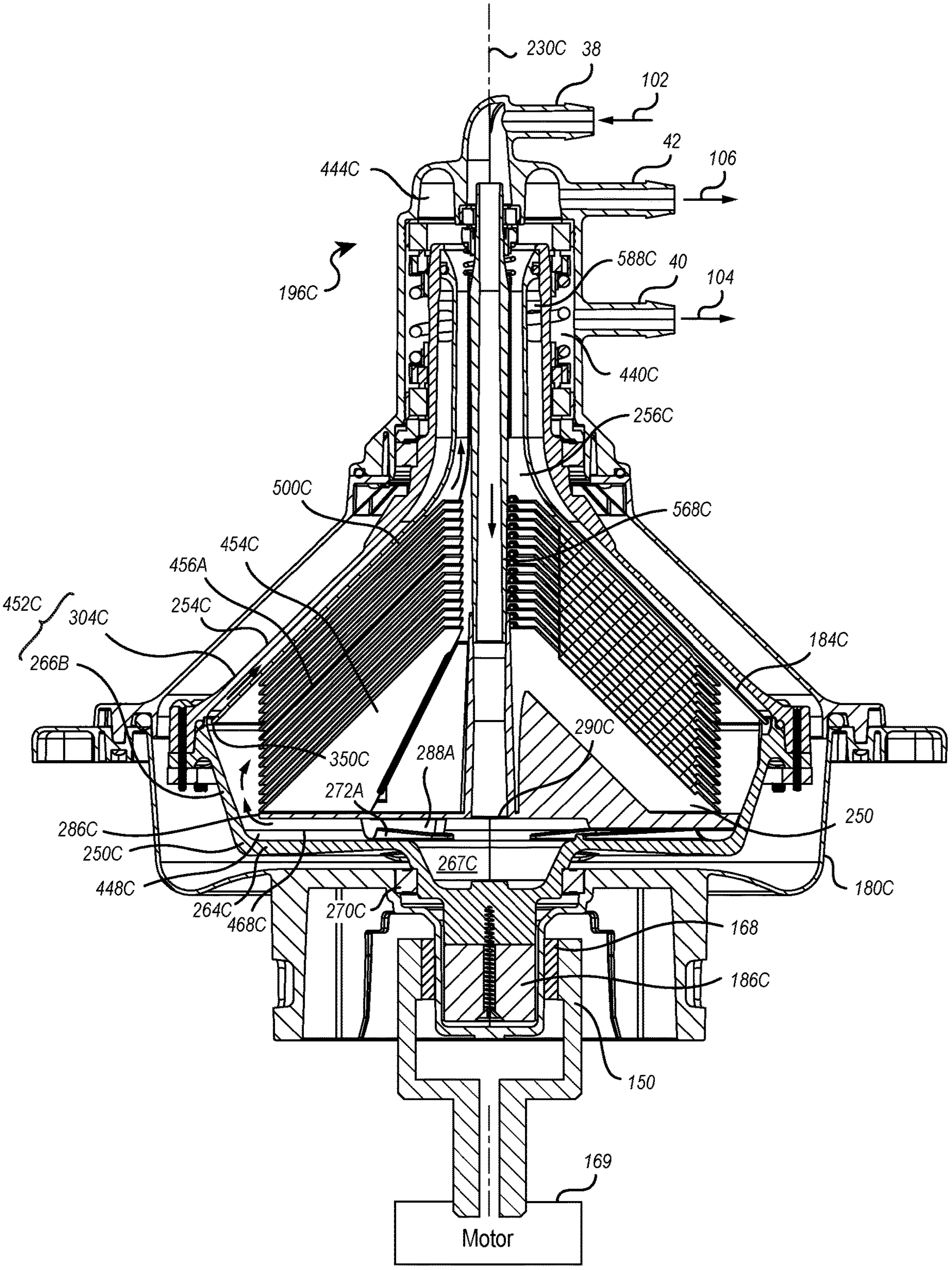
FIG. 38 is a further cross sectional view of the centrifugal separator shown in FIG. 22.

Turning to FIG. 38, during operation motor 169 is active so as to rotate drive rotor 150 relative to separation stator 180C about central axis 230C. In turn, the magnetic force produced by magnet 168 acts on drive coupling 186C, as previously discussed, so as to concurrently rotate drive coupling 186C and separation rotor 184C about central axis 230 and relative to separation stator 180. During operation, separation rotor 184C typically rotates at a rate of at least 1,000; 2,000; 2,500; 3,000; or 3,500 rotations per minute (RPM) or in a range between any two of the foregoing values. Depending on the application, other speeds can also be used.

Once rotation of separation rotor 184C is activated, inlet stream 102 (FIGS. 1, 3, and 5) of suspension 18 is passed into inlet port 38 and travels through conduit 568C along central axis 230C and through opening 290C of dispersion member 252C so as to enter space 448C between dispersion member 252C and floor 264C of separation rotor 184C. Inlet stream 102 radially outwardly flows in all directions within space 448C toward the perimeter edge 286C of dispersion member 252C. In part, dispersion member 252D functions to force inlet stream 102 to flow radially outward away from central axis 230C so as to maximize the rate and force at which inlet stream 102C begins to separate into a heavy component and a light component. Specifically, as inlet stream 102 moves radially outward away from central axis 230C, inlet stream 102 become subject to an increasing greater centrifugal force caused by the rotation of separation rotor 184C. Thus, as inlet stream 102 passes around perimeter edge 286C of dispersion member 252C, the centrifugal force causes inlet stream 102 to separate into a heavier component that travels radially outward and a lighter component that travels radially inward.

In addition, radially extending spacers 272 and lower partitions 288 extend between dispersion member 252C and floor 264C so as to divide space 448 in a plurality of inlet fluid paths 460C that extend from conduit 420C to perimeter edge 286C of dispersion member 252C. Each inlet fluid path 460C is bounded between an adjacent pair of spacers 272C/lower partitions 288C so as to force inlet stream 102 to flow radially outward along a generally linear path as opposed to swirling in a circle within space 448C about central axis 230. This linear, radial flow of inlet stream 102 again assists to quickly move inlet stream 102 away from central axis 230C so as to increase the rate of separation of inlet stream 102 into heavier and lighter components. In addition, the linear, radial flow helps to maintain inlet stream 102 in a laminar flow, as opposed to a turbulent flow, which further assists in the separation of inlet stream 102 into the heavier and lighter components. In the depicted embodiment, six inlet fluid path 460C (FIG. 27) are formed. In alternative embodiments, other numbers of inlet fluid paths 460C can be formed, such as at least 3, 4, 5, 6, 7, 8, 9, or 10 or in a range between any two of the foregoing numbers. Furthermore, as inlet steam 102 flows radially outward along inlet fluid paths 460C, the fluid also flows through recess 267C formed on floor 264C. As previously discussed, the fluid flowing through recess 267C assist in cooling adjacent bearing assembly 270C.

Lower sidewall 266C of base 250C and upper sidewall 304C of cap 254C combine to form an outer sidewall 450C of separation rotor 184C while inner sidewall 320C of insert 256C forms an inner sidewall 320C of separation rotor 184C. Outer sidewall 450C and inner sidewall 320C combine to form a sidewall assembly 452C of separation rotor 184C that encircles a compartment 454C of which space 448C forms a portion.

Figure 39:
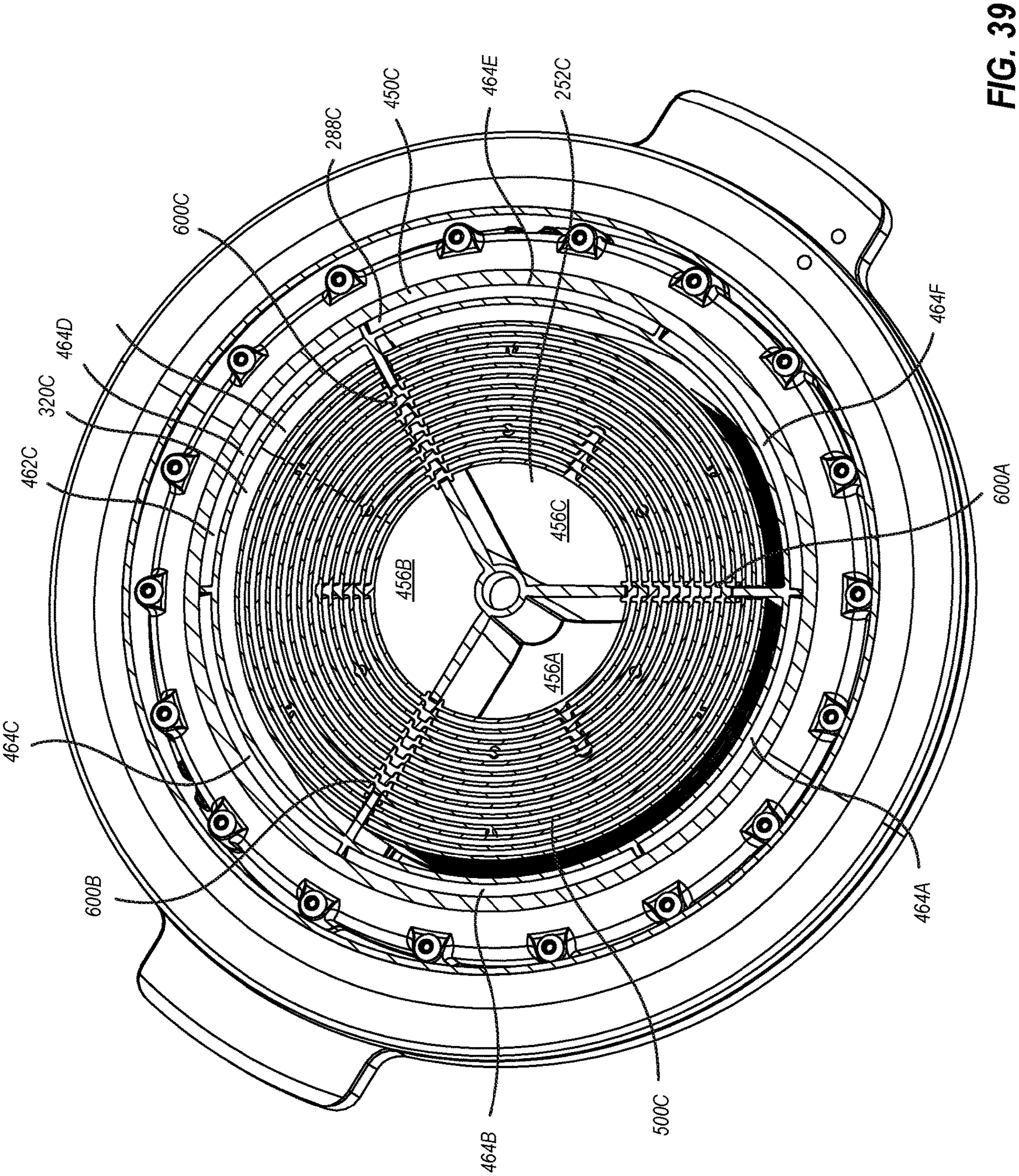
FIG. 39 is a lateral cross sectional view of the centrifugal separator shown in FIG. 22.

As better depicted in the cross-sectional view of FIG. 39, lower partitions 288C radially outwardly project within space 448C from or toward opening 290C of dispersion member 252C to sidewall assembly 452C and, more specifically, to outer sidewall 450C/lower sidewall 216C. As a result, lower partitions 288 create three isolated inlet fluid paths 460 below dispersion member 252C.

Similarly, as depicted in FIGS. 24 and 29, three walls 600A-C are formed within compartment 454C that radially outwardly extend from conduit 568C to both inner sidewall 320C and to lower sidewall 266C and that longitudinally extend from top surface 282C of base 280C to the first end 238C of insert 256C, typically to above side openings 558C. Walls 600A-C bound a plurality of light component fluid paths 456A-C that extend longitudinally along separation rotor 184C and through which a portion of the fluid travels. Walls 600A-C prevent or limit fluid traveling within fluid paths 456A-C from radially encircling conduit 568C. Depicted in FIG. 24 is a side view of wall 600A. As shown therein, wall 600A is formed from the combination of retention rail 296A, outer partition 578A, upper partition 574A and stacked guides 516A. The other walls 600B and C are similarly formed from corresponding retention rail 296, outer partition 578, upper partition 574 and stacked guides 516 B and C, respectively.

Walls 600A-C also align with and intersect with lower partitions 288A-C respectively. As a result, each inlet fluid path 460 bounded between adjacent lower partitions 288 aligns with a corresponding light component fluid path 456 and fluid does not mix as it passes therebetween. That is, fluid traveling along an inlet fluid path 460 to a corresponding light component fluid path 456 does not mix with a separated fluid traveling along a separate inlet fluid path 460 to a separate corresponding light component fluid path 456. Again, this configuration helps the fluid to continually flow along a generally linear path as opposed to swirling in a circle around conduit 568C/central axis 230C and helps to keep the fluid flowing in a more laminar flow, as opposed to a turbulent flow, both of which help separation of the fluid into the heavy component and the light component. In the depicted embodiment, three walls 600 and three lower partitions 288 are shown. In alternative embodiments, separation rotor 184 can be formed with at least 3, 4, 5, 6, 7, 8, 9, 12, 15, 18, 21 or more walls 600 and lower partitions 288 or in a range between any two of the foregoing.

With reference to FIGS. 33, 35, 38 and 39, a plurality of heavy component fluid paths are formed between insert 256C and cap 254C. Specifically, as a result of dividers 350A-F outwardly projecting from exterior surface 324C of insert 256C, an annular, frustoconical gap 462C is formed between inner sidewall 320C of insert 256C and the interior surface 300C of cap 254C. The outer edge of dividers 350A-F sit against interior surface 300C of cap 254C so that dividers 350A-F divide annular, frustoconical gap 462C into a plurality of separate heavy component fluid paths 464A-F. That is, sidewall assembly 452C bounds the plurality of separate heavy component fluid paths 464A-F. Each heavy component fluid paths 464 has an opening 466C disposed at perimeter edge 330C of insert 256C/inner sidewall 320C. For example, FIG. 38 shows heavy component fluid paths 464A. Walls 600A-C typically align with dividers 350A, C, and E, respectively.

Using dividers 350C to form and isolate heavy component fluid paths 464A-F helps the heavy component flowing into and along heavy component fluid paths 464 to continually flow along a generally linear path, as opposed to swirling in a circle around central axis 230C and also assists with keeping the heavy components in a more laminar flow, as opposed to a turbulent flow, both of which help separation of the fluid and which also limits the application of undue force on the separated cells or microorganisms which can be damaging or detrimental. In the depicted embodiment, six dividers 350A-F are used forming six heavy component fluid paths 464A-F. In alternative embodiments, separation rotor 184C can be formed with at least 3, 4, 5, 6, 7, 8, 9, 12, 15, 18, 21, 26, 32, 38 or more dividers 350 and/or heavy component fluid paths 464 or can be in a range between any two of the foregoing.

Turing to FIG. 38, as a result of the centrifugal force produced by the rotation of separation rotor 184C, the lighter components of inlet stream 102 initially flow radially outward away from opening 290C, pass around perimeter edge 286C of dispersion member 252C and then flow radially inward into a corresponding one of light component fluid paths 456 at second end 242C of separation rotor 184C. As the lighter components flow into fluid paths 456, the fluid travels between disc 500C where the fluid can be further separated. That is, as the fluid travels between disc 500C, the heavier aspects of the light components separate toward bottom face 506C of discs 500C and flow down and radially outward toward one of heavy component fluid paths 464 while the lighter aspects separate toward top face 504C of disc 500C and flow radially inward toward conduit 568C. As the lighter components flow out from between disc 500C, the lighter components flow along the channel between conduit 568C and insert 256C toward first end 196C, through the end of insert 256C, through light component collection recess 444C and out through second outlet port 42 as second outlet stream 106 (FIGS. 1, 3, and 5,). Second outlet stream 106 can then be further processed or transferred as previously discussed.

In contrast to the light components, which flow radially inward into light component fluid paths 456, the heavier components, which typically include the cells, microorganism, particles thereof, and other solids, flow radially outward toward sidewall assembly 452C/outer sidewall 450C and, more specifically, the heavy components of the fluid flow into a corresponding heavy component fluid paths 464 through an opening 466C. The heavy components then flow within heavy component fluid paths 464 toward first end 196C of separation rotor 184C. As the heavy components reach first end 196C, the heavy components flow out through side openings 558C, through heavy component collection recess 446C and then out through first outlet port 40 as first outlet stream 104 (FIGS. 1, 3, and 5,). First outlet stream 104 can then be further processed or transferred as previously discussed.

Returning to FIG. 34, as previously discussed, the heavy components pass through openings 466C into the heavy component fluid paths 464. Openings 466C and the heavy component fluid paths 464 are bounded between outer sidewall 450C and inner sidewall 320C. During operation, particles of the heavy component can collect at the constricted opening 466C and form pellets. These pellets can block or restrict flow of the heavy components through opening 466C and into heavy component fluid paths 464. Separator 12C and the other separators disclosed herein can be operated in different manners and/or be modified into different designs to help minimize the formation of the pellets and/or remove the pellets after formation. For example, a pump 100A, such as shown in FIG. 5, can be applied to first outlet stream 104 to draw the heavy component fluid through heavy component fluid paths 464. Elevating the flow rate of pump 100A can minimize the formation of the pellets and/or draw the formed pellets through openings 466 and out first outlet port 40. For example, pump 100A may be operated at a first flow rate and then periodically operated at a second flow rate that is higher than the first flow rate. The periodic operation at the higher flow rate can minimize the formation of the pellets and/or draw the formed pellets through openings 466 and out first outlet port 40. The operation of pump 100A at the higher flow rate can be based on a set time interval or based on sensed operating parameters, such as flow rates and/or pressure readings. The operation at the higher flow rates can be for only short time intervals so as to not significantly disrupt the natural separation process. For example, pump 100A may be operated at the high flow rate for period time intervals of less than 30 seconds, 20 seconds, 10 seconds, 5 seconds or in a range between any two of the foregoing.

Figure 40:
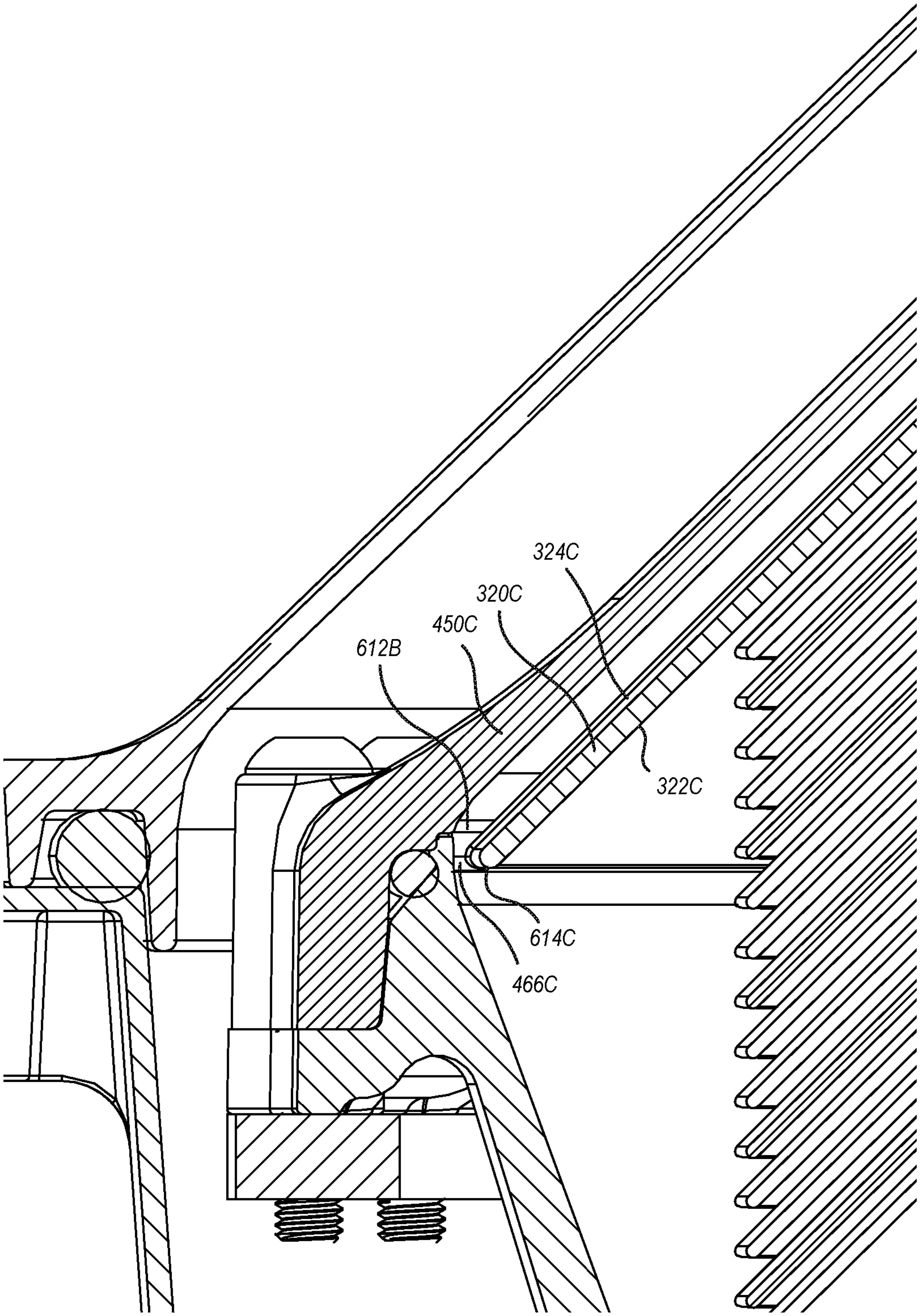
FIG. 40 is an enlarged cross sectional side view of a perimeter edge of an alternative separation rotor.

The shape of inner sidewall 320C can also be modified to help control the formation and/or removal of pellets. For example, in the embodiment depicted in FIG. 34, the second end of inner sidewall 320C has an annular tip end 612A that terminates at a rounded end face 614C. In the depicted embodiment, the opposing sides 322C/324C of tip end 612A remaining parallel and in alignment with the opposing sides 322C/324C of a central portion of inner sidewall 320C. In an alternative embodiment depicted in FIG. 40, inner sidewall 320C can be formed with an annular tip end 612B that curves or bends radially inward toward axis 230C. For example, an inside corner or curve can be formed on interior surface 322C of inner sidewall 320C at tip end 612B. This configuration results in tip end 612B having an orientation similar to the orientation of the adjacent outer sidewall 450C and can help feed larger particles and/or pellets through opening 466C.

Figure 41:
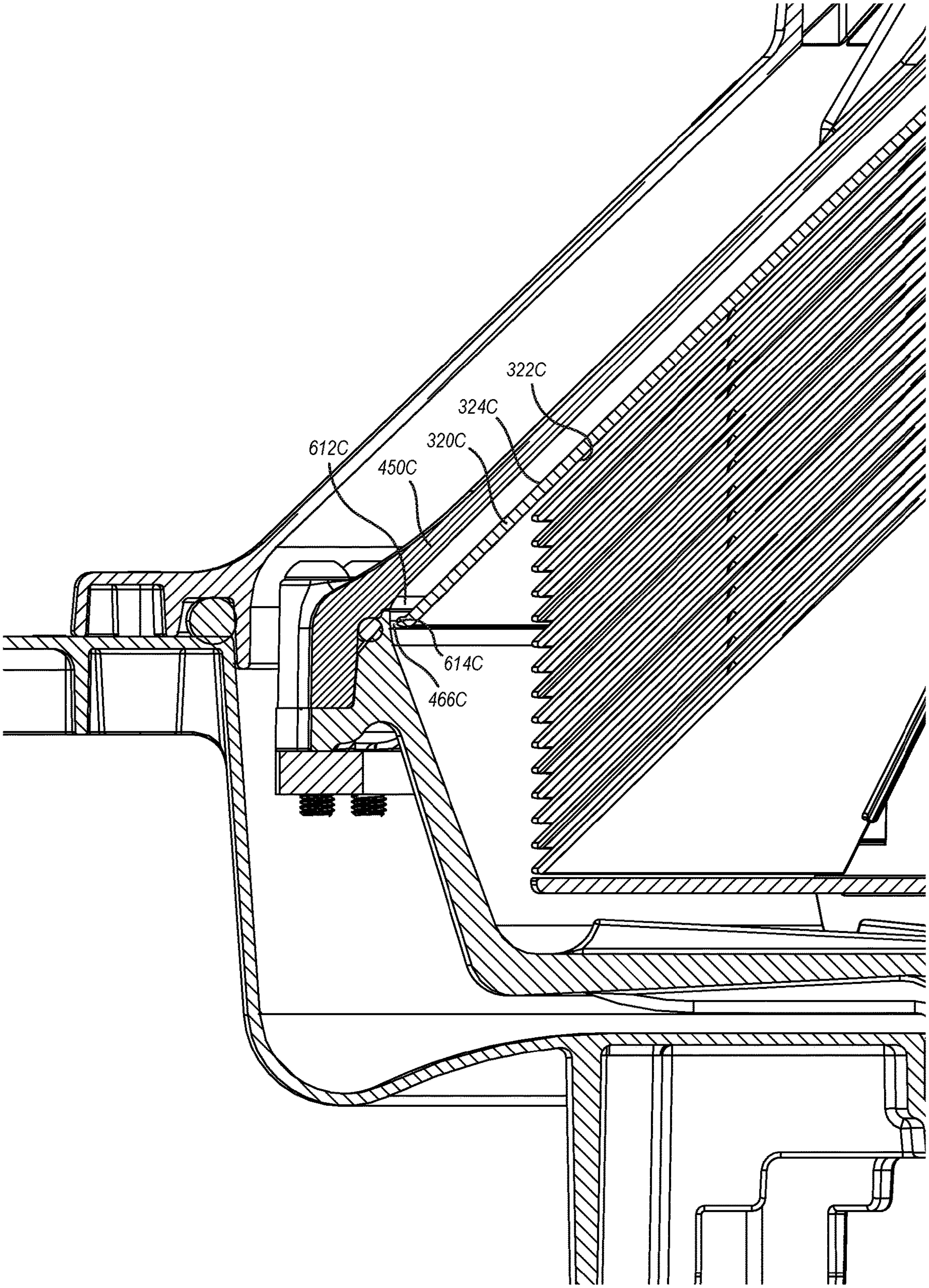
FIG. 41 is an enlarged cross sectional side view of a perimeter edge of another alternative separation rotor.

In another alternative embodiment depicted in FIG. 41, inner sidewall 320C can be formed with an annular tip end 612C at the second end that curves or bends radially outward away from axis 230C. For example, an inside corner or curve can be formed on exterior surface 324C of inner sidewall 320C at tip end 612C. This configuration results in the width of opening 466C being constricted. The constricting of opening 466C increases the flow rate directly at opening 466C which can help draw larger solid particles and/or pellets through opening 466C which then travel downstream.

Centrifugal separators 12A, 12B and/or 12C have a number of unique benefits in addition to those previously discussed. For example, many prior art centrifuges that are used to separate cells from medium can only operate in batch mode as opposed to continuous flow. That is, the centrifuge is loaded with a defined batch of suspension, operated to facilitate separation of the defined batch and then stopped and reloaded with a new batch of suspension for separation. In other prior art centrifugal separators, the centrifugal separator must be temporarily stopped after a period of operation to either backflush the system or to remove components collected therein. In contrast, the inventive centrifugal separators 12A-C can be operated continuously without the need for stopping to reload new suspension, remove a collected component or flush the system. Thus, as used in the specification and appended claims, a "continuous flow" centrifugal separator is a centrifugal separator that can continuously separate a fluid stream without the need for stopping the centrifugal separator to remove a collected component therein or to flush the separator. For example, centrifugal separators 12A-C can be operated to continuously separate inlet stream 102 of suspension 18 into both outlet streams 104 and 106 for extended periods of at least 30 minutes, 1 hour, 2 hours, 3 hours, 6 hours, 12 hours, 24 hours, 48 hours or longer without the need for stopping to remove a collected component or flush the system. Thus, one of the benefits of the present disclosure is that outlet streams 104 and 106 can concurrently be flowing out of centrifugal separators 12A-C while inlet stream 102 is flowing into centrifugal separators 12A-C.

Furthermore, because centrifugal separators 12A-C operate in a continuously flow process, processing of suspension 18 is quicker because there is less down time. As such, cells and microorganism are subject to less stress. For example, in the perfusion system of FIG. 1, centrifugal separators 12A-C are able to quickly and continuously separate inlet stream 102 into outlet streams 104 and 106 and return outlet stream 104 back to container 14 so that the amount of time that the cells and microorganisms are separated from the sparging gas and nutrients within container 14 is minimized, thereby minimizing stress on the cells and microorganisms. Furthermore, because of the configuration of centrifugal separators 12A-C, minimal mechanical stress is applied to the cells and microorganisms as they pass through the separator.

An additional benefit of embodiments of the centrifugal separators is that they have few parts and are simple and inexpensive to produce, thereby making them disposable after a single use. For example, because separation stator 180 and separation rotor 184 can simply be molded from a polymer, the material cost to produce body assembly 130 is relatively inexpensive. Accordingly, once suspension 18 has been completely processed from container 14, body assembly 130 can simply be disposed of, such as by being recycled, thereby avoiding any need for cleaning or sterilization. A new body assembly 130 can then be used with magnet driver 132 for processing a new container 14 holding a new quantity of suspension 18. Because magnet driver 132 never directly contacts suspension 18, magnet driver 132 can be repeatedly reused without the need for sterilization or cleaning.

Another benefit of centrifugal separators 12A-C is that body assembly 130 can be easily sterilized prior to shipment and use. For example, once body assembly 130 is assembled, as discussed above, it can be sealed closed and then sterilized by irradiation such as gamma irradiation. Depending on the materials used, some embodiments could also be sterilized by autoclave. As used in the specification and appended claims, the terms "sterile" and "sterilized" mean to be free from bacteria or other living microorganisms. Because body assembly 130 includes minimal metal part, there is minimal interference to the irradiation process.

Finally, the unique configuration of centrifugal separators 12A-C enables highly efficient separation of solids. Other benefits also exist.

Figure 42:
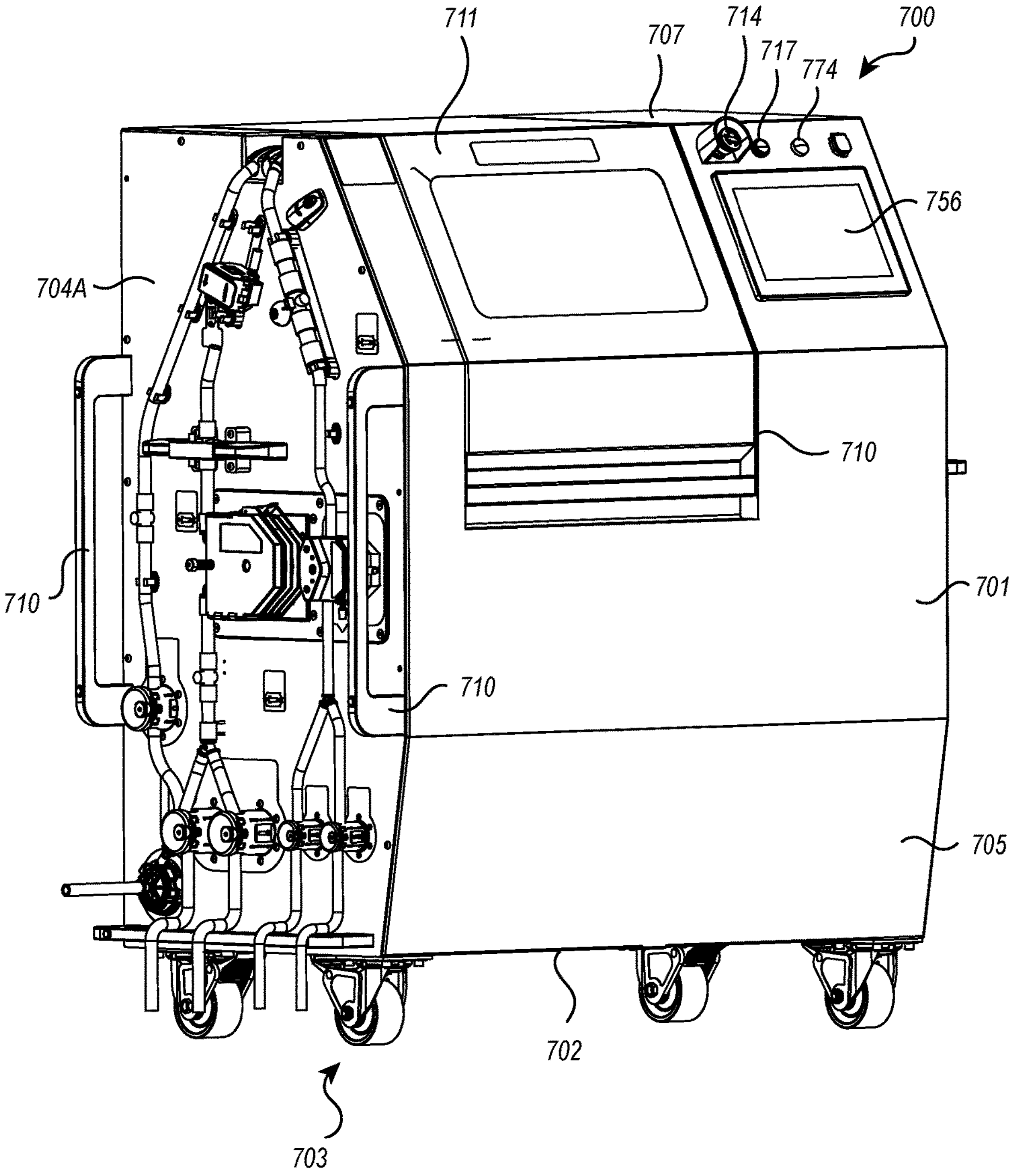
FIG. 42 is a front perspective view of a skid for use with the centrifugal separator of FIG. 22.
Figure 43:
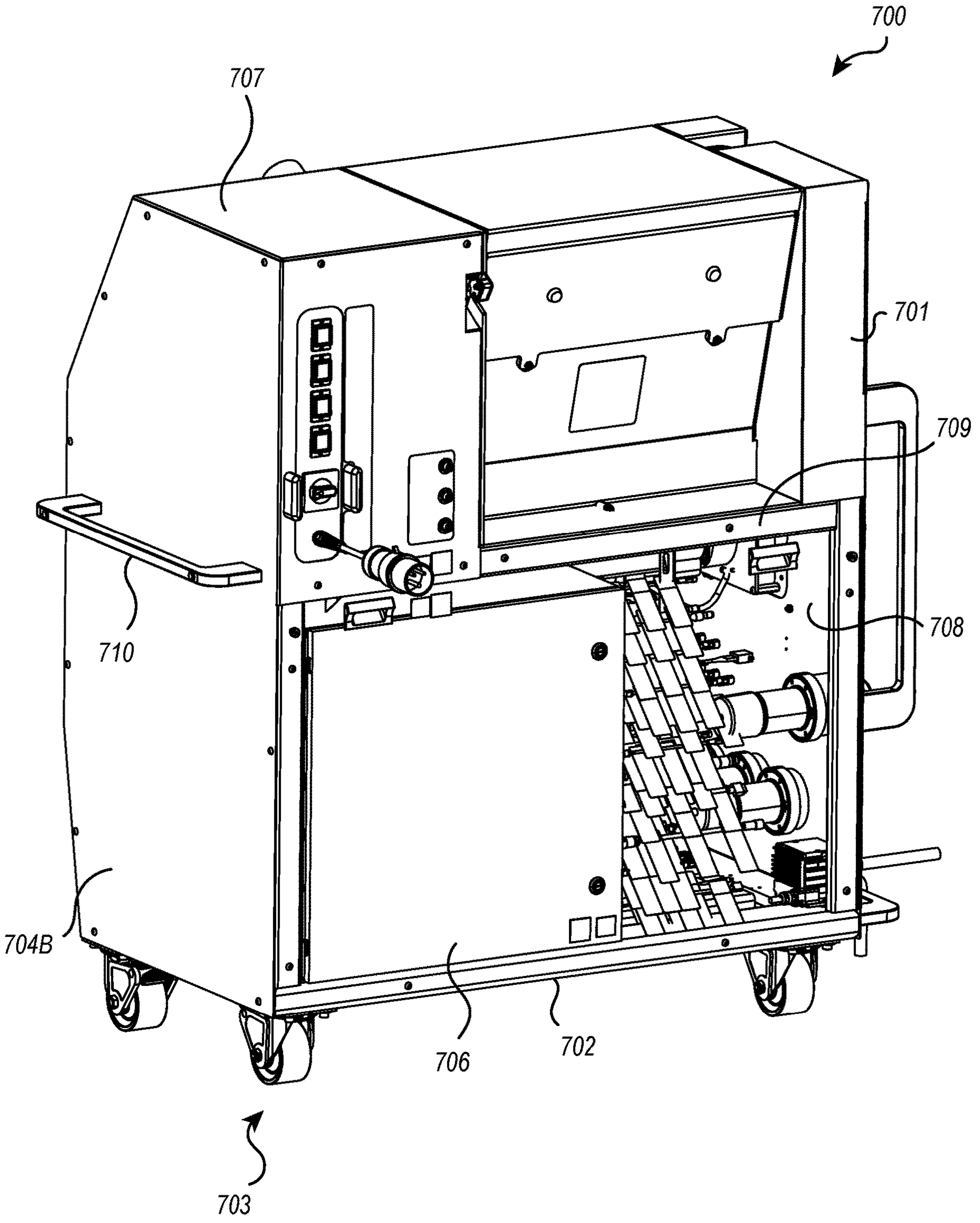
FIG. 43 is a rear perspective view of the skid shown in FIG. 42.

The centrifugal separators and assemblies disclosed herein can be incorporated into a portable and modular skid that will be described in detail. FIGS. 42 and 43 depict a front perspective and rear perspective view, respectively, of an exemplary centrifugal separator skid 700. Skid 700 can include a platform or base 702 with wheel assemblies 703 that provide portability, ease of movement and positioning of skid 700 such as to or within a bioproduction facility and/or during processing. Wheel assemblies 703 can come with caster red urethane wheels with bearings and a mounting plate to mount the wheel assemblies 703 to the base 702. In other embodiments, wheel assemblies 703 can be eliminated.

Skid 700 further comprises a housing 701 supported on base 702. Housing 701 can include opposing side panels 704A and 704B that extend between a front panel 705 and an opposing back panel 706. Panels 704, 705 and 706 extend between base 702 at a lower end and a top panel 707 at an upper end so as to form an enclosed and contained unit having one or more compartments 708 within skid 700/housing 701. Panels 704, 705, 706, and 707 can be made from one unitary piece or several pieces of metal, plastic or other rigid material that forms walls of one or more compartments 708 of skid 700.

A bumper and/or handle 710 can be mounted on one or both of opposing side panels 704A and 704B of housing 701 or on other panels so that an operator or automated system can grip handle 710 while moving skid 700 into an optimal position for integration into a bioproduction process.

Figure 46:
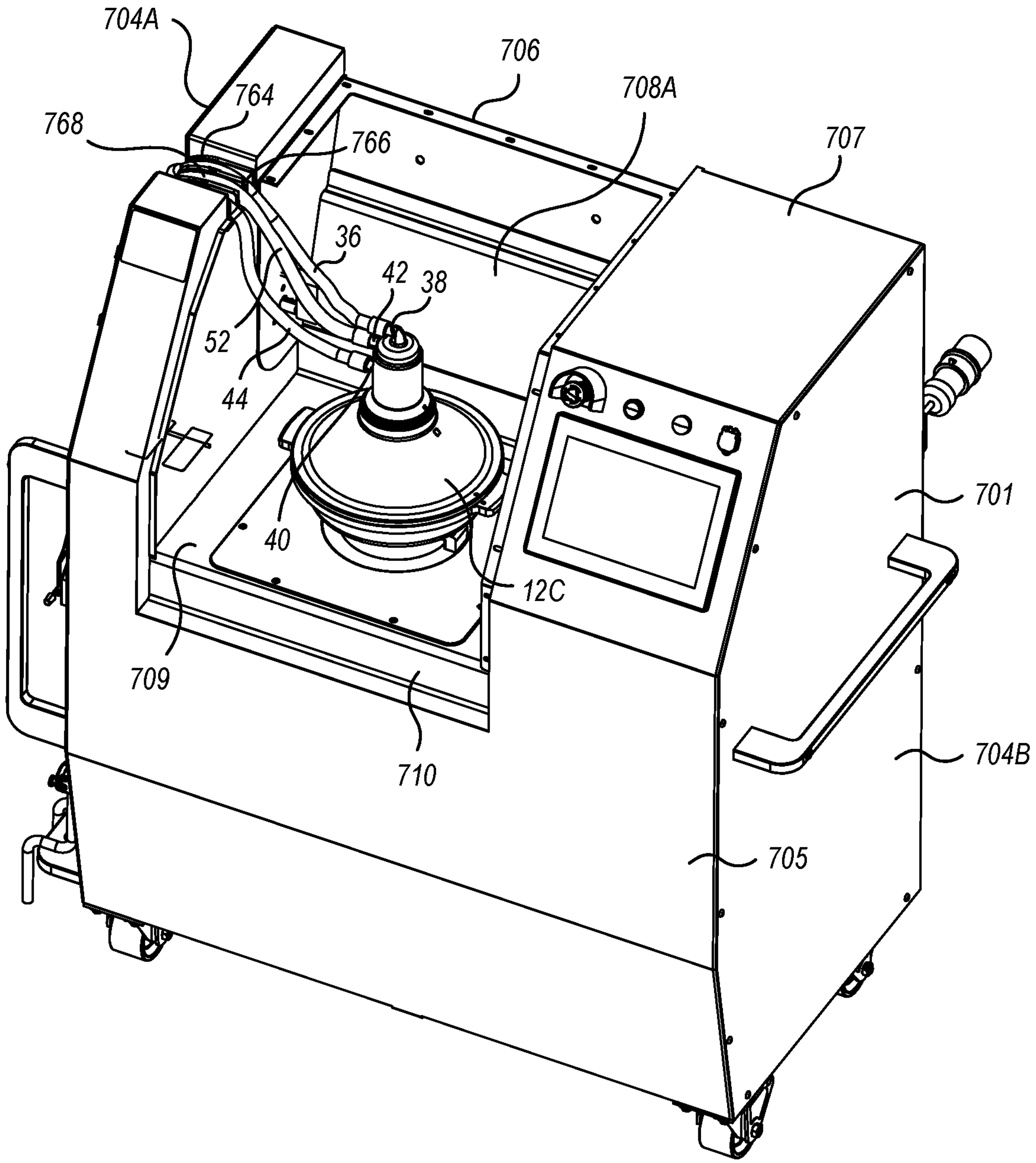
FIG. 46 is a front perspective view of the skid shown in FIG. 42 with the door removed.

As shown in FIG. 46, a mounting platform 709 can be disposed within housing 701 and can extend laterally between the panels 704, 705, and 706 of skid 700/housing 701 for mounting centrifugal separator 12 thereon. Although any of the centrifugal separators disclosed herein can be used on skid 700, separator 12C is depicted and discussed with skid 700. The mounting platform 709 divides the compartment 708 into a top compartment 708A and a bottom compartment 708B (FIG. 43). The top compartment 708A and/or the bottom compartment 708B can be hermitically sealed from the environment, but it is not required. In one exemplary embodiment, the top compartment 708A and the bottom compartment 708B are hermitically sealed from each other and the environment.

As also shown in FIG. 46, a doorway 710 is formed on housing 701 and provides communication and access to top compartment 708A. Doorway 710 is sized and configured to enable separator 12C to be manually inserted and removed from top compartment 708A. Doorway 710 is shown extending through a portion of front panel 705 and top panel 707. In other embodiments, doorway 710 can extends solely through front panel 705 or top panel 707 or can extend through other panels. With reference to FIG. 42, a door assembly 711 can be disposed on housing 701 to selectively open and close doorway 710. More specifically, in one exemplary embodiment door assembly 711 includes door 716 that can be movably mounted to housing 701, such as being hingedly mounted to housing 701, so that door 716 can be moved between an open position where doorway 710 is open (FIG. 46) and a closed position where doorway 710 is closed (FIG. 42). When in the open position, mounting platform 709 is openly exposed so that separator 12C can be mounted on or removed from platform 709 within top compartment 708A or can otherwise be accessed within top compartment 708A. In the closed position, doorway 710 is covered by door 716 so as to act as a shield or cover in case of failure of separator 12C during operation. In one embodiment, the door assembly 711/door 716 can be automatically locked during operation of the centrifugal separator 12C, e.g., door assembly 711 can be self-locking or programmed to automatically lock.

Figure 45:
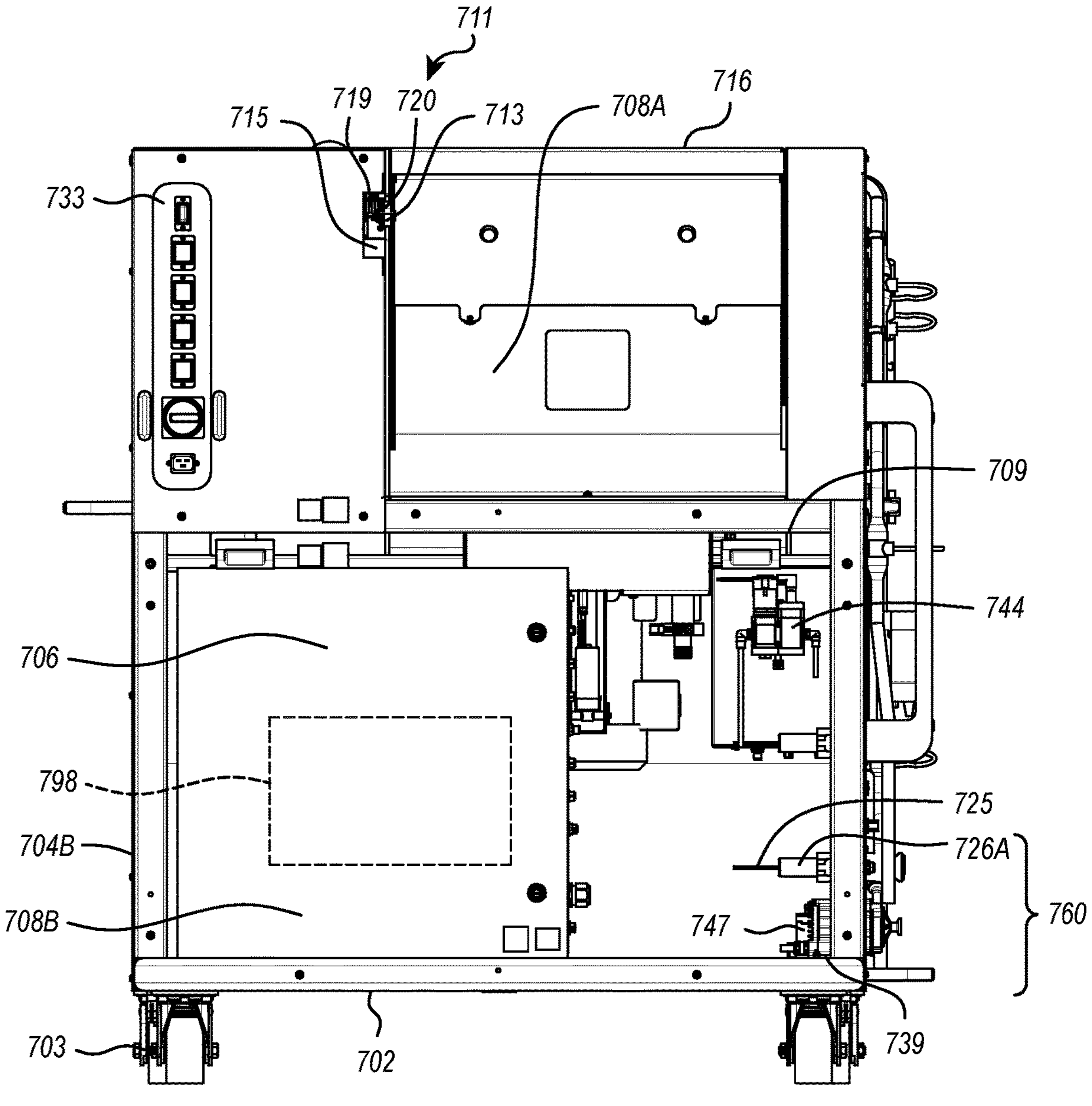
FIG. 45 is an elevated rear view of the skid shown in FIG. 42.

In an exemplary embodiment, as shown in FIG. 45, the door assembly 711 can include a switch block 715, a latch 713, a locking guard switch 719 and an actuating locking key 720, which interact with door 716. The switch block 712 and locking guard switch 719 are in wired or wireless communication with a controller 798 comprising a programmable processor and non-transitory memory programmed to actuate the switch block 715 and locking guard switch 719 and move the latch 713 from a locked position to an unlocked position. In an exemplary embodiment, the switch block 712 and locking guard switch 719 form a key or tongue operated, solenoid interlock switch with key entry slots. The actuating locking key 720 can be inserted into one or more key entry slots to unlock the door 716, or the door 716 can be automatically unlocked with the controller 798. The door assembly 711 can further include hinges, bearings, bushings and/or or radial dampers 762 (shown in FIG. 48) that facilitate rotation of the door 716 about an axis of rotation, radially and upward to open it and radially and downward to close it. The radial dampers 762 also prevent the door 716 from opening or closing with too much velocity or force so as to prevent damage. The door assembly 711/door 716 acts as a containment shield that can withstand maximum forces associated with the failure of the centrifugal separator 12C at maximum speed or rpm.

In an exemplary embodiment, the controller 798 is programmed to automatically lock the door assembly 711/door 716 when the centrifugal separator 12C is in operation and automatically unlock the door assembly 711/door 716 when the centrifugal separator 12C is not in operation. The controller 798 is also programmed to preclude lock-down of the centrifugal separator 12C (described in detail with respect to a loading assembly 800) and actuation of mounting clips 804 if the door 716 is open.

The centrifugal separator skid 700 is a modular and portable unit including single-use process equipment and components that can be easily mounted, installed and removed from the skid 700/housing 701 through quick release and easy-connect ports and mounting assemblies. As a result, an exemplary skid 700 can come fully equipped with a diverse set of process components and equipment necessary for efficient integration of the centrifugal separator 12C into a variety of bioproduction processes. An exemplary skid 700 can also be provided without process equipment, but with ports and mounting assemblies so the operator or end-user can select a custom set of process components and equipment to install through the quick release and easy-connect ports and mounting assemblies of the skid 700.

Exemplary quick release and easy-connect ports and mounting assemblies include tubing and piping holders, cable management systems, mounts, connectors and ports for centrifugal separators, controllers, sensors, valves, power sources and pumps. Exemplary process equipment and components include tubing, piping, cabling and electronics, controllers, pumps, power sources, sensors, probes, valves and centrifugal separators. In one preferred embodiment, one or more exemplary process components are single-use and/or disposable components. The exemplary quick release and easy-connect ports and mounting assemblies, process equipment and components can be installed and mounted on any surface of the skid 700/housing 701, including the side 704, front 705, back 706 and top 707 panels of the skid 700/housing 701, in the compartment(s) 708 of the skid 700/housing 701 or on the mounting platform 709 of the skid 700.

In an exemplary embodiment, a power supply 733 (FIG. 45) is provided on the back panel 706 of the skid 700/housing 701. The power supply 733 can provide power to all process equipment installed on the skid 700, including the centrifugal separator, centrifugal separator motor, controllers, door assembly, fieldbus, fieldbus nodes and switches, linear actuators, linear actuator motor, pumps, pump motors, sensors, switches, valves and valve control systems. The power supply 733 can be a unitary power supply, multiple power supply units, a programable power supply, a DC power supply, a variable AC power supply, a switch mode power supply (SMPS) or an uninterruptible power source (UPS). In an exemplary embodiment, the power supply 733 is a variable AC, 240 voltage power supply.

With reference to FIG. 22A, one or more and commonly a plurality of tubing holders 722 are mounted on housing 701 and, in one exemplary embodiment, to the sidewall panel 704A of the skid 700. The tubing holders 722 can be shaped as clips configured to retain tubing and/or piping used to flow biologic fluids and solids to and from process equipment installed on the skid 700.

As shown in FIG. 46, separator 12C is removably secured within top compartment 708A. Mounted to and outwardly projecting from separator 12C are fluid lines 36, 44 and 52 as previously discussed with regard to FIG. 1-5. Fluid line 36 inlet port and is used to deliver an inlet stream to separator 12C such as from bioproduction vessel 10. Fluid line 44 couples to first outlet port 40 and is used to transport a heavy component outlet stream downstream. Finally, fluid line 52 couples to second outlet port 42 and is used to transport a light component outlet stream downstream. Each of fluid lines 36, 44 and 52 pass through a notch 764 that extends through side panel 704A and/or top panel 707 so as to communicate with top compartment 708A. Upstanding within notch 764 are guide rails 766 that separate channels 768. Typically, three separate channel 768 are formed. Each channel 768 is sized to receive a corresponding one of fluid lines 36, 44 and 52. Notch 764 is configured so that when door 716 is moved to the open position, separator 12 having fluid lines previously connected thereto can be positioned within top compartment 708A and fluid lines 36, 44 and 52 laid within corresponding channels 768. Door 716 can then be moved to the closed position to operate separator 12C while fluid lines 36, 44 and 52 pass out of top compartment 708A through notch 764. In part, guide rails 766 are formed so as to minimize any open space between fluid lines 36, 44 and 52 passing through notch 764, thereby minimizing the risk of any matter flying out of top compartment 708A upon failure of separator 12.

Figure 44:
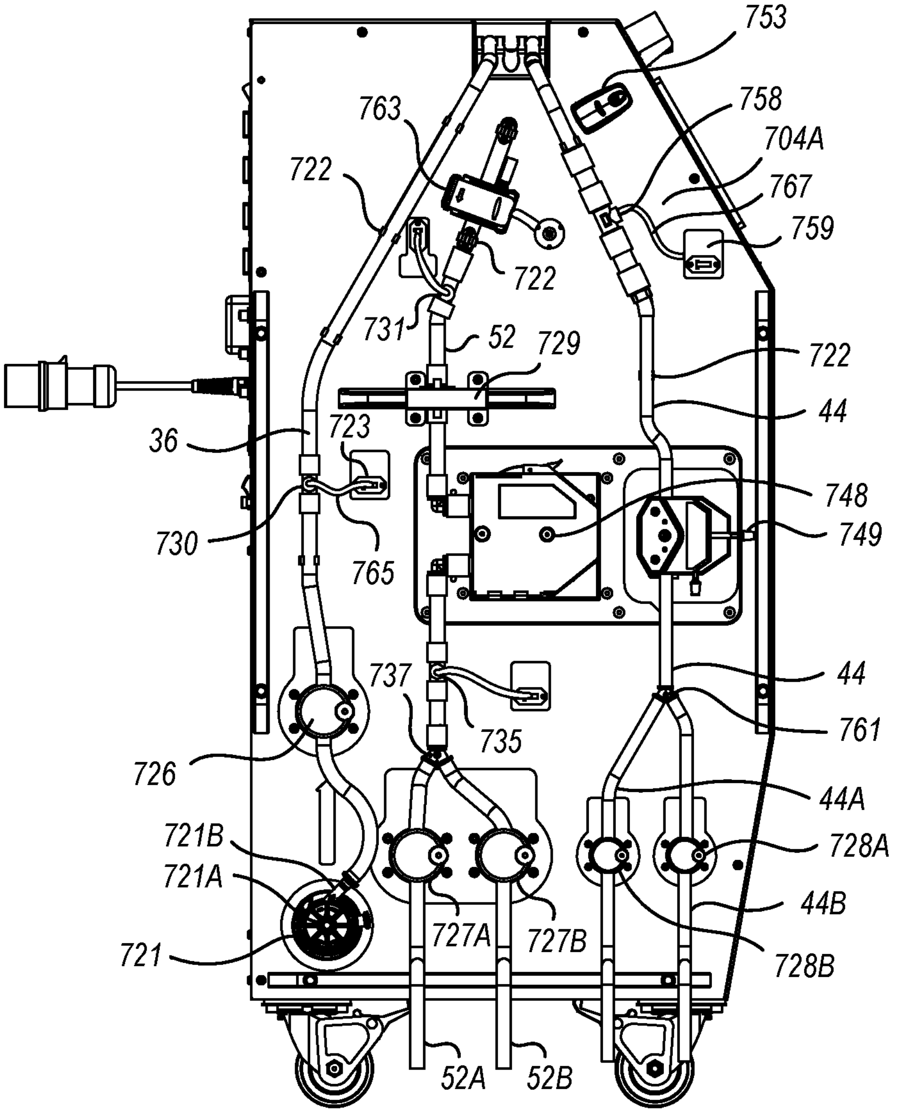
FIG. 44 is an elevated side view of the skid shown in FIG. 42.

As depicted in FIG. 44, fluid lines 36, 44 and 52, which can also be referred to as line sets, can be removably mounted along the height of side panel 704A by tubing holders 722. As previously discussed, fluid lines 36, 44 and 52 are typically formed from flexible tubing but could also comprise rigid tubing. Fluid line 36 carrying the inlet fluid is removably coupled to pinch valve 726 mounted side panel 704A. Pinch valve 726 can selectively pinch fluid line 36 closed to prevent fluid flow therethrough or release fluid line 36 so as to allow fluid to flow therethrough. Coupled with fluid line 36 is an inlet pump 721 and one or more sensors 730.

Inlet pump 721 can be removably mounted to the housing 501/sidewall panel 504A of the skid 700 to pump biological fluids, solids, mixtures, solutions and suspensions through inlet line 36 to centrifugal separator 12. The inlet pump 721 can include a pump assembly box with quick-release connecters that interface an inlet port 721A and an outlet port 721B of the pump 721 and a motor for driving the pump 721. The pump assembly box can enclose and provide a hermetical seal around the pump 721. Inlet port 721A can be fluidly connected to bioproduction vessel 10. The bioproduction vessel 10 can be any bioproduction vessel, including but not limited to mixers, cell factories, bioreactors, fermenters, lab and bench scale vessels and other vessels that can feed fluids, solids or mixed phase biocomponents to the skid 700 for separation.

The inlet pump 721 can be a centrifugal pump or a positive displacement pump, such as peristaltic pump. Preferably, the inlet pump 721 is a single-use, disposable centrifugal pump with no bearings or seals. The inlet pump 721 can be enclosed in an aseptically sealed casing, such as the pump assembly box, and equipped with a suspended impeller driven by the magnetic field of an inlet pump motor. Inlet pump 721 is commonly a centrifugal pump so as to provide a high flow rate of fluid to and through separator 12C for efficient processing. However, in other applications other types of pumps can be used. Pump 721 is removably coupled to housing 701. This enables separator 12C, fluid lines 36, 44 and 52 and pump 721 to be preassembled and sterilized, such as by irradiation, and then subsequently mounted on skid 700 as a unitary assembly.

The one or more sensors 730 can comprise one or more of a pressure sensor, conductivity sensor, flow meter sensor, pH sensor, temperature sensor, or turbidity sensor which can be spaced along fluid line 36. The one or more sensors 730 can be removably plugged into a corresponding electrical outlet 723 by an electrical cable 765. In various embodiments, the sensors 730 can be equipped with quick release bulk-head connectors for easy connection and release for single-use. The electrical outlet 723 can provide power to the one or more sensors 730 and can couple one or more sensors 730 to controller 798 for operating and monitoring one or more sensors 730. Controller 798 can convert electrical signals from the sensors into measurable process parameters. In other embodiments, the one or more sensors 730 can be wireless.

Fluid line 44 carrying the heavy component outlet stream is removably coupled to a pump 749, which is typically a peristaltic pump, that is mounted on housing 701/side panel 704A. One or more sensors 758 are coupled with fluid line 44. The one or more sensors 758 can comprise one or more of a pressure sensor, conductivity sensor, flow meter sensor, pH sensor, temperature sensor, or turbidity sensor which can be spaced along fluid line 44. The one or more sensors 758 can be removably plugged into an electrical outlet 759 by an electrical cable 767. In various embodiments, the sensors 758 can be equipped with quick release bulk-head connectors for easy connection and release for single-use. The electrical outlet 759 can provide power to the one or more sensors 758 and can couple the one or more sensors 758 to controller 798 for operating and monitoring the one or more sensors 758. Controller 798 can convert electrical signals from the sensors into measurable process parameters. In other embodiments, the one or more sensors 758 can be wireless. The lower end of fluid line 44 forks at a tee fitting 761 with fluid lines 44A and 44B extending therefrom. Fluid lines 44A and 44B are each removably coupled with a pinch valve 728A and 728B, respectively, mounted to housing 701. Accordingly, by controlling the operation of pinch valves 728A and 728B, the heavy component outlet stream can be delivered to different locations, such as either back to bioproduction vessel 10 or to a collection container, waste container, or other downstream processing equipment. In other embodiments, tee fitting 761 can be eliminated and fluid line 44 can be coupled to a single pinch valve 728.

Fluid line 52 which carries the light component outlet stream is removably coupled to a pump 748, which is typically a peristaltic pump, that is mounted on housing 701/side panel 704A. Coupled with fluid line 52 is a flow meter sensor 763, a pressure sensors 731, a turbidity sensor 729 and a sensor 735. Sensor 735 can comprise one or more of a pressure sensor, conductivity sensor, flow meter sensor, pH sensor, temperature sensor, or turbidity sensor. Sensors 763, 731, 729, and 735 can each be removably plugged into an electrical outlet disposed on housing 701 by an electrical cable. The electrical outlet can provide power to the sensors 763, 731, 729, and 735 and can couple the sensors 763, 731, 729, and 735 to controller 798 for operating and monitoring the sensors. In other embodiments, the sensors 763, 731, 729, and 735 can be wireless. The lower end of fluid line 52 forks at a tee fitting 761 with fluid lines 52A and 52B extending therefrom. Fluid lines 52A and 52B are each removably coupled with a pinch valve 727A and 727B, respectively, mounted to housing 701. Accordingly, by controlling the operation of pinch valves 727A and 727B, the heavy component outlet stream can be delivered to different locations, such as either back to bioproduction vessel 10 or to a collection container, waste container, or other downstream processing equipment. In other embodiments, tee fitting 737 can be eliminated and fluid line 52 can be coupled to a single pinch valve 727.

The various sensors discussed above with regard to fluid lines 36, 44 and 52 can measure and provide signals indicative of pressure, flow rate, turbidity, density, motor power, rotor rpm, temperature, pH, $O_2$ concentration, $CO_2$ concentration and other process parameters at various locations throughout the process flow lines, within the centrifugal separator and other tubing and equipment upstream and downstream from the centrifugal separator 12.

One or more cable management modules 753 can also be mounted at various desired locations on housing 701/sidewall panel 704A of the skid 700. The one or more cable management modules 753 can be a low-profile, breakthrough, multi-cord cable management system that provide a spool or other surface for winding and retaining the electrical cabling. One or more liquid-tight sealing grommets can also be used together with or independent of the cable management modules 753 and tubing holders 722. The grommets form liquid-tight seals around tubing, wiring, cabling, and cords routed to and from process equipment installed on the skid 700. One or more ports can be provided to allow protraction of tubing holders 722 and cable management modules 753 out of the port during installation, retraction into the port, (e.g., flush to the sidewall panel 704A/housing 701 of the skid 700) or during storage. Exemplary tubing holders 722, and cable management modules 753 provide enhanced equipment access, operational efficiency and safety for the operator of the skid 700.

The skid 700 can also be equipped with a valve control system 760 including a flow control valve 726A and tubing 725 (shown also in FIG. 48), a series of working valves 726, 727, 728, 744, a valve terminal 739 and a fieldbus node 747. The valve control system 760 can be an electrical or pneumatic control system and the valves 726, 727, 728, 744 can be electrically actuated or pneumatically actuated. In an exemplary embodiment the valves 726, 727, 728, 744 are pneumatic pinch valves or pinch clamps. The valves 726, 727, 728, 744 can also be gate valves, globe valves, check valves, plug valves, ball valves, butterfly valves, needle valves, pinch valves, or solenoid valves equipped with solenoid elements for opening and closing the valves. The valves 726, 727, 728, 744 can also be equipped with optical digital position feedback sensors for detecting whether the valves are open or closed. Exemplary pneumatic valve control systems can include tubing 725 and flow control valve 726A through which air or other gas or hydraulic fluid is distributed through a manifold to each of the valves 726, 727, 728, 744 to facilitate actuation of the valves. The valves 726, 727, 728, 744 can be in wired or wireless communication with the controller 98. The valves can also be self-actuating or manually operated.

The valves 726, 727, 728, 744 can be arranged on and mounted to any surface of the skid 700, including the sidewall panel 704A of the skid 700 to control the flow of biological fluids, solids, mixtures, solutions and suspensions through flowlines, to and from the centrifugal separator assembly 12C and through other process equipment. The valves 726, 727, 728, 744 can also include snap-in tube slots for quick loading and unloading of tubing into and out of the valves. In an exemplary embodiment, the valves 726, 727, 728, 744 are single-use valves made of disposable materials to allow for cheap and easy replacement after use.

The valve terminal 739 can be mounted to the base 702, panels 704, 705, 706, 707 or mounting platform 709 of the skid 700. In an exemplary embodiment, the valve terminal 739 is mounted in the bottom compartment 708B of the skid 700. The valve terminal 739 can include a communications port, communications link, a circuit board, and a manifold with multiple pneumatic ports pneumatically coupled to inlet and outlet ports of the valves 726, 727, 728, 744. In one embodiment, a gas or hydraulic fluid can be fed through tubing 725 and a flow control valve 726A and manifold to distribute the gas hydraulic fluid to and actuate each of the valves 726, 727, 728, 744.

In an exemplary embodiment, the communications port and link can be an I/O port and link coupled to the fieldbus node 747. The valve terminal 739 and fieldbus node 747 can be in wired or wireless communication with the controller 798 that controls the actuation of the valves 726, 727, 728, 744 with electrical signals or pneumatic or hydraulic pressure applied through the valve terminal 739 and manifold. The valve control system 760 can use a specific communications protocol to facilitate data and electrical signal transmission between the valve terminal 739, fieldbus node 747, valves 726, 727, 728, 744 and a controller 798. Exemplary industrial fieldbus and Ethernet protocols include, but are not limited to, Profibus, Modbus, DeviceNET, Profinet, Ethernet/IP, Ethernet CAT and Modbus TCP. In an exemplary embodiment, the communications protocol used by the valve control system 760 is Profinet.

The one or more process flow lines, including the inlet line 36 and outlet lines 44, 52, and valves 726, 727, 728, 744 can be configured and actuated to route biocomponents to the centrifugal separator assembly 12C for separation. In an exemplary embodiment, the inlet line 36 and an inlet valve 726 located upstream from the inlet pump 721 can be configured and actuated by controller 798 to bypass the centrifugal separator 12C and route air, others gases, liquids, solids or biocomponents downstream from the inlet pump assembly 721 and centrifugal separator assembly 12C during start-up. This operation can be used to flush the system of air and gas before or after use. The inlet line 36 and an inlet valve 726 located upstream from the inlet pump 721 can also be configured and actuated by controller 798 to route biocomponents from a bioproduction vessel to the centrifugal separator 12C for separation.

The light outlet line 52 and one light outlet valve 727 can be configured and controlled via controller 798 to flow and route light biological components separated from the centrifugal separator assembly 12C downstream for processing, while the other light outlet valve 727 can be configured to recycle and route light biological components separated from the centrifugal separator assembly 12C back to the bioproduction vessel that fed the system.

Likewise, the heavy outlet line 44 and one heavy outlet valve 728 can be configured and controlled via controller 798 to flow and route heavy biological components separated from the centrifugal separator assembly 12C downstream for processing, while the other heavy outlet valve 728 can be configured to recycle and route heavy biological components separated from the centrifugal separator assembly 12C back to the bioproduction vessel that fed the system.

Recycled biocomponents exiting the bioprocess vessel can be flowed and routed through the inlet pump 721 and to the centrifugal separator 12C or bypass the centrifugal separator 12C via a split in the inlet line-set.

The skid 700 can be equipped with an emergency shut-off valve 744 (FIG. 45) that closes off one or more outlet lines 44, 52 exiting the centrifugal separator assembly 12C during emergencies, leaks or otherwise. Each of the valves 726, 727, 728, 744 can function as emergency shut-off valves.

As shown in FIG. 42, the skid 700 can include a user input and digital display 756, a switch block 717, a switch reset button 74, and an emergency stop button 714 which can be used to start, stop and otherwise control operation of centrifugal separator 12C and/or the components of skid 700. In one embodiment, if the emergency stop button 714 is actuated to stop centrifugal separator 12C, the user may be required to actuate the switch reset button 774 to reset the switch block 717 for operation. The user input and digital display 756 allows an operator to provide process parameter inputs and read process parameter outputs that control and indicate process parameters, such as pressure, flow rate, turbidity, density, temperature, pH, motor power, rotor rpms and other process parameters throughout the flow lines and process equipment on skid 700.

In exemplary embodiments, process equipment and components including tubing, piping, cabling and electronics, controllers, motors, pumps, power sources, sensors, probes, valves and centrifugal separators can be mounted to various locations on the skid 700 depending on the specific requirements and configuration of the bioprocess within which the skid 700 is integrated. For example, process equipment and components can be installed and mounted on any surface of the skid 700, including the side 704, front 705, back 706 and top 707 panels of the skid 700, in the compartment(s) 708 of the skid 700 or on the mounting platform 709 of the skid 700.

Figure 48:
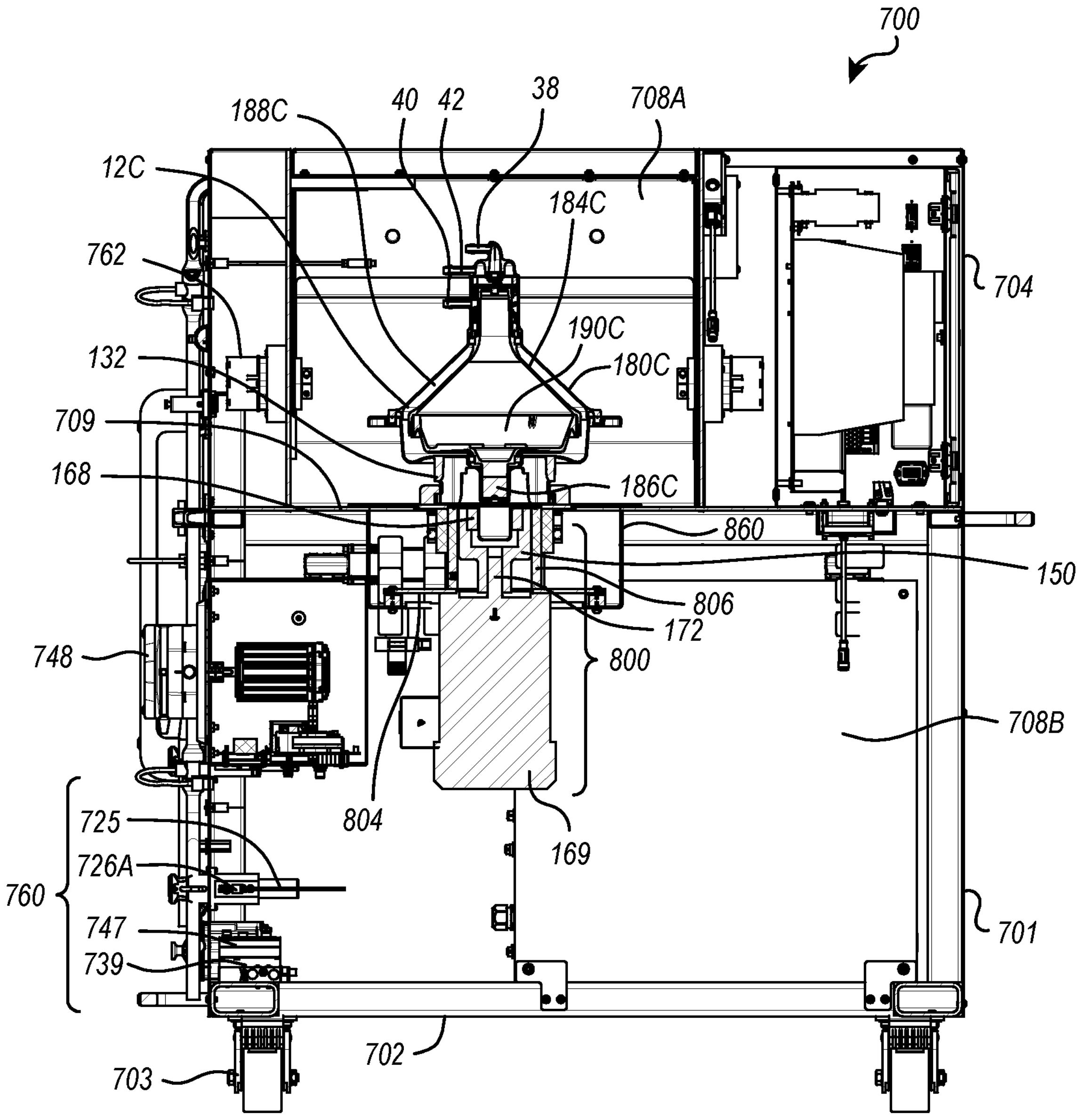
FIG. 48 is a cross sectional view of the skid shown in FIG. 45.
Figure 49:
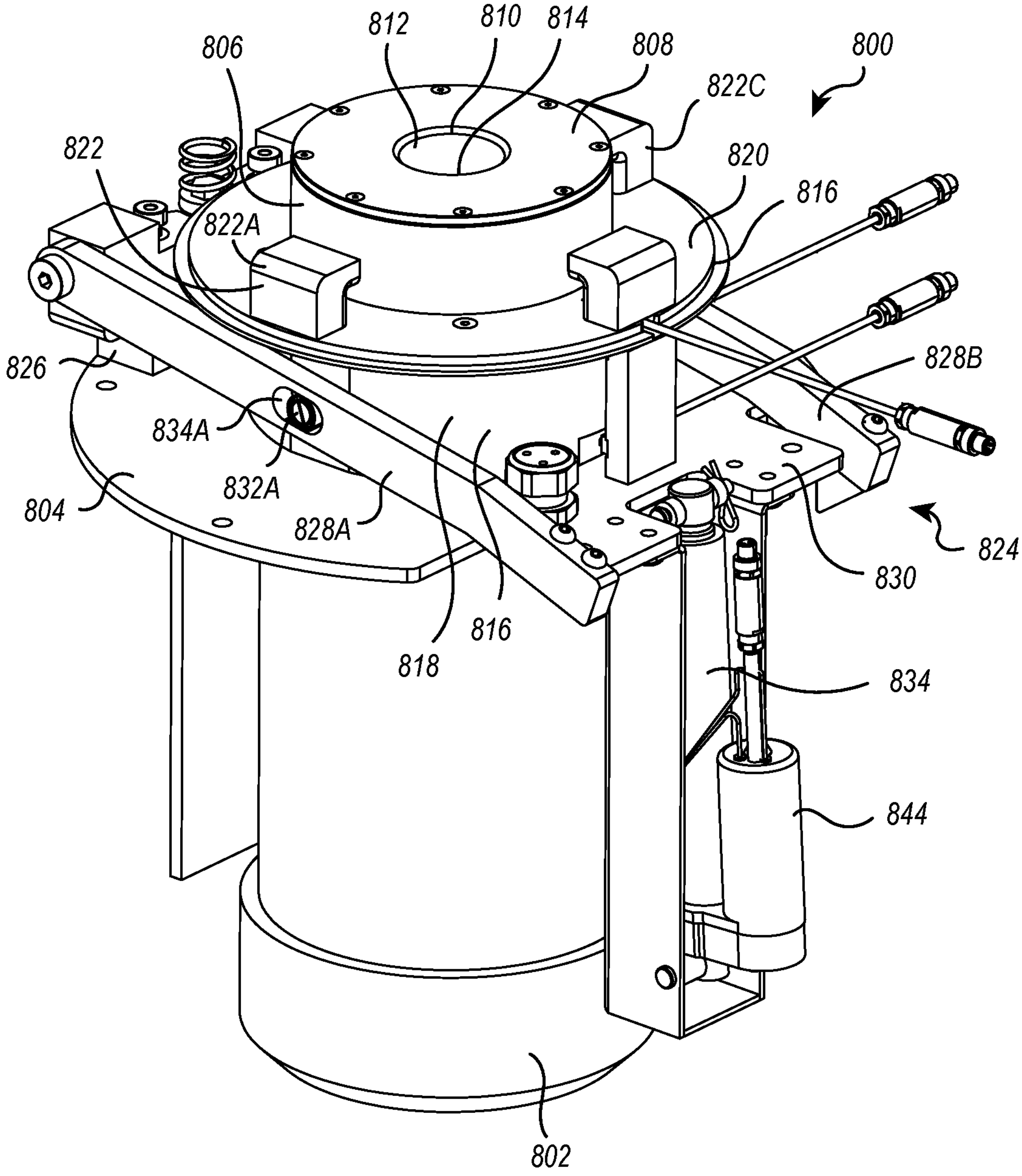
FIG. 49 is a front perspective view of a loading assembly of the skid shown in FIG. 42 in lowered position.

FIGS. 48 and 49 depict front and side cross-sectional views, respectively, of the exemplary centrifugal separator skid 700. Additional components and functionality of the skid 700 are depicted by the cross-sectional views.

The mounting platform 709 can be used to mount the centrifugal separator 12C to the skid 700. The mounting platform 709 can be a flat table with a recess 812 that accepts and interfaces with a loading assembly 800. The loading assembly 800 can releasably load, mount, center and lock the centrifugal separator assembly 12C to the skid 700. The skid 500 houses centrifugal separator assembly 12C within top compartment 708A. The housed centrifugal separator can be any centrifugal separator disclosed and described herein or in related U.S. Provisional Patent Ser. No. 63/115,938, which is herein incorporated by reference in its entirety for all purposes.

As previously discussed, centrifugal separator assembly 12C can include a separation stator 180C that forms a stator chamber 188C and a separation rotor 184C rotatably mounted and/or coupled to the stator chamber 188C. The separation rotor 184C forms a separation container 190C within which biocomponents are separated during rotation of the separation rotor 184C. A mounting surface 804 can be fixed to or integral to the separation stator 180C and is used to mount and/or lock the separation stator 180C and centrifugal separator 12C to the skid 700. The mounting surface 804 can be a flange, cavity, elbow, recess or slot on the separation stator 180C. A drive coupling 186C with two ends, and preferably a magnet on one end, is coupled to the separation rotor 184C at one end and magnetically coupled to a magnetic driver 148 on its other end. The magnetic driver 148 can include an outer housing 134 and a drive rotor 150 with one end coupled to a motor 169. The drive rotor 150 includes a magnet that creates a magnetic field capable of interacting with and magnetically coupling the drive rotor to the drive coupling 186C and/or a magnet on the drive coupling 186C. As the motor 169 rotates the drive rotor 150, the rotation of the drive rotor 150 and magnetic field rotates the drive coupling 186C and separation rotor 184C. The stator chamber 188C can form an aseptic seal and a hermetic seal around the separation rotor 184C and the drive coupling 186C to provide a sterile chamber sealed from the environment.

The centrifugal separator 12C is preferably housed in the top compartment 708A of the skid 700 where the door assembly 711 is located. A hermetic seal can be formed in the top compartment 708A of the skid 700 around all components of the centrifugal separator assembly 12C. The separation stator 180C acts as a containment shield and can withstand maximum forces associated with the failure of the separation rotor 180C at maximum speed or rpm. The top compartment 708A and the door assembly 711 act as a second containment shield and can also withstand maximum forces associated with the failure of the separation rotor 180C at maximum speed or rpm. Therefore, the skid 700 and centrifugal separator 12C together provide dual containment with two containment shields for enhanced safety. Dual containment is especially appropriate when dealing with potentially hazardous material, like viral, vaccine and clinical stage products and compositions.

The drive coupling 186C has one end coupled to the separation rotor 184C and the other end magnetically centered and coupled to the magnetic driver 148. The drive coupling 186C can be mechanically attached to the separation rotor 184C on one end. The drive coupling 186C can be made of metal, magnetic material or similar magnetics as those attached to the magnetic driver 148 so that the magnetic field generated by the magnets on the magnetic driver 148 can interact with, magnetically couple to and rotate the drive coupling 186C, which in turn rotates the separation rotor 184C.

The drive coupling 186C can be disposed within the separation stator 180C or outside of the separation stator 180C. The drive coupling 186C can also be disposed within a drive coupling sleeve 187C that is mounted to the separation stator 180C. The drive coupling sleeve 187C and/or the separation stator 184C can partially or fully form an aseptic seal and a hermetic seal around the drive coupling 186C, the separation rotor 184C and the separation container 190C so that no seals are required to create an airtight and watertight seal around the separation rotor 184C and the drive coupling 186C. The separation rotor 184C can then be driven magnetically by the drive coupling 186C and magnetic driver 148 without the need for seals between the drive coupling 186C and the magnetic driver 148 or the need for seals between the top and bottom compartments 708A, 708B of the skid 700. This configuration prevents contamination of the contents of the separation container 190C and components of the centrifugal separator assembly 12C and allows the operator to easily dispose of all or part of the centrifugal separator assembly 12C after use.

One or more magnets (not shown) can be mounted and attached to the drive coupling 186C. In exemplary embodiments, the drive coupling 186C is annular and partially or fully encircles an annular cavity. One or more magnets are secured to an interior surface of the cavity. The magnets can be a plurality of magnet sections that are spaced apart and secured to interior surface as to encircle cavity. In exemplary embodiments, the magnet can include at least 2, 4, 6, 12, 18, 24, or 30 separate magnet sections. Magnetic sections can be vertically orientated with respect to the axis of rotation, such that the poles of a magnetic section are axially oriented. The poles of each magnetic section are preferentially alternated in axially orientation. The magnet can also be a magnetic ring secured to and encircling the cavity. The magnetic ring can be dipole, quadripole, hexapole, or octapole, and the poles can be preferentially radially disposed. The one or more magnets can be made of one or more magnetic materials, including neodymium.

Other details of exemplary centrifugal separator assemblies 12, including drive couplings 186C, are described in related U.S. Provisional Patent Ser. No. 63/115,938, which is herein incorporated by reference in its entirety for all purposes.

The skid 700 is equipped with the loading assembly 800 to releasably load, mount, and lock the centrifugal separator assembly 12C to the skid 700. With reference to FIG. 49-52, the loading assembly 800 includes a housing 802 with a support 804 outwardly projecting from an upper end thereof. In one embodiment, support 804 can be annular and radially outwardly project from housing 802. Upstanding from support 804 in alignment with housing 802 is a tubular inner sleeve 806. An alignment plate 808 is secured at an upper end inner sleeve 806 and encircles a central opening 810. As best depicted in FIG. 52, receiver 812 is secured to and downwardly projects from an interior surface of alignment plate 808 in alignment with opening 810. Receiver 812 bounds a cavity 814 that communicates with opening 810. In one embedment, alignment plate 808 and central opening 810 are circular while cavity 814 has a cylindrical configuration.

Figure 50:
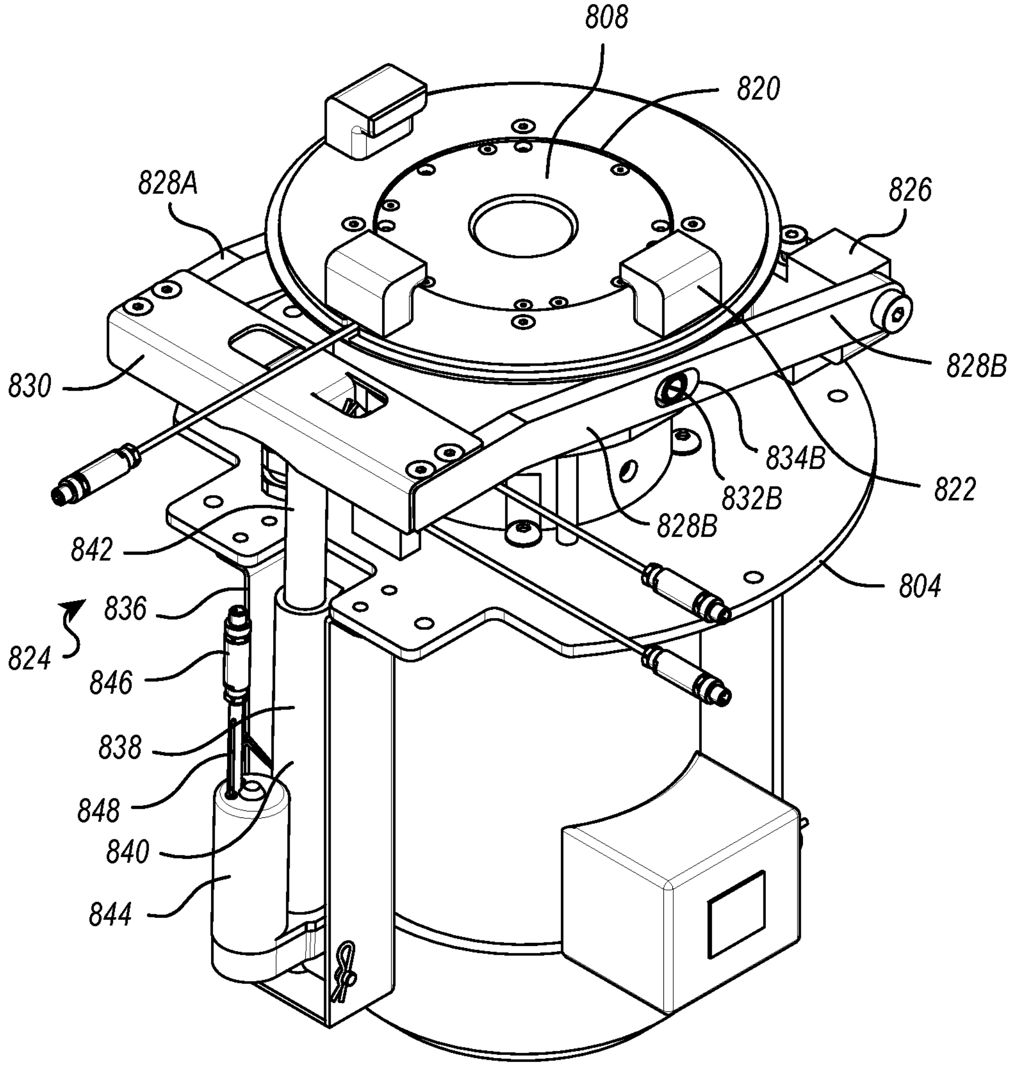
FIG. 50 is a front perspective view of the loading assembly shown in FIG. 49 in a raised position.

At least partially encircling inner sleeve 806 is amount 816. In one embodiment, mount 816 includes an outer sleeve 818 having an annular mounting plate 820 disposed at an upper end thereof. Both outer sleeve 818 and mounting plate 820 can completely or at least partially encircle inner sleeve 806 and can be circular. Mounting plate 820 can encircle and radially outwardly project a distance from outer sleeve 818. Disposed on and upwardly projecting from a top surface of mounting plate 820 is one or more mounting elements 822. In the depicted embodiments, one or more mounting elements 822 comprises three radially spaced apart clips 822A-C each having a substantially L-shaped configuration. As will be discussed below in greater detail, in alternative embodiments, one or more mounting elements 822 can have a variety of different configurations. Mount 816 is slidable relative to inner sleeve 806. Furthermore, mount 816/outer sleeve 118 has a height that is shorter than inner sleeve 806. As such, mount 816/outer sleeve 118 can be moved between a lowered position, as shown in FIG. 49, wherein mounting plate 820 is disposed at a lower elevation, and a raised position, as shown in FIG. 50, wherein the top surface of mounting plate 820 and alignment plate 808 can be disposed within substantially the same plane.

A lift assembly 824 is used for selectively moving mount 816 between the lowered and raised positions. Lift assembly 824 includes a pivot mount block 826 secured to and upstanding on support 804. A pair of pivot arms 828A and 828B each have a first end that is hingedly mounted to opposing ends of mount block 826. Pivot arms 828A and 828B project from mount block 826 so as to extend past opposing sides of mount 816/outer sleeve 118 to a second end of pivot arms 828A and 828B. A brace 830 extends between the second ends of pivot arms 828A and 828B. In this configuration, pivot arms 828A and 828B are disposed on opposing sides of mount 816/outer sleeve 118 while pivot mount block 826 and brace 830 are disposed on opposite opposing sides of mount 816/outer sleeve 118. Opening 834A and 834B are centrally formed on or extend through pivot arms 828A and 828B. Support pins 832A and 832B outwardly project from opposing sides of mount 816/outer sleeve 118 and are received within openings 834A and 834B, respectively. Openings 834A and 834B are sized/configured so that pivot arms 828A and 828B can be both supported by but pivot about support pins 832A and 832B. In one embodiment, opening 834A and 834B are elongated so that support pins 832A and 832B can also laterally slide a distance within opening 834A and 834B.

Downwardly projecting from support 804 in alignment with brace 803 is a mount bracket 836. Extending between a lower end of mount bracket 836 and brace 803 is a linear actuator 838. Linear actuator 838 generally includes a housing 840, a linear actuator rod 842 which can expand out of and retract into housing 840, and an electrical motor 844 that controls movement of linear actuator rod 842 relative to housing 840. Housing 840 is secured to mount bracket 836 while linear actuator rod 842 is secured to brace 836. Linear actuator 838 is electrically coupled to controller 798, which can control operation of linear actuator 838 either automatically or through manual or sensed prompts.

During operation, linear actuator 838 can be activated to raise linear actuator rod 842 which in turn lifts brace 830 and the second end of pivot arms 828A and 828B. Pivot arms 828A and 828B pivot on pivot mount block 826 and concurrently lift mount 816 through engagement with support pins 832. Mount 816 is lifted to a raised or unlocked position wherein mounting plate 820 is flush with alignment plate 808. When needed, linear actuator 838 can be activated to lower linear actuator rod 842 which then lowers mount 816 to a lowered or locked position where mounting plate 820 is disposed at an elevation below alignment plate 808.

A proximity sensor 846, mounted via a proximity sensor mount 848, can be positioned proximate to the pivot arms 828 and/or brace 830 to sense whether the linear actuator 838 is actuated up or down and whether the loading assembly 800 is in the locked or unlocked position.

Figure 51:
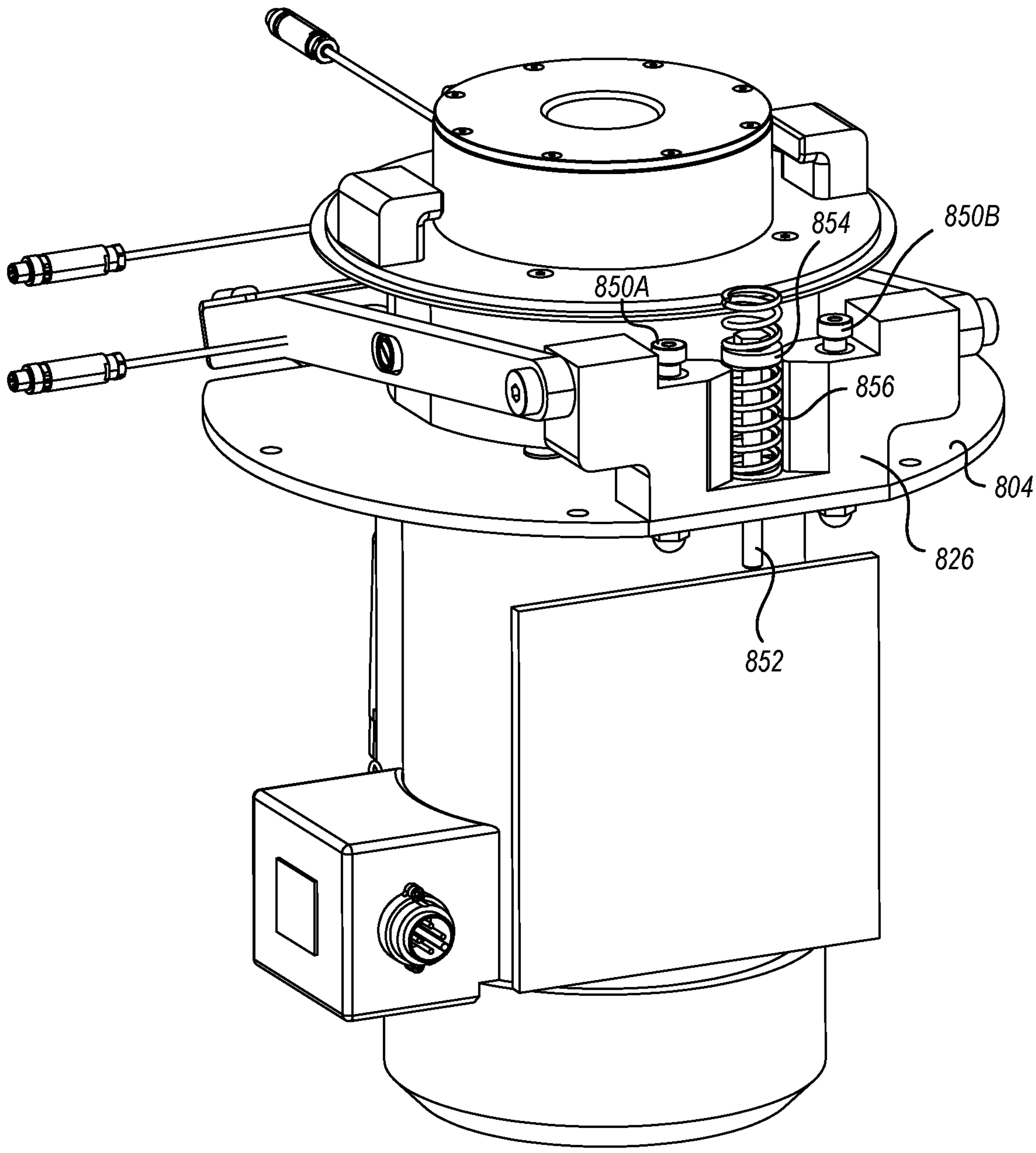
FIG. 51 is a rear perspective view of the loading assembly shown in FIG. 49.
Figure 52:
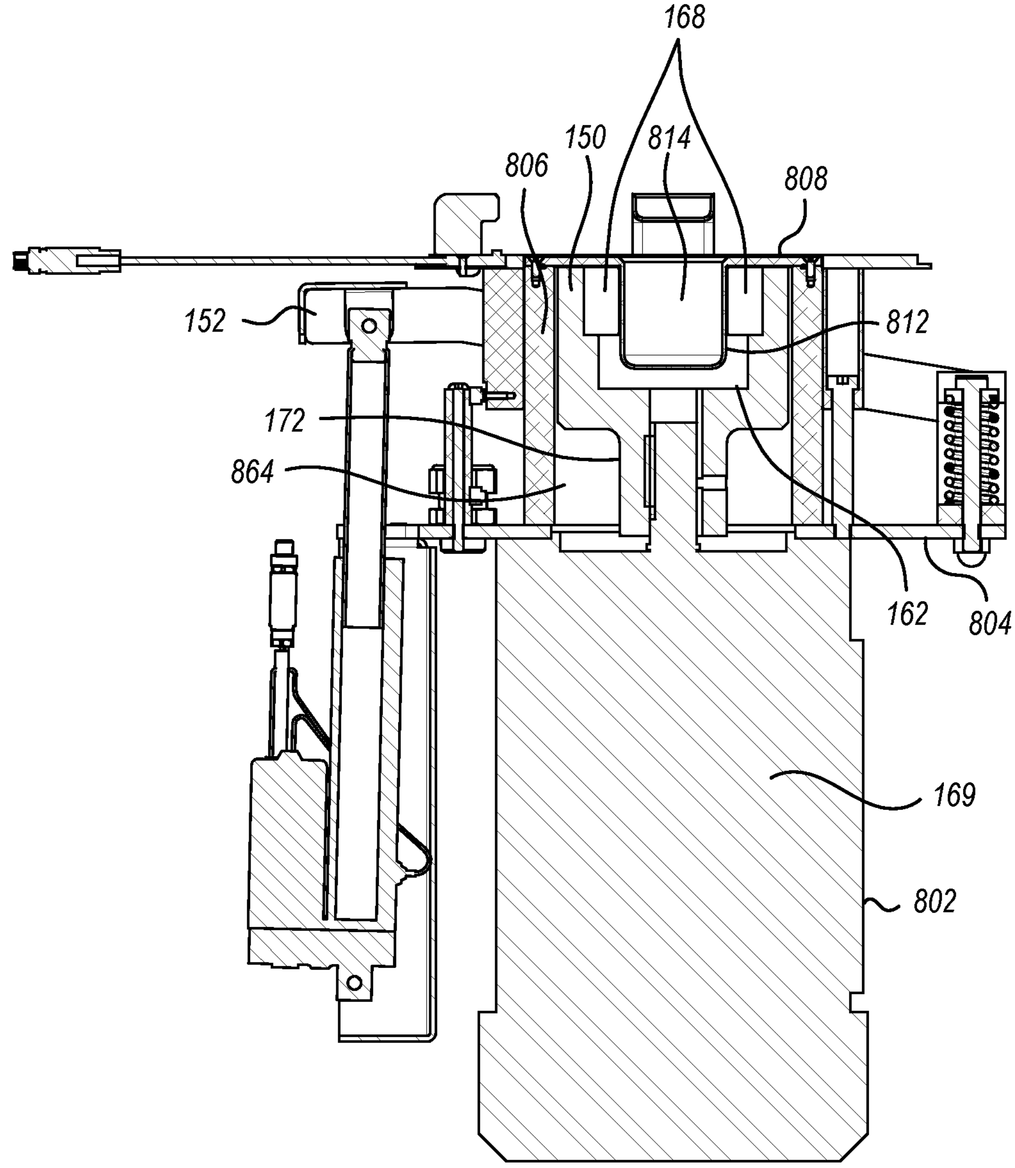
FIG. 52 is a cross sectional view of the loading assembly shown in FIG. 49.

Turning to FIG. 51, pivot mount block 826 can be spring loaded to enable resilient movement. Specifically, in one embodiment, pivot mount block 826 can be slidably secured to a pair of guide pins 850 which are secured to support 804 and pass through pivot mount block 826. A retention pin 852 is also secured to support 804 and freely passes through a portion of pivot mount block 826. An enlarged head 854 is formed at an upper end of retention pin 852 with a spring 856 encircling retention pin 852 and extending between enlarged head 854 and pivot mount block 826. Thus, as needed during movement of lift assembly 824, such as to prevent binding and overloading, pivot mount block 826 can resiliently slide upward along pins 850 and 852 and subsequently resiliently return to original positioning under the force of spring 856. Thus, the pivot mount block 826 moves in accordance with the spring rate, tension and force, which provides clearance between the mounting plate 820 and other components of the loading assembly 800 during lock-down of the centrifugal separator.

Figure 47:
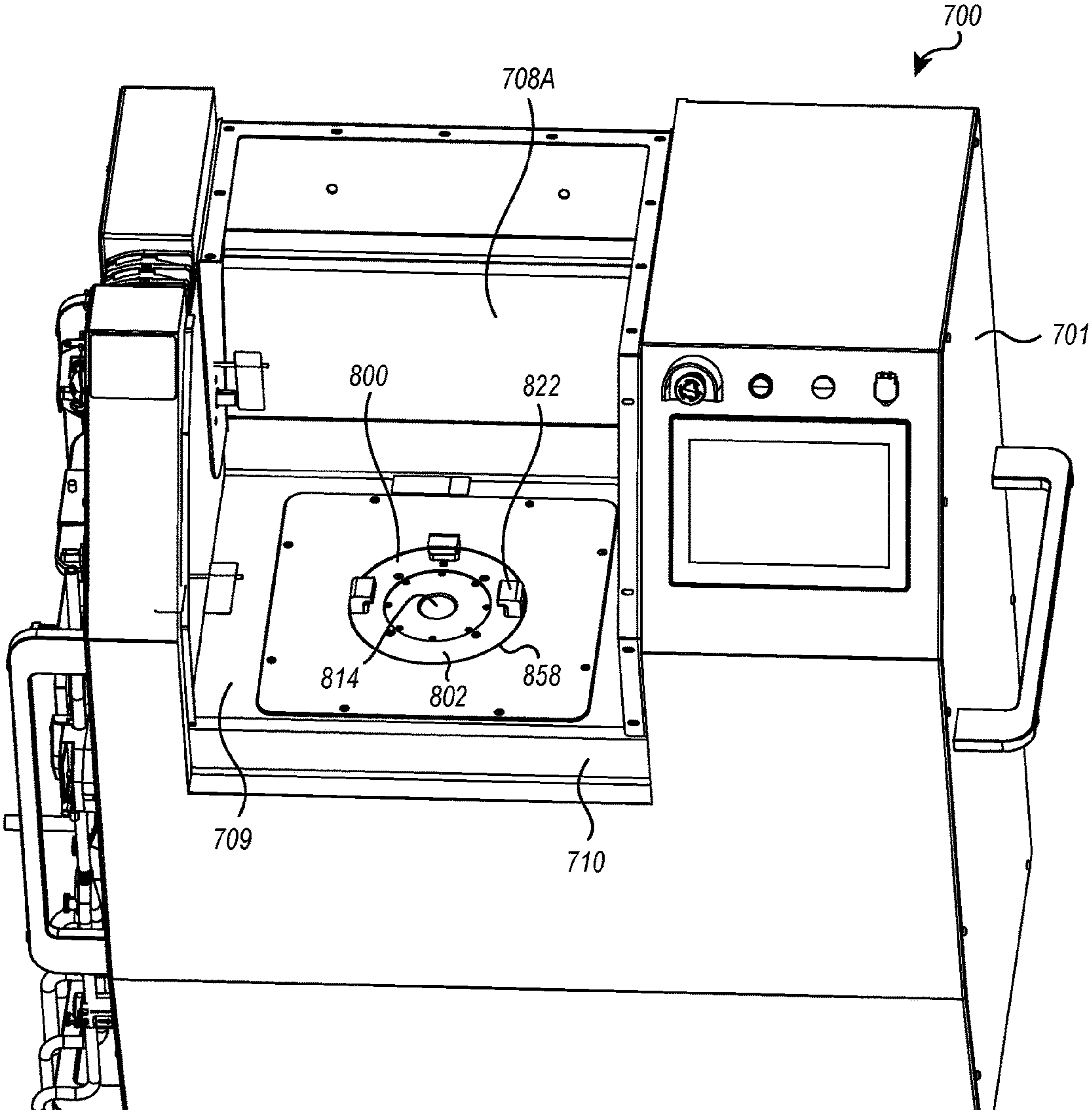
FIG. 47 is a front perspective view of the skid shown in FIG. 46 with the centrifugal separator removed.

Returning to FIGS. 47 and 48 an opening 858 extends through mounting platform 709 within top compartment 708A so as to communicate with bottom compartment 708B. Loading assembly 800 is secured within bottom compartment 708B such as by one or more brackets 860 extending between support 804 and platform 709 or some other portion of housing 701. Loading assembly 800 is positioned in alignment with opening 858 and so that the top surface of alignment plate 808 is substantially flush with the top surface of platform 709 within top compartment 708A. In this installed position, linear actuator 838 can again be activated to move loading assembly 800 between the raised or unlocked position, as shown in FIG. 47, or to the lowed and locked position as shown in FIG. 49.

Returning to FIG. 52, housed within loading assembly 800 is previously discussed magnetic driver 148. More specifically, magnetic driver 148 includes driver rotor 150 that is rotatably housed within an opening 864 encircled by inner sleeve 806. The drive rotor 150 can include sleeve 152 having one or more magnets 168 secured thereto, as previously discussed. Stem 172 projects from sleeve 152 and couples with motor 169 that is disposed within housing 802. In an exemplary embodiment, the motor 169 is 2 HP, 3 Phase, 230/460 VAC, 3600 RPM induction motor. The motor 169 can be housed within or at least partially housed within the bottom compartment 708B of the skid 700. The bottom compartment 708B can form a hermetic and aseptic seal around the motor 169, magnetic driver 148 or both. Motor 169 can be electrically coupled to and operated by controller 798 or can be otherwise manually controlled. Accordingly, operation of magnetic driver 150 facilitates rotation of drive rotor 150/one or more magnets 168 about receiver 812.

The one or more magnets 168 can be mounted and attached to the drive rotor 150 or the sleeve 152 of the drive rotor 150. As will be described in further detail, the magnet or magnets 168 are configured to create a magnetic field around components of the skid 700 that interacts with the separation rotor 184C and drive coupling 186C to magnetically couple, center and rotate the rotor 184C during loading and operation. Exemplary embodiments of the magnetic driver 148 are disclosed and described in U.S. Provisional Patent Ser. No. 63/115,938 (e.g., FIG. 8), which is herein incorporated by reference in its entirety for all purposes.

In exemplary embodiments, the drive rotor 150 and/or sleeve 152 is annular and partially or fully encircles an annular cavity or cup 162. The cavity of cup 162 can form part or all of a hermetic seal that prevents water ingress into component parts of the magnetic driver 148. One or more magnets are secured to an interior surface of the cavity 162. The one or more magnets 168 can be a plurality of magnet sections that are spaced apart and secured to the interior surface of drive rotor 150 and/or sleeve 152. In exemplary embodiments, one or more magnet 168 can comprise at least 2, 4, 6, 12, 18, 24, or 30 separate magnet sections. Magnetic sections can be vertically orientated with respect to the axis of rotation, such that the poles of a magnetic section are axially oriented. The poles of each magnetic section are preferentially alternated in axially orientation. The one or more magnet 168 can also be a magnetic ring secured to and encircling the cavity 162 of drive rotor 150 and/or sleeve 152. The magnetic ring can be dipole, quadripole, hexapole, or octapole, and the poles can be preferentially radially disposed. The one or more magnets 168 can be made of one or more magnetic materials, including neodymium.

In an exemplary embodiment, several magnets are circumferentially spaced and mounted in the annular cavity 162 of the drive rotor 150. In this and all other exemplary configurations, the magnet arrangement generates a magnetic field around the magnetic driver 148, mount 816, mounting plate 820, the cavity 814 and/or part of the mounting platform 709. When the drive coupling 186 is positioned within proximity of the magnetic field, a magnetic pull and/or vertical load-assist force loads the centrifugal separator assembly 12C, including separation rotor 184C and drive coupling 186C, to the skid 700 and centers the separation rotor 184C to the drive rotor 150.

The one or more magnets 168 mounted and attached to the drive rotor 150 or the sleeve 152 of the drive rotor 150 provide optimal centering of the separation rotor 184C during loading and torque during operation. The magnetic coupling between the drive rotor 150 and drive coupling 186C can be comprised of any magnetic pairing that provides sufficient torque to meet the process torque requirements. For example, torque requirements in one example embodiment range from 10 to 70 in-$lb_f$. Magnets can be comprised of material capable of carrying a permanent magnetic field on the rotor side and either a permanent magnet or electro-magnet on the motor side of the coupling. In exemplary embodiments, the magnets can be comprised of neodymium.

The magnetic driver 148 is coupled to the motor 844 and can be mounted to the skid 700 via the motor 169/housing 802, support 804 or via another surface of loading assembly 800. The magnetic driver 148, motor 169, and/or loading assembly 800 can be mounted to any surface of the skid 700, including the base 7022, panels (704, 705, 706, 707,) or mounting platform 709. In a preferred embodiment, the magnetic driver 148 and motor 169 coupled together are mounted to the bottom of the mounting platform 709 or to support 804 attached to the mounting platform 9. The motor 169 can be disposed partially or fully within the bottom compartment 708B of the skid 700. The mounting plate 820 and/or a portion of the drive rotor 150 can be mounted to extend through and past the opening 858 in the mounting platform 709. The mounting plate 820 and/or a portion of the drive rotor 150 can also be mounted to sit flush with the opening in the mounting platform 709.

One or more magnets 168 attached to the drive rotor 150 and/or sleeve 152 of the drive rotor 150 create a magnetic field proximate to and/or around the drive rotor 150, opening 810, mounting plate 820, receiver 812, cavity 814, and/or mounting platform 709. The strength and position of the magnetic field proximate to and/or around the drive rotor 150 opening 810, mounting plate 820, receiver 812, cavity 814, and/or mounting platform 709 can be varied to create a load-assist effect that draws the centrifugal separator assembly 12C and specifically the drive coupling 186C towards the cavity 814 and mounting plate 820.

In an exemplary method for loading the centrifugal separator assembly 12C on to the skid 800, load assembly 800 is moved to the raised, unlocked position as shown in FIG. 47. Mounting plate 820 is now flush with mounting platform 709 with mounting elements 822 upstanding therefrom. An operator or automated control system can open the door assembly 711 and place the centrifugal separator 12C on the mounting platform 709 proximate the mounting plate 820 (accessible through opening 885 in the mounting platform 9). Specifically, the lower end of driver sleeve 132C, as depicted in FIG. 23, is positioned on mounting platform 709 and is used to support separator assembly 12C. The mounting platform 709 provides a horizontal surface that allows horizontal translation/sliding of the centrifugal separator assembly 12C/driver sleeve 132C across the platform 709 and towards the cavity 814 and mounting plate 820. As the centrifugal separator assembly 12C is moved horizontally across the mounting platform 709 and/or placed close enough to the drive rotor 150, opening 858 or mounting plate 820 to encounter the drive rotor 150 magnetic field, a horizontal and/or downward vertical load-assist force draws the drive coupling 186C (FIG. 24) and the centrifugal separator 12C towards the cavity 814, mounting plate 820, drive rotor 150. As separator assembly 12C is moved toward mounting plate 820, separator assembly 12C can be orientated so that apertures 146 on driver sleeve 132C (FIG. 23) are orientated toward mounting elements 822 upstanding from mounting plate 820.

The magnetic field applies a downward vertical force to the drive coupling 186 and centrifugal separator 12C that helps to self-position and magnetically position the centrifugal separator assembly 12C for lockdown. Specifically, centrifugal separator 12C is manipulated and moved laterally on mounting platform 709 until mounting elements 822 are received within corresponding apertures 146 on driver sleeve 132C. The magnetic field assists with the horizontal movement and centering. The magnetic field and load-assist force also automatically and magnetically aligns the central axis of rotation of the separation rotor 184C with the central axis of rotation of the drive rotor 150. The driver sleeve 132C supports and alleviates the downward vertical force on the drive coupling 186 caused by the magnetic field during loading and as the centrifugal separator 12C is moved horizontally across the mounting platform 709.

Figure 53:
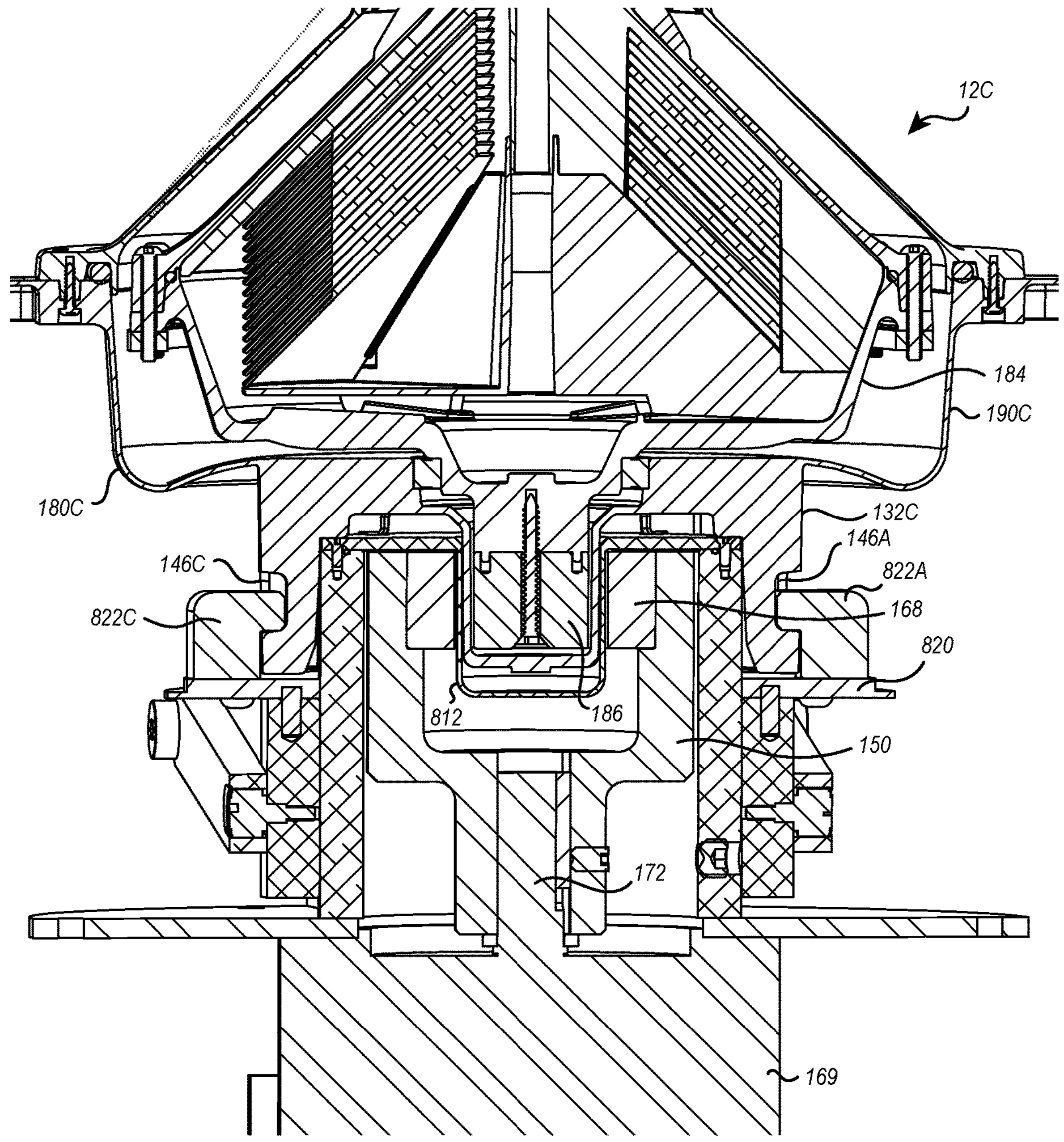
FIG. 53 is an enlarged cross sectional view of the loading assembly of FIG. 49 coupled with the centrifugal separator.

With reference to FIG. 53, after mounting elements 822 are received within corresponding apertures 146 on driver sleeve 132C and separation rotor 184C self-aligns with drive rotor 150 via the magnet and magnetic field, the centrifugal separator 12C can be locked down. Specifically, linear actuator 838 is actuated causing loading assembly 800/mount 816 move to the lowered, locked position, as previously discussed. In so doing, mounting plate 820 with mounting elements 822 and centrifugal separator 12C disposed thereon is lowered below mounting platform 709 which causes drive coupling 186 to be directly received within cavity 814 of receiver 812. In turn, drive coupling 186 is encircled or laterally aligned with the one or more magnets 168 attached to the drive rotor 150. This positioning optimizes the magnetic force of the one or more magnets 168 on drive coupling 186 so as to optimize rotation of separation rotor 184C. Furthermore, as loading assembly 800/mount 816 moves to the lowered, locked position, base 190C of separation stator 180C butts against a portion of mounting platform 709 so as to effectively lock centrifugal separator 12C to skid 700, i.e., mounting elements 822 received in apertures 146 are pulling down on driver sleeve 132C while mounting platform 709 pushes upward against base 190C of separation stator 180C. Linear actuator 838 holds loading assembly 800 in this lowered, locked position during operation of centrifugal separator 12C. Here it is again appreciated that the spring loading of the pivot mount block 826, as previously discussed, prevents over loading of centrifugal separator 12C during the locking process and operation of centrifugal separator 12C.

It is appreciated that a variety of alternative structures can be used to facilitate engagement between mounting elements 822 and driver sleeve 132C. For example, mounting elements 822 could be replaced with a single semi-circular L-shaped member that is received within a corresponding notch on driver sleeve 132C. In other embodiments, one or more extensions could outwardly extend from driver sleeve 132C and be received within notches or openings formed on one or more mounting elements 822. In other embodiments, different types of fasteners or clamps could be used to secure mounting elements 822 to driver sleeve 132C. Thus, driver sleeve 132C can be formed with one or more flanges, elbows, cavities, slots or recesses for engagement with mounting elements 822. The present design, however, has unique benefits in that it facilitates and easy lateral sliding connection.

Once operation of centrifugal separator 12C is completed, the linear actuator 838 can be used to move loading assembly 800 back to raised, unlocked position and to enable removal of centrifugal separation 12C from skid 700 in the reverse process of how it was attached. It is appreciated that due to the strong magnetic force, manual separation of centrifugal separation 12C from drive rotor 150 would be difficult when drive coupling 186 is received within receive 812 and engaged with one or more magnets 168. As such, skid 700 and loading assembly 800 has the unique benefit of using a mechanic force to at least partially separate centrifugal separation 12C from drive rotor 150 before having to manually manipulate centrifugal separation 12C.

Figure 54:
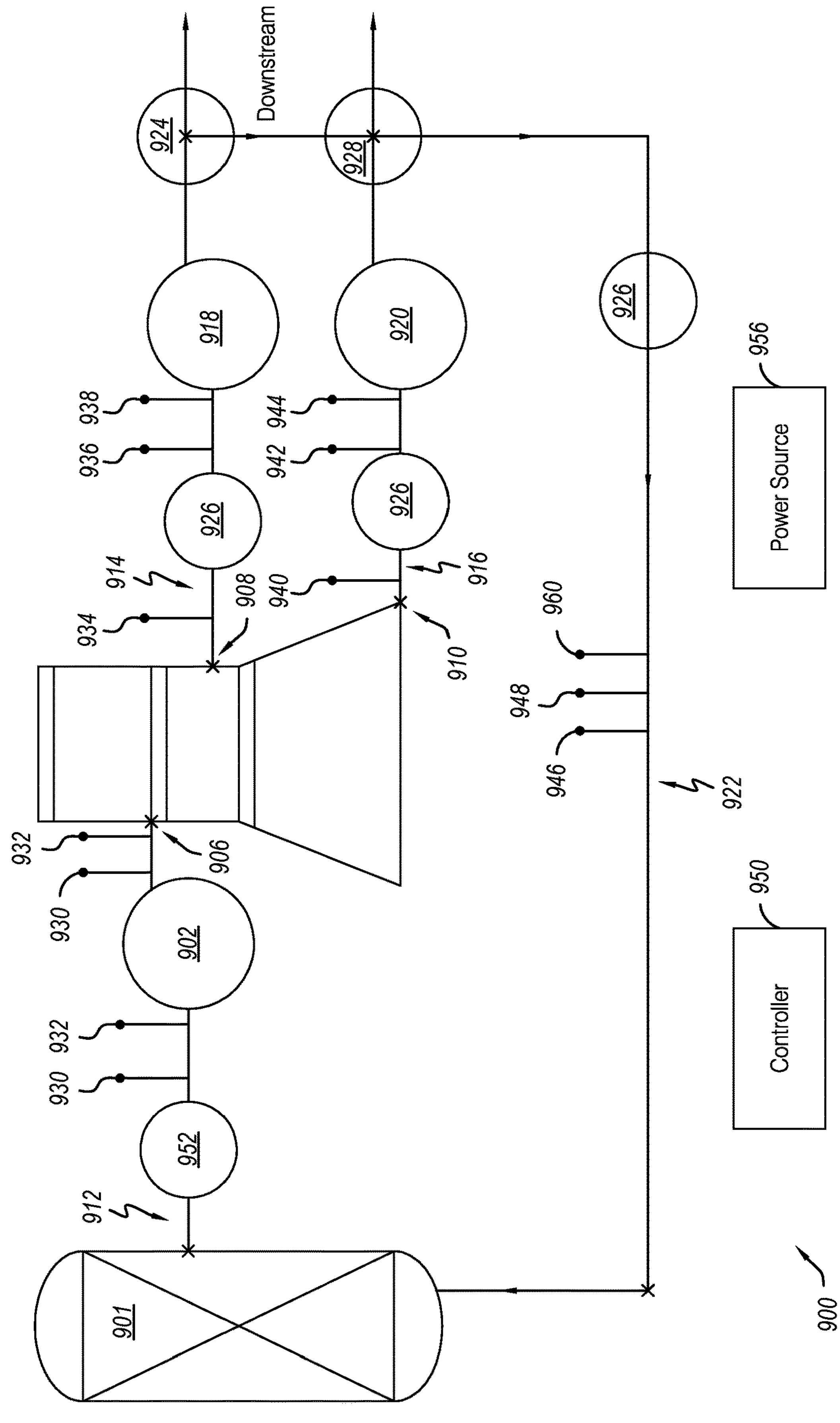
FIG. 54 is a schematic representation of an exemplary centrifugal separator skid integrated in an exemplary bio-production process.

FIG. 54 is a schematic representation of an exemplary centrifugal separator skid 900 integrated in an exemplary bioproduction process including a bioproduction vessel 901. The bioproduction vessel 901 can be any bioproduction vessel, including but not limited to, mixers, cell factories, bioreactors, fermenters, lab and bench scale vessels and other vessels that can feed fluid, solid or mixed phase biocomponents to the skid 900 for separation. The skid 900 can include an inlet pump 902, a centrifugal separator assembly 904, an inlet line-set 912, a light outlet line-set 914, a heavy outlet line-set 916, a light outlet pump 918, a heavy outlet pump 920, a recycle line-set 922, a series of valves 924, 926, 928, a series of sensors 930-948, 960, a controller 950, a programable power source 956 and other process equipment and components described with respect to FIGS. 43-46.

The centrifugal separator assembly 904 can be the same centrifugal separator 12 and alternatives discussed herein, including all component parts and equipment, described herein or anyone of the centrifugal separators disclosed and described in related U.S. Provisional Patent Ser. No. 63/115,938, which is herein incorporated by reference in its entirety for all purposes. As previously described, the centrifugal separator assembly 904 can have an inlet port 906, a light outlet port 908 and a heavy outlet port 910. The ports 906, 908, 910 are fluidly coupled to and in communication with an internal chamber or separation container 190C of the separation rotor 184C (shown in FIG. 48) where biocomponents are separated.

The inlet line or line-set 912 connects the bioproduction vessel 901, the inlet line valve 952, inlet pump 902, and the inlet port 906 of the centrifugal separator assembly 904. The inlet line valve 952 can be positioned upstream or downstream from the inlet pump 902 and can be actuated to block or flow biocomponents to the inlet port 910 of the centrifugal separator assembly 904 for separation. The inlet pump 902 is used to pump and flow liquids, solids, gases and mixed phased biocomponents from the bioproduction vessel 901, through the inlet line-set 912, the inlet line valve 952 and to the centrifugal separator assembly 904. The inlet pump 902 can be a centrifugal pump or a positive displacement pump, such as peristaltic pump. Preferably, the inlet pump 902 is a single-use, disposable centrifugal pump.

The light outlet line-set 914 connects the light outlet port 908 of the centrifugal separator assembly 904, the light outlet pump 918, the light recycle valve 924 and the recycle line-set 922. Lighter components separated in the centrifugal separator assembly 904 naturally flow and are routed through the light outlet port 908 and light outlet line-set 914 during operation of the centrifugal separator assembly 904. The light outlet line-set 914 can include a light recycle valve 924 positioned at a split in the light outlet line-set 914. The light recycle valve 924 can be actuated to flow and route light biocomponents separated in the centrifugal separator assembly 904 downstream from the skid 900 for further processing, harvesting and removal. The light recycle valve 924 can also be actuated to flow and route light biocomponents separated in the centrifugal separator assembly 904 through the recycle line-set 922 and back to the bioproduction vessel 901.

The light outlet pump 918 can be driven (by electrical motor or other means) to pump light biocomponents separated in the centrifugal separator assembly 904 downstream from the skid 900 for further processing or through the recycle line-set 922 for recycling to the bioproduction vessel 901. The light outlet pump 918 can also act as a stop valve for the light outlet line-set 914 by reversing the operation and flow through the pump 918 to prevent any biocomponents from flowing past the pump 918. The light outlet pump 918 can be a centrifugal pump or a positive displacement pumps, such as peristaltic pump. Preferably, light outlet pump 918 is a single-use, disposable peristaltic pump.

The heavy outlet line-set 916 connects the heavy outlet port 910 of the centrifugal separator assembly 904, the heavy outlet pump 920, the heavy recycle valve 928, and the recycle line-set 922. Heavier components separated in the centrifugal separator assembly 904 naturally flow and are routed through the heavy outlet port 910 and heavy outlet line-set 916 during operation of the centrifugal separator assembly 904. The heavy outlet line-set 916 can include a heavy recycle valve 928 positioned at a split in the heavy outlet line-set 916. The heavy recycle valve 928 can be actuated to flow and route heavy biocomponents separated in the centrifugal separator assembly 904 downstream from the skid 900 for further processing, harvesting and removal. The heavy recycle valve 928 can also be actuated to flow and route heavy biocomponents separated in the centrifugal separator assembly 904 through the recycle line-set 922 and back to the bioproduction vessel 901.

The heavy outlet pump 920 can be driven (by electrical motor or other means) to pump heavy biocomponents separated in the centrifugal separator assembly 904 downstream from the skid 900 for further processing or through the recycle line-set 922 for recycling to the bioproduction vessel 901. The heavy outlet pump 920 can also act as a stop valve for the heavy outlet line-set 916 by reversing the operation and flow through the pump 920 to prevent any biocomponents from flowing past the pump 920. The heavy outlet pump 920 can be a centrifugal pump or a positive displacement pumps, such as peristaltic pump. Preferably, heavy outlet pump 920 is a single-use, disposable peristaltic pump.

The exemplary centrifugal separator skid 900 and line-sets 918, 920, 922, 958 can be equipped and coupled with a series of sensors 930-948, 960 for measuring process parameters at various locations within the skid 900. For example, inlet pressure sensors 930 can measure the pressure in the inlet line-set 912 upstream or downstream from the inlet pump 902 and upstream from the centrifugal separator assembly 904. Inlet flow sensors 932 can measure the flow rate of biocomponents upstream or downstream from the inlet pump 902 and upstream from the centrifugal separator assembly 904.

The light outlet line set 914 is equipped with sensors that measure process parameters and send signals to the controller 950 for process control functions. For example, a light line-set pressure sensor 934 can measure the pressure downstream from the centrifugal separator assembly 904 and upstream from the light outlet pump 918. A light line-set turbidity sensor 936 can measure the turbidity downstream from the centrifugal separator assembly 904 and upstream from the light outlet pump 918. A light line-set flow sensor 938 can measure the flow rate of biocomponents in the light outlet line-set 914 downstream from the centrifugal separator assembly 904 and upstream from the light outlet pump 918.

The heavy outlet line set 916 is also equipped with sensors that measure process parameters and send signals to the controller 950 for process control functions. For example, a heavy line-set pressure sensor 940 can measure the pressure downstream from the centrifugal separator assembly 904 and upstream from the heavy outlet pump 920. A heavy line-set turbidity sensor 942 can measure the turbidity downstream from the centrifugal separator assembly 904 and upstream from the heavy outlet pump 920. A heavy line-set flow sensor 944 can measure the flow rate of biocomponents in the heavy outlet line-set 916 downstream from the centrifugal separator assembly 904 and upstream from the heavy outlet pump 920.

The recycle line set 922 is also equipped with sensors that measure process parameters and send signals to the controller 950 for process control functions. For example, a recycle line pressure sensor 946 can measure the pressure in the recycle line-set 922. A recycle line flow sensor 948 can measure the flow rate of biocomponents in the recycle line-set 922. A recycle line turbidity sensor 960 can measure the turbidity in the recycle line-set 922. The series of exemplary sensors 930-948, 960 can be positioned at multiple locations along the line-sets 918, 920, 922 and upstream and downstream from the process equipment of the skid 900, including the pumps 902, 918, 920 and centrifugal separator assembly 904. Preferably, the exemplary sensors 930-948, 960 are single use, disposable sensors that are easily mounted, removed and replaced on the skid 900. In addition to pressure, flow and turbidity sensors, the skid 900 can be equipped with conductivity sensors, $O_2$ sensors, $CO_2$ sensors, pH sensors, temperature sensors, proximity sensors, rpm sensors and other sensors selected by the operator and necessary for the bioproduction process.

The skid can also be equipped with one or more emergency shut-off valves 926 throughout the skid 900, including upstream from the inlet pump 902, coupled to the light outlet line-set 914 or heavy outlet line-set 916 downstream from the centrifugal separator assembly 904, downstream from the light and heavy outlet pumps 918, 920, coupled to the recycle line-set 922 or at other locations to prevent biocomponents from flowing through line and process equipment.

The exemplary valves 924, 926, 928, 952 equipped on the skid can be controlled by a valve control system 760 described in reference to FIG. 48. The valve control system 760 can include a flow control valve 726, tubing 725, a valve terminal 739 and a fieldbus node 747. The valve control system 760 can be a pneumatic control system and the valves 924, 926, 928, 952 can be pneumatic pinch valves or pinch clamps equipped. The valve control system 760 can also be an electrical control system and the valves 924, 926,

928, 952 can have solenoid elements for opening and closing various ports on the valves and optical digital position feedback sensors for detecting whether the ports are open or closed. In exemplary embodiments, the valves 924, 926, 928, 952 include snap-in tube slots for quick loading and unloading of tubing into and out of the valves.

The valve terminal 739 (shown in FIG. 48) can include a communications port, communications link, a circuit board, and a manifold with multiple ports electrically or pneumatically coupled to inlet and outlet ports of the valves 924, 926, 928, 952. In an exemplary embodiment, the communications port and link can be an I/O port and link coupled to a fieldbus node 747. The valve terminal 739, fieldbus node 747 can be in wired or wireless communication with a controller 950 that controls the actuation of the valves 924, 926, 928, 952 with electrical signals or pneumatic pressure applied through the valve terminal 39 and manifold based on process parameters measured by the sensors 930-948, 960. The valve control system 60 and controller 950 can use a specific communications protocol to facilitate data and electrical signal transmission between the valve terminal 739, fieldbus node 747, valves 924, 926, 928, 952 and the controller 950. In an exemplary embodiment, the communications protocol is Profinet.

The controller 950 equipped on the skid 900 can include a programmable processor and non-transitory memory programmed to actuate the valves 924, 926, 928, 952 and supply power to pumps 902, 918, 920, the centrifugal separator assembly 904, valve control system 760 and other process equipment through a programable power source 956 based on process parameters measured by sensors 930-948, 960. The controller 950 can be in wired or wireless communication with the exemplary sensors 930-948, 960, valve terminal 739 (shown in FIG. 48), the pumps 902, 918, 920 and associated motors, and the motor 169 (shown in FIG. 48) that drives the centrifugal separator assembly 904. The controller 950 can receive and convert signals received from the sensors 930-948, 960 into readable process parameters. The signals are indicative of process parameters, such as pressure, flow rate, turbidity, density, temperature, pH, motor power, rotor rpms, $O_2$ concentration and/or $CO_2$ concentration throughout the skid 900, line-sets 912, 914, 916, 922 and process equipment on the skid 900. The controller 950 can automatically actuate, open and close exemplary valves 924, 926, 928, 952 equipped on the skid 900 based on the process parameter signals measured and transmitted by the sensors 930-948, 960 and read and translated by the controller 950. The controller 950 can also automatically control the programable power source 956 to increase or decrease power to the pumps 902, 918, 920, the centrifugal separator assembly 904 and/or associated motors based on the process parameter signals measured and transmitted by the sensors 930-948, 960 and read and translated by the controller 950.

In an exemplary embodiment, separation rotor 184C (shown in FIG. 48) of the centrifugal separator assembly 904 is coupled to an rpm sensor (e.g., accelerometer) proximate the separation rotor 184C to measure the rotations per minute and/or rotational speed of the separation rotor 184C. The controller 950 can automatically control the programable power source 956 to increase or decrease power to the motor 169 (shown in FIG. 48), and in-turn, increase or decrease the rotational speed of the separation rotor 184C based on process parameter signals measured and transmitted by the sensors 930-948, 960 and received, read and translated by the controller 950.

Figure 55A:
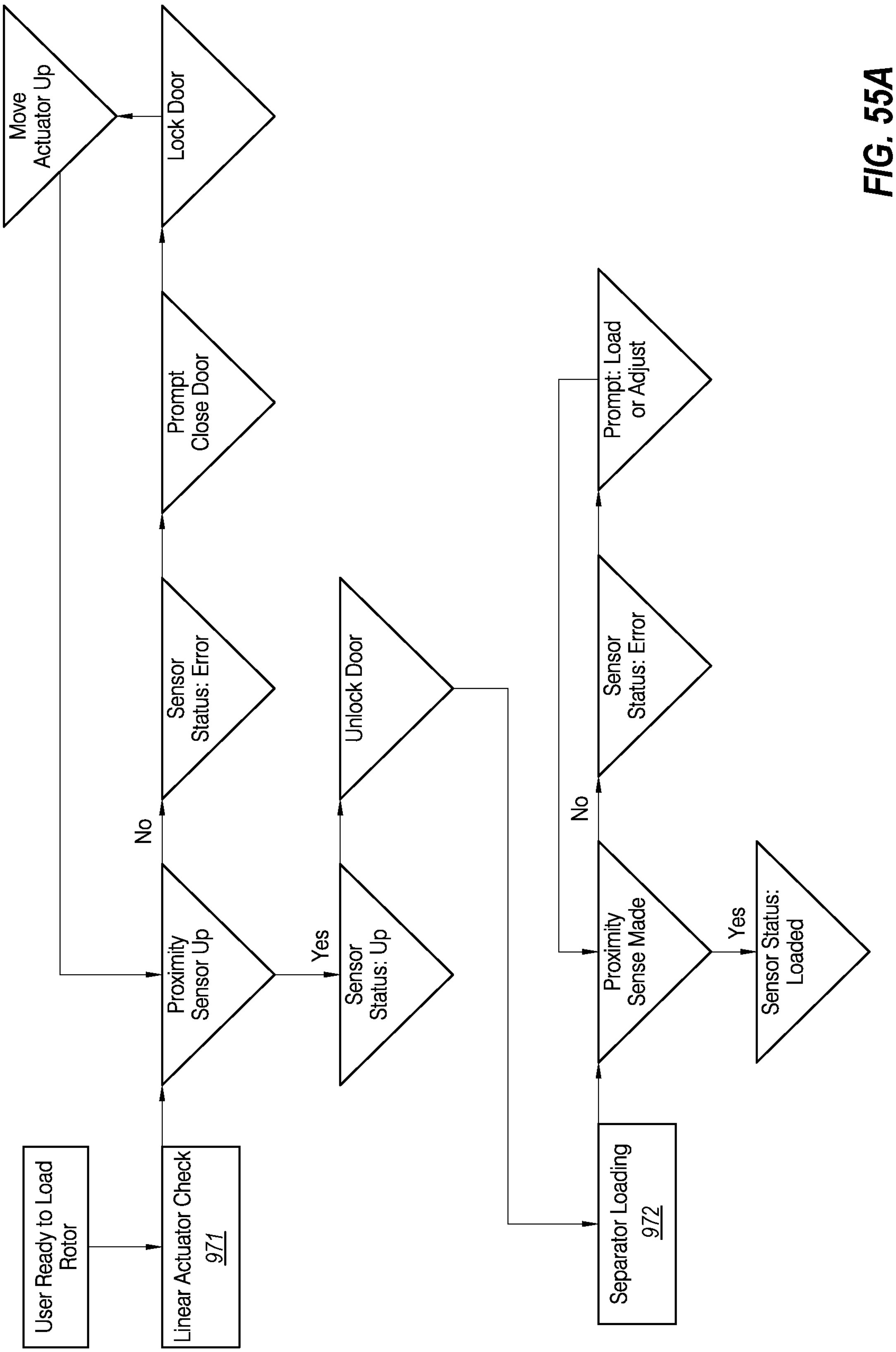
FIGS. 55A-55C illustrate a process flow diagrams of exemplary processes for operating an exemplary centrifugal separator skid.
Figure 55B:
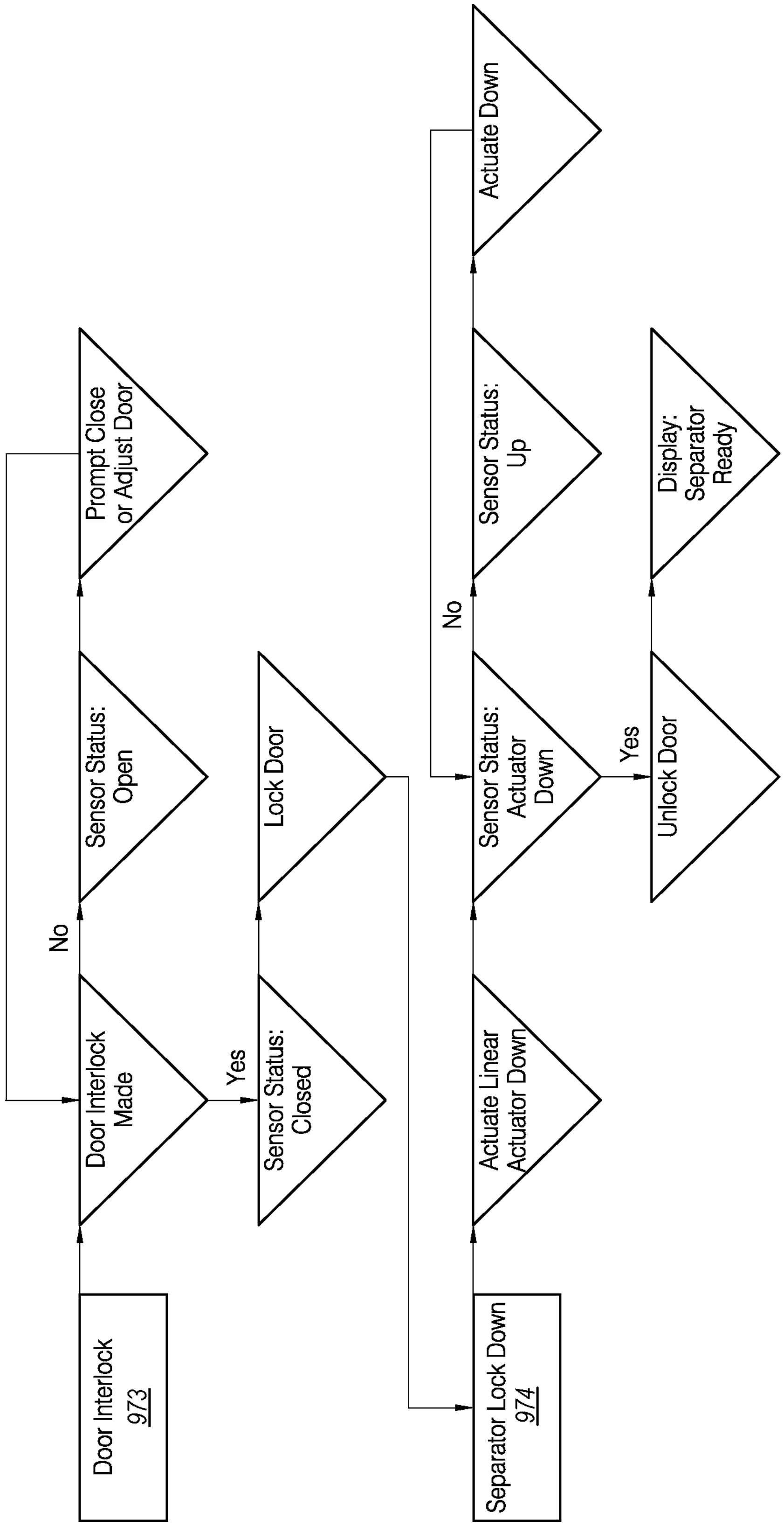
Figure 55C:
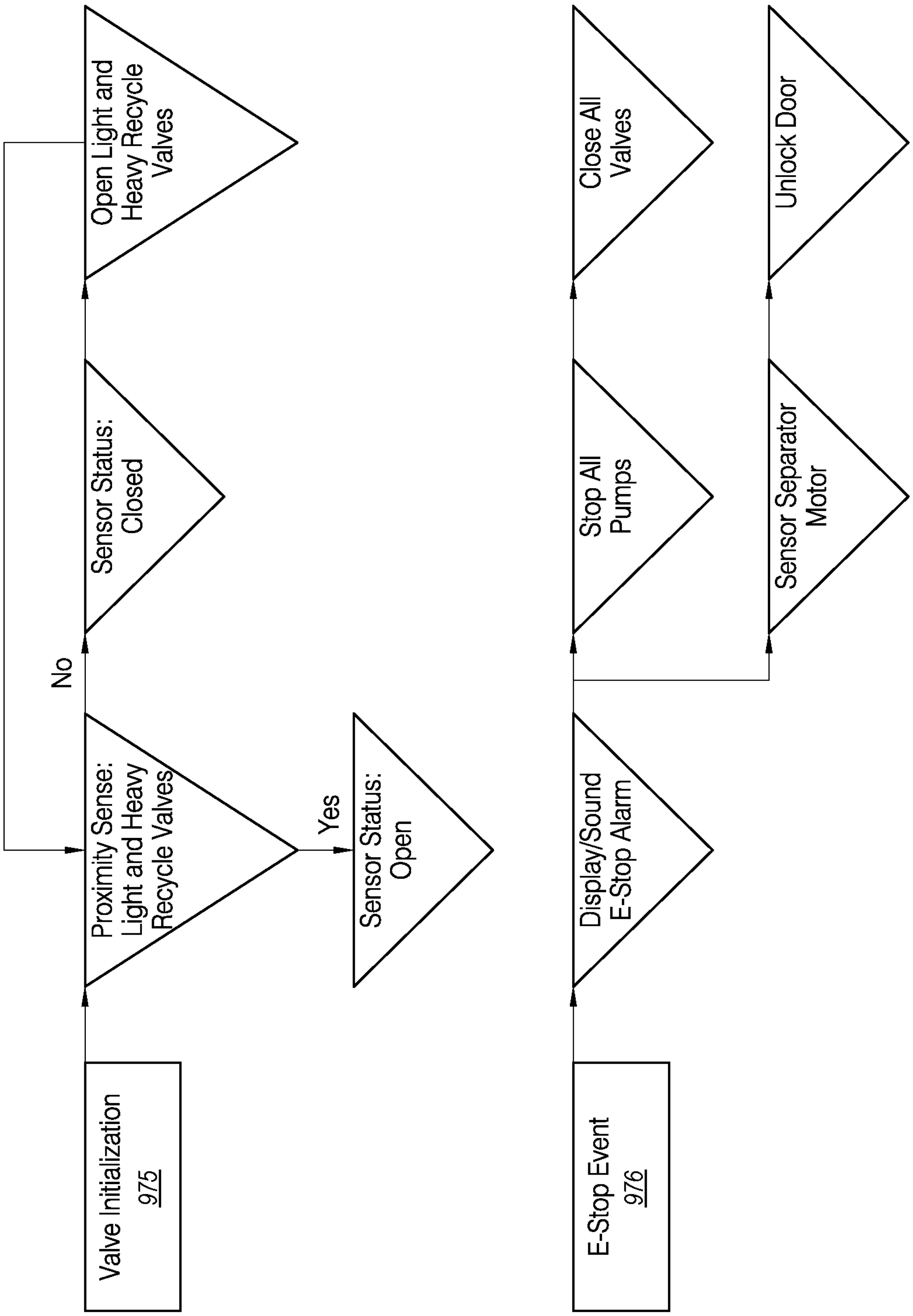

FIGS. 55A-55C illustrate process flow diagrams of exemplary operations for loading and locking down the centrifugal separator skid (700, 900), initializing the valves (924, 926, 928, 952), interlocking the door assembly (711) and performing an emergency system stop operation. The exemplary operations and processes can be run by a controller (798, 950) that includes a programmable processor and non-transitory memory programmed to automatically run start-up, separation, discharge, recycle and downs stream operations of the exemplary process. Aspects of the process can also be manually operated. As described in reference to FIGS. 45 and 54, the controller (798, 950) can be in wired or wireless communication with a programmable power source (733), the valves (924, 926, 928, 952), valve control system (760), sensors (930-948, 960), pumps (721, 748, 749, 902, 918, 920), motors (108, 169) and actuators (838) equipped on the exemplary centrifugal separator skids (700, 900). The controller (798, 950) is programmed to run start-up, separation, discharge, recycle and downs stream operations of the exemplary process by actuating, opening, closing, moving and/or supplying signals or power to valves, motors, pumps, the centrifugal separator, linear actuator and other equipment on the skid (700, 900).

The controller (798, 950) is programmed to request data and signals from all sensors in the system, including proximity sensors located at and coupled to the centrifugal separator skid (700, 900), the valves (924, 926, 928, 952) and the door assembly (711) to determine if equipment has been loaded, locked down and configured properly for operation.

Centrifugal Separator Loading and Lockdown Operations

With reference to FIG. 55A, the centrifugal separator skids (700, 900) of FIGS. 42-44 and 54, the controller (798, 950) is programmed to run a centrifugal separator loading operation by conducting the following steps.

At step 971, the controller (798, 950) is programmed to run control logic that triggers a proximity sensor to sense whether the linear actuator (838) is actuated in the up and unlocked position or the down and locked position. If the linear actuator (838) is in the down and locked position, the control logic can display an error message and prompt the user or automatically close and lock the door assembly (711). The control logic can send a signal to the linear actuator (838) to actuate into the up and unlocked position, triggering an output or notification via the digital display unit (762) that indicates that the linear actuator (838) is in the unlocked and up position. At this time, the control logic initiated by the controller (798, 950) can unlock the door assembly (711) for loading the centrifugal separator assembly (12, 904).

At step 972, the door assembly (711) can be manually or automatically opened and the centrifugal separator assembly (12, 904) can be loaded, which triggers a proximity sensor to sense whether the centrifugal separator assembly (12, 904) is loaded and centered properly. The centrifugal separator assembly (12, 904) can be magnetically loaded and centered as described with respect to FIGS. 49-53. If the centrifugal separator assembly (12, 904) is not loaded properly, the controller (798, 950) can display an error message on the digital display unit (762) and prompt the user to adjust the centrifugal separator assembly (12, 904). A notification and display can be provided when the assembly (12, 904) is properly loaded.

With reference to FIG. 55B at step 973, the operator can be prompted to close the door assembly (711), or the door assembly (711) can be automatically closed, which triggers a proximity sensor to sense whether the door assembly (711)

achieves proper interlock. If the door assembly (711) does not achieve proper interlock, the digital display unit (762) can provide a notification that the door is open or not locked and prompt the user or automatically to adjust the door assembly (711) for proper interlock. Once proper interlock is achieved, the digital display unit (762) can provide a notification that interlock has been achieved.

At step 974, once the door assembly (711) is locked, a control logic is initiated by the controller (798, 950) that moves the linear actuator down and into the locked position to lock the centrifugal separator assembly (12, 904) to the skid (700, 900). This triggers a proximity sensor to sense whether linear actuator (838) is in the down and locked position, and if not, to provide a display that the linear actuator is up. The controller (798, 950) can actuate the linear actuator (838) to continue movement of the linear actuator (838) down. Once the centrifugal separator assembly (12, 904) is locked down to the skid (700, 900), the control logic can provide a display that the separator is locked down and ready for start-up, separation, discharge, recycle and downs stream operations.

With reference to FIG. 55C at step 975, a valve initialization process can be run by a control logic initiated by the controller (798, 950) that triggers proximity sensors associated with light and heavy recycle valves (924, 928) to sense whether the valves are actuated to recycle biocomponents back to the bioproduction vessel (901). If the recycle valves (924, 928) are not actuated to recycle biocomponents back to the bioproduction vessel (901), the digital display unit (762) can provide a notification that the valves are not open or configured to recycle. A control logic initiated by the controller (798, 950) can automatically actuate the recycle valves (924, 928) to recycle biocomponents back to the bioproduction vessel (901). Once the recycle valves (924, 928) are actuated to recycle mode, the digital display unit (762) can provide a notification that the valves are open or in recycle mode.

Figure 56:
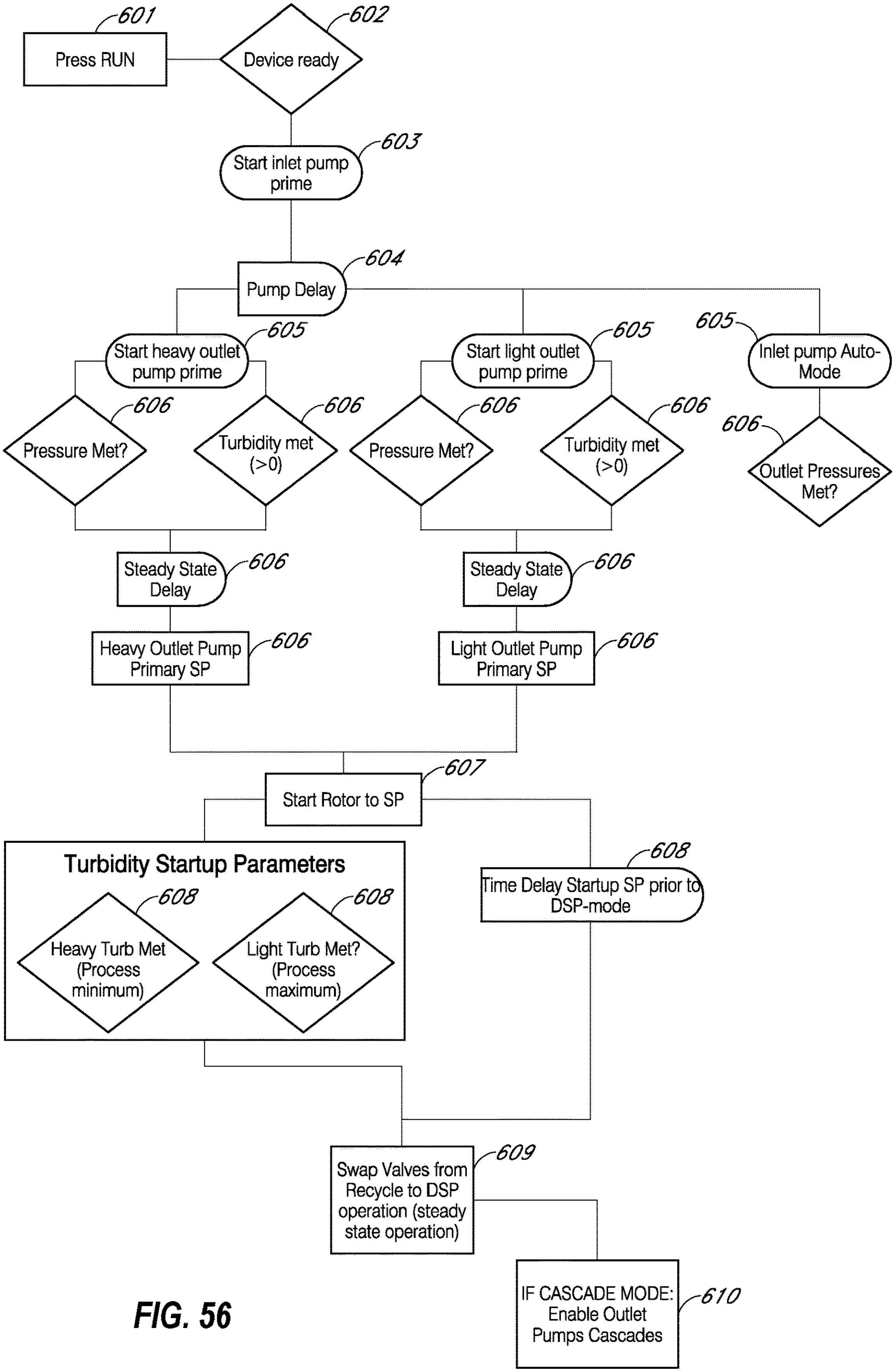
FIG. 56 illustrates a process flow diagram of an exemplary process for operating an exemplary centrifugal separator skid.

FIG. 56 illustrates a process flow diagram of an exemplary process for operating an exemplary centrifugal separator skid (700, 900). The exemplary process can be run by a controller (798, 950) described herein that includes a programmable processor and non-transitory memory programmed to automatically run start-up, separation, discharge, recycle and downs stream operations of the exemplary process. As discussed in reference to FIGS. 45 and 54, the controller (798, 950) can be in wired or wireless communication with a programmable power supply (733, 956), the valves (924, 926, 928, 952), valve control system (760), sensors (930-948, 960), pumps (721,748, 749, 902, 918, 920), motors (108, 169) and actuators (838) equipped on the exemplary centrifugal separator skids (700, 900). The controller (798, 950) is programmed to run start-up, separation, discharge, recycle and downs stream operations of the exemplary process by actuating, opening, closing, moving and/or supplying signals or power to valves, pumps, the centrifugal separator, linear actuator and other equipment on the skid (700, 900). With reference to the centrifugal separator skids (700, 900) of FIGS. 42-54, the controller (798, 950) is programmed to run a start-up operation by conducting the following steps.

Centrifugal Separator Start-Up Operation

At step 601, the operator can supply a RUN or START input through a user input and digital display unit 762 (shown in FIG. 42) of the skid (700, 900) that is in wired or wireless communication with the controller (798, 950), or the operator can actuate an on-switch of the skid (700, 900).

At step 602, the controller (798, 950) can provide a device ready output or notification via the user input and digital display unit (762) that indicates that the inlet pump (721, 902) can be primed.

At step 603, a control logic is initiated by the controller (798, 950) that starts the inlet pump (721, 902) by providing power to the motor of the inlet pump (721, 902). If the proper ports of the valves (924, 926, 928, 952) are not already open, the controller (798, 950) can be programmed to open and/or actuate valves (924, 926, 928, 952) and create a fluid path from the bioprocess vessel (901), to the centrifugal separator assembly (12, 904) and through light and heavy outlet line-sets (36, 44, 52, 914, 916, 958) downstream from the centrifugal separator assembly (12, 904). The controller (798, 950) can be programmed to arrange the valves (924, 926, 928, 952) in accordance with a default start-up valve position and mode. In an exemplary embodiment, the default position of the valves (924, 926, 928, 952) prior to start-up creates a flow path from the bioproduction vessel (901), to the centrifugal separator assembly (12, 904), through the light and heavy outlet line-sets (36, 44, 52, 914, 916) and through a recycle line-set (922) leading back to the bioprocess vessel (901). The start-up of the inlet pump (721, 902) flows fluid, that may or may not include biocomponents and/or solids for separation, from the bioprocess vessel 901 and through the inlet pump (721, 902) to prime the inlet pump (721, 902). The controller can be programmed to actuate the valves (924, 926, 928, 952) to route fluid through the centrifugal separator assembly (12, 904) and thought the recycle line set 922 (shown in FIG. 54). The flow of fluid through the system primes the pump and pushes gas out of the system. Fluid, gas or biocomponents can be recycled back to the bioprocess vessel 901 during priming of the inlet pump (521, 902).

At step 604, a control logic is initiated by the controller (598, 950) that time-delays the start-up of light and heavy outlet pumps (36, 44, 52, 918, 920) for a short duration (e.g., 2-10 seconds) or until the inlet pump (721, 902) is primed. Either the time-delay and/or the logic in the next process steps 605 and/or 606 can be used to assure that the inlet pump (721, 902) is primed. If pressure measurements are being used to determine whether the inlet pump (721, 902) is primed, the time delay can be increased. Once the time delay has reached a minimum time limit, the control logic can proceed to the next process steps.

At step 605, a control logic is initiated by the controller (798, 950) that starts the outlet pumps (748, 749, 918, 920) and places the inlet pump (721, 902) in auto-mode where a constant power is applied to the inlet pump (721, 902). In auto-mode, a control logic is initiated by the controller (798, 950) that applies and adjusts power from the programmable power supply (733) to the motor of the inlet pump (721, 902) to maintain pressure(s) downstream from the inlet pump (721, 902) or downstream from the centrifugal separator (12, 904) at the set-point pressure.

At step 606, a control logic is initiated by the controller (798, 950) triggers one or more of the light line-set turbidity sensor (936) or the heavy line-set turbidity sensor (942) to measure the turbidity in the light and/or heavy outlet line-sets (36, 44, 52, 914, 916) respectively downstream from the centrifugal separator assembly (12, 904). The light line-set turbidity sensor (936) and/or the heavy line-set turbidity sensor (942) send a signal(s) to the controller (98, 950) that is indicative of the turbidity downstream from the centrifugal separator assembly (12, 904). The controller (798, 950) receives, translates, reads and compares the turbidity measurement(s) to a set-point turbidity within the light and/or heavy outlet line-sets (914, 916) downstream from the centrifugal separator assembly (12, 904). If the turbidity measurement(s) matches the required set-point turbidity, priming is complete and the inlet pump (721, 902) continues to run and pump biocomponents from the bioproduction vessel (910), through the system and back through the recycle loop. The set-point turbidity in the light and heavy outlet line-sets (36, 44, 52, 914, 916) downstream from the centrifugal separator assembly (12, 904) can be set to a minimum turbidity. In an exemplary embodiment, the set-point turbidity in the light and heavy outlet line-sets (36, 44, 52, 914, 916) downstream from the centrifugal separator assembly (12, 904) are both greater than 0 FTU. One or more turbidity measurements can be made overtime to confirm that the turbidity is not fluctuating over time and to assure that the inlet pump (721, 902) is primed and the outlet pumps (748, 749, 918, 920) and system have reached steady state. The controller (798, 950) can provide a "pump is primed" or "prime complete" output or notification via the user input and digital display unit (762) that indicates that the inlet pump (721, 902) is primed.

At step 606, alternatively or in addition to measuring turbidity in the light and/or heavy outlet line-sets (36, 44, 52, 914, 916), a control logic is initiated by the controller (798, 950) that triggers one or more of the inlet pressure sensor (930) downstream from the inlet pump (721, 902), the light line-set pressure sensor (934) or the heavy line-set pressure sensor (940) to measure the pressure downstream from the inlet pump (721, 902) or in the light and/or heavy outlet line-sets (36, 44, 52, 914, 916) respectively downstream from the centrifugal separator assembly (12, 904). The inlet pressure sensor 930, light line-set pressure sensor (934) and/or the heavy line-set pressure sensor (940) send a signal(s) to the controller (798, 950) that is indicative of the pressure downstream from the inlet pump (721, 902) or centrifugal separator assembly (12, 904). The controller (798, 950) receives, translates, reads and compares the pressure measurement(s) to a set-point pressure downstream from the inlet pump (721, 902) and/or within the light and/or heavy outlet line-sets (36, 44, 52, 914, 916) downstream from the centrifugal separator assembly (12, 904). If the pressure measurement(s) matches the required set-point pressure, priming is complete, the system has reached steady state, and the inlet pump (721, 902) continues to run and pump biocomponents from the bioproduction vessel (910), through the system and back through the recycle loop. The set-point pressure can be set to a minimum pressure. One or more pressure measurements can be made over time to confirm that the pressure is not fluctuating over time and to assure that the inlet pump (721, 902) is primed and system has reached steady state. If pressure measurements are being used to confirm priming and steady state, the time delay at step 604 can be increased to assure steady state and priming has been accomplished. In an exemplary embodiment, the set-point pressure is greater than or equal to a minimum pressure of 2 psi. The controller (798, 950) can provide a "pump is primed" output or notification via the user input and digital display unit (62) that indicates that the inlet pump (721, 902) is primed.

At step 607, after the inlet pump (721, 902) is primed and both outlet pumps (748, 749, 918, 920) and the system have reached a steady state, a control logic is initiated by the controller (798, 950) that applies power from the programmable power supply (733) to the motor (169) that magnetically drives and rotates the separation rotor (184) of the centrifugal separator assembly (12, 904). The start-up of the separation rotor (184) can affect process parameters, including pressure, turbidity and flow rate in the system, resulting in a perturbation away from steady state achieved prior to start-up of the centrifugal separator assembly (12, 904).

At step 608, a control logic is initiated by the controller (798, 950) that triggers one or more of the light line-set turbidity sensor (936), the heavy line-set turbidity sensor (942), the light line-set pressure sensor (934) or the heavy line-set pressure sensor (940), all located upstream from the light and heavy outlet pumps (36, 44, 52, 918, 920), to measure pressure and/or turbidity in the light and heavy outlet line-sets (36, 44, 52, 914, 916) downstream from the centrifugal separator assembly (12, 904). The one or more sensors (934, 936, 940, 942) send signals to the controller (98, 950) that are indicative of the pressure or turbidity in the light and heavy outlet line-sets (36, 44, 52, 914, 916) downstream from the centrifugal separator assembly (12, 904). The controller (798, 950) receives, translates, reads and compares the turbidity and/or pressure measurement(s) to an outlet pump set-point turbidity and/or pressure requirement that has to be satisfied at a location downstream from the centrifugal separator assembly (12, 904). If the turbidity and/or pressure measurements match the required outlet pump set-point turbidity and/or pressure, the system has reached a safe steady state. The pressure and turbidity set-points can be set to a minimum or maximum pressure or turbidity. For example, the outlet pump set-point pressure can be set at a minimum pressure requirement measured at the light line-set pressure sensor (934) or the heavy line-set pressure sensor (940).

In an exemplary embodiment, the light outlet set-point turbidity measured at the light line-set turbidity sensor (936) is set at a predetermined maximum turbidity. The heavy outlet set-point turbidity measured at the heavy line-set turbidity sensor (942) is set at a predetermined minimum turbidity. Both the maximum and minimum turbidity set points measured in light and heavy outlet line-sets (36, 44, 52, 914, 916) and by the light and heavy line-set turbidity sensors (934, 940) respectively, must be satisfied to achieve a safe steady state and before the control logic can proceed to the next process steps.

One or more pressure and/or turbidity measurements can be made downstream from the centrifugal separator assembly (12, 904) over time to confirm that the pressure or turbidity is not fluctuating over time and to assure that the system has reached a safe steady state with all pumps and the centrifugal separator on. The controller (98, 950) can provide a "steady state" output and notification via the user input and digital display unit (762) that indicates that the system has reached a safe steady state with all pumps and the centrifugal separator on. Once one or more steady state set-point requirements governing this step are met, the control logic can proceed to the next process steps, including downstream process mode where biocomponents are routed downstream of the centrifugal separator assembly (12, 904) and skid (700, 900).

Alternatively at step 608, a control logic is initiated by the controller (798, 950) that time-delays the initiation of a downstream process mode where biocomponents are routed downstream of the centrifugal separator assembly (12, 904) and skid (700, 900) instead of routing biocomponents from the bioprocess vessel (901), through the recycle line set (922) and back the bioprocess vessel (901). Initiation of the downstream process mode is delayed until a confirmed steady state has been reached after start-up of the centrifugal separator assembly (12, 904) and all pumps. Either the time-delay and/or the other logic in this process step 613 can be used to assure that the system has reached a safe steady state after start-up of the centrifugal separator assembly (12, 904). If pressure measurements are being used to determine whether steady state has been reached, the time delay can be increased. Once the time delay has reached a minimum time limit, the control logic can proceed to the next process steps.

At step 609 and after steady state has been reached with all pumps and the centrifugal separator on, a control logic is initiated by the controller (798, 950) that initiates downstream process mode by actuating one or more valves to route separated biocomponents downstream of the centrifugal separator assembly (12, 904) and skid (700, 900) instead of routing biocomponents from the bioprocess vessel (901), through the recycle line set (922) and back the bioprocess vessel (901). In an exemplary embodiment, the controller (798, 950) is programmed to run logic that causes actuation of the light recycle valve (924) and the heavy recycle valve (928) (for example with a valve control system 760) to route separated biocomponents downstream of the centrifugal separator assembly (12, 904) and skid (700, 900).

At step 610, another set of pressure and turbidity measurements can be made as discussed with respect to previous steps to verify that the system has not perturbated away from steady state or that the system has again reached steady state after the downstream process mode is initiated. Once steady state is reached and confirmed after initiating the downstream process mode a control logic is initiated by the controller (798, 950) to enter cascade mode. Cascade mode can also be initiated at the same time as downstream process mode. In cascade mode, the controller (798, 950) continuously applies and adjusts power from the programmable power supply (733) to the inlet pump (721, 902), the light outlet pump (748, 918) and the heavy outlet pump (749, 920) to maintain steady state set points, including operating set points for pressure, turbidity and flow rate upstream and downstream from the centrifugal separator assembly (12, 904).

With reference to FIG. 5C at step 506, an emergency stop event can be initiated by the controller (798, 950) if equipment fails, process parameters are not optimized or if the separation process is not running properly. During an E-STOP event, a control logic initiated by the controller (798, 950) can display and/or sound an alarm and error message indicating that an E-STOP needs to or will occur. The controller (798, 950) can then cut off all power and stop all pumps and the centrifugal separator assembly (12, 904). The controller (798, 950) can also close all valves (924, 926, 928, 952) to assure no biocomponents exit the system or skid (700, 900).

EXAMPLES

Example Separation 1

Figure 57:
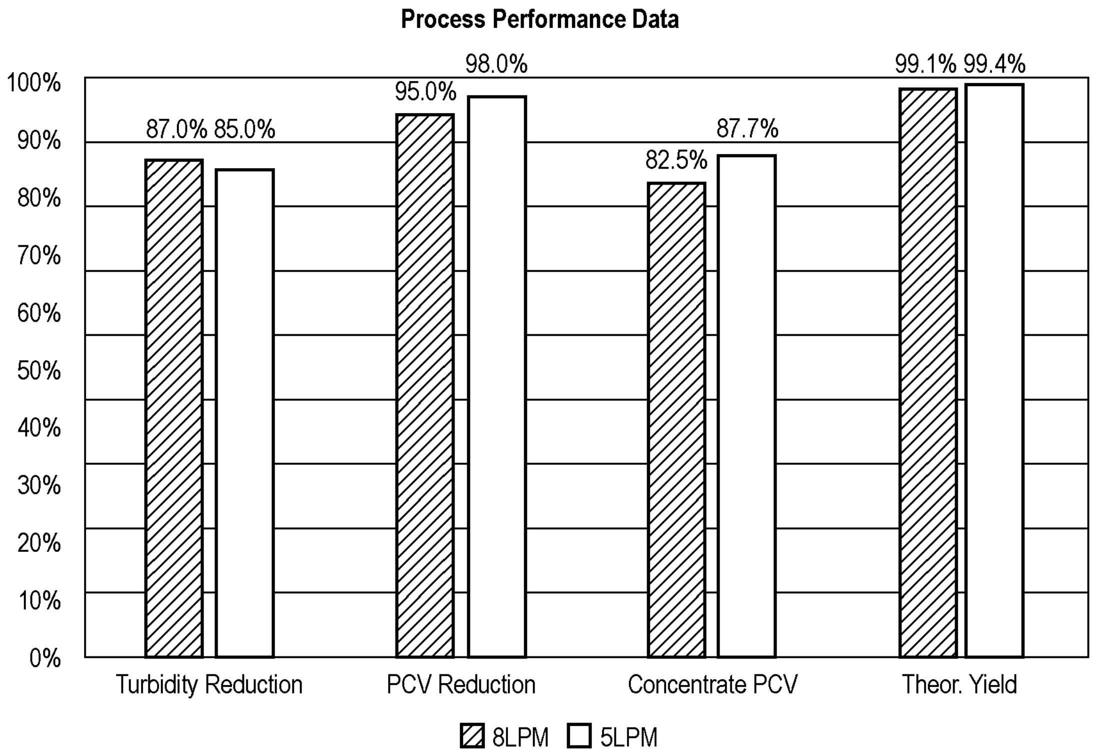
FIG. 57 illustrates a bar graph of process performance parameters generated from example separation processes run with an exemplary centrifugal separator loaded on a skid.

After loading, lockdown and start-up operations performed in accordance with the present disclosure, a CHO cell culture suspension was pumped at 8 liters/min to the inlet of an exemplary centrifugal separator loaded on a skid. The cell culture suspension was separated by the centrifugal separator into a centrate of light components exiting the light outlet and a concentrate of heavy components exiting the heavy outlet of the centrifugal separator. FIG. 57 illustrates a bar graph of several process performance parameters, including percent reduction in turbidity; percent reduction in packed cell volume (PCV); PCV enriched in concentrate stream; and theoretical yield of soluble product (in this case a secreted protein), measured from the inlet to the outlet of the centrifugal separator. The process performance parameters of Example Separation 1 are depicted in the first set of bars in the bar graph of FIG. 57.

The packed cell volume is an indication of the volume percentage of cells in the cell culture suspension and was calculated using the following equation:

$$PCV = \frac{\text{Cell pellet volume}}{\text{Sample Volume}} \cdot 100\%$$

The theoretical yield of soluble product separated from the cell culture suspension was calculated using the following equation:

$$\text{Theoretical Yield} = 1 - \frac{\text{Liquid } vol. \text{ out concentrate}}{\text{Liquid } vol. \text{ in inlet}} \cdot 100\% = 1 - \frac{PCV_{inlet} \cdot (1 - PCV_{conc.})}{(1 - PCV_{inlet})} 100\%$$

Example Separation 1 resulted in a reduction in turbidity of the cell culture suspension of 87%; reduction in PCV of 95%; PCV enriched in concentrate of 82.5%; and theoretical yield of 99.1% of soluble product recovery.

Example Separation 2

After loading, lockdown and start-up operations, a CHO cell culture suspension was pumped at 5 liters/min to the inlet of an exemplary centrifugal separator loaded on a skid. The cell culture suspension was separated by the centrifugal separator into a centrate of light components exiting the light outlet and a concentrate of heavy components exiting the heavy outlet of the centrifugal separator. FIG. 57 illustrates a bar graph of several process performance parameters, including percent reduction in turbidity; percent reduction in packed cell volume (PCV); PCV enriched in concentrate; and theoretical yield of soluble product, measured from the inlet to the outlet of the centrifugal separator. The process performance parameters of Example Separation 2 are depicted in the second set of bars in the bar graph of FIG. 57.

The packed cell volume is an indication of the volume percentage of cells in the cell culture suspension and was calculated using the following equation:

$$PCV = \frac{\text{Cell pellet volume}}{\text{Sample Volume}} \cdot 100\%$$

The theoretical yield of soluble product separated from the cell culture suspension was calculated using the following equation:

$$\text{Theoretical Yield} = 1 - \frac{\text{Liquid } vol. \text{ out concentrate}}{\text{Liquid } vol. \text{ in inlet}} \cdot 100\% = 1 - \frac{PCV_{inlet} \cdot (1 - PCV_{conc.})}{(1 - PCV_{inlet})} 100\%$$

Example Separation 2 resulted in reduction in turbidity of the cell culture suspension of 85%; reduction in PCV of 98%; PCV enriched in concentrate of 87.7%; and theoretical yield of 99.4% of soluble product.

Example Separation 3

After loading, lockdown and start-up operations, a CHO cell culture suspension was pumped at 8 liters/min to the inlet of an exemplary centrifugal separator loaded on a skid. The cell culture suspension was separated by the centrifugal separator into a centrate of light components exiting the light outlet and a concentrate of heavy components exiting the heavy outlet of the centrifugal separator. The centrate exiting the light outlet of the centrifugal separator was subjected to depth filtration using a cellulose-based depth filter with diatomaceous earth filter aide.

Figure 58:
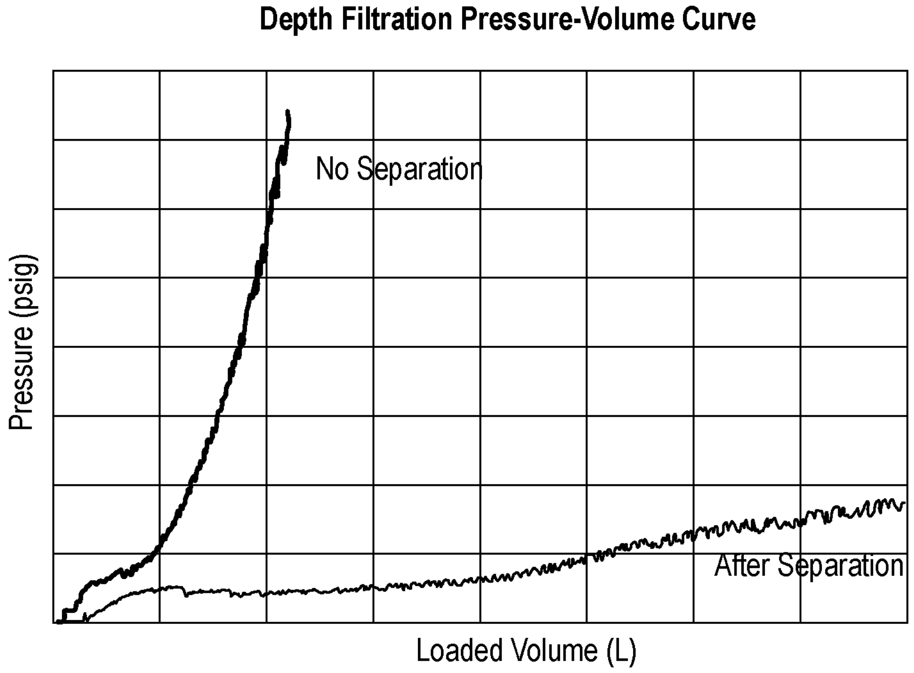
FIG. 58 illustrates exemplary pressure-volume depth filtration curves.

The same CHO cell culture suspension was also subjected to depth filtration under the same conditions without first running the cell culture suspension through the centrifugal separator. FIG. 58 illustrates a pressure-volume curve corresponding to depth filtration of cell culture suspension without separation and a pressure volume curve corresponding to depth filtration of centrate yielded from Example Separation 3. As shown in FIG. 58, the pressure over a given volume of depth filtration is much lower for cell culture suspension that has undergone separation using the exemplary centrifugal separator. These depth filtration results are indicative of high separation performance.

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems, processes, and/or products according to certain embodiments of the present disclosure may include, incorporate, or otherwise comprise properties features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features without necessarily departing from the scope of the present disclosure.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims.

All changes which come within the meaning and range of equivalency of the claims are to be embraced within their scope.

What is claimed is:

1. A skid for use in separating biocomponents, the skid comprising:

a housing bounding a compartment, the compartment being partially bounded by a mounting platform; and a loading assembly secured to the housing so as to communicate with the compartment, the loading assembly comprising:

an alignment plate having a top surface with a cavity recessed therein, the cavity communicating with the compartment;

a drive rotor rotatably disposed below the alignment plate and at least partially encircling the cavity, the drive rotor including one or more magnets;

a motor coupled to the drive rotor for selectively rotating the drive rotor about the cavity; and a mount at least partially encircling the drive rotor and communicating with the compartment, the mount including a mounting plate having one or more mounting elements upstanding therefrom, the mount being movable between a first raised position wherein the mounting plate is aligned with the alignment plate and a second lowered position wherein the mounting plate is disposed at an elevation lower than the alignment plate.

2. The skid as recited in claim 1, further comprising:

a doorway formed on the housing and communicating with the compartment; and a door mounted on the housing, the door being movable between an open position wherein the doorway is openly exposed and a closed position wherein the door covers the doorway.

3. The skid as recited in claim 2, further comprising a notch recessed into an exterior surface of the housing and extending between a side face of the housing and the doorway, the notch bounding a channel that communicates with the compartment whether the door is in the open position or the closed position.

4. The skid as recited in claim 1, wherein the mounting platform comprises an opening extending therethrough; and wherein the loading assembly is secured to the housing so that the alignment plate is aligned with the opening extending through the mounting platform.

5. The skid as recited in claim 4, wherein at least a portion of a top surface of the mounting platform, a top surface of the alignment plate, and a top surface of the mounting plate are horizontally aligned when the mount is in the raised position.

6. The skid as recited in claim 1, wherein the loading assembly further comprises:

an annular inner sleeve that encircles an opening, the inner sleeve having an upper end with the alignment plate mounted thereon;

a receiver extending from a bottom surface of the alignment plate and projecting into the opening of the annular sleeve, the receiver bounding the cavity; and the drive rotor being at least partially disposed within the opening of the inner sleeve.

7. The skid as recited in claim 6, wherein the loading assembly further comprises an annular outer sleeve encircling the inner sleeve, the outer sleeve having an upper end with the mounting plate mounted thereon, the outer sleeve and the mounting plate being movable relative to the inner sleeve.

8. The skid as recited in claim 7, further comprising:

a support from which the inner sleeve upstands;

a pivot mount block secured to the support at a location spaced apart from the inner sleeve;

a pair of pivot arms each having a first end pivotably mounted to the pivot mount block so that the pair of pivot arms extend along opposing sides of the outer sleeve; and a pair of support pins outwardly projecting from the opposing sides of the outer sleeve and coupling with a corresponding one of the pair of pivot arms.

9. The skid as recited in claim 7, further comprising a linear actuator positioned to selectively raise and lower the outer sleeve relative to the inner sleeve.

10. The skid as recited in claim 1, wherein the one or more mounting elements comprise one or more L-shaped clips upstanding from the mounting plate and facing toward the cavity.

11. The skid as recited in claim 1, further comprising one or more peristaltic pumps mounted on an exterior surface of the housing.

12. The skid as recited in claim 1, further comprising one or more pinch valves mounted on an exterior surface of the housing.

13. The skid as recited in claim 1, further comprising one or more of a pressure sensor, conductivity sensor, flow meter sensor, pH sensor, temperature sensor, or turbidity sensor mounted on an exterior surface of the housing.

14. A system for separating biocomponents, the system comprising:

the skid as recited in claim 1; and a centrifugal separator removably disposed within the compartment of the skid, the centrifugal separator being supported on the mounting plate of the loading assembly.

15. The system as recited in claim 14, further comprising a first fluid line fluidically coupled to the centrifugal separator within the compartment of the skid, the first fluid line passing out of the compartment and being removably secured to an exterior surface of the housing.

16. A method for separating biocomponents, the method comprising:

positioning a centrifugal separator on a top surface of the mounting platform of the skid as recited in claim 1;

laterally moving the centrifugal separator within the compartment of the housing so that the centrifugal separator is supported on the mounting plate of the mount and the mounting elements engage the centrifugal separator;

moving the mounting plate to the lowered position so that centrifugal separator is lowered relative to the alignment plate, a drive coupling of the centrifugal separator being received within the cavity of the alignment plate as the mounting plate is moved to the lowered position; and activating the motor to rotate the drive rotor which magnetically rotates a separation rotor of the centrifugal separator.

17. The method as recited in claim 16, wherein laterally moving the centrifugal separator comprises laterally sliding the centrifugal separator on the mounting platform proximate a magnetic field produced by the one or more magnets of the drive rotor, wherein the magnetic field assists in positioning of the centrifugal separator.

18. The method as recited in claim 16, wherein moving the mounting plate to the lowered position rigidly locks the centrifugal separator to the housing of the skid.

19. The method as recited in claim 16, wherein the step of positioning a centrifugal separator on the top surface of the mounting platform comprises:

passing the centrifugal separator through a doorway formed on the housing and into the compartment; and closing a door that covers the doorway after the centrifugal separator is within the compartment.

20. The method as recited in claim 16, wherein the centrifugal separator is positioned on the top surface of the mounting platform so that a first fluid line coupled with centrifugal separator passes out of the compartment of the housing, the method further comprising removably securing the first fluid line to a pinch valve and/or a peristaltic pump mounted on an exterior surface of the housing.

* * * * *